(12) United States Patent
Anderson et al.

(10) Patent No.: US 10,053,497 B2
(45) Date of Patent: Aug. 21, 2018

(54) THERAPEUTIC EPITOPES AND USES THEREOF

(75) Inventors: Robert Paul Anderson, Parkville (AU); Adrian Vivian Sinton Hill, Oxford (GB); Derek Parry Jewell, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 2011 days.

(21) Appl. No.: 10/516,837

(22) PCT Filed: Jun. 5, 2003

(86) PCT No.: PCT/GB03/02450
§ 371 (c)(1),
(2), (4) Date: Aug. 9, 2005

(87) PCT Pub. No.: WO03/104273
PCT Pub. Date: Dec. 18, 2003

(65) Prior Publication Data
US 2006/0178299 A1    Aug. 10, 2006

(30) Foreign Application Priority Data
Jun. 5, 2002  (GB) .................... 0212885.8

(51) Int. Cl.
| | | |
|---|---|---|
| *A61K 38/00* | (2006.01) | |
| *A61K 39/00* | (2006.01) | |
| *C07K 2/00* | (2006.01) | |
| *C07K 4/00* | (2006.01) | |
| *C07K 5/00* | (2006.01) | |
| *C07K 7/00* | (2006.01) | |
| *C07K 14/00* | (2006.01) | |
| *C07K 16/00* | (2006.01) | |
| *C07K 17/00* | (2006.01) | |
| *C07K 14/415* | (2006.01) | |

(52) U.S. Cl.
CPC ............ *C07K 14/415* (2013.01); *A61K 38/00* (2013.01)

(58) Field of Classification Search
None
See application file for complete search history.

(56) References Cited

U.S. PATENT DOCUMENTS

| | | |
|---|---|---|
| 4,459,355 A | 7/1984 | Cello et al. |
| 4,536,475 A | 8/1985 | Anderson |
| 4,710,461 A | 12/1987 | Komano et al. |
| 4,886,753 A | 12/1989 | Marcker et al. |
| 4,943,674 A | 7/1990 | Houck et al. |
| 4,945,050 A | 7/1990 | Sanford et al. |
| 5,036,006 A | 7/1991 | Sanford et al. |
| 5,086,169 A | 2/1992 | Mascarenhas |
| 5,097,025 A | 3/1992 | Benfey et al. |
| 5,100,792 A | 3/1992 | Sanford et al. |
| 5,107,065 A | 4/1992 | Shewmaker et al. |
| 5,110,732 A | 5/1992 | Benfey et al. |
| 5,177,010 A | 1/1993 | Goldman et al. |
| 5,179,022 A | 1/1993 | Sanford et al. |
| 5,187,073 A | 2/1993 | Goldman et al. |
| 5,187,267 A | 2/1993 | Comai et al. |
| 5,202,257 A | 4/1993 | Heinemann et al. |
| 5,204,253 A | 4/1993 | Sanford et al. |
| 5,250,515 A | 10/1993 | Fuchs et al. |
| 5,356,799 A | 10/1994 | Fabijanski et al. |
| 5,371,014 A | 12/1994 | Matsuyama et al. |
| 5,405,765 A | 4/1995 | Vasil et al. |
| 5,428,146 A | 6/1995 | Logemann et al. |
| 5,459,252 A | 10/1995 | Conkling et al. |
| 5,464,763 A | 11/1995 | Schilperoort et al. |
| 5,478,744 A | 12/1995 | Sanford et al. |
| 5,484,956 A | 1/1996 | Lundquist et al. |
| 5,489,520 A | 2/1996 | Adams et al. |
| 5,495,007 A | 2/1996 | Thompson et al. |
| 5,508,468 A | 4/1996 | Lundquist et al. |
| 5,510,318 A | 4/1996 | Patel et al. |
| 5,538,877 A | 7/1996 | Lundquist et al. |
| 5,554,798 A | 9/1996 | Lundquist et al. |
| 5,565,346 A | 10/1996 | Facciotti |
| 5,589,583 A | 12/1996 | Klee et al. |
| 5,589,610 A | 12/1996 | De Beuckeleer et al. |
| 5,618,988 A | 4/1997 | Hauptmann et al. |
| 5,629,183 A | 5/1997 | Saunders et al. |
| 5,633,363 A | 5/1997 | Colbert et al. |
| 5,646,333 A | 7/1997 | Dobres et al. |
| 5,670,349 A | 9/1997 | Cramer et al. |
| 5,689,044 A | 11/1997 | Ryals et al. |

(Continued)

FOREIGN PATENT DOCUMENTS

| | | |
|---|---|---|
| EP | 0242236 | 10/1987 |
| EP | 0255378 | 2/1988 |

(Continued)

OTHER PUBLICATIONS

US 5,792,925, 08/1998, de Framond (withdrawn)
Cornell et al. 'In vitro Mucosal Digestion of Synthetic Giiadin-Derived Peptides in Celiac Disease.' Journal of Protein Chemistry, vol. 14, No. 5, 1995.*
Ngo et, al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*

(Continued)

*Primary Examiner* — Nora Rooney
(74) *Attorney, Agent, or Firm* — Arrigo, Lee, Guttman & Mouta-Bellum LLP

(57) ABSTRACT

The invention herein disclosed is related to epitopes useful in methods of diagnosing, treating, and preventing coeliac disease. Therapeutic compositions which comprise at least one epitope are provided.

1 Claim, 60 Drawing Sheets

(13 of 60 Drawing Sheet(s) Filed in Color)

(56) References Cited

U.S. PATENT DOCUMENTS

| | | | |
|---|---|---|---|
| 5,859,328 | A | 1/1999 | Nasrallah et al. |
| 6,036,983 | A | 3/2000 | Nielsen |
| 6,232,445 | B1 | 5/2001 | Rhode et al. |
| 7,144,569 | B1 * | 12/2006 | Anderson et al. ............ 424/9.81 |
| 7,202,216 | B2 | 4/2007 | Sollid et al. |
| 7,303,871 | B2 * | 12/2007 | Hausch et al. ............... 435/6.18 |
| 7,307,871 | B2 | 12/2007 | Liaw |
| 2003/0215438 | A1 * | 11/2003 | Hausch et al. ............. 424/94.63 |
| 2005/0249719 | A1 * | 11/2005 | Shan et al. ................. 424/94.63 |
| 2005/0256054 | A1 | 11/2005 | Sollid et al. |
| 2006/0240475 | A1 | 10/2006 | Khosla et al. |
| 2008/0318852 | A1 | 12/2008 | Anderson et al. |

FOREIGN PATENT DOCUMENTS

| | | |
|---|---|---|
| EP | 267159 | 5/1988 |
| EP | 0293358 | 11/1988 |
| EP | 0369367 | 5/1990 |
| EP | 442174 | 8/1991 |
| EP | 486233 | 5/1992 |
| EP | 486234 | 5/1992 |
| EP | 293358 | 4/1993 |
| EP | 604662 | 7/1994 |
| EP | 672752 | 9/1995 |
| EP | 0693119 | 1/1997 |
| EP | 905 236 | 3/1999 |
| EP | 0905518 | 3/1999 |
| EP | 539563 | 10/2001 |
| EP | 0536330 | 2/2002 |
| WO | WO 91/02071 | 2/1991 |
| WO | WO 92/000377 | 1/1992 |
| WO | WO 92/17580 | 10/1992 |
| WO | WO 92/20809 | 11/1992 |
| WO | WO 94/13863 | 6/1994 |
| WO | WO 95/06128 | 3/1995 |
| WO | WO97/20058 | 6/1997 |
| WO | WO97/47745 | 12/1997 |
| WO | WO 98/23960 | 6/1998 |
| WO | WO 98/45460 | 10/1998 |
| WO | WO 98/45461 | 10/1998 |
| WO | WO98/56811 | 12/1998 |
| WO | WO 99/20775 | 4/1999 |
| WO | WO99/53075 | 10/1999 |
| WO | WO99/58681 | 11/1999 |
| WO | WO00/47614 | 8/2000 |
| WO | WO 01/25793 | 4/2001 |
| WO | WO 02/083722 | 10/2002 |
| WO | WO 03/066079 | 8/2003 |
| WO | 03/096984 A2 | 11/2003 |
| WO | 03096979 | 11/2003 |
| WO | WO 03/096984 | 11/2003 |
| WO | WO 03/104273 | 12/2003 |
| WO | 04045392 | 6/2004 |
| WO | 2010060155 | 6/2010 |

OTHER PUBLICATIONS

Skolnick et al. 'From genes to protein structure and function: novel applications of computational approaches in the genomic era.' Trends in Biotech. 18:34-39, 2000.*

Attwood et al. 'The Babel of Bioinformatics.' Science. 290(5491):471-473, 2000.*

Di Sabatino et al. 'The function of tissue transglutaminase in celiac disease.' Autoimmunity Reviews. 11:746-753, 2012.*

Anderson et al. 'In vivo antigen challenge in celiac disease identifies a single transglutaminase-modified peptide as the dominant A-gliadin T-cell epitope.' Nature Maed. 6(3):337-342, 2000.* von der Muelbe et al. 'Deamidation within alpha-gliadin-derived peptide enhances its recognition by serum antibodies of CD patients.' Peptides: The Wave of the Future, Proceedings of the Second International and the Seventeenth American Peptide Symposium, San Diego, CA, United States, 2001. pp. 1037-1038.*

Cournoyer et al. 'Analysis of Deamidation in Proteins.' Comprehensive Analytical Chemistry, vol. 52, pp. 375-410, 2009.*

Ach, et al., "RRB1 and RRB2 encode maize retinoblastoma-related proteins that interact with a plant D-type cyclin and geminivirus replication protein," Mol. Cell Biol. (1997) 17:5077-5086.

Albani, et al., "DcE2F, a functional plant E2F-like transcriptional activator from Daucus carota," J. Biol. Chem. (2000) 275:19258-19267.

Bandara, et al., "Functional synergy between DP-1 and E2F-1 in the cell cycle-regulating transcription factor DRTF1/E2F," EMBO J. (1993) 12:4317-4324.

Bogre, et al., "Wounding induces the rapid and transient activation of a specific MAP kinase activity," Plant Cell (1997) 9:75-83.

Breeden and Nasmyth, "Regulation of the yeast HO gene," Cold Spring Harbor Symp. Quant. Biol. (1985) 50:643-650.

Breeden, "Start-specific transcription in yeast," Curr. Topics Microbiol. Immunol. (1996) 208:95-127.

de Jager, et al., "Retinoblastoma proteins implants," Plant Mol. Biol. (1999) 41:295-299.

de la Luna, et al., "Nuclear accumulation of the E2F heterodimer regulated by subunit composition and alternative splicing of a nuclear localization signal," J. Cell Sci. (1996) 109:2443-2452.

Denecke, et al., "Plant and mammalian sorting signals for protein retention in the endoplasmic reticulum contain a conserved epitope," EMBO J. (1992) 11:2345-2355.

Doonan and Folbert, "Conserved and novel regulators of the plant cell cycle," Curr. Opin. Cell Biol. (1997) 9:824-830.

Dynlacht B.D. et al., "DNA-binding and trans-activation properties of *Drosphila* E2F and DP proteins," Proc Natl Acad Sci U S A Jul. 5, 1994;91(14):6359-63.

Dyson, "The regualtion of E2F by pRB-family proteins," Genes Dev. (1998) 12:2245-2262.

Fields and Song, "A novel genetic system to detect protein-protein interactions," Nature (1989) 340:245-246.

Fountain, et al., "Isolation and characterization of a plant retinoblastoma-related gene from photoautotrophic cell suspension culture of *Chenopodium rubrum* L.," Plant Physiol. (1999) 119:363.

Fuerst, et al., "Modulation of cyclin transcript levels in cultured cells of *Arapidopsis thaliana*," Plant Physiol. (1996) 112:1023-1033.

Gillaspy G.E. et al., GenEmbl Accesion No. U39059, Nov. 18, 1996.

Gillespie D. "The magic and challenge of DNA probes as diagnostic reagents," *Vet Microbiol* (1990), (3.

Girling, et al., "A new component of transcription factor DRTF1/E2F," Nature (1993) 362:83-87.

Grafi, et al., "A maize cDNA encoding a member of the retinoblastoma protein family: involvement in endoreduplication," Proc. Natl. Acad. Sci. USA (1996) 93:8962-8967.

Gutierrez, "DNA replication and cell cycle in plants: learning from geminiviruses," EMBO J. (2000) 19:792-799.

Gutierrez, "The retinoblastoma patway in plant cell cycle and development," Curr. Opin. Plant Biol. (1998) 1:492-497.

Hiebert S.W. et al., "E2F-1: DP-1 induces P53 and overrides survival factors to trigger apoptosis," Mol Cell Biol (1995), 15(12): 6864-74.

Helin, et al., "Heterodimerization of the transcription factors E2F-1 and DP-1 leads to cooperative trans-activation," Genes Dev. (1993) 7:1850-1861.

Helin, et al., "Inhibition of E2F-1 trans-activation by direct binding of the retinoblastoma protein," Mol. Cell Biol. (1993) 13:6501-6508.

Helin, et al., A cDNA encoding a pRB-binding protein with properties of the transcription factor E2F, Cell (1992) 70:337-350.

Huntley and Murray, "The plant cell cycle," Curr. Opin. Plant Biol. (1999) 2:440-446.

Huntley, et al., "The maize retinoblastoma protein homologue ZmRb1 is regulated during leaf development and display conserved interactions with G1/S regulators and plant cyclins (D-type) proteins," Plant Mol. Biol. (1998) 37:155-169.

Kosugi and Obashi, "PCF1 and PCF2 specifically bind to cis elements in the rice proliferating cell nuclear antigen gene," Plant Cell (1997) 9:1607-1619.

(56) References Cited

OTHER PUBLICATIONS

Kozak, "At least six nucleotides preceding the AUG initiator codon enhance translation in mammalian cell," J Mol Biol (1987), 196:947-950.
Krek, et al., "Binding to DNA and the retinoblastoma gene product promoted by complex formation of different E2F family members," Science (1993) 262:1557-1560.
Lipman, et al., "Rapid and sensitive protein similarity searches," Science (1985) 227:1435-1441.
Lowndes, et al., "Control of DNA synthesis genes in fission yeast by the cell cycle gene cdc10," Nature (1992) 355:449-453.
Lui, et al., "The *Aradiopsis* Cdc2a-interacting protein ICK2 is structurally related to ICK1 and is a potent inhibitor of cyclin-dependent kinase activity in vitro," Plant J. (2000) 21:379-386.
Magyar Z. et al., "Characterization of two distinct DP-related genes from *Arabidopsis thaliana*," FEBS Lett. Dec. 1, 2000; 486(1):79-87.
Mariconti L. et al., "The E2F family of transcription factors from *Arabidopsis thaliana*. Novel and conserved components of the retinoblastoma/E2F pathway in plants," J Biol Chem (2002), 277(12):9911-9. EPub Jan. 10, 2002
Martinez-Balbos, et al., "Regulation of E2F1 activity by acetylation," EMBO J. (2000) 19:662-671.
Marzio, et al., "E2F family members are differently regulated by reversible acetylation," J. Biol. Chem. (2000) 275:10887-10892.
Mironov, et al., "Cyclin-dependent kinases and cell division in plants: the nexus," Plant Cell (1999) 11:509-521.
Nakagami, et al., "Tobacco retinoblastoma-related protein phosphorylated by a distinct cyclin-dependent kinase complex with Cdc2/cyclin D in vitro," Plant J. (1999) 18:243-252.
Nevins, "E2F: A link between the Rb tumor suppression protein and viral oncoproteins," Science (1992) 258:424-429.
Ormonroyd, et al., "A new member of the DP family, DP-3, with distinct protein products suggests regulatory role for alternative splicaing in the cell cycle transcription factor DRTF1/E2F," Oncogene (1995) 11:1437-1446.
Othani and Nevins, "Functional properties of a *Drosophila* homolog of the E2F-1 gene," Mol. Cell Biol. (1994) 14:1603-1612.
Ouelette, et al., (Title Unkown) Oncogene (1992) 7:1075-1081.
Ramirez-Parra, et al., "Characterization of wheat DP, a heterodimerization partner of the palnt E2F transcription factor which stimulates E2F-DNA binding," FEBS Lett. (2000) 486:73-78.
Ramirez-Parra, et al., "The cloning of plant E2F, a retinoblastoma-binding protein, reveals unique and conserved features with animal G1/S regulators," Nucl. Acids, Res. (1999) 27:3527-3533.
Riou-Kamlichi, et al., "Cytokinin activation of *Aradiopsis* cell division through a D-type cyclin," Science (1999) 283:1541-1544.
Sandler SJ et al., "Inhibition of gene expression in transformed plants by antisense RNA," Plant Molecular Biology (1988), 11(3): 301-310.
Sanford, et al., "Optimizing the biolistic process for diffesent biological applications," Methods Enzymol. (1993) 217:483-509.
Sardet, et al., "E2F-4 and E2F-5, to members of the E2F family, are expressed in the early phases of the cell cycle," Proc. Natl. Acad. Sci. USA (1995) 92:2403-2407.
Sawado T et al., "dE2F2, a novel E2F-family transcription factor in *Drosophila melanogaster*," Biochem Biophys Res Coimmun Oct. 20, 1998;251(2):409-415.
Scott, et al, "Model system for plant cell biology: GFP imaging in living onion epidermal cells," Biotechniques (1999) 26:1125-1132.
Sekine, et al., "Isolation and characterization of the E2F-like gene in plants," FEBS Lett. (1999) 460:117-122.
Shoemaker, et al., EMBL Acc. No. AI939068, Aug. 3, 1999.
Slansky and Farnum, "Introduction to the E2F family: protein structure and gene reguation," Curr. Topics Microbiol. Immunol. (1996) 208:1-30.
Smith and Waterman, "Comparison of biosequences", Adv. Mathematics (1981) 2:482-489.

Suarez-Lopez and Gutierrez, "DNA replication of wheat dwarfgeminivirus vectors: effects of origin structure and size," Virology (1997) 227:389-399.
Tao, et al., "Subunit composition determines E2F DNA-binding site specificity," Mol. Cell Biol. (1997) 17:6994-7007.
Umada, et al., "A distinct cyclin-dependent kinase-activating kinase of *Aradiopsis thaliana*," Proc. Natl. Acad. Sci. USA (1998) 95:5021-5026.
Van der Krol A.R. et al., "Inhibition of flower pigmentation by antisense CHS genes: promoter and minimal sequences requirements for antisense effect," Plant Mol Biol (1990), 14(4): 457-466.
Varagona, et al., "Nuclear localization signal(s)-required for nuclear targeting of the maize regulatory protein Opaque-2," Plant Cell (1992) 4:1213-1227.
von Armin et al., "Cloning vectors for expression of green fluorescent protein fusion proteins in transgenic plants," Gene (1998) 221:35-43.
von Armin, et al., "Light inactivation of *Arabiopsis* photomorphoenic repressor COP1 involves a cell-specific regulation of its nucleocytoplasmic partitioning," Cell (1994) 79:1035-1045.
Wang, et al., "ICK1, a cyclin-dependent protein kinase inhibitor from *Arabidopsis thaliana* interacts with both cdc2a and CycD3, and its expression is induced by abcsic acid," Plant J. (1998) 15:501-510.
Waterhouse et al., "Virus resistance and gene silencing : killing the messenger," Trends Plant Sci. (1999), 4(11); 452-457.
Whisstock J.C. et al., "Prediction of protein function from protein sequence and structure," Q Rev Biophys (2003) 36(3):307 Review.
Wu CL et al., "In vivo association of E2F-family transcription factor in *Drosophila melanogaster*," Mol Cell Biol (1995); 15(5) : 2536-46.
Xie, et al., "GRAB proteins, novel members of the NAC domain family, isolated by their interaction with a geminivirus protein," Plant Mol. Biol. (1999) 39:647-656.
Xie, et al., "Identification and analysis of a retinoblastoma binding motif in the replication protein of a plant DNA virus: requirement for efficient viral DNA replication," EMBO J. (1995) 14:4073-4082.
Xie, et al., "Plant cells contain a novel member of the retinoblastoma family of growth regulatory proteins," EMBO J. (1996) 15:4900-4908.
Zheng, et al., "Structural basis of DNA recognition by the heterodimeric cell cycle transcription factor E2F-DP," Genes Dev. (1999) 13:666-674.
Fleckenstein "Gliadin T cell epitope selection by tissue transglutaminase in celiac disease. Role of enzyme specificity and pH influence on the transamidation versus deamidation process," J Biol Chem (2002) 277(37):34109-34116.
Fraser et al., "Coeliac disease: In vivo toxicity of the putative immunodominant epitope," Gut (2003) 52(12):1698-1702.
Lundin et al., "Oats induced villous atrophy in coeliac disease," Gut (2003) 52(11):1649-1652.
van de Wal, "Glutenin is involved in the gluten-driven mucosal T cell response," Eur J Immunol (1999) 29(10):3133-3139.
Altschul "A protein alignment scoring system sensitive at all evolutionary distances," J Mol Evol (1993) 36(3):290-300.
Altschul et al., "Basic local alignment search tool," J Mol Biol (1990) 215(3):403-410.
Bunce et al., "Phototyping: comprehensive DNA typing for HLA-A, B, C, DRB1, DRB3, DRB4, DRB5 & DQB1 by PCR with 144 primer mixes utilizing sequence-specific primers (PCR-SSP)," Tissue Antigens (1995) 46(5):355-367.
Dalta et al., "Plant promoters for transgene expression," Biotechnology Ann Rev (1997) 3:269-296.
Devereux et al., "A comprehensive set of sequence analysis programs for the VAX," Nucleic Acids Research (1984) 12(1 Pt 1):387-395.
Greenberg et al., "Transglutaminases: multifunctional cross-linking enzymes that stabilize tissues," FASEB (1991) 5(15):3071-3077.
Henikoff "Amino acid substitution matrices from protein blocks," Proc. Natl. Acad Sci USA (1992) 89(22):10915-10919.

(56) References Cited

OTHER PUBLICATIONS

Karlin et al., "Applications and statistics for multiple high-scoring segments in molecular sequences," *Proc Natl Acad USA* (1993) 90(12):5873-5887.

Kohler et al., "Continuous cultures of fused cells secreting antibody of predefined specificity," *Nature* (1975) 256(5517):495-497.

Kricka "Prospects for chemiluminescent and bioluminescent immunoassay and nucleic acid assays in food testing and the pharmaceutical industry," *J Biolumin Chemilumin* (1998) 13(4):189-193.

Lalvani et al., "Rapid effector function in CD8+ memory T cells," *J Exp Med* (1997) 186(6):859-865.

Mantzaris et al., "In vivo toxicity of a synthetic dodecapeptide from A gliadin in patients with coeliac disease," *Gastroenterol.* (1991) 26(4):392-398.

Maiuri et al., "In vitro activities of A-gliadin-related synthetic peptides: damaging effect on the atrophic coeliac mucosa and activation of mucosal immune response in the treated coeliac mucosa," *Scand J Gastroenterol.* (1996) 31(3):247-253.

Molberg et al., "Tissue transglutaminase selectively modifies gliadin peptides that are recognized by gut-derived T cells in celiac disease," *Nature Med* (1998) 4(6):713-717.

Mullighan et al., "High-resolution HLA-DQB1 typing using the polymerase chain reaction and sequence-specific primers," *Tissue Antigens* (1997) 50(6):688-692.

Olerup et al., "HLA-DQB1 and -DQA1 typing by PCR amplification with sequence-specific primers (PCR-SSP) in 2 hours," *Tissue Antigens* (1993) 41(3):119-137.

Ota et al., "T-cell recognition of an immunodominant myelin basic protein epitope in multiple sclerosis," *Nature* (1990) 346(6280):183-187.

Quarsten et al., "HLA binding and T cell recognition of a tissue transglutaminase-modified gliadin epitope," *Eur J Immunol* (1999) 29(8):2506-2514.

Thurau et al., "Oral tolerance in a murine model of relapsing experimental autoimmune uveoretinitis (EAU): induction of protective tolerance in primed animals," *Clin Exp Immunol* (1997) 109(2):370-376.

Vasil et al., "Herbicide Resistant Fertile Transgenic Wheat Plants Obtained by Microprojectile Bombardment of Regenerable Embryogenic Callus ," *Biotechnology* (1992) 10:667-674.

Weiner et al., "Oral tolerance: cytokine milieu in the gut and modulation of tolerance by cytokines," *Res Immunol* (1997) 148(8-9):528-533.

Yoshida et al., "The oral administration of low-dose antigen induces activation followed by tolerization, while high-dose antigen induces tolerance without activation," *Clin Immunol Immunopathol* (1997) 82:207-215.

Sambrook et al., *Molecular Cloning: A Laboratory Manual* (1989).

Vader et al., *Proceedings 8th International Symposium Coeliac Disease.*

Anderson "Identification of the Immunodominant T-Cell Epitope in Agliadin Recognized by Coeliac Disease (CD) Patients in Vivo," (1999) A165.

Dieterich et al., "Identification of tissue transglutaminase as the autoantigen of celiac disease," *Nature Medicine* (1997) 3(7):797-801.

Gutgemann et al., "Induction of rapid T cell activation and tolerance by systemic presentation of an orally administered antigen," *Immunity* (1998) 8:667-673.

McAdam et al., "Gliadin Specific Response by Small Intestinal T Cells," *Peptide Binding to HLA Molecules and T Cells,* Eighth International Symposium on Coeliac Disease, p. 17, (1999).

Sjostrom et al., "Identification of a gliadin T-cell epitope in coeliac disease: general importance of gliadin deamidation for intestinal T-cell recognition," *Scand J Immunol* (1998) 48(2):111-115.

Tian et al., "Antigen-based immunotherapy for autoimmune disease: from animal models to humans?" *Immunology Today* (1999) 20(4):190-195.

Van de Wal et al., "Selective deamidation by tissue transglutaminase strongly enhances gliadin-specific T cell reactivity," *The Journal of Immunology* (1998) 161(4):1585-1588.

Arentz-Hansen et al., "Celiac lesion T cells recognize epitopes that cluster in regions of gliadins rich in proline residues," *Gastroenterology* (2002) 123(3):803-809.

Jung et al., "From combinatorial libraries to MHC ligand motifs, T-cell superagonists and antagonists," *Biologicals* (2001) 29(3-4):179-181.

Mowat et al., "Coeliac disease—a future for peptide therapy?," *Lancet* (2000) 356(9226):270-271.

Madsen et al., "A humanized model for multiple sclerosis using HLA-DR2 and a human T-cell receptor," *Nature Genetics* (1999) 23(3):343-347.

Van de Wal et al., "Coeliac disease: it takes three to tango!," *Gut* (2000) 46(5):734-737.

Vader et al., "Specificity of Tissue Transglutaminase Explains Cereal Toxicity in Celiac Disease," *Journal of Experimental Medicine* (2002) 195(5):643-649.

Wieser et al., "Coeliac active peptides from gliadin: large-scale preparation and characterization," *Z Lebensm Unters Forsch* (1992) 194(3):229-234.

Kumar et al., "Human genome search in celiac disease: mutated gliadin T-cell-like epitope in two human proteins promotes T-cell activation," *Journal of Molecular Biology* (2002) 319(3):579-599.

Moustakas et al., "Structure of celiac disease-associated HLA-DQ8 and non-associated HLA-DQ9 alleles in complex with two disease-specific epitopes," *International Immunology* (2000) 12(8):1157-1166.

Piper et al., "High Selectivity of Human Tissue Transglutaminase for Immunoactive Gliadin Peptides: Implications for Celiac Sprue," *Biochemistry* (2002) 41(1):386-393.

Plebanski et al., "Protection from Plasmodium berghei infection by priming and boosting T cells to a single class I-restricted epitope with recombinant carriers suitable for human use," *Eur J Immunol* (1998) 28(12):4345-4355.

Anderson et al., "The a-gliadin gene family. II. DNA and protein sequence variation, subfamily structure, and origins of pseudogenes," *Theor Appl Genet* (1997) 95:59-65.

Vader et al., "The gluten response in children with celiac disease is directed toward multiple gliadin and glutenin peptides ," *Gastroenterology* (2002) 122:1729-1737.

Arentz-Hansen, Helene; The Intestinal T Cell Response to α-Gliadin in Adult Celiac Disease is Focused on a Single Deamidated Glutamine targeted by Tissue Glutaminase; *J. Exp. Med.* vol. 191, No. 4,2-200-603-612.

Anderson, Robert et al.; In vivo antigen challenge in celiac disease identifies a single transglutaminase-modified peptide as the dominant a-gliadin T-cell epitope; *Nature Medicine* vol. 6, No. 3, Mar. 2000; 337-342.

Uhlig, H. et al., Role of Tissue Transglutaminase in Gliadin Binding to Reticular Extracellular Matrix and Relation to Coeliac Disease Autoantibodies; *Autoimmunity,* vol. 28, pp. 185-195.

Database SwissProt Online! ID: GDA4-Wheat ACC:P04724, Aug. 13, 1987 (Abstract).

Okita, T. et al., Evolution and Heterogeneity of the α-1β-type and Y-type Gliadin DNA Sequences; *The Journal of Biological Chemistry;* vol. 260, No. 13, Jul. 5, 1985; pp. 8203-8213.

Godkin, A.S. et al., Identification of Coeliac Disease-Specific T Cell Epitope from A-Gliadin; *Gut;* vol. 44, Suppl. 1, p. A72, Apr. 1999.

Troncone, R. et al., Cytokines produced by Gliadin-Specific T Cell Clines from the Coeliac Mucosa; *Gastroenterology,* vol. 110, No. 4, p. A103, Apr. 1996.

Van De Wal, Y et al., Small intestinal T cells of celiac disease patients recognize a natural pepsin fragment of gliadin; *Proc. Natl. Acad. Sci.* vol. 95, pp. 10050-10054, Aug. 1998; Immunology.

O'Keeffe, J. et al. T cell proliferation, MGC class II restriction and cytokine products of gliadin-stimulated peripheral blood mononuclear cells (PBMC); *Clin. Exp. Immunol.;* 1999; 117:269-276.

*Gastroenterology* (1996) 110(4):A103.

Chevalier et al., "The Electronic Plant Gene Register," *Plant Physiology* (1999) 119:363-364.

(56) References Cited

OTHER PUBLICATIONS

Office action dated Sep. 17, 2013 received in copending U.S. Appl. No. 13/541,864.

Terreaux, "Increased HLA-DQ2-affinity of a synthetic gliadin peptide by acid-induced deamidation of glutamine residues," Bioorganic and Medicinal Chemistry Letters 8 (1998) 2039-2044.

Saito "New immunotherapy for allergic diseases—Allergen-peptide immunotherapy and DNA-based vaccine," The Allergy in Practice (2003) 23(12):26-30.

Itoh "An Analysis of Allergy Research and Treatment," Immunology Frontier (2001) 11(4):57-63.

Anderson et al., "Lesion volume, injury severity, and thalamic integrity following head injury," Theor Appl Genet (1997) 95:59-65.

Hirahara "New Specific Imunotherapies for Japanese Cedar Pollinosis," The Society for Bioscience and Bioengineering Japan (2002) pp. 152-155.

Osman et al., "B Cell Epitopes of Gliadin," Clinical and Experimental Immunology (2000) 121:248-254.

Lodish et al., Chapter 27: Immunity; Molecular Cell Biology (1995) pp. 1328-1329.

Janeway et al., Chapter 3: Antigen Recognition by B-cell and T-cell Receptors; Immuno Biology, 5th Ed. (2001) pp. 114-115.

Tye-Din et al., Comprehensive, Quantitative Mapping of T-Cell Epitopes in Gluten in Celiac Disease, Sci Trans Med (2010) 2:41-51.

Anderson et al.—XP2638432.

Scheets et al.—XP-002638433.

Rafalski—XP-002638434.

Skerritt "Antigenicity of Wheat Prolamins: Detailed Epitope Analysis using a Panel of Monoclonal Antibodies," (2000) Journal of Cereal Science (2000) 32:259-279.

Mazzarella "Cytokines Produced by Gliadin-Specific T Cell Clones from the Coeliac Mucosa," (1996) A1031.

Biagi et al., "A non-toxic analogue of a coeliac-activating gliadin peptide: a basis for immunomodulation?" Aliment Pharmacol Ther (1999) 13:945-950.

Weiner et al., "Oral tolerance: cytokine milieu in the gut and modulation of tolerance by cytokines," Res Immunol (1997) 10:667-674.

Notice of Allowance dated Aug. 8, 2012 received in copending U.S. Appl. No. 11/556,208.

Godkin et al., "Identification of Coeliac Disease-Specific T Cell Epitope from A-Gliadin," Gut (1999) 44(Suppl 1):72.

Wang et al., "ICK1, a cyclin-dependent protein kinase inhibitor from *Arabidopsis thaliana* interacts with both Cdc2a and CycD3, and its expression is induced by abscisic acid," Plant J (1998) 15:501-510.

Waterhouse et al., "Virus resistance and gene silencing: killing the messenger," (1999) 4(11):452-457.

Whisstock et al., "Prediction of protein function from protein sequence and structure," Q Rev Biophs (2003) 36 (3):307-340 Review.

Final Office Action dated May 22, 2014 received in copending U.S. Appl. No. 13/541,864.

Vader L.W. et al., Specificity of Tissue Transglutaminase Explains Cereal Toxicity in Celiac Disease, J. Exp. Med. 195(5):643 (Mar. 4, 2002).

Final Office Action dated Jan. 20, 2011 received in co-pending U.S. Appl. No. 11/556,208.

Evavold, et al., Separation of IL-4 Production from Th Cell Proliferation by an Altered T Cell Receptor Ligand, Science, 1991;252:1308-1310.

Arentz-Hansen, et al., The Molecular Basis for Oat Intolerance in Patients with Celiac Disease, PLoS Med. Oct. 2004;1(1):e1.

NCBI_BLAST search results for instant SEQ ID No. 1787 (last accessed Aug. 16, 2010).

\* cited by examiner

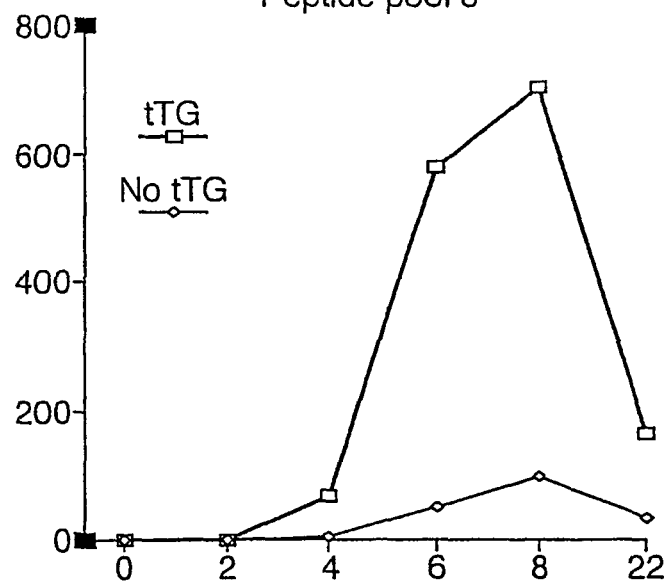
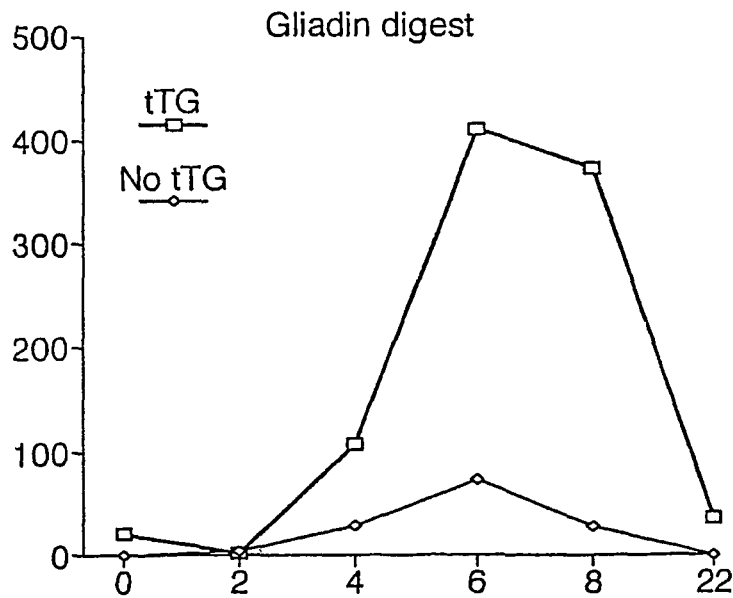
Fig.1a.

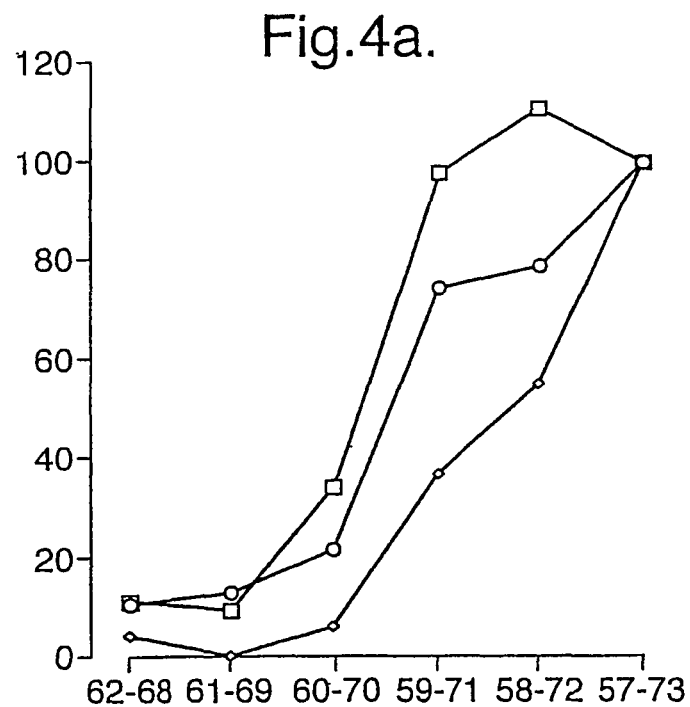
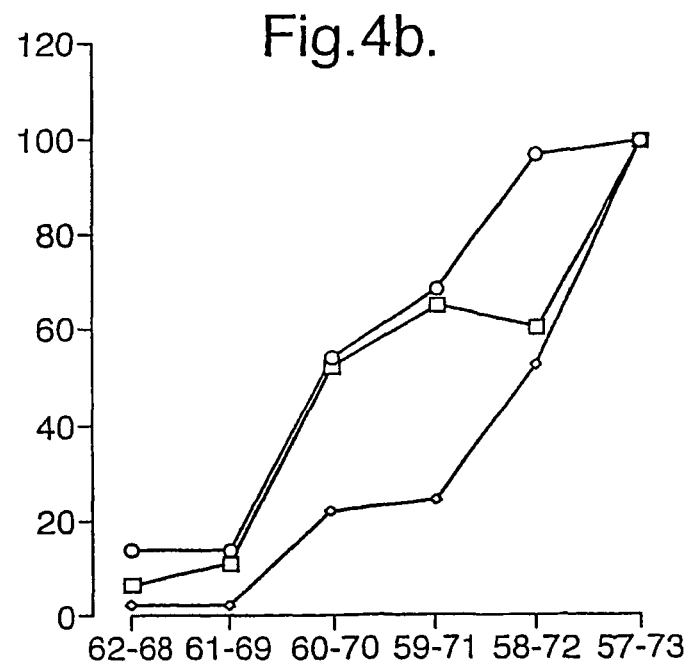

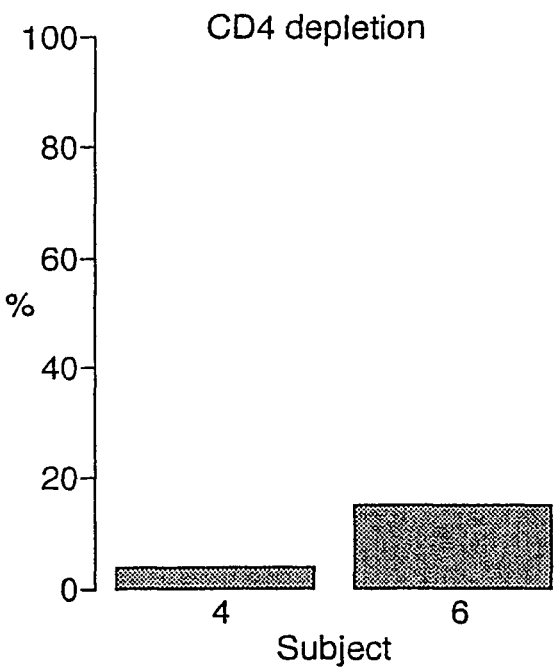
Fig. 7a. CD4 depletion
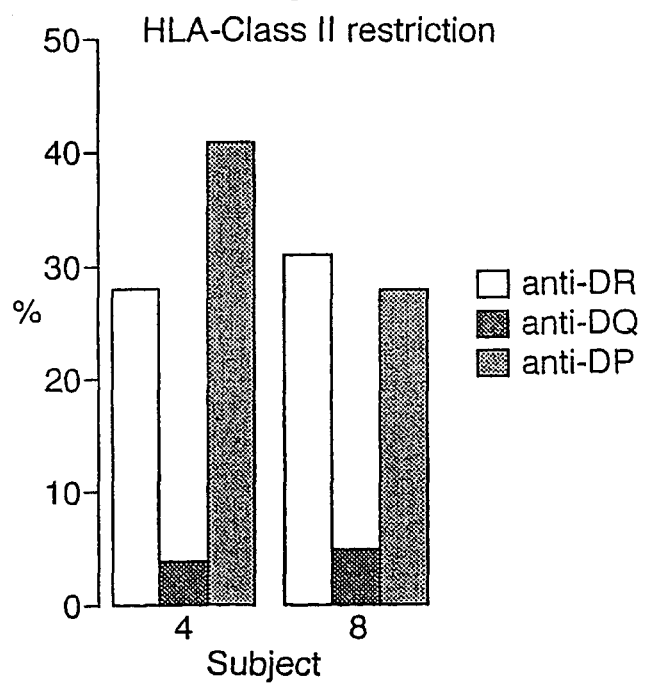
Fig. 7b. HLA-Class II restriction

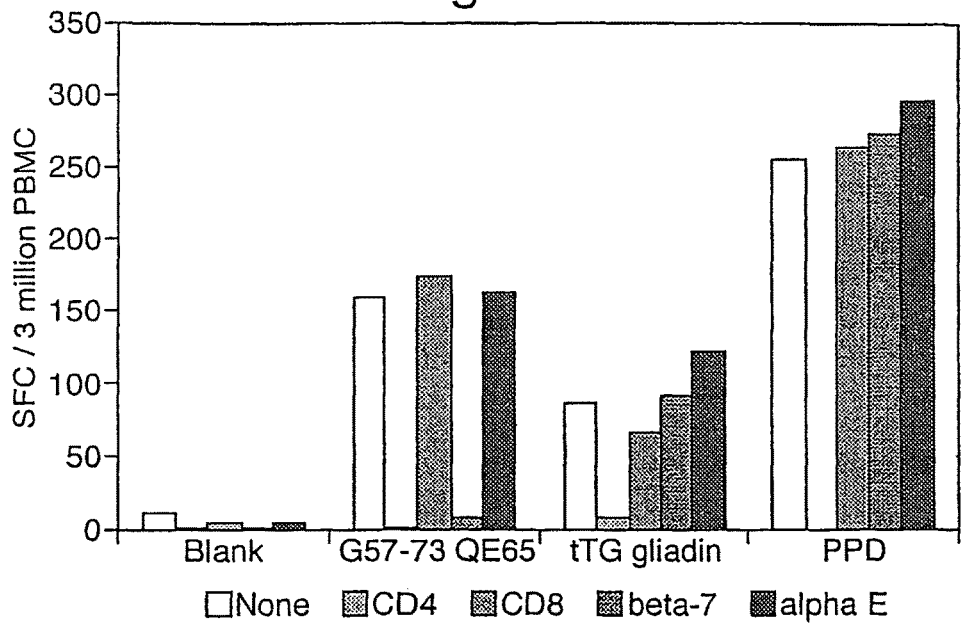
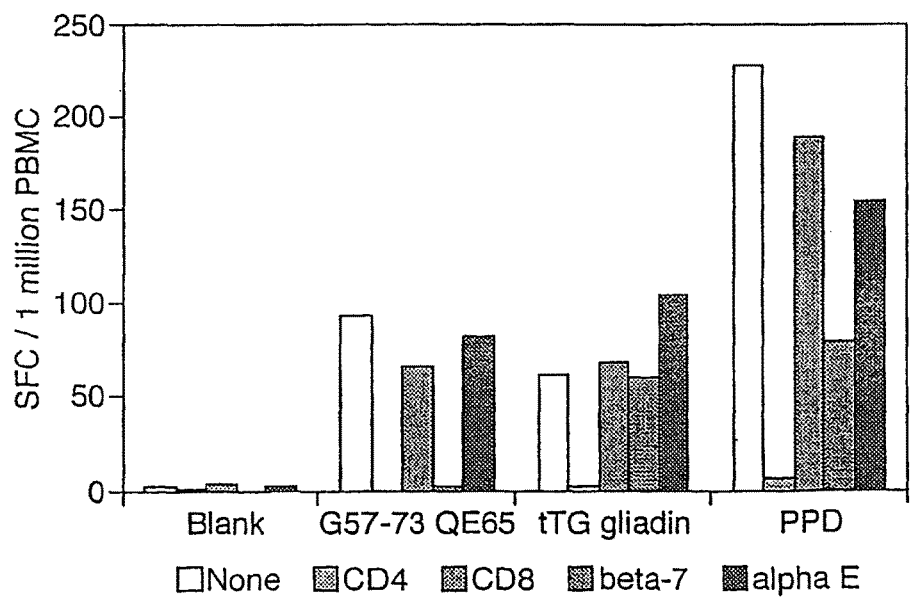
Fig. 10.

Dose response to A-gliadin 57-73 QE65:
QLQPFPQPELPYPQPQS.

Dose response to GDA4_WHEAT P04724 84-100 QE92:
PQLPYPQPELPYPQPQP.

Dose response to A-gliadin 57-73:
QLQPFPQPQLPYPQPQS (2.5, 25 & 250 mcg/ml),
and A-gliadin 57-73 (25 mcg/ml) + tTG treatment.

Dose response to GDA4_WHEAT P04724 84-100:
PQLPYPQPQLPYPQPQP (2.5, 25 & 250 mcg/ml),
and P04724 84-100 (25 mcg/ml) + tTG treatment.

Dose response to the DQ2-restricted α gliadin T cell epitope A-gliadin 57-68 QE65: QLQPFPQPELPY (E65) (2.5, 25 & 250 mcg/ml), and A-gliadin 57-68: QLQPFPQPQLPY (Q65) (25 mcg/ml) +/- tTG treatment.

Dose response to the DQ2-restricted α gliadin T cell epitope α-2 62-75 QE65 & QE72: PQPELPYPQPELPY (E65) (2.5, 25 & 250 mcg/ml), and α-2 62-75: PQPQLPYPQPQLPY (Q65) (25 mcg/ml) +/- tTG treatment.

Dose response to the DQ8-restricted α gliadin T cell epitope GDA9 202-219: QE208 & 216: QQYPSGEGSFQPSQENPQ (E) (25 & 250 mcg/ml), and to GDA9 202-219 QQYPSGQGSFQPSQQNPQ (Q) (25 mcg/ml) +/- tTG treatment.

Dose response to the DQ2-restricted γ gliadin T cell epitope GDB2 134-153 QE140, 148,150: QQLPQPEQPQQSFPEQERPF (E) (25 & 250 mcg/ml), and to GDB2 134-153: QQLPQPQQPQQSFPQQQRPF (Q) (25 mcg/ml) +/- tTG treatment.

Dose response to gliadin digest by chymotrysin.

Dose response to gliadin digested by chymotrysin then treated with tTG.

Total ELISpot responses to A-gliadin 57-73 QE65 (25mcg/ml) versus A-gliadin 57-73 QE65 responses as percent of tTG gliadin (500mcg/ml) responses.

(Fig.14.)
Bioactivity of gliadin polymorphisms of A-gliadin 57-73
(A) in coeliac subjects 6/7 days after gluten challenge
(Gamma-Interferon Elispot) (n=4).

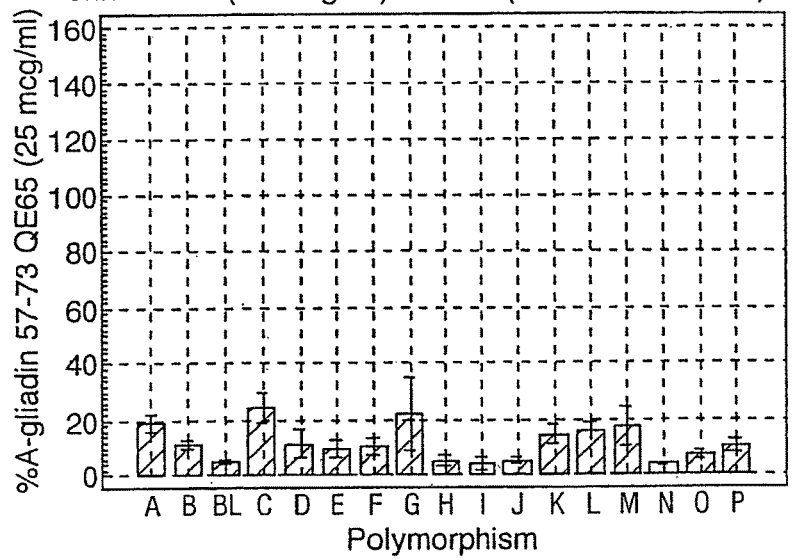

Fig.14a.

| | |
|---|---|
| A QLQPFPQPQLPYPQPQS | I QLQPFPQPQLSYSQPQP |
| B QLQPFPQPQLPYPQPQP | J QPQPFPPPQLPYPQTQP |
| C QLQPFPQPQLPYPQPQL | K PQLPYPQPQLPYPQPQP |
| D QLQPFPQPQLPYLQPQS | L PQLPYPQPQLPYPQPQL |
| E QLQPFPRPQLPYPQPQP | M PQPQPFLPQLPYPQPQS |
| F QLQPFPQPQLPYSQPQP | N PQPQPFPPQLPYPQPQS |
| G QLQPFLQPQLPYSQPQP | O PQPQPFPPQLPYPQTQP |
| H QLQPFSQPQLPYSQPQP | P PQPQPFPPQLPYPQPPP |

A QLQPFPQPQLPYPQPQS
B QLQPFPQPQLPYPQPQP
C QLQPFPQPQLPYPQPQL
D QLQPFPQPQLPYLQPQS
E QLQPFPRPQLPYPQPQP
F QLQPFPQPQLPYSQPQP
G QLQPFLQPQLPYSQPQP
H QLQPFSQPQLPYSQPQP
I QLQPFPQPQLSYSQPQP
J QPQPFPPPQLPYPQTQP
K PQLPYPQPQLPYPQPQP
L PQLPYPQPQLPYPQPQL
M PQPQPFLPQLPYPQPQS
N PQPQPFPPQLPYPQPQS
O PQPQPFPPQLPYPQTQP
P PQPQPFPPQLPYPQPPP

A  QLQPFPQPQLPYPQPQS
B  QLQPFPQPQLPYPQPQP
C  QLQPFPQPQLPYPQPQL
D  QLQPFPQPQLPYLQPQS
E  QLQPFPRPQLPYPQPQP
F  QLQPFPQPQLPYSQPQP
G  QLQPFLQPQLPYSQPQP
H  QLQPFSQPQLPYSQPQP
I  QLQPFPQPQLSYSQPQP
J  QPQPFPPQLPYPQTQP
K  PQLPYPQPQLPYPQPQP
L  PQLPYPQPQLPYPQPQL
M  PQPQPFLPQLPYPQPQS
N  PQPQPFPPQLPYPQPQS
O  PQPQPFPPQLPYPQTQP
P  PQPQPFPPQLPYPQPPP

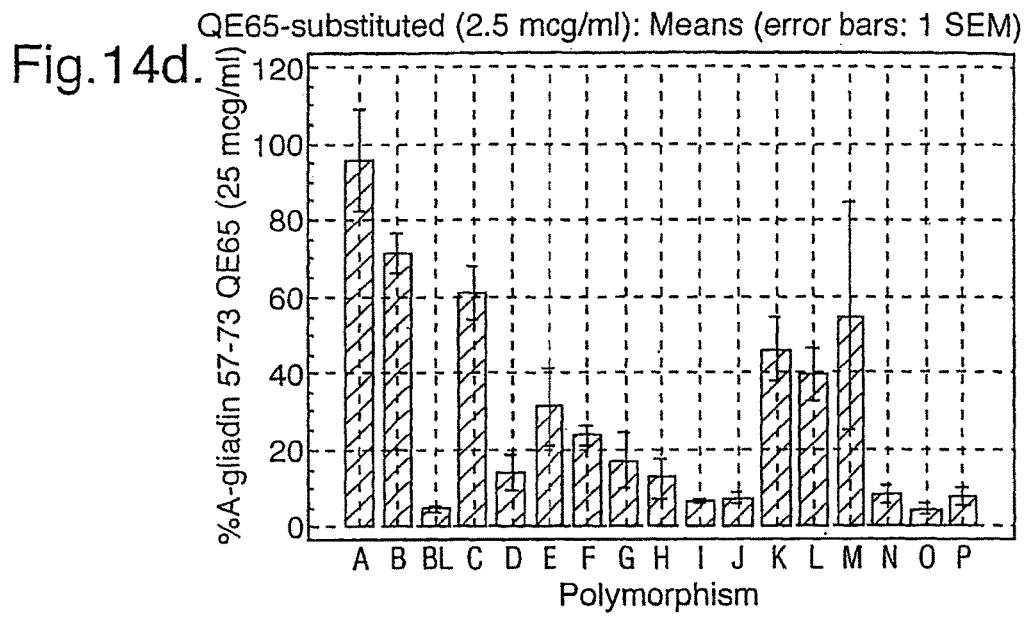

Fig. 14d. QE65-substituted (2.5 mcg/ml): Means (error bars: 1 SEM)

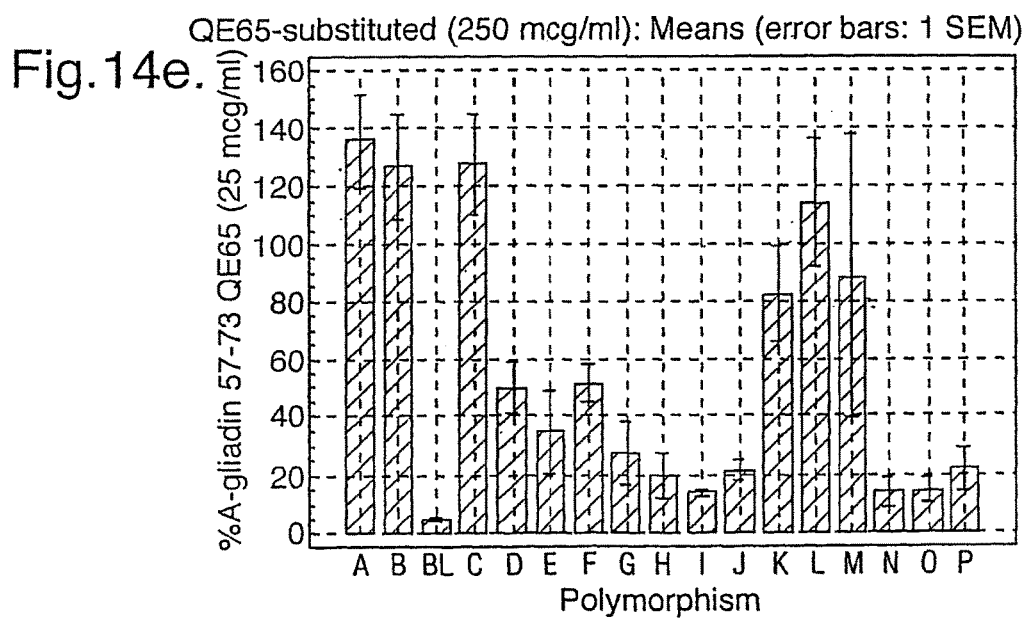

Fig. 14e. QE65-substituted (250 mcg/ml): Means (error bars: 1 SEM)

A  QLQPFPQPQLPYPQPQS
B  QLQPFPQPQLPYPQPQP
C  QLQPFPQPQLPYPQPQL
D  QLQPFPQPQLPYLQPQS
E  QLQPFPRPQLPYPQPQP
F  QLQPFPQPQLPYSQPQP
G  QLQPFLQPQLPYSQPQP
H  QLQPFSQPQLPYSQPQP
I  QLQPFPQPQLSYSQPQP
J  QPQPFPPPQLPYPQTQP
K  PQLPYPQPQLPYPQPQP
L  PQLPYPQPQLPYPQPQL
M  PQPQPFLPQLPYPQPQS
N  PQPQPFPPQLPYPQPQS
O  PQPQPFPPQLPYPQTQP
P  PQPQPFPPQLPYPQPPP

Agonist activity of A-gliadin 57-73 QE65 variants according to position substituted (Mean of 8 coeliac subjects' PBMC responses in interferon gamma ELISPOT after gluten challenge)
QLQP<u>FPQPELPYPQ</u>PQS
60................70

Fig.18.

Agonist activity of A-gliadin 57-73 QE65 variants according to position substituted (Mean of 8 coeliac subjects' PBMC responses in interferon gamma ELISPOT after gluten challenge)
QLQPFPQPELPYPQPQS
60................70

Agonist activity of A-gliadin 57-73 QE65 variants according to position substituted (Mean of 8 coeliac subjects' PBMC responses in interferon gamma ELISPOT after gluten challenge)
QLQPFPQPELPYPQPQS
60.................70

Fig.20.

Agonist activity of A-gliadin 57-73 QE65 variants according to position substituted (Mean of 8 coeliac subjects' PBMC responses in interferon gamma ELISPOT after gluten challenge)

QLQPFPQPELPYPQPQS
60................70

Q63 Means (error bars: 95% CI for mean)

Fig.21.

Agonist activity of A-gliadin 57-73 QE65 variants according to position substituted (Mean of 8 coeliac subjects' PBMC responses in interferon gamma ELISPOT after gluten challenge)
QLQPFPQPELPYPQPQS
60...................70

Agonist activity of A-gliadin 57-73 QE65 variants according to position substituted (Mean of 8 coeliac subjects' PBMC responses in interferon gamma ELISPOT after gluten challenge)
QLQPFPQPELPYPQPQS
60.................70

Agonist activity of A-gliadin 57-73 QE65 variants according to position substituted (Mean of 8 coeliac subjects' PBMC responses in interferon gamma ELISPOT after gluten challenge)
QLQPFPQPELPYPQPQS
60..................70

Agonist activity of A-gliadin 57-73 QE65 variants according to position substituted (Mean of 8 coeliac subjects' PBMC responses in interferon gamma ELISPOT after gluten challenge)
QLQPFPQPELPYPQPQ

Fig. 25.

Agonist activity of A-gliadin 57-73 QE65 variants according to position substituted (Mean of 8 coeliac subjects' PBMC responses in interferon gamma ELISPOT after gluten challenge)
QLQPFPQPELPYPQPQS
60..................70

Fig.26.

Agonist activity of A-gliadin 57-73 QE65 variants according to position substituted (Mean of 8 coeliac subjects' PBMC responses in interferon gamma ELISPOT after gluten challenge)
QLQPFPQPELPYPQPQS
60.................70

P69 Means (error bars: 95% CI for mean)

Fig.27.

Agonist activity of A-gliadin 57-73 QE65 variants according to position substituted (Mean of 8 coeliac subjects' PBMC responses in interferon gamma ELISPOT after gluten challenge)
QLQPFPQPELPYPQPQS
60................70

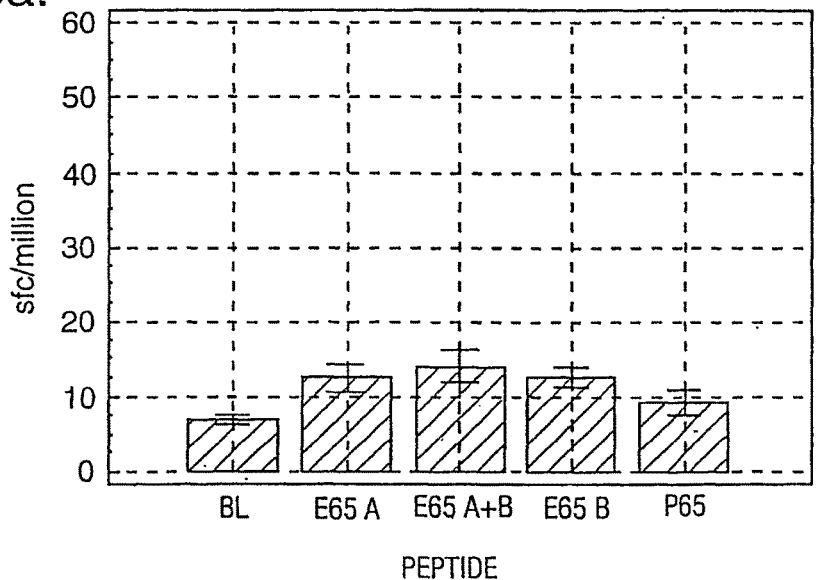
(Fig.28.)
Interferon gamma ELISpot responses in newly diagnosed and treated coeliac subjects, before and after gluten challenge.
Fig.28a. Untreated, newly diagnosed coeliacs (Mean+SEM, n=9)

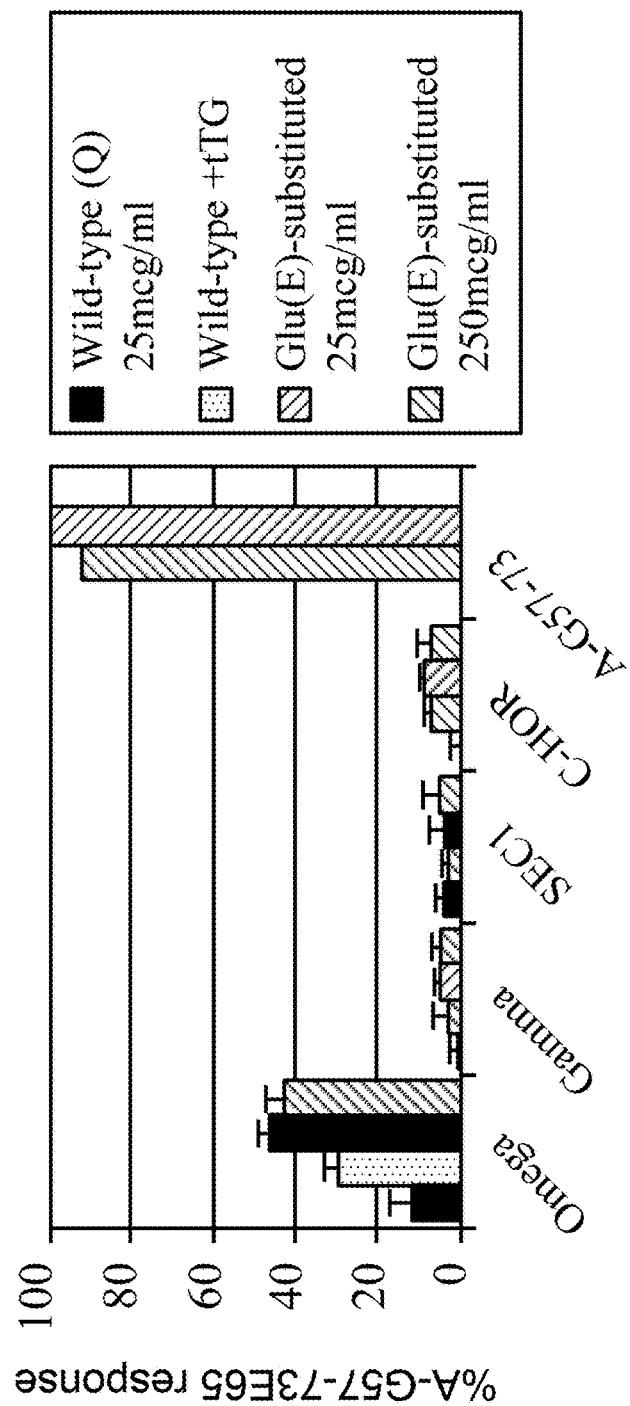
Figure 29. Bioactivity of prolamin homologues of A-gliadin 57-73 (IFNg-ELISpot, mean+SEM, n=6)
Omega: AAG17702 (141-157), Gamma: P21292 (96-112), SEC1: Q43639 (335-351), C-HOR: Q40055 (166-182). E-substituted peptides were synthesized with E for Q at position 9.

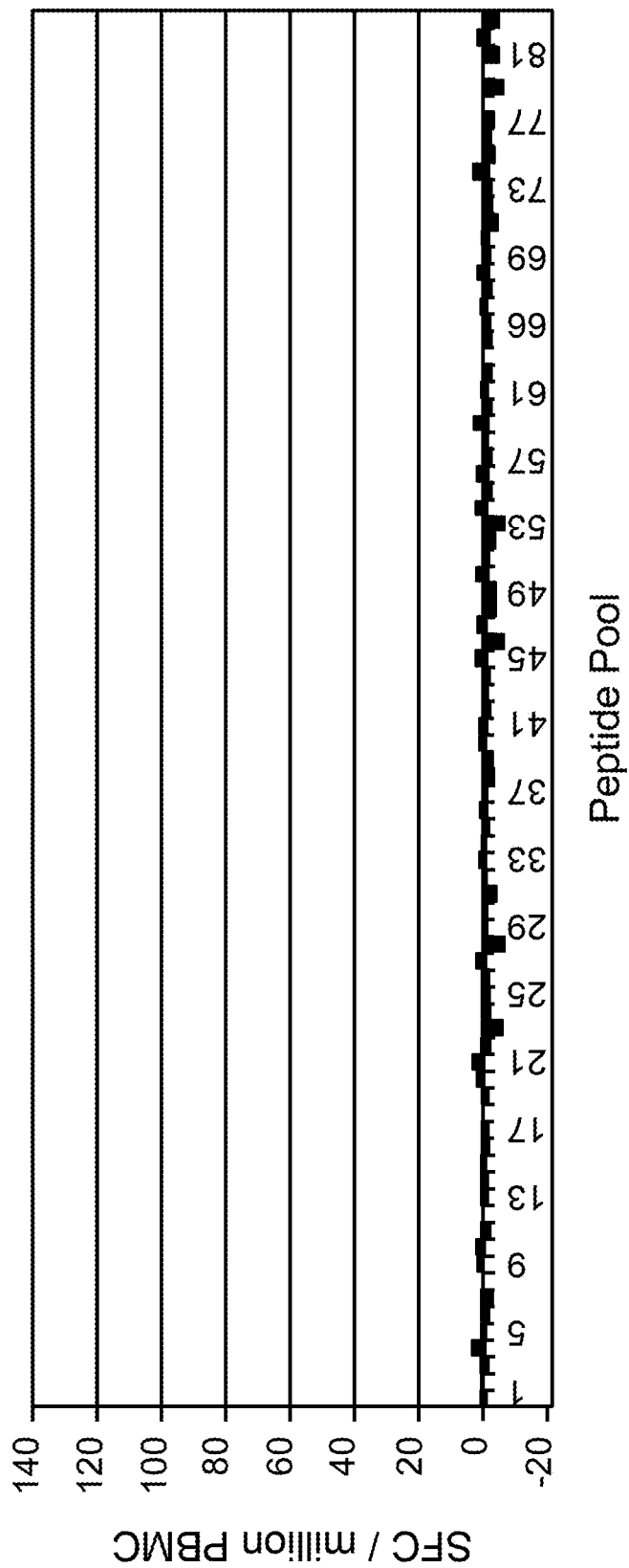
Figure 30. Healthy HLA-DQ2 Subjects: Change in IFNgamma ELISpot Responses to tTG-deamidated Gliadin Peptide Pools (median change Day 6 vs Day 0, n=10)

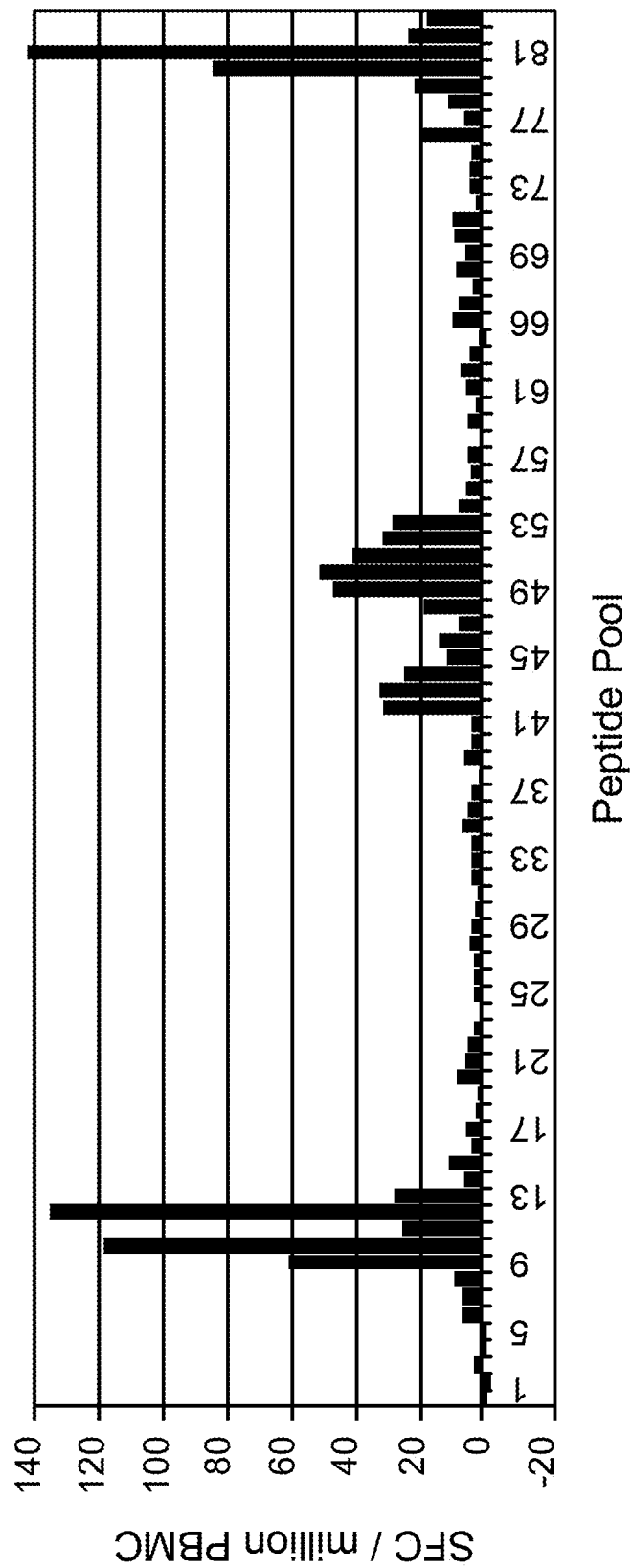

Figure 32. Individual Peptide Contributions to "Summed" Gliadin Peptide Response

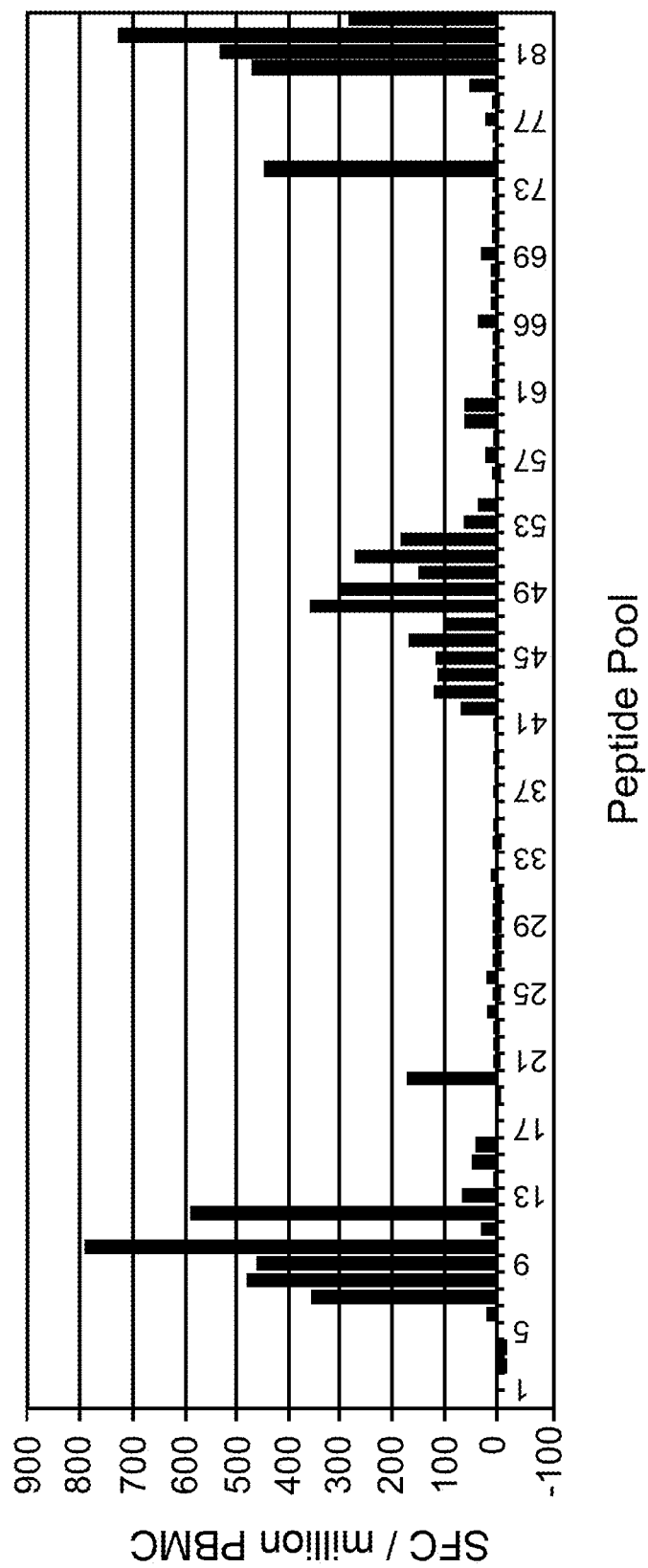
Figure 33. Coeliac HLA-DQ2/8 Subject COS: Gluten challenge induced IFNgamma ELISpot Responses to tTG-deamidated Gliadin Peptide Pools

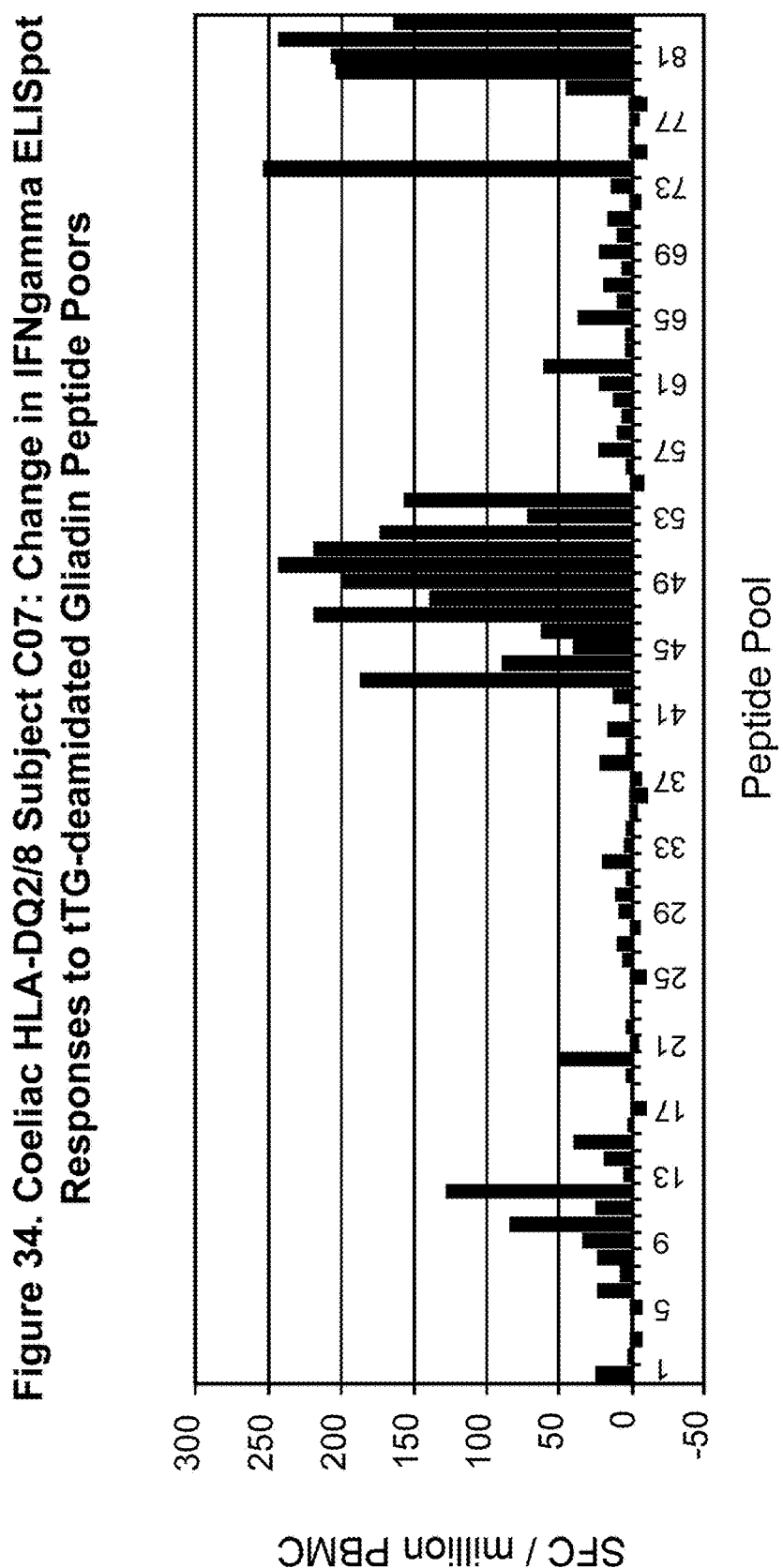
Figure 34. Coeliac HLA-DQ2/8 Subject C07: Change in IFNgamma ELISpot Responses to tTG-deamidated Gliadin Peptide Poors

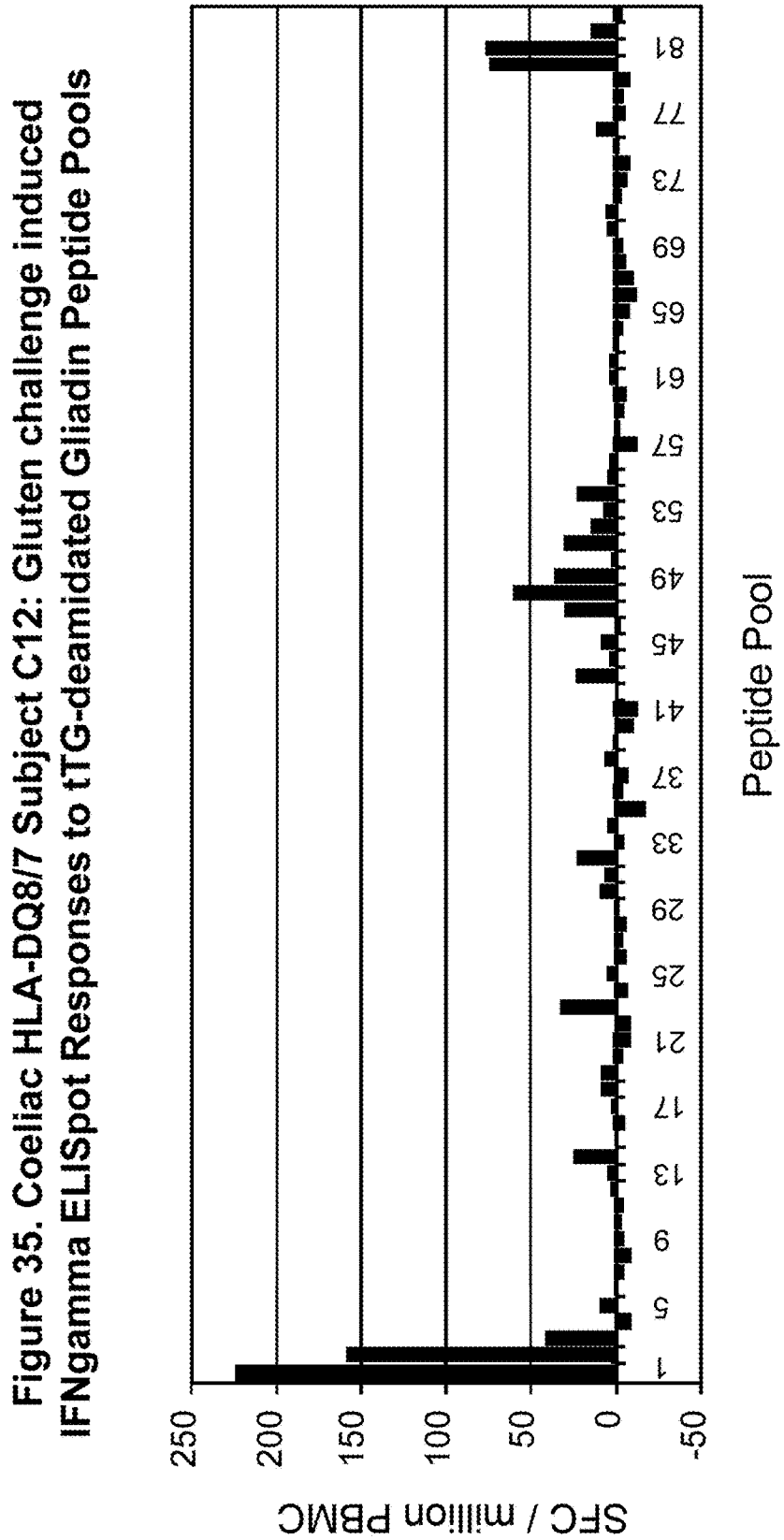
Figure 35. Coeliac HLA-DQ8/7 Subject C12: Gluten challenge induced IFNgamma ELISpot Responses to tTG-deamidated Gliadin Peptide Pools

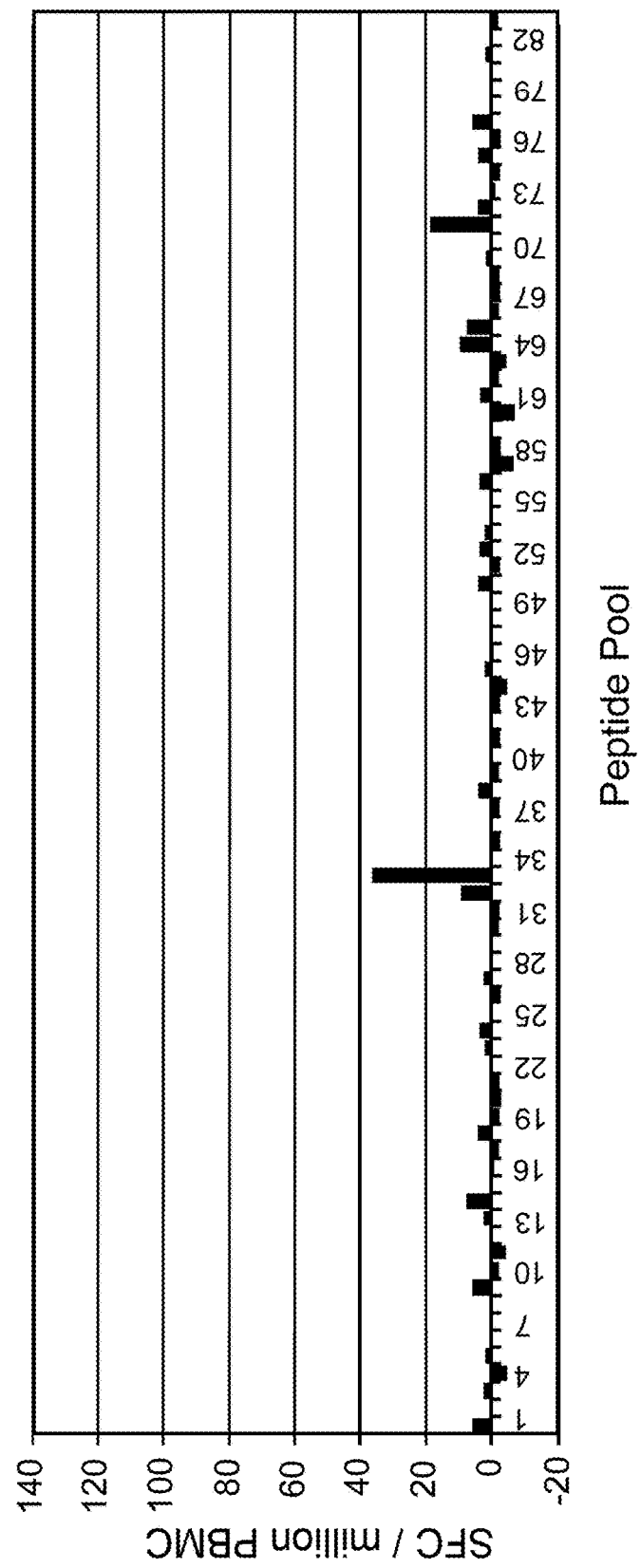
Figure 36. Coeliac HLA-DQ6/8 Subject C11: Change in IFNgamma ELISpot Responses to tTG-deamidated Gliadin Peptide Pools

FIGURE 37

| COELIAC SUBJECT | C14 | C15 | C16 | C17 | C18 | C19 | C20 | C21 | C22 | C23 | C24 | C25 | C26 | C27 | C28 |
|---|---|---|---|---|---|---|---|---|---|---|---|---|---|---|---|
| HLA-DQ | 2Z | 2Z | 22 | 22 | 22 | 22 | 2X | 2X | 2X | 2X | 28 | 28 | 2X | 2X | 2X |
| ANTIGEN CHALLENGE | WHEAT | | | | | | | | | | | | RYE | | |
| DURATION OF CHALLENGE (DAYS) | 3 | 3 | 6 | 3 | 6 | 3 | 3 | 3 | 3 | 0.5 | 3 | 1 | 3 | 3 | 3 |
| DOMINANT PEPTIDE ELISPOT SFC | 203 | 46 | 96 | 195 | 114 | 136 | 29 | 57 | 129 | 259 | 50 | 18 | 163 | 52 | 229 |
| BLANK ELISPOT SFC | 1 | 2 | 4 | 0.5 | 3 | 1 | 1 | 4 | 3 | 2 | 1 | 2 | 1 | 2 | 6 |

| SEQ ID NO: | Pept. NO: | Sequence |
|---|---|---|
| 107 | 1 | AVRFPVPQLQPQNPSQQLPQ |
| 108 | 2 | MVRVPVPQLQPQNPSQQQPQ |
| 109 | 3 | MVRVPVPQLQPQNPSQQHPQ |
| 110 | 4 | MVRVPMPQLQPQDPSQQQPQ |
| 111 | 5 | MVRVTVPQLQPQNPSQQQPQ |
| 112 | 6 | AVRVSVPQLQPQNPSQQQPQ |
| 113 | 7 | AVRVPVPQLQPQNPSQQQPQ |
| 114 | 8 | AVRWPVPQLQPQNPSQQQPQ |
| 115 | 9 | AVRVFVPQLQLQNPSQQQPQ |
| 116 | 10 | MVRVPVPQLQLQNPSQQQPQ |
| 117 | 11 | AVRVPVPQPQPQNPSQPQPQ |
| 118 | 12 | AVRVFVPQLQPKNPSQQQPQ |
| 119 | 13 | LQPQNPSQQLPQEQVPLVQQ |
| 120 | 14 | LQPQNPSQQQPQEQVPLVQQ |
| 121 | 15 | LQPQNPSQQHPQEQVPLVQQ |
| 122 | 16 | LQPQDPSQQQPQEQVPLVQQ |
| 123 | 17 | LQPQNPSQQQPQKQVPLVQQ |
| 124 | 18 | LQLQNPSQQQPQEQVPLVQE |
| 125 | 19 | LQLQNPSQQQPQEQVPLVQE |
| 126 | 20 | PQPQNPSQPQPQGQVPLVQQ |
| 127 | 21 | PQPQNPSQPQPQRQVPLVQQ |
| 128 | 22 | LQPKNPSQQQPQEQVPLVQQ |
| 129 | 23 | LQPQNPSQQQPQEQVPLMQQ |
| 130 | 24 | QLPQEQVPLVQQQQFLGQQQ |
| 131 | 25 | QHPQEQVPLVQQQQFLGQQQ |
| 132 | 26 | QQPQEQVPLVQQQQFLGQQQ |
| 133 | 27 | QQPQEQVPLVQQQQFLGQQQ |
| 134 | 28 | QQPQEQVPLVQQQQFPGQQQ |
| 135 | 29 | QQPQKQVPLVQQQQFPGQQQ |
| 136 | 30 | QQPQEQVPLVQEQQFQGQQQ |
| 137 | 31 | PQPQGQVPLVQQQQFPGQQQ |
| 138 | 32 | PQPQRQVPLVQQQQFPGQQQ |
| 139 | 33 | QQPQEQVPLMQQQQQFPGQQ |
| 140 | 34 | LVQQQQFLGQQQPFPPQQPY |
| 141 | 35 | LVQQQQFLGQQQSFPPQQPY |
| 142 | 36 | LVQQQQFLGQQQPFPPQQPY |
| 143 | 37 | LVQQQQFPGQQQPFPPQQPY |
| 144 | 38 | LVQEQQFQGQQQPFPPQQPY |
| 145 | 39 | LVQQQQFPGQQQPFPPQQPY |
| 146 | 40 | LMQQQQQFPGQQEQFPPQQP |
| 147 | 41 | LMQQQQQFPGQQERFPPQQP |
| 148 | 42 | GQQQPFPPQQPYPQPQPFPS |
| 149 | 43 | GQQQPFPPQQPYPQPQPFSQ |
| 150 | 44 | GQQQSFPPQQPYPQPQPFPS |

FIGURE 37 (continued)

| # | # | Sequence |
|---|---|---|
| 151 | 45 | GQQQPFPPQQPYPQQPFPS |
| 152 | 46 | GQQQQFPPQQPYPQPQPFPS |
| 153 | 47 | GQQEQFPPQQPYPHQQPFPS |
| 154 | 48 | GQQSRFPPQQPYPHQQPFPS |
| 155 | 49 | QQPYPQPQPFPSQLPYLQLQ |
| 156 | 50 | QQPYPQPQFPSQLPYLQLQP |
| 157 | 51 | QQPYPQPQPFPSQQPYLQLQ |
| 158 | 52 | QQPYPQQQPFPSQQPYMQLQ |
| 159 | 53 | QQPYPHQQPFPSQQPYPQPQ |
| 160 | 54 | PFPSQLPYLQLQPFPQPQLP |
| 161 | 55 | PFPSQQPYLQLQPFPQPQLP |
| 162 | 56 | PFPSQQPYLQLQPFSQPQLP |
| 163 | 57 | PFPSQQPYLQLQPFLQPQLP |
| 164 | 58 | PFPSQQPYLQLQPFLQPQPF |
| 165 | 59 | PFPSQQPYLQLQPFPQPQLP |
| 166 | 60 | PFPSQQPYMQLQPFPQPQLP |
| 167 | 61 | PFPSQQPYMQLQPFPQPQPF |
| 168 | 62 | PFPSQQPYLQLQPFPQPQPF |
| 169 | 63 | PFPSQQPYLQLQPFPRPQLP |
| 170 | 64 | PFPSQQPYPQPQPFPPQLPY |
| 171 | 65 | PFPSQQPYPQPQPFPQPQPF |
| 172 | 66 | LQLQPFPQPQLPYSQPQPFR |
| 173 | 67 | LQLQPFPQPQLPYSQPQQFR |
| 174 | 68 | LQLQPFPQPQLPYLQPQPFP |
| 175 | 69 | LQLQPFPQPQLSYSQPQPFR |
| 176 | 70 | LQLQPFSQPQLPYSQPQPFR |
| 177 | 71 | LQLQPFLQPQLPYSQPQPFR |
| 178 | 72 | LQLQPFLQPQPFPPQLPYSQ |
| 179 | 73 | LQLQPFPQPQLFYPQPQLPY |
| 180 | 74 | MQLQPFPQPQLPYPQPQLPY |
| 181 | 75 | MQLQPFPQPQPFPPQLPYPQ |
| 182 | 76 | LQLQPFPQPQLPYPQPQPFP |
| 183 | 77 | LQLQPFPQPQPFPPQLPYPQ |
| 184 | 78 | LQLQPFPRPQLPYPQPQPFR |
| 185 | 79 | LQLQPFPQPQPFLPQLPYPQ |
| 186 | 80 | LQLQPFPQPQPFPPQLPYPQ |
| 187 | 81 | PQPQPFPPQLPYPQTQPFPP |
| 188 | 82 | PQPQPFPQPQPFPPQLPYPQ |
| 189 | 83 | PQLPYSQPQPFRPQQPYPQP |
| 190 | 84 | PQLPYSQPQQFRPQQPYPQP |
| 191 | 85 | PQLPYLQPQPFRPQQPYPQP |
| 192 | 86 | PQLSYSQPQPFRPQQPYPQP |
| 193 | 87 | PQLSYSQPQPFRPQQLYPQP |
| 194 | 88 | PQPFPPQLPYSQPQPFRPQQ |
| 195 | 89 | PQLPYPQPQLPYPQPQLPYP |
| 196 | 90 | PQLPYPQPQLPYPQPQPFRP |
| 197 | 91 | PQPFPPQLPYPQPQLPYPQP |
| 198 | 92 | PQLPYPQPQPFRPQQPYPQP |
| 199 | 93 | PQPFPPQLPYPQPQPFRPQQ |
| 200 | 94 | PQPFPPQLPYPQPPPFSPQQ |
| 201 | 95 | PQPFLPQLPYPQPQSFPPQQ |
| 202 | 96 | PQPFFPQLPYPQPQSFPPQQ |
| 203 | 97 | QLPYPQTQPFPPQQPYPQPQ |
| 204 | 98 | PQPFPPQLPYPQTQPFPPQQ |
| 205 | 99 | LPYPQPQPFRPQQPYPQSQP |

FIGURE 37 (continued)

| | | |
|---|---|---|
| 206 | 100 | LPYPQPQPFRPQQSYPQPQP |
| 207 | 101 | LPYPQPPPFHPQQPYPQPQP |
| 208 | 102 | LPQLPYPQPQSFPPQQPYPQ |
| 209 | 103 | PPQLPYPQTQPFPPQQPYPQ |
| 210 | 104 | QPFRPQQPYPQPQPQYSQPQ |
| 211 | 105 | QPFRPQQLYPQPQPQYSQPQ |
| 212 | 106 | QPFRPQQPYPQSQPQYSQPQ |
| 213 | 107 | QPFRPQQSYPQPQPQYSQPQ |
| 214 | 108 | PPFSPQQPYPQPQPQYPQPQ |
| 215 | 109 | QSFPPQQPYPQQRPKYLQPQ |
| 216 | 110 | QSFPPQQPYPQQRPMYLQPQ |
| 217 | 111 | QSFPPQQPYPQQQPQYLQPQ |
| 218 | 112 | QPFPPQQPYPQPQPQYPQPQ |
| 219 | 113 | YPQPQPQYSQPQQPISQQQQ |
| 220 | 114 | YPQPQPQYSQPQPISQQQQ |
| 221 | 115 | YPQSQPQYSQPQQPISQQQQ |
| 222 | 116 | YPQPQPQYPQPQQPISQQQA |
| 223 | 117 | YPQQRPKYLQPQQPISQQQA |
| 224 | 118 | YPQQRPMYLQPQQPISQQQA |
| 225 | 119 | YPQQPQYLQPQQPISQQQA |
| 226 | 120 | SQPQQPISQQQKKQQQQQQ |
| 227 | 121 | SQPQEPISQQQQQQQQQQI |
| 228 | 122 | PQPQQPISQQQAQQQQQQQ |
| 229 | 123 | QQQQQQQQQQQQQQQILQQ |
| 230 | 124 | QQQQQQQQQQQQEQQILQQ |
| 231 | 125 | QQQQQQQQQQQQQQTLQQ |
| 232 | 126 | QQQQQQQQQKQQQQQQQT |
| 233 | 127 | AQQQQQQQQQQQQQQTLQQ |
| 234 | 128 | QQQQQQQQILQQILQQQLIP |
| 235 | 129 | QQQQQEQQTLQQTLQQQLIP |
| 236 | 130 | QQQQQEQQILQQMLQQQLIP |
| 237 | 131 | QQQQQEQQTLQQTLQQQLTP |
| 238 | 132 | QQQQQQQIIQQILQQQLIP |
| 239 | 133 | QQKQQQQQQQTLQQILQQQ |
| 240 | 134 | QQQQQQQQILPQILQQQLIP |
| 241 | 135 | QQQQQQQTLQQILQQQLIP |
| 242 | 136 | ILQQILQQQLIPCMDVVLQQ |
| 243 | 137 | ILQQMLQQQLIPCMDVVLQQ |
| 244 | 138 | ILQQILQQQLIPCMDVVLQQ |
| 245 | 139 | ILQQILQQQLIPCRDVVLQQ |
| 246 | 140 | ILPQILQQQLIPCRDVVLQQ |
| 247 | 141 | TLQQILQQQLIPCRDVVLQQ |
| 248 | 142 | QLIPCMDVVLQQHNIAHGRS |
| 249 | 143 | QLIPCMDVVLQQHNKAHGRS |
| 250 | 144 | QLIPCMDVVLQQHNLAHGRS |
| 251 | 145 | QLIPCMDVVLQQHNIVHGRS |
| 252 | 146 | QLIPCMDVVLQQHNIAPGRS |
| 253 | 147 | QLIPCMDVVLQQHNIVHGKS |
| 254 | 148 | QLIPCRDVVLQQHSIAYGSS |
| 255 | 149 | QLIPCRDVVLQQHSIAHGSS |
| 256 | 150 | QLIPCRDVVLQQHNIAHGSS |
| 257 | 151 | QLIPCRDVVLQQHNIAHARS |
| 258 | 152 | QLIPCRDVVLQQHNIAHASS |
| 259 | 153 | VLQQHNIAHGRSQVLQQSTY |
| 260 | 154 | VLQQHNKAHGRSQVLQQSTY |

FIGURE 37 (continued)

| | | | | | | | | | | | | | |
|---|---|---|---|---|---|---|---|---|---|---|---|---|---|
| 261 | 155 | VLQQHNLAHGRSQVLQQSTY | | | | | | | | | | | |
| 262 | 156 | VLQQHNIVHGRSQVLQQSTY | | | | | | | | | | | |
| 263 | 157 | VLQQHNIARGRSQVLQQSTY | | | | | | | | | | | |
| 264 | 158 | VLQQHNIVHGKSQVLQQSTY | | | | | | | | | | | |
| 265 | 159 | VLQQHSIAYGSSQVLQQSTY | | | | | | | | | | | |
| 266 | 160 | VLQQHSIAHGSSQVLQQSTY | | | | | | | | | | | |
| 267 | 161 | VLQQHNIAHGSSQVLQESTY | | | | | | | | | | | |
| 268 | 162 | VLQQHNIAHARSQVLQQSTY | | | | | | | | | | | |
| 269 | 163 | VLQQHNIAHASSQVLQQSTY | | | | | | | | | | | |
| 270 | 164 | VLQQHNIAHASSQVLQQSSY | | | | | | | | | | | |
| 271 | 165 | HGRSQVLQQSTYQLLQELCC | | | | | | | | | | | |
| 272 | 166 | HGRSQVLQQSTYQLLRELCC | | | | | | | | | | | |
| 273 | 167 | HGRSQVLQQSTYQLLRELCC | | | | | | | | | | | |
| 274 | 168 | HGKSQVLQQSTYQLLQELCC | | | | | | | | | | | |
| 275 | 169 | YGSSQVLQQSTYQLVQQLCC | | | | | | | | | | | |
| 276 | 170 | HGSSQVLQQSTYQLVQQFCC | | | | | | | | | | | |
| 277 | 171 | HGSSQVLQESTYQLVQQLCC | | | | | | | | | | | |
| 278 | 172 | HARSQVLQQSTYQPLQQLCC | | | | | | | | | | | |
| 279 | 173 | HASSQVLQQSTYQLLQQLCC | | | | | | | | | | | |
| 280 | 174 | HASSQVLQQSSYQQLQQLCC | | | | | | | | | | | |
| 281 | 175 | QSTYQLLQELCCQHLWQIPE | | | | | | | | | | | |
| 282 | 176 | QSTYQLLRELCCQHLWQIPE | | | | | | | | | | | |
| 283 | 177 | QSTYQLLRELCCQHLWQIPE | | | | | | | | | | | |
| 284 | 178 | QSTYQLVQQLCCQLWQIPE | | | | | | | | | | | |
| 285 | 179 | QSTYQLVQQFCCQQLWQIPE | | | | | | | | | | | |
| 286 | 180 | QSTYQPLQQLCCQQLWQIPE | | | | | | | | | | | |
| 287 | 181 | QSTYQLLQQLCCQQLLQIPE | | | | | | | | | | | |
| 288 | 182 | QSSYQQLQQLCCQQLFQIPE | | | | | | | | | | | |
| 289 | 183 | ELCCQHLWQIPEQSCQAIH | | | | | | | | | | | |
| 290 | 184 | ELCCQHLWQILEQSQCQAIH | | | | | | | | | | | |
| 291 | 185 | ELCCQHLWQIPEKLQCQAIH | | | | | | | | | | | |
| 292 | 186 | QLCCQQLWQIPEQSRCQAIH | | | | | | | | | | | |
| 293 | 187 | QFCCQQLWQIPEQSRCQAIH | | | | | | | | | | | |
| 294 | 188 | QLCCQQLLQIPEQSRCQAIH | | | | | | | | | | | |
| 295 | 189 | GLCCQQLLQIPEQSQCQAIH | | | | | | | | | | | |
| 296 | 190 | QLCCQQLFQIPEQSRCQAIH | | | | | | | | | | | |
| 297 | 191 | QIPEQSQCQAIHNVVHAIIL | | | | | | | | | | | |
| 298 | 192 | QIPEQSQCQAIQNVVHAIIL | | | | | | | | | | | |
| 299 | 193 | QILEQSQCQAIHNVVHAIIL | | | | | | | | | | | |
| 300 | 194 | QIPEQSQCQAIHKVVHAIIL | | | | | | | | | | | |
| 301 | 195 | QIPEKLQCQAIHNVVHAIIL | | | | | | | | | | | |
| 302 | 196 | QIPEQSRCQAIHNVVHAIIL | | | | | | | | | | | |
| 303 | 197 | QIPEQSQCQAIHNVAHAIIM | | | | | | | | | | | |
| 304 | 198 | QIPEQSRCQAIHNVVHAIIL | | | | | | | | | | | |
| 305 | 199 | QAIHNVVHAIILHQQQKQQQ | | | | | | | | | | | |
| 306 | 200 | QAIHNVVHAIILHQQQKQQ | | | | | | | | | | | |
| 307 | 201 | QAIQNVVHAIILHQQQKQQQ | | | | | | | | | | | |
| 308 | 202 | QAIHKVVHAIILHQQQKQQ | | | | | | | | | | | |
| 309 | 203 | QAIHNVVHAIILHQQQQQQQ | | | | | | | | | | | |
| 310 | 204 | QAIHNVVHAIILHQQHHHQ | | | | | | | | | | | |
| 311 | 205 | QAIHNVVHAIILHQQQRQQQ | | | | | | | | | | | |
| 312 | 206 | QAIHNVVHAIIMHQQEQQQ | | | | | | | | | | | |
| 313 | 207 | QAIHNVAHAIIMHQQQQQQQ | | | | | | | | | | | |
| 314 | 208 | QAIHNVVHAIILHHHQQQQ | | | | | | | | | | | |
| 315 | 209 | AIILHQQQKQQQPSSQVSF | | | | | | | | | | | |

FIGURE 37 (continued)

| | | | | | | | | | | | | | | | | |
|---|---|---|---|---|---|---|---|---|---|---|---|---|---|---|---|---|
| 316 | 210 | AIILHQQQKQQQQPSSQFS | | | | | | ▓ | | | | | | | | |
| 317 | 211 | AIILHQQQKQQQQLSSQVSF | | | | | | | | | | | | | | |
| 318 | 212 | AIILHQQQKQQQPSSQVSFQ | | | | | | | | | | | | | | |
| 319 | 213 | AIILHQQQQQQEQKQQLQQ | | | | | | | | | | | | | | |
| 320 | 214 | AIILHQQQQQQQQQQQFLS | | | | | | | | | | | | | | |
| 321 | 215 | AIILHQQHHHQQQQQQQQQ | | | | | | ░ | | | | | | | | |
| 322 | 216 | AIILHQQHHHHQEQKQQLQQ | | | | | | | | | | | | | | |
| 323 | 217 | AIILHQQRQQQPSSQVSLQ | | | | | | ▓ | | | ▓ | | | | | |
| 324 | 218 | AIIMHQQEQQQLQQQQQQQ | | | | ▓ | | | ▓ | | | | | | | ▓ |
| 325 | 219 | AIIMHQQQQQQEQKQQLQQ | | | | | | | | | | | | | | |
| 326 | 220 | AIILHHHQQQQQPSSQVSY | | | | | | ░ | | | | | | | | |
| 327 | 221 | KQQQQPSSQVSFQQPLQQYP | | | | | | | | | | | | | | |
| 328 | 222 | KQQQQPSSQFSFQQPLQQYP | | | | | | | | | | | | | | |
| 329 | 223 | KQQQQLSSQVSFQQPQQQYP | | | | | | | | | | | | | | |
| 330 | 224 | KQQQPSSQVSFQQPQQQYPL | | | | | | | | | | | | | | |
| 331 | 225 | QQQQEQKQQLQQQQQQQQL | | | | | | | | | | | | | | |
| 332 | 226 | HHHQEQKQQLQQQQQQQQL | | | | | | | | | | | | | | |
| 333 | 227 | KQQQPSSQVSLQQPQQQYPS | | | | | | | | | | | | | | |
| 334 | 228 | QQQQLQQQQQQLQQQQQQQ | ░ | | | ░ | | | ░ | | | | | | | |
| 335 | 229 | KQQQQPSSQVSYQQPQEQYP | | | | | | | | | | | | | | |
| 336 | 230 | QLQQQQQQQQLQQQQQKQQ | ░ | | | ▓ | ░ | | ■ | | | | | | | ▓ |
| 337 | 231 | QQQLQQQQKQQQQPSSQVS | | | | | | | | | | | | | | |
| 338 | 232 | QQQQQQQQPLSQVSFQQPQ | ░ | | | ▓ | | | ■ | | | | | | | ■ |
| 339 | 233 | QQQQQQQQQPLSQVCFQQSQ | ░ | | | | | | | | | | | | | ░ |
| 340 | 234 | HHHQQQQQQQQQQPLSQVSF | | | | | | | | | | | | | | |
| 341 | 235 | QQQQQQQQQPSSQVSFQQPQ | | | | | | ░ | | | | | | | | |
| 342 | 236 | QPLSQVSFQQPQQQYPSGQG | | | | | | | | | | | | | | |
| 343 | 237 | QPLSQVCFQQSQQQYPSGQG | | | | | ░ | | | | | | | | | |
| 344 | 238 | QPSSQVSFQQPQQQYPSSQV | | | | | | | | | | | | | | |
| 345 | 239 | KVSFQQPLQQYPLGQGSFRP | | | | | | | | | | | | | | |
| 346 | 240 | QFSFQQPLQQYPLGQGSFRP | | | | | | | | | | | | | | |
| 347 | 241 | QVSFQQPQQQYPLGQGSFRP | ░ | | | | | | | | | | | | ░ | |
| 348 | 242 | QVSFQQPQQQYPSGQGSFQP | | | | | ░ | | | | | | | | | |
| 349 | 243 | QVCFQQSQQQYPSGQGSFQP | | | | | ░ | | | | | | | | | |
| 350 | 244 | QVSFQQPQQQYPSGQGFFQP | | | | | | | | | | | | | | |
| 351 | 245 | QVSFQQPQQQYPSGQGFFQP | | | | | | | | | | | | | | |
| 352 | 246 | QVSLQQPQQQYPSGQGFFQP | | | | | | | | | | | | | | |
| 353 | 247 | QVSFQQPQQQYPSSQVSFQP | | | | | | | | | | | | | | |
| 354 | 248 | QVSFQQPQQQYPSSQGSFQP | | | | | | | | | ▓ | | | | | ░ |
| 355 | 249 | QVSYQQPQEQYPSGQVSFQS | | | | | | | | | | | | | | |
| 356 | 250 | QQYPLGQGSFRPSQNPQAQ | | | | | | | | | | | | | | |
| 357 | 251 | QQYPLGQGSFRPSQNSQAQ | | | | | | | | | | | | | | |
| 358 | 252 | QQYPSGQSSFQPSQNPQAQ | | | | | | | | | | | | | | |
| 359 | 253 | QQYPSGQGFFQPSQNPQAQ | | | | | ░ | | | ▓ | | | | | | ▓ |
| 360 | 254 | QQYPSGQGFFQPFQNPQAQ | | | | | | ░ | | | | | | | | |
| 361 | 255 | QQYPSGQGFFQPSQNPQAQ | ░ | | | | | | | | | | | | | |
| 362 | 256 | QQYPSSQVSFQPSQLNPQAQ | | | | | | | | | | | | | | |
| 363 | 257 | QQYPSSQGSFQPSQNPQAQ | | | | | | | | | | | | | | |
| 364 | 258 | EQYPSGQVSFQSSQQNPQAQ | ░ | | | | | | | | | | | ░ | | |
| 365 | 259 | SFRPSQQNPLAQGSVQPQQL | | | | | | | | | | | | | | |
| 366 | 260 | SFRPSQQNPQAQGSVQPQQL | | | | | | | | ░ | | | | | | |
| 367 | 261 | SFRPSQQNPQTQGSVQPQQL | | | | | | | | | | | | | | |
| 368 | 262 | SFRPSQQNSQAQGSVQPQQL | | | | | | | | | | | | | | |
| 369 | 263 | SFRPSQQNPQDQGSVQPQQL | | | | | | | | | | | | | | ░ |
| 370 | 264 | SFRPSQQNPRAQGSVQPQQL | | | | | | | | | | | | | | |

FIGURE 37 (continued)

| | | | | | | | | | | | | | | |
|---|---|---|---|---|---|---|---|---|---|---|---|---|---|---|
| 371 | 265 | SFQPSQQNPQAQGSVQPQQL | | | | | | | | | ▒ | | | |
| 372 | 266 | FFQPSQQNPQAQGSFQPQQL | | | | | | | | | | | | |
| 373 | 267 | FFQPFQQNPQAQGSFQPQQL | | | | ▒ | | | | | | | | |
| 374 | 268 | FFQPSQQNPQAQGSVQPQQL | | | | | ▒ | | | | | | | |
| 375 | 279 | SFQPSQLNPQAQGSVQPQQL | | | | | | | | | | | | |
| 376 | 280 | SFQPSQLNPQAQGSVQPQQL | | | | | | | | | | | | |
| 377 | 271 | SFQPSQQNPQAQGSVQPQQL | | | | | | | | | | | | |
| 378 | 272 | SFQSSQQNPQAQGSVQPQQL | | | | | | | | ▒ | | | | |
| 379 | 273 | PQAQGSVQPQQLPQFEEIRN | | | | | | | | | | | | |
| 380 | 274 | PQTQGSVQPQQLPQFEEIRN | | | | | | | | | | | | |
| 381 | 275 | PQAQGSVQPQQLPQFEEIRNL | ▒ | | | | | | | | | | | |
| 382 | 276 | PLAQGSVQPQQLPQFEEIRN | | | | | | | | | | | | |
| 383 | 277 | PQDQGSVQPQQLPQFEEIRN | | | | | | | | | | | | |
| 384 | 278 | PRAQGSVQPQQLPQFEEIRN | | | | | | | | | | | | |
| 385 | 279 | PQAQGSFQPQQLPQFEEIRN | | | | | | | | | | | | |
| 386 | 280 | PQAQGSSFQPQQLPQFEAIRN | | | | | | | | | | | | |
| 387 | 281 | PQAQGSVQPQQLPQFAEIRN | | | | | | | | | | | | |
| 388 | 282 | PQAQGSVQPQQLPQFQEIPN | ▒ | | | | | | | | | | | |
| 389 | 283 | PQQLPQFEEIRNLALQTLPA | | | | | | | | | | | | |
| 390 | 284 | PQQLPQFEEIRNLALQTLPAM | | | | | | | | | | | | |
| 391 | 285 | PQQLPQFEEIRNLAPK | | | | | | | | | | | | |
| 392 | 286 | PQQLPQFEEIRNLALETLPA | | | | | | | | | | | | |
| 393 | 287 | PQQLPQFEAIRNLALQTLPA | | | | | | | | | ▒ | | | |
| 394 | 288 | PQQLPQFAEIRNLALQTLPA | | | | | | | | | | | | |
| 395 | 289 | PQQLPQFQEIRNLALQTLPA | | | | | | | | | | | | |
| 396 | 290 | EIRNLALQTLPAMCNVYIPP | | | | ■ | | | ▓ | | | | ■ | |
| 397 | 291 | EIRNLALQTLPSMCNVYIPP | | | | | | | | | | | | |
| 398 | 292 | EIRNLALETLPAMCNVYIPP | | | | | ■ | | | | | | | |
| 399 | 293 | EIRNLALQTLPRMCNVYIPP | | | | | | | | | | | | |
| 400 | 294 | ILPAMCNVYIPPYCTIAPFG | | | | | | | | | | | | |
| 401 | 295 | TLPSMCNVYIPPYCTIAPFG | | | | | | | | | | | | |
| 402 | 296 | TLPAMCNVYIPPYCTIVPFG | | | | | | | | | | ▒ | | |
| 403 | 297 | ILPAMCNVYIPPYCAMAPFG | | | | | | | | | | | | |
| 404 | 298 | TLPAMCNVYIPPYCTITPFG | | | | | | | | | | | | |
| 405 | 299 | TLPAMCNVYIPPYCTIAPVG | | | | | | | | | | | | |
| 406 | 300 | TLPAMCNVYIPPYCSTTIAP | | | | | | | | | | | | |
| 407 | 301 | TLPRMCNVYIPPYCSTTIAP | | | | | | | | | | | | |
| 408 | 302 | TLPRMCNVYIPPYCSTTTAP | | | | | | | | | | | | |
| 409 | 303 | TLPAMCNVYIPPHCSTTIAP | ▒ | | | | | | | | | | | |
| 410 | 3045 | YIPPYCTIAPFGIFGTNYR | | | | | | | | | | | | |
| 411 | 305 | YIPPYCTIVPFGIFGTNYR | | | | | ▒ | | | | | | | |
| 412 | 306 | YIPPYCAMAPFGIFGTNYR | | | | | | | | | | | | |
| 413 | 307 | YIPPYCTMAPFGIFGTNYR | | | | | | | | | | | | |
| 414 | 308 | YIPPYCTITPFGIFGTN | | | | | ▒ | | | | | | | |
| 415 | 309 | YIPPYCTIAPVGIFGTNYR | | | | | | | | | | | | |
| 416 | 310 | YIPPYCSTTIAPVGIFGTN | ▒ | | | | | | ▒ | | | | ▒ | |
| 417 | 311 | YIPPYCSTTTAPFGIFGTN | | | | | | | | | | | | |
| 418 | 312 | YIPPHCSTTIAPFGIFGTN | | | | ▒ | ▒ | | | | | | | |
| 419 | 313 | YIPPHCSTTIAPFGISGTN | | | | | | | | | | | | |
| 420 | 314 | IPPYCSTTIAPFGIFGTNYR | ▒ | | | | | | | | | | | |
| 421 | 315 | GIANMQVDPSSQVQWPQQQP | | | | | | | | ▒ | | | ■ | ▒ |
| 422 | 316 | GIANIQVDPSGQVQWLQQQL | | | | | | | | | | | | |
| 423 | 317 | ATANMQVDPSGQVPWPQQQP | | | | ▒ | | | | | | | | |
| 424 | 318 | MNIQVDPSGQVPWPQQQPFP | | | | | | | | | | | | |
| 425 | 319 | ATANMQADPSGQVQWPQQQP | | | | | | | | ▒ | | | ■ | |

FIGURE 37 (continued)

| | | | | | | | | | | | | | | |
|---|---|---|---|---|---|---|---|---|---|---|---|---|---|---|
| 426 | 320 | TTANIQVDPSGQVQWPQQQQ | | | | | | | | | | | | |
| 427 | 321 | ATANMQVDPSGQVQWPQQQP | | | | | | | | | | | | |
| 428 | 322 | QIVPPSGQVQWPQQQPFP | | | | | | | | | | | | |
| 429 | 323 | PSGQVQWPQQQPVPQPHQPF | | | | | | | | | | | | |
| 430 | 324 | PSGQVQWLQQQLVPQLQQPL | | | | | | | | | | | | |
| 431 | 325 | PSGQVPWPQQQPFPQPHQPF | | | | | | | | | | | | |
| 432 | 326 | PSGQVQWPQQQPFLQPHQPF | | | | | | | | | | | | |
| 433 | 327 | PSGQVQWPQQQPFFQPQQP | | | | | | | | | | | | |
| 434 | 328 | PSGQVQWPQQQPFRQPQQPF | | | | | | | | | | | | |
| 435 | 329 | PSGQVQWPQQQPFPQPQQPF | | | | | | | | | | | | |
| 436 | 330 | QQQPVPQPHQPFSQQPQQTF | | | | | | | | | | | | |
| 437 | 331 | QQQLVPQLQQPLSQQPQQTF | | | | | | | | | | | | |
| 438 | 332 | QQQPFFQPHQPFSQQPQQTF | | | | | | | | | | | | |
| 439 | 333 | QQQPFLQPHQPFSQQPQQIF | | | | | | | | | | | | |
| 440 | 334 | QQQPFFQPQQPFSQQPQQI | | | | | | | | | | | | |
| 441 | 335 | QQQQPFPQPQQPQQPFPQPQ | | | | | | | | | | | | |
| 442 | 336 | QQQPFRQPQQPFYQQPQHTP | | | | | | | | | | | | |
| 443 | 337 | QQQPFPQPQQPFCQQPQRII | | | | | | | | | | | | |
| 444 | 338 | QQQPFPQPQQPFCEQPQRTI | | | | | | | | | | | | |
| 445 | 339 | HQPFSQQPQQTFPQPQQTFP | | | | | | | | | | | | |
| 446 | 340 | QQPLSQQPQQIFPQPQQTFP | | | | | | | | | | | | |
| 447 | 341 | HQPFSQQPQQIFPQPQQTFP | | | | | | | | | | | | |
| 448 | 342 | QQPFSQQPQQIFPQPQQTFP | | | | | | | | | | | | |
| 449 | 343 | QQPQQPFFQPQQPQLPFPQQ | | | | | | | | | | | | |
| 450 | 344 | QQPFYQQPQHTFPQPQQICP | | | | | | | | | | | | |
| 451 | 345 | QQPFCQQPQRTIPQPHQTFH | | | | | | | | | | | | |
| 452 | 346 | QQPFCQQPQQTIPQPHQTFH | | | | | | | | | | | | |
| 453 | 347 | QQPFCEQPQRTIPQPHQTFH | | | | | | | | | | | | |
| 454 | 348 | QQIFPQPQQTFPHQPQQQFP | | | | | | | | | | | | |
| 455 | 349 | QQIFPQPQQTFPHQPQQQFP | | | | | | | | | | | | |
| 456 | 350 | QQIFPQPQQTFPHQPQQAFP | | | | | | | | | | | | |
| 457 | 351 | QRTIPQPHQTFHHQPQQTFP | | | | | | | | | | | | |
| 458 | 352 | QTFPHQPQQAFPQPQQTFPH | | | | | | | | | | | | |
| 459 | 353 | QIFHHQPQQTFPQPQQIYPH | | | | | | | | | | | | |
| 460 | 354 | QTFHHQPQQIFPQPEQTYPH | | | | | | | | | | | | |
| 461 | 355 | QAFPQPQQTFPHQPQQQFPQ | | | | | | | | | | | | |
| 462 | 356 | QHTFPQPQQICPHQPQQQFP | | | | | | | | | | | | |
| 463 | 357 | QTFPQPQQTYPHQPQQQFPQ | | | | | | | | | | | | |
| 464 | 358 | QTFPQPEQTYPHQPQQQFPQ | | | | | | | | | | | | |
| 465 | 359 | QTFPHQPQQQFPQPQQPQQQ | | | | | | | | | | | | |
| 466 | 360 | QTFPHQPQQQVPQPQQPQQP | | | | | | | | | | | | |
| 467 | 361 | QTFPHQPQQQFSQPQQPQQQ | | | | | | | | | | | | |
| 468 | 362 | QTCPHQPQQQFPQPQQPQQP | | | | | | | | | | | | |
| 469 | 363 | QTYPHQPQQQFPQTQQPQQP | | | | | | | | | | | | |
| 470 | 364 | QQFPQPQQPQQQFLQPQQPF | | | | | | | | | | | | |
| 471 | 365 | QQVPQPQQPQQPFLQPQQPF | | | | | | | | | | | | |
| 472 | 366 | QQFSQPQQPQQQFIQPQQPF | | | | | | | | | | | | |
| 473 | 367 | QQFPQPQQPQQQFLQPHQPF | | | | | | | | | | | | |
| 474 | 368 | QQFPQPQQPQQQFPQPQQQ | | | | | | | | | | | | |
| 475 | 369 | QQFPQTQQPQQPFPQPQQTF | | | | | | | | | | | | |
| 476 | 370 | PQQQFLQPQQPFPQPQGPY | | | | | | | | | | | | |
| 477 | 371 | FQQQFIQPQQPFPQPQQTY | | | | | | | | | | | | |
| 478 | 372 | PQQQFIQPQQPQQTYPQPQ | | | | | | | | | | | | |
| 479 | 373 | PQQQFLQPRQPFPQPQQPY | | | | | | | | | | | | |
| 480 | 374 | PQQPFPQQPQQQFPQPQQPQ | | | | | | | | | | | | |

FIGURE 37 (continued)

| | | |
|---|---|---|
| 481 | 375 | PQQPFPQPQQPQQPFPQPQQ |
| 482 | 376 | PQQPFPQPQQTFFQQPQLPF |
| 483 | 377 | FQQQFPQPQQPQQPFPQQPQ |
| 484 | 378 | QQPQQPFPQQPQQGFPQPQQ |
| 485 | 379 | QQPQQQFPQPQQPQQPFPQP |
| 486 | 380 | QPQQPQQPFPQPQQPQLFFP |
| 487 | 381 | QQPFPQQPQQPYPQQPQQPF |
| 488 | 382 | QQPFPQQPQQPFPQTQQPQQ |
| 489 | 383 | QQPFPQQPQQTYPQRPQQPF |
| 490 | 384 | PQPFPQQPQQPYPQQPQQPF |
| 491 | 385 | QQPFPQPQQPQLFFPQQPQQ |
| 492 | 386 | QQPFPQPQQAQLPFPQQPQQ |
| 493 | 387 | QQTFPQQPQLPFPQQPQQPF |
| 494 | 388 | QQPYFQQPQQPFPQTQQPQQ |
| 495 | 389 | QQPFPQTQQPQQPFPQQPQQ |
| 496 | 390 | QQTYPQRPQQPFPQTQQPQQ |
| 497 | 391 | QPQLPFPQQPQQPQQPFPQ |
| 498 | 392 | QAQLPFPQQPQQFLPQPQQP |
| 499 | 393 | QLPFPQQPQQPFPQPQQPQQ |
| 500 | 394 | QPQQPFPQQPQQPFPQTQQP |
| 501 | 395 | QFQQPFPQTQQPQQPFPQQP |
| 502 | 396 | TQQPQQPFPQQPQQPFFQTQ |
| 503 | 397 | PQQPQQPFFPQTQQPQQPFPQ |
| 504 | 398 | QQPFPQTQQPQQLFPQFQQP |
| 505 | 399 | QQPFFQTQQPQQFFPQLQQP |
| 506 | 400 | QQPFPQTQQPQQPFPQSQQP |
| 507 | 401 | QQPFPQTQQPQQFFPQSKQP |
| 508 | 402 | QQPFPQPQQPQQPFPQLQQP |
| 509 | 403 | QQPLPQPQQPQQFFPQSQQP |
| 510 | 404 | QQPFPQPQQPQQPFPQSQQP |
| 511 | 405 | QPQQLFPQSQQPQQQFSQPQ |
| 512 | 406 | QPQQPFPQLQQPQQPFPQPQ |
| 513 | 407 | QPQQPFPQSQQPQQPFPQPQ |
| 514 | 408 | QPQQPFPQSKQPQQPFPQPQ |
| 515 | 409 | QPQQPFPQLQQPQQPLPQPQ |
| 516 | 410 | SQQPQQQFSQPQQQFFPQPQQ |
| 517 | 411 | LQQPQQPFPQPQQQLPQPQQ |
| 518 | 412 | SQQPQQPFPQPQQQFPQPQQ |
| 519 | 413 | SKQPQQFFPQPQQPQQSFPQ |
| 520 | 414 | LQQPQQPLPQPQQPQQPFPQ |
| 521 | 415 | SQQPQQPFPQPQQPQQSFPQQ |
| 522 | 416 | SQPQQQFPQPQQPQQSFPQQ |
| 523 | 417 | PQPQQQLPQPQQPQQSFPQQ |
| 524 | 418 | PQPQQQFPQPQQPQQSFPQQ |
| 525 | 419 | PQPQQPQQSFPQQQPSLIQQ |
| 526 | 420 | PQPQQPQQPFPQQQQPLIQP |
| 527 | 421 | PQPQQPQQSFPQQQPLIQP |
| 528 | 422 | QPQQPQQSFPQQQPPFIQPS |
| 529 | 423 | QPQQPQQSFPQQQRPFIQPS |
| 530 | 424 | QPQQPQQSFPQQQPSLIQQS |
| 531 | 425 | FPQQQPPFIQPSLQQQVNPC |
| 532 | 426 | FPQQQRPFIQPSLQQQLNPC |
| 533 | 427 | FPQQQPSLIQQSLQQQLNPC |
| 534 | 428 | FPQQQPLIQPYLQQQMNPC |
| 535 | 429 | FPQQQPAIQSFLQQQMNPC |

| | | |
|---|---|---|
| 591 | 485 | QQQQQQQQQGMHIFLPLSQQ |
| 592 | 486? | QEQQEQPQGVQILVPLSQQQ |
| 593 | 487 | QEQQEQLQGVQTILVPLSQQQ |
| 594 | 488 | QSQQQQQQQQQQQGIQIM |
| 595 | 489 | QEQQQGIQILRPLFQLVQGQ |
| 596 | 490 | QEQQQGVPILRPLFQLAQGL |
| 597 | 491 | QQQQQQQGIQIMRPLFQLVQ |
| 598 | 492 | GMHILLPLYQQQQVGQGTLV |
| 599 | 493 | GIDYFLPLSQHEQVGQGSLV |
| 600 | 494 | GMHIFLPLSQQQQVGQGSLV |
| 601 | 495 | GVQILVPLSQQQQVGQGTLV |
| 602 | 496 | GVQILVPLSQQQQVGQGILV |
| 603 | 497 | GIQIMRPLFQLVQGQGIIQP |
| 604 | 498 | GIQILRPLFQLVQGQGIIQP |
| 605 | 499 | GVPILRPLFQLAQGLGIIQP |
| 606 | 500 | YQQQQVGQGTLVQGQGIIQP |
| 607 | 501 | SQHEQVGQGSLVQGQGIIQP |
| 608 | 502 | SQQQQVGQGSLVQGQGIIQP |
| 609 | 503 | SQQQQVGQGTLVQGQGIIQP |
| 610 | 504 | SQQQQVGQGILVQGQGIIQP |
| 611 | 505 | GTLVQGQGIIQPQQPAQLEA |
| 612 | 506 | GSLVQGQGIIQPQQPAQLEA |
| 613 | 507 | FQLVQGQGIIQPQQPAQLEV |
| 614 | 508 | FQLAQGLGIIQPQQPAQLEG |
| 615 | 509 | IIQPQQPAQLEAIRSLVLQT |
| 616 | 510 | IIQPQQPAQLEVIRSLVLQT |
| 617 | 511 | IIQPQQPAQLEVIRSSVLQT |
| 618 | 512 | IIQPQQPAQYEVIRSLVLRT |
| 619 | 513 | IIQPQQPAQLEGIRSLVLKT |
| 620 | 514 | QLEAIRSLVLQTLPTMCNVY |
| 621 | 515 | QLEAIRSLVLQTLPSMCNVY |
| 622 | 516 | QLEVIRSLVLQTLATMCNVY |
| 623 | 517 | QLEVIRSSVLQTLATMCNVY |
| 624 | 518 | QLEVIRSLVLGTLPTMCNVF |
| 625 | 519 | QYEVIRSLVLRTLPNMCNVY |
| 626 | 520 | QLEGIRSLVLKTLPTMCNVY |
| 627 | 521 | VLQTLPTMCNVYVPPECSII |
| 628 | 522 | VLQTLPSMCNVYVPPECSIM |
| 629 | 523 | VLQTLATMCNVYVPPYCSTI |
| 630 | 524 | VLGTLPTMCNVFVPPECSTT |
| 631 | 525 | VLRTLPNMCNVYVRPDCSTI |
| 632 | 526 | VLKTLPTMCNVYVPPDCSTI |
| 633 | 527 | CNVYVPPECSIIKAPFSSVV |
| 634 | 528 | CNVYVPPECSIMRAPFASIV |
| 635 | 529 | CNVYVPPYCSTIRAPFASIV |
| 636 | 530 | CNVFVPPECSTTKAPFASIV |
| 637 | 531 | CNVYVRPDCSTINAPFASIV |
| 638 | 532 | CNVYVPPDCSTINVPYANID |
| 639 | 533 | CSIIKAPFSSVVAGIGGQ |
| 640 | 534 | CSIMRAPFASIVAGIGGQ |
| 641 | 535 | CSTIRAPFASIVAGIGGQYR |
| 642 | 536 | CSTIRAPFASIVASIGGQ |
| 643 | 537 | CSTTKAPFASIVADIGGQ |
| 644 | 538 | CSTINAPFASIVAGISGQ |
| 645 | 539 | CSTINVPYANIDAGIGGQ |

FIGURE 37 (continued)

| | | | | | | | | | | | | | |
|---|---|---|---|---|---|---|---|---|---|---|---|---|---|
| 646 | 540 | QQFFPLQPQQSFLWQSQQF | | | | | | | | | | | |
| 647 | 541 | PQQSFLWQSQQPFLQQPQQP | | | | | | | | | | | |
| 648 | 542 | SQQPFLQQPQQPSFQFQQVV | | | | | | | | | | | |
| 649 | 543 | PQQPSPQFQQVVQIISPAIP | | | | | | | | | | | |
| 650 | 544 | QQVVQIISPATPTTIPSAGE | | | | | | | | | | | |
| 651 | 545 | PATPTTIPSAGKPTSAPFPQ | | | | | | | | | | | |
| 652 | 546 | SAGKPTSAPFPQQQQQRQQI | | | | | | | | | | | |
| 653 | 547 | FFPQQQQRQQIAQQQIPVV | | | | | | | | | | | |
| 654 | 548 | HQQLAQQQIPVVQPSILQQL | | | | | | | | | | | |
| 655 | 549 | IPVVQPSILQQLNPCKVFLQ | | | | | | | | | | | |
| 656 | 550 | LQQLNPCKVFLQQQCSPVAM | | | | | | | | | | | |
| 657 | 551 | VFLQQQCSPVAMPQRLARSQ | | | | | | | | | | | |
| 658 | 552 | PVAMPQRLARSQMLQSSCH | | | | | | | | | | | |
| 659 | 553 | ARSQMLQSSCHVMQQQCCQ | | | | | | | | | | | |
| 660 | 554 | SSCHVMQQQCCQQLPQIPQQ | | | | | | | | | | | |
| 661 | 555 | QCCQQLPQIPQQSRYQAIRA | | | | | | | | | | | |
| 662 | 556 | PQIPQQSRYQAIRAIIYSII | | | | | | | | | | | |
| 663 | 557 | IPQQSRYQAIRAIIYSIILQ | | | | | | | | | | | |
| 664 | 558 | AIRAIIYSIILQEQQVQGS | | | | | | | | | | | |
| 665 | 559 | IILQEQQVQGSIQSQQQQP | | | | | | | | | | | |
| 666 | 560 | VQGSIQSQQQPQQLGQCVS | | | | | | | | | | | |
| 667 | 561 | QSPQQLGQCVSQPQQSQQ | | | | | | | | | | | |
| 668 | 562 | QCVSQPQQSQQLGQQPQQ | | | | | | | | | | | |
| 669 | 563 | QSQQLGQQPQQQLAQGTF | | | | | | | | | | | |
| 670 | 564 | QPQQQLAQGTFLQPSQIAQ | | | | | | | | | | | |
| 671 | 565 | QGTFLQPSQIAQLEVMTSIA | | | | | | | | | | | |
| 672 | 566 | QIAQLEVMTSIALRILPTMC | | | | | | | | | | | |
| 673 | 567 | TSIALRILPTMCSVNVPLYR | | | | | | | | | | | |
| 674 | 568 | PTMCSVNVPLYRTTTSVPFG | | | | | | | | | | | |
| 675 | 569 | PLYRTTTSVPFGVGTGVGAY | | | | | | | | | | | |
| 676 | 570 | TIIRTFPIPTISSNNNHHFS | | | | | | | | | | | |
| 677 | 571 | PIISSNNNHHFPSNSNHHFH | | | | | | | | | | | |
| 678 | 572 | HHFPSNSNHHFHSNNNQFYR | | | | | | | | | | | |
| 679 | 573 | HHFHSNNNQFYRNNNSPGHN | | | | | | | | | | | |
| 680 | 574 | QFYRNNNSPGHNNPLNNNNS | | | | | | | | | | | |
| 681 | 575 | PGHNNPLNNNNSPNNNSPSN | | | | | | | | | | | |
| 682 | 576 | NNNSPNNNSPSNHHNNSPNN | | | | | | | | | | | |
| 683 | 577 | SPSNHHNNSPNNNFQYHTHF | | | | | | | | | | | |
| 684 | 578 | SPNNNFQYHTHFSNHKNLPH | | | | | | | | | | | |
| 685 | 579 | HTHFSNHKNLPHTNNIQQQQ | | | | | | | | | | | |
| 686 | 580 | NLPHTNNIQQQQPPFSQQQQ | | | | | | | | | | | |
| 687 | 581 | QQQQPPFSQQQQPPFSQQQQ | | | | | | | | | | | |
| 688 | 582 | QQQQPPFSQQQQPVLPQQSP | | | | | | | | | | | |
| 689 | 583 | QQQQPVLPQQSPFSQQQQLV | | | | | | | | | | | |
| 690 | 584 | QQSPFSQQQQLVLPPQQQQQ | | | | | | | | | | | |
| 691 | 585 | QQLVLPPQQQQQLVQQQIP | | | | | | | | | | | |
| 692 | 586 | QQQQLVQQQIPIVQPSVLQ | | | | | | | | | | | |
| 693 | 587 | QQIPIVQPSVLQQLNPCKVF | | | | | | | | | | | |
| 694 | 588 | SVLQQLNPCKVFLQQQCSPV | | | | | | | | | | | |
| 695 | 589 | CKVFLQQQCSPVAMPQRLAR | | | | | | | | | | | |
| 696 | 590 | CSPVAMPQRLARSQMWQQSS | | | | | | | | | | | |
| 697 | 591 | PLARSQMWQQSSCHVMQQQC | | | | | | | | | | | |
| 698 | 592 | QQSSCHVMQQQCCQQLQQIP | | | | | | | | | | | |
| 699 | 593 | QQCCQQLQQIPEQSRYEAI | | | | | | | | | | | |
| 700 | 594 | QQIPEQSRYEAIRAIIYSII | | | | | | | | | | | |

FIGURE 37 (continued)

| 756 | 650 | SRLLSPRGKELHTPQEQFPQ | | | | | | | | | | | | | | ▒ | |
| 757 | 651 | KELHTPQEQFPQQQQFFQFQ | | | | | | | | | | | | | | | |
| 758 | 652 | QFPQQQQFPQPQQFPQ | | | | | | | | | | | | | | | |

70.1 to 100
40.1 to 70
25.1 to 40
10.1 to 25
5.1 to 10
<5

>3 x B1

SEQUENCE LISTING

<160> NUMBER OF SEQ ID NOS: 808

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 1

Pro Gln Pro Glu Leu Pro Tyr
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 2

Gln Leu Gln Pro Phe Pro Gln Pro Glu Leu Pro Tyr Pro Gln Pro Gln
1               5                   10                  15

Ser

<210> SEQ ID NO 3
<211> LENGTH: 266
<212> TYPE: PRT
<213> ORGANISM: Homo sapiens

<400> SEQUENCE: 3

Val Arg Val Pro Val Pro Gln Leu Gln Pro Gln Asn Pro Ser Gln Gln
1               5                   10                  15

Gln Pro Gln Glu Gln Val Pro Leu Val Gln Gln Gln Gln Phe Pro Gly
                20                  25                  30

Gln Gln Gln Gln Phe Pro Pro Gln Gln Pro Tyr Pro Gln Pro Gln Pro
                35                  40                  45

Phe Pro Ser Gln Gln Pro Tyr Leu Gln Leu Gln Pro Phe Pro Gln Pro
            50                  55                  60

Gln Leu Pro Tyr Pro Gln Pro Gln Ser Phe Pro Pro Gln Gln Pro Tyr
65              70                  75                  80

Pro Gln Pro Gln Pro Gln Tyr Ser Gln Pro Gln Gln Pro Ile Ser Gln
                85                  90                  95

Gln Gln Ala Gln Gln Gln Gln Gln Gln Gln Gln Gln Gln Gln Gln Gln
                100                 105                 110

Gln Ile Leu Gln Gln Ile Leu Gln Gln Gln Leu Ile Pro Cys Met Asp
            115                 120                 125

```
Val Val Leu Gln Gln His Asn Ile Ala His Ala Arg Ser Gln Val Leu
    130                 135                 140
Gln Gln Ser Thr Tyr Gln Leu Leu Gln Glu Leu Cys Cys Gln His Leu
145                 150                 155                 160
Trp Gln Ile Pro Glu Gln Ser Gln Cys Gln Ala Ile His Asn Val Val
                165                 170                 175
His Ala Ile Ile Leu His Gln Gln Lys Gln Gln Gln Pro Ser
            180                 185                 190
Ser Gln Val Ser Phe Gln Pro Leu Gln Gln Tyr Pro Leu Gly Gln
        195                 200                 205
Gly Ser Phe Arg Pro Ser Gln Gln Asn Pro Gln Ala Gln Gly Ser Val
    210                 215                 220
Gln Pro Gln Gln Leu Pro Gln Phe Glu Glu Ile Arg Asn Leu Ala Leu
225                 230                 235                 240
Gln Thr Leu Pro Ala Met Cys Asn Val Tyr Ile Ala Pro Tyr Cys Thr
                245                 250                 255
Ile Ala Pro Phe Gly Ile Phe Gly Thr Asn
            260                 265

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 4

Pro Gln Pro Gln Leu Pro Tyr
1               5

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 5

Leu Gln Leu Gln Pro Phe Pro Gln Pro Gln Leu Pro Tyr Pro Gln Pro
1               5                   10                  15

Gln Ser Phe Pro
            20

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 6

Glu Leu Gln Pro Phe Pro Gln Pro Glu Leu Pro Tyr Pro Gln Pro Gln
1               5                   10                  15

Ser

<210> SEQ ID NO 7
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      wheat gliadin peptide

<400> SEQUENCE: 7

Gln Leu Gln Pro Phe Pro Gln Pro Glu Leu Pro Tyr Pro Gln Pro Glu
1               5                   10                  15

Ser

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 8

Glu Leu Gln Pro Phe Pro Gln Pro Glu Leu Pro Tyr Pro Gln Pro Glu
1               5                   10                  15

Ser

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 9

Gln Pro Gln Leu Pro
1               5

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 10

Gln Leu Gln Pro Phe Pro Gln Pro Gln Leu Pro Tyr Pro Gln Pro Gln
1               5                   10                  15

Ser

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 11

Leu Gln Leu Gln Pro Phe Pro Gln Pro Glu Leu Pro Tyr Pro Gln Pro
1               5                   10                  15

Gln Ser Phe Pro
            20

<210> SEQ ID NO 12
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      wheat gliadin peptide

<400> SEQUENCE: 12

Pro Gln Leu Pro Tyr
1               5

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 13

Gln Leu Gln Pro Phe Pro Gln Pro Glu Leu Pro Tyr
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 14

Pro Phe Pro Gln Pro Glu Leu Pro Tyr Pro Gln
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 15

Pro Arg Ala Pro Trp Ile Glu Gln Glu Gly Pro Glu Tyr Trp
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 16

Ile Asp Val Trp Leu Gly Gly Leu Leu Ala Glu Asn Phe Leu Pro Tyr
1               5                   10                  15

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 17

Pro Gln Pro Gln Pro Phe Pro Pro Glu Leu Pro Tyr Pro Gln Pro Gln
1               5                   10                  15
```

Ser

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 18

Phe Pro Gln Pro Gln Leu Pro Tyr Pro
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 19

Phe Pro Gln Pro Gln Gln Pro Phe Pro
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 20

Pro Gln Gln Pro Gln Gln Pro Phe Pro
1               5

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 21

Leu Gln Pro Gln Asn Pro Ser Gln Gln Gln Pro Gln
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 22

Leu Gln Pro Glu Asn Pro Ser Gln Glu Gln Pro Glu
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic

```
      wheat gliadin peptide
<220> FEATURE:
<221> NAME/KEY: MOD_RES
<222> LOCATION: (1)..(7)
<223> OTHER INFORMATION: Any amino acid
<220> FEATURE:
<221> NAME/KEY: MOD_RES
<222> LOCATION: (10)..(10)
<223> OTHER INFORMATION: Ile, Leu, Met or Pro
<220> FEATURE:
<221> NAME/KEY: MOD_RES
<222> LOCATION: (11)..(11)
<223> OTHER INFORMATION: Pro, Ser or Thr
<220> FEATURE:
<221> NAME/KEY: MOD_RES
<222> LOCATION: (12)..(17)
<223> OTHER INFORMATION: Any amino acid

<400> SEQUENCE: 23

Xaa Xaa Xaa Xaa Xaa Xaa Xaa Pro Gln Xaa Xaa Xaa Xaa Xaa Xaa Xaa
1               5                   10                  15

Xaa

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 24

Val Leu Gln Gln His Asn Ile Ala His Gly Ser Ser Gln Val Leu Gln
1               5                   10                  15

Glu Ser Thr Tyr
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 25

Ile Lys Asp Phe His Val Tyr Phe Arg Glu Ser Arg Asp Ala Leu Trp
1               5                   10                  15

Lys Gly Pro Gly
            20

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 26

Gln Leu Gln Pro Phe Pro Gln Pro Gln Leu Pro Tyr Pro Gln Pro Gln
1               5                   10                  15

Pro

<210> SEQ ID NO 27
<211> LENGTH: 17
<212> TYPE: PRT
```

<213> ORGANISM: Artificial Sequence
<220> FEATURE:
<223> OTHER INFORMATION: Description of Artificial Sequence: Synthetic wheat gliadin peptide

<400> SEQUENCE: 27

Gln Leu Gln Pro Phe Pro Gln Pro Glu Leu Pro Tyr Pro Gln Pro Gln
1               5                   10                  15
Pro

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 28

Gln Leu Gln Pro Phe Pro Gln Pro Gln Leu Pro Tyr Ser Gln Pro Gln
1               5                   10                  15
Pro

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 29

Gln Leu Gln Pro Phe Pro Gln Pro Glu Leu Pro Tyr Ser Gln Pro Gln
1               5                   10                  15
Pro

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 30

Gln Gln Thr Tyr Pro Gln Arg Pro Gln Pro Phe Pro Gln Thr Gln
1               5                   10                  15
Gln Pro Gln Gln
        20

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 31

Pro Gln Gln Pro Gln Gln Pro Gln Gln Pro Phe Pro Gln Pro Gln Gln
1               5                   10                  15
Pro Phe Pro Trp
        20

```
<210> SEQ ID NO 32
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 32

Gln Gln Pro Gln Gln Pro Phe Pro Gln Pro Gln Gln Pro Gln Leu Pro
1               5                   10                  15

Phe Pro Gln Gln
            20

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 33

Gln Ala Phe Pro Gln Pro Gln Gln Thr Phe Pro His Gln Pro Gln Gln
1               5                   10                  15

Gln Phe Pro Gln
            20

<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 34

Thr Gln Gln Pro Gln Gln Pro Phe Pro Gln Gln Pro Gln Gln Pro Phe
1               5                   10                  15

Pro Gln Thr Gln
            20

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 35

Pro Ile Gln Pro Gln Gln Pro Phe Pro Gln Gln Pro Gln Gln Pro Gln
1               5                   10                  15

Gln Pro Phe Pro
            20

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 36

Pro Gln Gln Ser Phe Ser Tyr Gln Gln Gln Pro Phe Pro Gln Gln Pro
```

```
1               5                  10                  15
Tyr Pro Gln Gln
            20

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      wheat gliadin peptide
<220> FEATURE:
<221> NAME/KEY: MOD_RES
<222> LOCATION: (2)..(2)
<223> OTHER INFORMATION: Any amino acid

<400> SEQUENCE: 37

Gln Xaa Pro Phe
1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      wheat gliadin peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (4)..(4)
<223> OTHER INFORMATION: Phe or Tyr

<400> SEQUENCE: 38

Gln Xaa Xaa Xaa
1

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 39

Gln Gln Pro Phe Pro Gln Pro Gln Gln Pro Phe Pro
1               5                  10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 40

Gln Gln Pro Phe Pro Gln Gln Pro Gln Gln Pro Phe Pro
1               5                  10

<210> SEQ ID NO 41
<211> LENGTH: 12
<212> TYPE: PRT
<213> ORGANISM: Artificial Sequence
<220> FEATURE:
```

<223> OTHER INFORMATION: Description of Artificial Sequence: Synthetic
      wheat gliadin peptide

<400> SEQUENCE: 41

Pro Ile Gln Pro Gln Gln Pro Phe Pro Gln Gln Pro
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 42

Leu Gln Pro Gln Asn Pro Ser Gln Gln Gln Pro Gln
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 43

Leu Gln Pro Gln Asn Pro Ser Gln Gln Gln Pro Gln
1               5                   10

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 44

Gln Gln Tyr Pro Ser Gly Gln Gly Ser Phe Gln Pro Ser Gln Gln Asn
1               5                   10                  15

Pro Gln

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      wheat gliadin peptide
<220> FEATURE:
<221> NAME/KEY: MOD_RES
<222> LOCATION: (3)..(3)
<223> OTHER INFORMATION: Gln or Leu
<220> FEATURE:
<221> NAME/KEY: MOD_RES
<222> LOCATION: (5)..(5)
<223> OTHER INFORMATION: Phe or Tyr

<400> SEQUENCE: 45

Pro Gln Xaa Pro Xaa Pro
1               5

<210> SEQ ID NO 46
<211> LENGTH: 12
<212> TYPE: PRT
<213> ORGANISM: Artificial Sequence

```
<220> FEATURE:
<223> OTHER INFORMATION: Description of Artificial Sequence: Synthetic
      wheat gliadin peptide

<400> SEQUENCE: 46

Leu Gln Pro Gln Asn Pro Ser Gln Gln Gln Pro Gln
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 47

Pro Gln Pro Glu Leu Pro Tyr Pro Gln Pro Glu Leu Pro Tyr
1               5                   10

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 48

Gln Gln Leu Pro Gln Pro Glu Gln Pro Gln Gln Ser Phe Pro Glu Gln
1               5                   10                  15

Glu Arg Pro Phe
            20

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 49

Gln Leu Gln Pro Phe Pro Gln Pro Glu Leu Pro Tyr Pro Gln Pro Gln
1               5                   10                  15

Leu

<210> SEQ ID NO 50
<211> LENGTH: 22
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 50

Pro Gln Gln Pro Gln Gln Pro Gln Gln Pro Phe Pro Gln Pro Gln Gln
1               5                   10                  15

Pro Phe Pro Trp Gln Pro
            20

<210> SEQ ID NO 51
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      wheat gliadin peptide

<400> SEQUENCE: 51

Gln Leu Gln Pro Phe Pro Gln Pro Gln Leu Pro Tyr Pro Gln Pro Gln
1               5                   10                  15

Leu

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 52

Gln Pro Gln Gln Pro Phe Pro Gln Pro Gln Gln Pro Phe Pro Trp
1               5                   10                  15

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 53

Gln Leu Gln Pro Phe Pro Gln Pro Gln Leu Pro Tyr
1               5                   10

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 54

Pro Phe Pro Gln Pro Gln Leu Pro Tyr
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 55

Pro Gln Pro Gln Leu Pro Tyr Pro Gln
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 56

Pro Tyr Pro Gln Pro Gln Leu Pro Tyr
1               5
```

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 57

Pro Gln Gln Pro Tyr Pro Gln Pro Gln Pro Gln
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 58

Pro Gln Gln Ser Phe Pro Gln Gln Gln
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 59

Ile Ile Pro Gln Gln Pro Ala Gln
1               5

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 60

Phe Pro Gln Gln Pro Gln Gln Pro Tyr Pro Gln Gln Pro
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 61

Phe Ser Gln Pro Gln Gln Gln Phe Pro Gln Pro Gln
1               5                   10

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 62

Leu Gln Pro Gln Gln Pro Phe Pro Gln Gln Pro Gln Gln Pro Tyr Pro
1               5                   10                  15
Gln Gln Pro Gln
            20

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 63

Gln Ser Glu Gln Ser Gln Gln Pro Phe Pro Gln Gln Phe
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      wheat gliadin peptide
<220> FEATURE:
<221> NAME/KEY: MOD_RES
<222> LOCATION: (2)..(2)
<223> OTHER INFORMATION: Ile or Leu

<400> SEQUENCE: 64

Gln Xaa Pro Gln Gln Pro Gln Gln Phe
1               5

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 65

Pro Phe Ser Gln Gln Gln Gln Ser Pro Phe
1               5                   10

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 66

Pro Phe Ser Gln Gln Gln Gln Gln
1               5

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 67

```
<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 68

Gln Leu Gln Pro Phe Pro Arg Pro Gln Leu Pro Tyr Pro Gln Pro Gln
1               5                   10                  15

Pro

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 69

Gln Leu Gln Pro Phe Leu Gln Pro Gln Leu Pro Tyr Ser Gln Pro Gln
1               5                   10                  15

Pro

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 70

Gln Leu Gln Pro Phe Ser Gln Pro Gln Leu Pro Tyr Ser Gln Pro Gln
1               5                   10                  15

Pro

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 71

Gln Leu Gln Pro Phe Pro Gln Pro Gln Leu Ser Tyr Ser Gln Pro Gln
1               5                   10                  15

Pro

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide
```

```
Gln Leu Gln Pro Phe Pro Gln Pro Gln Leu Pro Tyr Leu Gln Pro Gln
1               5                   10                  15

Pro
```

```
<400> SEQUENCE: 72

Pro Gln Leu Pro Tyr Pro Gln Pro Gln Leu Pro Tyr Pro Gln Pro Gln
1               5                   10                  15

Pro

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 73

Pro Gln Leu Pro Tyr Pro Gln Pro Gln Leu Pro Tyr Pro Gln Pro Gln
1               5                   10                  15

Leu

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 74

Pro Gln Pro Gln Pro Phe Leu Pro Gln Leu Pro Tyr Pro Gln Pro Gln
1               5                   10                  15

Ser

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 75

Pro Gln Pro Gln Pro Phe Pro Pro Gln Leu Pro Tyr Pro Gln Pro Gln
1               5                   10                  15

Ser

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 76

Pro Gln Pro Gln Pro Phe Pro Pro Gln Leu Pro Tyr Pro Gln Tyr Gln
1               5                   10                  15

Pro

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide
```

<400> SEQUENCE: 77

Pro Gln Pro Gln Pro Phe Pro Pro Gln Leu Pro Tyr Pro Gln Pro Pro
1               5                   10                  15

Pro

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 78

Val Pro Gln Leu Gln Pro Gln Asn Pro Ser Gln Gln Gln Pro Gln Glu
1               5                   10                  15

Gln Val

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 79

Val Pro Gln Leu Gln Pro Glu Asn Pro Ser Gln Gln Gln Pro Gln Glu
1               5                   10                  15

Gln Val

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 80

Val Pro Gln Leu Gln Pro Arg Asn Pro Ser Gln Gln Gln Pro Gln Glu
1               5                   10                  15

Gln Val

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 81

Val Pro Gln Leu Gln Pro Gln Asn Pro Ser Gln Glu Gln Pro Gln Glu
1               5                   10                  15

Gln Val

<210> SEQ ID NO 82
<211> LENGTH: 18
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 82

Val Pro Gln Leu Gln Pro Gln Asn Pro Ser Gln Arg Gln Pro Gln Glu
1               5                   10                  15

Gln Val

<210> SEQ ID NO 83
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 83

Val Pro Gln Leu Gln Pro Gln Asn Pro Ser Gln Gln Gln Pro Glu Glu
1               5                   10                  15

Gln Val

<210> SEQ ID NO 84
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 84

Val Pro Gln Leu Gln Pro Gln Asn Pro Ser Gln Gln Gln Pro Arg Glu
1               5                   10                  15

Gln Val

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 85

Val Pro Gln Leu Gln Pro Gln Asn Pro Ser Gln Glu Gln Pro Glu Glu
1               5                   10                  15

Gln Val

<210> SEQ ID NO 86
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 86

Val Pro Gln Leu Gln Pro Glu Asn Pro Ser Gln Gln Gln Pro Glu Glu
1               5                   10                  15

Gln Val

<210> SEQ ID NO 87
<211> LENGTH: 18
<212> TYPE: PRT
<213> ORGANISM: Artificial Sequence
<220> FEATURE:

<223> OTHER INFORMATION: Description of Artificial Sequence: Synthetic
      wheat gliadin peptide

<400> SEQUENCE: 87

Val Pro Gln Leu Gln Pro Glu Asn Pro Ser Gln Glu Gln Pro Gln Glu
1               5                   10                  15

Gln Val

<210> SEQ ID NO 88
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 88

Val Pro Gln Leu Gln Pro Glu Asn Pro Ser Gln Glu Gln Pro Glu Glu
1               5                   10                  15

Gln Val

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 89

Arg Trp Pro Val Pro Gln Leu Gln Pro Gln Asn Pro Ser Gln Gln
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 90

Trp Pro Val Pro Gln Leu Gln Pro Gln Asn Pro Ser Gln Gln Gln
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 91

Pro Val Pro Gln Leu Gln Pro Gln Asn Pro Ser Gln Gln Gln Pro
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 92

Val Pro Gln Leu Gln Pro Gln Asn Pro Ser Gln Gln Gln Pro Gln
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 93

Pro Gln Leu Gln Pro Gln Asn Pro Ser Gln Gln Gln Pro Gln Glu
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 94

Gln Leu Gln Pro Gln Asn Pro Ser Gln Gln Gln Pro Gln Glu Gln
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 95

Leu Gln Pro Gln Asn Pro Ser Gln Gln Gln Pro Gln Glu Gln Val
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 96

Gln Pro Gln Asn Pro Ser Gln Gln Gln Pro Gln Glu Gln Val Pro
1               5                   10                  15

<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 97

Pro Gln Pro Gln Pro Phe Pro Pro Gln Leu Pro Tyr Pro Gln Thr Gln
1               5                   10                  15

Pro

<210> SEQ ID NO 98
<211> LENGTH: 19
<212> TYPE: PRT

<210> SEQ ID NO 99
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 98

Leu Gly Gln Gln Gln Pro Phe Pro Pro Gln Gln Pro Tyr Pro Gln Pro
1               5                   10                  15

Gln Pro Phe

<210> SEQ ID NO 99
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 99

Gln Gln Tyr Pro Ser Gly Glu Gly Ser Phe Gln Pro Ser Gln Glu Asn
1               5                   10                  15

Pro Gln

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 100

Gly Gln Gln Gly Tyr Tyr Pro Thr Ser Pro Gln Gln Ser Gly Gln
1               5                   10                  15

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 101

Pro Gln Leu Pro Tyr Pro Gln Pro Glu Leu Pro Tyr Pro Gln Pro Gln
1               5                   10                  15

Pro

<210> SEQ ID NO 102
<211> LENGTH: 14
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 102

Pro Gln Pro Gln Leu Pro Tyr Pro Gln Pro Gln Leu Pro Tyr
1               5                   10

<210> SEQ ID NO 103
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 103

Gln Gln Leu Pro Gln Pro Gln Gln Pro Gln Gln Ser Phe Pro Gln Gln
1               5                   10                  15

Gln Arg Pro Phe
            20

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 104

Gln Leu Gln Pro Phe Pro Gln Pro Gln Leu Pro Tyr Leu Gln Pro Gln
1               5                   10                  15

Ser

<210> SEQ ID NO 105
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 105

Gln Pro Gln Pro Phe Pro Pro Pro Gln Leu Pro Tyr Pro Gln Thr Gln
1               5                   10                  15

Pro

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 106

Pro Gln Pro Gln Pro Phe Pro Pro Gln Leu Pro Tyr Pro Gln Thr Gln
1               5                   10                  15

Ser

<210> SEQ ID NO 107
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 107

Ala Val Arg Phe Pro Val Pro Gln Leu Gln Pro Gln Asn Pro Ser Gln
1               5                   10                  15

Gln Leu Pro Gln
            20

<210> SEQ ID NO 108
<211> LENGTH: 20
<212> TYPE: PRT

```
<213> ORGANISM: Artificial Sequence
<220> FEATURE:
<223> OTHER INFORMATION: Description of Artificial Sequence: Synthetic
      wheat gliadin peptide

<400> SEQUENCE: 108

Met Val Arg Val Pro Val Pro Gln Leu Gln Pro Gln Asn Pro Ser Gln
1               5                   10                  15

Gln Gln Pro Gln
            20

<210> SEQ ID NO 109
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 109

Met Val Arg Val Pro Val Pro Gln Leu Gln Pro Gln Asn Pro Ser Gln
1               5                   10                  15

Gln His Pro Gln
            20

<210> SEQ ID NO 110
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 110

Met Val Arg Val Pro Met Pro Gln Leu Gln Pro Gln Asp Pro Ser Gln
1               5                   10                  15

Gln Gln Pro Gln
            20

<210> SEQ ID NO 111
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 111

Met Val Arg Val Thr Val Pro Gln Leu Gln Pro Gln Asn Pro Ser Gln
1               5                   10                  15

Gln Gln Pro Gln
            20

<210> SEQ ID NO 112
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 112

Ala Val Arg Val Ser Val Pro Gln Leu Gln Pro Gln Asn Pro Ser Gln
1               5                   10                  15

Gln Gln Pro Gln
```

20

<210> SEQ ID NO 113
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 113

Ala Val Arg Val Pro Val Pro Gln Leu Gln Pro Gln Asn Pro Ser Gln
1               5                   10                  15

Gln Gln Pro Gln
            20

<210> SEQ ID NO 114
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 114

Ala Val Arg Trp Pro Val Pro Gln Leu Gln Pro Gln Asn Pro Ser Gln
1               5                   10                  15

Gln Gln Pro Gln
            20

<210> SEQ ID NO 115
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 115

Ala Val Arg Val Pro Val Pro Gln Leu Gln Leu Gln Asn Pro Ser Gln
1               5                   10                  15

Gln Gln Pro Gln
            20

<210> SEQ ID NO 116
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 116

Met Val Arg Val Pro Val Pro Gln Leu Gln Leu Gln Asn Pro Ser Gln
1               5                   10                  15

Gln Gln Pro Gln
            20

<210> SEQ ID NO 117
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

```
<400> SEQUENCE: 117

Ala Val Arg Val Pro Val Pro Gln Pro Gln Pro Gln Asn Pro Ser Gln
1               5                   10                  15

Pro Gln Pro Gln
            20

<210> SEQ ID NO 118
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 118

Ala Val Arg Val Pro Val Pro Gln Leu Gln Pro Lys Asn Pro Ser Gln
1               5                   10                  15

Gln Gln Pro Gln
            20

<210> SEQ ID NO 119
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 119

Leu Gln Pro Gln Asn Pro Ser Gln Gln Leu Pro Gln Glu Gln Val Pro
1               5                   10                  15

Leu Val Gln Gln
            20

<210> SEQ ID NO 120
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 120

Leu Gln Pro Gln Asn Pro Ser Gln Gln Pro Gln Glu Gln Val Pro
1               5                   10                  15

Leu Val Gln Gln
            20

<210> SEQ ID NO 121
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 121

Leu Gln Pro Gln Asn Pro Ser Gln Gln His Pro Gln Glu Gln Val Pro
1               5                   10                  15

Leu Val Gln Gln
            20

<210> SEQ ID NO 122
<211> LENGTH: 20
```

<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 122

Leu Gln Pro Gln Asp Pro Ser Gln Gln Gln Pro Gln Glu Gln Val Pro
1               5                   10                  15

Leu Val Gln Gln
            20

<210> SEQ ID NO 123
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 123

Leu Gln Pro Gln Asn Pro Ser Gln Gln Gln Pro Gln Lys Gln Val Pro
1               5                   10                  15

Leu Val Gln Gln
            20

<210> SEQ ID NO 124
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 124

Leu Gln Leu Gln Asn Pro Ser Gln Gln Gln Pro Gln Glu Gln Val Pro
1               5                   10                  15

Leu Val Gln Glu
            20

<210> SEQ ID NO 125
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 125

Leu Gln Leu Gln Asn Pro Ser Gln Gln Gln Pro Gln Glu Gln Val Pro
1               5                   10                  15

Leu Val Gln Glu
            20

<210> SEQ ID NO 126
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 126

Pro Gln Pro Gln Asn Pro Ser Gln Pro Gln Pro Gln Gly Gln Val Pro
1               5                   10                  15

Leu Val Gln Gln
            20

<210> SEQ ID NO 127
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 127

Pro Gln Pro Gln Asn Pro Ser Gln Pro Gln Pro Gln Arg Gln Val Pro
1               5                   10                  15

Leu Val Gln Gln
            20

<210> SEQ ID NO 128
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 128

Leu Gln Pro Lys Asn Pro Ser Gln Gln Gln Pro Gln Glu Gln Val Pro
1               5                   10                  15

Leu Val Gln Gln
            20

<210> SEQ ID NO 129
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 129

Leu Gln Pro Gln Asn Pro Ser Gln Gln Gln Pro Gln Glu Gln Val Pro
1               5                   10                  15

Leu Met Gln Gln
            20

<210> SEQ ID NO 130
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 130

Gln Leu Pro Gln Glu Gln Val Pro Leu Val Gln Gln Gln Gln Phe Leu
1               5                   10                  15

Gly Gln Gln Gln
            20

<210> SEQ ID NO 131
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 131

Gln His Pro Gln Glu Gln Val Pro Leu Val Gln Gln Gln Phe Leu
1               5                   10                  15

Gly Gln Gln Gln
            20

<210> SEQ ID NO 132
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 132

Gln Gln Pro Gln Glu Gln Val Pro Leu Val Gln Gln Gln Phe Leu
1               5                   10                  15

Gly Gln Gln Gln
            20

<210> SEQ ID NO 133
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 133

Gln Gln Pro Gln Glu Gln Val Pro Leu Val Gln Gln Gln Phe Leu
1               5                   10                  15

Gly Gln Gln Gln
            20

<210> SEQ ID NO 134
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 134

Gln Gln Pro Gln Glu Gln Val Pro Leu Val Gln Gln Gln Phe Pro
1               5                   10                  15

Gly Gln Gln Gln
            20

<210> SEQ ID NO 135
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 135

Gln Gln Pro Gln Lys Gln Val Pro Leu Val Gln Gln Gln Phe Pro
1               5                   10                  15

Gly Gln Gln Gln
            20

<210> SEQ ID NO 136

```
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 136

Gln Gln Pro Gln Glu Gln Val Pro Leu Val Gln Glu Gln Gln Phe Gln
1               5                   10                  15

Gly Gln Gln Gln
            20

<210> SEQ ID NO 137
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 137

Pro Gln Pro Gln Gly Gln Val Pro Leu Val Gln Gln Gln Gln Phe Pro
1               5                   10                  15

Gly Gln Gln Gln
            20

<210> SEQ ID NO 138
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 138

Pro Gln Pro Gln Arg Gln Val Pro Leu Val Gln Gln Gln Gln Phe Pro
1               5                   10                  15

Gly Gln Gln Gln
            20

<210> SEQ ID NO 139
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 139

Gln Gln Pro Gln Glu Gln Val Pro Leu Met Gln Gln Gln Gln Gln Phe
1               5                   10                  15

Pro Gly Gln Gln
            20

<210> SEQ ID NO 140
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 140

Leu Val Gln Gln Gln Gln Phe Leu Gly Gln Gln Gln Pro Phe Pro Pro
1               5                   10                  15
```

Gln Gln Pro Tyr
            20

<210> SEQ ID NO 141
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 141

Leu Val Gln Gln Gln Gln Phe Leu Gly Gln Gln Ser Phe Pro Pro
1               5                   10                  15

Gln Gln Pro Tyr
            20

<210> SEQ ID NO 142
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 142

Leu Val Gln Gln Gln Gln Phe Leu Gly Gln Gln Pro Phe Pro Pro
1               5                   10                  15

Gln Gln Pro Tyr
            20

<210> SEQ ID NO 143
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 143

Leu Val Gln Gln Gln Gln Phe Pro Gly Gln Gln Pro Phe Pro Pro
1               5                   10                  15

Gln Gln Pro Tyr
            20

<210> SEQ ID NO 144
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 144

Leu Val Gln Glu Gln Gln Phe Gln Gly Gln Gln Pro Phe Pro Pro
1               5                   10                  15

Gln Gln Pro Tyr
            20

<210> SEQ ID NO 145
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 145

Leu Val Gln Gln Gln Gln Phe Pro Gly Gln Gln Gln Phe Pro Pro
1               5                   10                  15

Gln Gln Pro Tyr
            20

<210> SEQ ID NO 146
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 146

Leu Met Gln Gln Gln Gln Phe Pro Gly Gln Gln Glu Gln Phe Pro
1               5                   10                  15

Pro Gln Gln Pro
            20

<210> SEQ ID NO 147
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 147

Leu Met Gln Gln Gln Gln Phe Pro Gly Gln Gln Glu Arg Phe Pro
1               5                   10                  15

Pro Gln Gln Pro
            20

<210> SEQ ID NO 148
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 148

Gly Gln Gln Gln Pro Phe Pro Pro Gln Gln Pro Tyr Pro Gln Pro Gln
1               5                   10                  15

Pro Phe Pro Ser
            20

<210> SEQ ID NO 149
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 149

Gly Gln Gln Gln Pro Phe Pro Pro Gln Gln Pro Tyr Pro Gln Pro Gln
1               5                   10                  15

Phe Pro Ser Gln
            20

```
<210> SEQ ID NO 150
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 150

Gly Gln Gln Gln Ser Phe Pro Pro Gln Gln Pro Tyr Pro Gln Pro Gln
1               5                   10                  15

Pro Phe Pro Ser
            20

<210> SEQ ID NO 151
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 151

Gly Gln Gln Gln Pro Phe Pro Pro Gln Gln Pro Tyr Pro Gln Gln Gln
1               5                   10                  15

Pro Phe Pro Ser
            20

<210> SEQ ID NO 152
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 152

Gly Gln Gln Gln Gln Phe Pro Pro Gln Gln Pro Tyr Pro Gln Pro Gln
1               5                   10                  15

Pro Phe Pro Ser
            20

<210> SEQ ID NO 153
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 153

Gly Gln Gln Glu Gln Phe Pro Pro Gln Gln Pro Tyr Pro His Gln Gln
1               5                   10                  15

Pro Phe Pro Ser
            20

<210> SEQ ID NO 154
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 154

Gly Gln Gln Glu Arg Phe Pro Pro Gln Gln Pro Tyr Pro His Gln Gln
```

```
                  1               5                  10                 15
Pro Phe Pro Ser
            20

<210> SEQ ID NO 155
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 155

Gln Gln Pro Tyr Pro Gln Pro Gln Pro Phe Pro Ser Gln Leu Pro Tyr
1               5                  10                  15

Leu Gln Leu Gln
            20

<210> SEQ ID NO 156
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 156

Gln Gln Pro Tyr Pro Gln Pro Gln Phe Pro Ser Gln Leu Pro Tyr Leu
1               5                  10                  15

Gln Leu Gln Pro
            20

<210> SEQ ID NO 157
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 157

Gln Gln Pro Tyr Pro Gln Pro Gln Pro Phe Pro Ser Gln Gln Pro Tyr
1               5                  10                  15

Leu Gln Leu Gln
            20

<210> SEQ ID NO 158
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 158

Gln Gln Pro Tyr Pro Gln Gln Gln Pro Phe Pro Ser Gln Gln Pro Tyr
1               5                  10                  15

Met Gln Leu Gln
            20

<210> SEQ ID NO 159
<211> LENGTH: 20
<212> TYPE: PRT
<213> ORGANISM: Artificial Sequence
<220> FEATURE:
```

-continued

<223> OTHER INFORMATION: Description of Artificial Sequence: Synthetic
      wheat gliadin peptide

<400> SEQUENCE: 159

Gln Gln Pro Tyr Pro His Gln Gln Pro Phe Pro Ser Gln Gln Pro Tyr
1               5                   10                  15

Pro Gln Pro Gln
            20

<210> SEQ ID NO 160
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 160

Pro Phe Pro Ser Gln Leu Pro Tyr Leu Gln Leu Gln Pro Phe Pro Gln
1               5                   10                  15

Pro Gln Leu Pro
            20

<210> SEQ ID NO 161
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 161

Pro Phe Pro Ser Gln Gln Pro Tyr Leu Gln Leu Gln Pro Phe Pro Gln
1               5                   10                  15

Pro Gln Leu Pro
            20

<210> SEQ ID NO 162
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 162

Pro Phe Pro Ser Gln Gln Pro Tyr Leu Gln Leu Gln Pro Phe Ser Gln
1               5                   10                  15

Pro Gln Leu Pro
            20

<210> SEQ ID NO 163
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 163

Pro Phe Pro Ser Gln Gln Pro Tyr Leu Gln Leu Gln Pro Phe Leu Gln
1               5                   10                  15

Pro Gln Leu Pro
            20

<210> SEQ ID NO 164
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 164

Pro Phe Pro Ser Gln Gln Pro Tyr Leu Gln Leu Gln Pro Phe Leu Gln
1               5                   10                  15

Pro Gln Pro Phe
            20

<210> SEQ ID NO 165
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 165

Pro Phe Pro Ser Gln Gln Pro Tyr Leu Gln Leu Gln Pro Phe Pro Gln
1               5                   10                  15

Pro Gln Leu Pro
            20

<210> SEQ ID NO 166
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 166

Pro Phe Pro Ser Gln Gln Pro Tyr Met Gln Leu Gln Pro Phe Pro Gln
1               5                   10                  15

Pro Gln Leu Pro
            20

<210> SEQ ID NO 167
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 167

Pro Phe Pro Ser Gln Gln Pro Tyr Met Gln Leu Gln Pro Phe Pro Gln
1               5                   10                  15

Pro Gln Pro Phe
            20

<210> SEQ ID NO 168
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 168

```
Pro Phe Pro Ser Gln Gln Pro Tyr Leu Gln Leu Gln Pro Phe Pro Gln
1               5                   10                  15

Pro Gln Pro Phe
            20

<210> SEQ ID NO 169
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 169

Pro Phe Pro Ser Gln Gln Pro Tyr Leu Gln Leu Gln Pro Phe Pro Arg
1               5                   10                  15

Pro Gln Leu Pro
            20

<210> SEQ ID NO 170
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 170

Pro Phe Pro Ser Gln Gln Pro Tyr Pro Gln Pro Gln Pro Phe Pro Pro
1               5                   10                  15

Gln Leu Pro Tyr
            20

<210> SEQ ID NO 171
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 171

Pro Phe Pro Ser Gln Gln Pro Tyr Pro Gln Pro Gln Pro Phe Pro Gln
1               5                   10                  15

Pro Gln Pro Phe
            20

<210> SEQ ID NO 172
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 172

Leu Gln Leu Gln Pro Phe Pro Gln Pro Gln Leu Pro Tyr Ser Gln Pro
1               5                   10                  15

Gln Pro Phe Arg
            20

<210> SEQ ID NO 173
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      wheat gliadin peptide

<400> SEQUENCE: 173

Leu Gln Leu Gln Pro Phe Pro Gln Pro Gln Leu Pro Tyr Ser Gln Pro
1               5                   10                  15

Gln Gln Phe Arg
            20

<210> SEQ ID NO 174
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 174

Leu Gln Leu Gln Pro Phe Pro Gln Pro Gln Leu Pro Tyr Leu Gln Pro
1               5                   10                  15

Gln Pro Phe Arg
            20

<210> SEQ ID NO 175
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 175

Leu Gln Leu Gln Pro Phe Pro Gln Pro Gln Leu Ser Tyr Ser Gln Pro
1               5                   10                  15

Gln Pro Phe Arg
            20

<210> SEQ ID NO 176
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 176

Leu Gln Leu Gln Pro Phe Ser Gln Pro Gln Leu Pro Tyr Ser Gln Pro
1               5                   10                  15

Gln Pro Phe Arg
            20

<210> SEQ ID NO 177
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 177

Leu Gln Leu Gln Pro Phe Leu Gln Pro Gln Leu Pro Tyr Ser Gln Pro
1               5                   10                  15

Gln Pro Phe Arg
            20
```

<210> SEQ ID NO 178
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 178

Leu Gln Leu Gln Pro Phe Leu Gln Pro Gln Pro Phe Pro Pro Gln Leu
1               5                   10                  15

Pro Tyr Ser Gln
            20

<210> SEQ ID NO 179
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 179

Leu Gln Leu Gln Pro Phe Pro Gln Pro Gln Leu Pro Tyr Pro Gln Pro
1               5                   10                  15

Gln Leu Pro Tyr
            20

<210> SEQ ID NO 180
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 180

Met Gln Leu Gln Pro Phe Pro Gln Pro Gln Leu Pro Tyr Pro Gln Pro
1               5                   10                  15

Gln Leu Pro Tyr
            20

<210> SEQ ID NO 181
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 181

Met Gln Leu Gln Pro Phe Pro Gln Pro Gln Pro Phe Pro Pro Gln Leu
1               5                   10                  15

Pro Tyr Pro Gln
            20

<210> SEQ ID NO 182
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 182

Leu Gln Leu Gln Pro Phe Pro Gln Pro Gln Leu Pro Tyr Pro Gln Pro
1               5                   10                  15

Gln Pro Phe Arg
            20

<210> SEQ ID NO 183
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 183

Leu Gln Leu Gln Pro Phe Pro Gln Pro Gln Pro Phe Pro Pro Gln Leu
1               5                   10                  15

Pro Tyr Pro Gln
            20

<210> SEQ ID NO 184
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 184

Leu Gln Leu Gln Pro Phe Pro Arg Pro Gln Leu Pro Tyr Pro Gln Pro
1               5                   10                  15

Gln Pro Phe Arg
            20

<210> SEQ ID NO 185
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 185

Leu Gln Leu Gln Pro Phe Pro Gln Pro Gln Pro Phe Leu Pro Gln Leu
1               5                   10                  15

Pro Tyr Pro Gln
            20

<210> SEQ ID NO 186
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 186

Leu Gln Leu Gln Pro Phe Pro Gln Pro Gln Pro Phe Pro Pro Gln Leu
1               5                   10                  15

Pro Tyr Pro Gln
            20

<210> SEQ ID NO 187
<211> LENGTH: 20
<212> TYPE: PRT

<210> SEQ ID NO 188
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 187

Pro Gln Pro Gln Pro Phe Pro Pro Gln Leu Pro Tyr Pro Gln Thr Gln
1               5                   10                  15

Pro Phe Pro Pro
            20

<210> SEQ ID NO 188
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 188

Pro Gln Pro Gln Pro Phe Pro Gln Pro Gln Pro Phe Pro Pro Gln Leu
1               5                   10                  15

Pro Tyr Pro Gln
            20

<210> SEQ ID NO 189
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 189

Pro Gln Leu Pro Tyr Ser Gln Pro Gln Pro Phe Arg Pro Gln Gln Pro
1               5                   10                  15

Tyr Pro Gln Pro
            20

<210> SEQ ID NO 190
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 190

Pro Gln Leu Pro Tyr Ser Gln Pro Gln Gln Phe Arg Pro Gln Gln Pro
1               5                   10                  15

Tyr Pro Gln Pro
            20

<210> SEQ ID NO 191
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 191

Pro Gln Leu Pro Tyr Leu Gln Pro Gln Pro Phe Arg Pro Gln Gln Pro
1               5                   10                  15

Tyr Pro Gln Pro

20

<210> SEQ ID NO 192
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 192

Pro Gln Leu Ser Tyr Ser Gln Pro Gln Pro Phe Arg Pro Gln Gln Pro
1               5                   10                  15

Tyr Pro Gln Pro
            20

<210> SEQ ID NO 193
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 193

Pro Gln Leu Ser Tyr Ser Gln Pro Gln Pro Phe Arg Pro Gln Gln Leu
1               5                   10                  15

Tyr Pro Gln Pro
            20

<210> SEQ ID NO 194
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 194

Pro Gln Pro Phe Pro Pro Gln Leu Pro Tyr Ser Gln Pro Gln Pro Phe
1               5                   10                  15

Arg Pro Gln Gln
            20

<210> SEQ ID NO 195
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 195

Pro Gln Leu Pro Tyr Pro Gln Pro Gln Leu Pro Tyr Pro Gln Pro Gln
1               5                   10                  15

Leu Pro Tyr Pro
            20

<210> SEQ ID NO 196
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

```
<400> SEQUENCE: 196

Pro Gln Leu Pro Tyr Pro Gln Pro Gln Leu Pro Tyr Pro Gln Pro Gln
1               5                   10                  15

Pro Phe Arg Pro
            20

<210> SEQ ID NO 197
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 197

Pro Gln Pro Phe Pro Pro Gln Leu Pro Tyr Pro Gln Pro Gln Leu Pro
1               5                   10                  15

Tyr Pro Gln Pro
            20

<210> SEQ ID NO 198
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 198

Pro Gln Leu Pro Tyr Pro Gln Pro Gln Pro Phe Arg Pro Gln Gln Pro
1               5                   10                  15

Tyr Pro Gln Pro
            20

<210> SEQ ID NO 199
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 199

Pro Gln Pro Phe Pro Pro Gln Leu Pro Tyr Pro Gln Pro Gln Pro Phe
1               5                   10                  15

Arg Pro Gln Gln
            20

<210> SEQ ID NO 200
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 200

Pro Gln Pro Phe Pro Pro Gln Leu Pro Tyr Pro Gln Pro Pro Pro Phe
1               5                   10                  15

Ser Pro Gln Gln
            20

<210> SEQ ID NO 201
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 201

Pro Gln Pro Phe Leu Pro Gln Leu Pro Tyr Pro Gln Pro Gln Ser Phe
1               5                   10                  15

Pro Pro Gln Gln
            20

<210> SEQ ID NO 202
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 202

Pro Gln Pro Phe Pro Pro Gln Leu Pro Tyr Pro Gln Pro Gln Ser Phe
1               5                   10                  15

Pro Pro Gln Gln
            20

<210> SEQ ID NO 203
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 203

Gln Leu Pro Tyr Pro Gln Thr Gln Pro Phe Pro Pro Gln Gln Pro Tyr
1               5                   10                  15

Pro Gln Pro Gln
            20

<210> SEQ ID NO 204
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 204

Pro Gln Pro Phe Pro Pro Gln Leu Pro Tyr Pro Gln Thr Gln Pro Phe
1               5                   10                  15

Pro Pro Gln Gln
            20

<210> SEQ ID NO 205
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 205

Leu Pro Tyr Pro Gln Pro Gln Pro Phe Arg Pro Gln Gln Pro Tyr Pro
1               5                   10                  15
```

Gln Ser Gln Pro
            20

<210> SEQ ID NO 206
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 206

Leu Pro Tyr Pro Gln Pro Gln Pro Phe Arg Pro Gln Gln Ser Tyr Pro
1               5                   10                  15

Gln Pro Gln Pro
            20

<210> SEQ ID NO 207
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 207

Leu Pro Tyr Pro Gln Pro Pro Pro Phe Ser Pro Gln Gln Pro Tyr Pro
1               5                   10                  15

Gln Pro Gln Pro
            20

<210> SEQ ID NO 208
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 208

Leu Pro Gln Leu Pro Tyr Pro Gln Pro Gln Ser Phe Pro Pro Gln Gln
1               5                   10                  15

Pro Tyr Pro Gln
            20

<210> SEQ ID NO 209
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 209

Pro Pro Gln Leu Pro Tyr Pro Gln Thr Gln Pro Phe Pro Pro Gln Gln
1               5                   10                  15

Pro Tyr Pro Gln
            20

<210> SEQ ID NO 210
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 210

Gln Pro Phe Arg Pro Gln Gln Pro Tyr Pro Gln Pro Gln Pro Gln Tyr
1               5                   10                  15

Ser Gln Pro Gln
            20

<210> SEQ ID NO 211
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 211

Gln Pro Phe Arg Pro Gln Gln Leu Tyr Pro Gln Pro Gln Pro Gln Tyr
1               5                   10                  15

Ser Gln Pro Gln
            20

<210> SEQ ID NO 212
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 212

Gln Pro Phe Arg Pro Gln Gln Pro Tyr Pro Gln Ser Gln Pro Gln Tyr
1               5                   10                  15

Ser Gln Pro Gln
            20

<210> SEQ ID NO 213
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 213

Gln Pro Phe Arg Pro Gln Gln Ser Tyr Pro Gln Pro Gln Pro Gln Tyr
1               5                   10                  15

Ser Gln Pro Gln
            20

<210> SEQ ID NO 214
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 214

Pro Pro Phe Ser Pro Gln Gln Pro Tyr Pro Gln Pro Gln Pro Gln Tyr
1               5                   10                  15

Pro Gln Pro Gln
            20

<210> SEQ ID NO 215

```
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 215

Gln Ser Phe Pro Pro Gln Gln Pro Tyr Pro Gln Gln Arg Pro Lys Tyr
1               5                   10                  15

Leu Gln Pro Gln
            20

<210> SEQ ID NO 216
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 216

Gln Ser Phe Pro Pro Gln Gln Pro Tyr Pro Gln Gln Arg Pro Met Tyr
1               5                   10                  15

Leu Gln Pro Gln
            20

<210> SEQ ID NO 217
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 217

Gln Ser Phe Pro Pro Gln Gln Pro Tyr Pro Gln Gln Gln Pro Gln Tyr
1               5                   10                  15

Leu Gln Pro Gln
            20

<210> SEQ ID NO 218
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 218

Gln Pro Phe Pro Pro Gln Gln Pro Tyr Pro Gln Pro Gln Pro Gln Tyr
1               5                   10                  15

Pro Gln Pro Gln
            20

<210> SEQ ID NO 219
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 219

Tyr Pro Gln Pro Gln Pro Gln Tyr Ser Gln Pro Gln Gln Pro Ile Ser
1               5                   10                  15
```

Gln Gln Gln Gln
        20

<210> SEQ ID NO 220
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 220

Tyr Pro Gln Pro Gln Pro Gln Tyr Ser Gln Pro Gln Glu Pro Ile Ser
1               5                   10                  15

Gln Gln Gln Gln
        20

<210> SEQ ID NO 221
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 221

Tyr Pro Gln Ser Gln Pro Gln Tyr Ser Gln Pro Gln Gln Pro Ile Ser
1               5                   10                  15

Gln Gln Gln Gln
        20

<210> SEQ ID NO 222
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 222

Tyr Pro Gln Pro Gln Pro Gln Tyr Pro Gln Pro Gln Gln Pro Ile Ser
1               5                   10                  15

Gln Gln Gln Ala
        20

<210> SEQ ID NO 223
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 223

Tyr Pro Gln Gln Arg Pro Lys Tyr Leu Gln Pro Gln Gln Pro Ile Ser
1               5                   10                  15

Gln Gln Gln Ala
        20

<210> SEQ ID NO 224
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 224

Tyr Pro Gln Gln Arg Pro Met Tyr Leu Gln Pro Gln Gln Pro Ile Ser
1               5                   10                  15
Gln Gln Gln Ala
            20

<210> SEQ ID NO 225
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 225

Tyr Pro Gln Gln Gln Pro Gln Tyr Leu Gln Pro Gln Gln Pro Ile Ser
1               5                   10                  15
Gln Gln Gln Ala
            20

<210> SEQ ID NO 226
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 226

Ser Gln Pro Gln Gln Pro Ile Ser Gln Gln Gln Gln Gln Gln Gln Gln
1               5                   10                  15
Gln Gln Gln Gln
            20

<210> SEQ ID NO 227
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 227

Ser Gln Pro Gln Glu Pro Ile Ser Gln Gln Gln Gln Gln Gln Gln Gln
1               5                   10                  15
Gln Gln Gln Ile
            20

<210> SEQ ID NO 228
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 228

Pro Gln Pro Gln Gln Pro Ile Ser Gln Gln Gln Ala Gln Gln Gln Gln
1               5                   10                  15
Gln Gln Gln Gln
            20

```
<210> SEQ ID NO 229
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 229

Gln Gln Gln Gln Gln Gln Gln Gln Gln Gln Gln Gln Gln Gln Gln Gln
1               5                   10                  15

Ile Leu Gln Gln
            20

<210> SEQ ID NO 230
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 230

Gln Gln Gln Gln Gln Gln Gln Gln Gln Gln Gln Gln Gln Glu Gln Gln
1               5                   10                  15

Ile Leu Gln Gln
            20

<210> SEQ ID NO 231
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 231

Gln Gln Gln Gln Gln Gln Gln Gln Gln Gln Gln Gln Gln Gln Gln Gln
1               5                   10                  15

Ile Ile Gln Gln
            20

<210> SEQ ID NO 232
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 232

Gln Gln Gln Gln Gln Gln Gln Gln Gln Gln Lys Gln Gln Gln Gln Gln
1               5                   10                  15

Gln Gln Gln Ile
            20

<210> SEQ ID NO 233
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 233

Ala Gln Gln Gln Gln Gln Gln Gln Gln Gln Gln Gln Gln Gln Gln Gln
```

-continued

```
1               5                   10                  15

Thr Leu Gln Gln
            20

<210> SEQ ID NO 234
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 234

Gln Gln Gln Gln Gln Gln Gln Gln Ile Leu Gln Gln Ile Leu Gln Gln
1               5                   10                  15

Gln Leu Ile Pro
            20

<210> SEQ ID NO 235
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 235

Gln Gln Gln Gln Gln Glu Gln Gln Ile Leu Gln Gln Ile Leu Gln Gln
1               5                   10                  15

Gln Leu Ile Pro
            20

<210> SEQ ID NO 236
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 236

Gln Gln Gln Gln Gln Glu Gln Gln Ile Leu Gln Gln Met Leu Gln Gln
1               5                   10                  15

Gln Leu Ile Pro
            20

<210> SEQ ID NO 237
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 237

Gln Gln Gln Gln Gln Glu Gln Gln Ile Leu Gln Gln Ile Leu Gln Gln
1               5                   10                  15

Gln Leu Thr Pro
            20

<210> SEQ ID NO 238
<211> LENGTH: 20
<212> TYPE: PRT
<213> ORGANISM: Artificial Sequence
<220> FEATURE:
```

<223> OTHER INFORMATION: Description of Artificial Sequence: Synthetic
      wheat gliadin peptide

<400> SEQUENCE: 238

Gln Gln Gln Gln Gln Gln Gln Gln Ile Ile Gln Gln Ile Leu Gln Gln
1               5                   10                  15

Gln Leu Ile Pro
            20

<210> SEQ ID NO 239
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 239

Gln Gln Lys Gln Gln Gln Gln Gln Gln Gln Ile Leu Gln Gln Ile
1               5                   10                  15

Leu Gln Gln Gln
            20

<210> SEQ ID NO 240
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 240

Gln Gln Gln Gln Gln Gln Gln Gln Ile Leu Pro Gln Ile Leu Gln Gln
1               5                   10                  15

Gln Leu Ile Pro
            20

<210> SEQ ID NO 241
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 241

Gln Gln Gln Gln Gln Gln Gln Gln Thr Leu Gln Gln Ile Leu Gln Gln
1               5                   10                  15

Gln Leu Ile Pro
            20

<210> SEQ ID NO 242
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 242

Ile Leu Gln Gln Ile Leu Gln Gln Leu Ile Pro Cys Met Asp Val
1               5                   10                  15

Val Leu Gln Gln
            20

<210> SEQ ID NO 243
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 243

Ile Leu Gln Gln Met Leu Gln Gln Gln Leu Ile Pro Cys Met Asp Val
1               5                   10                  15

Val Leu Gln Gln
            20

<210> SEQ ID NO 244
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 244

Ile Leu Gln Gln Ile Leu Gln Gln Gln Leu Thr Pro Cys Met Asp Val
1               5                   10                  15

Val Leu Gln Gln
            20

<210> SEQ ID NO 245
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 245

Ile Leu Gln Gln Ile Leu Gln Gln Gln Leu Ile Pro Cys Arg Asp Val
1               5                   10                  15

Val Leu Gln Gln
            20

<210> SEQ ID NO 246
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 246

Ile Leu Pro Gln Ile Leu Gln Gln Gln Leu Ile Pro Cys Arg Asp Val
1               5                   10                  15

Val Leu Gln Gln
            20

<210> SEQ ID NO 247
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 247

-continued

Thr Leu Gln Gln Ile Leu Gln Gln Gln Leu Ile Pro Cys Arg Asp Val
1               5                   10                  15

Val Leu Gln Gln
            20

<210> SEQ ID NO 248
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 248

Gln Leu Ile Pro Cys Met Asp Val Val Leu Gln Gln His Asn Ile Ala
1               5                   10                  15

His Gly Arg Ser
            20

<210> SEQ ID NO 249
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 249

Gln Leu Ile Pro Cys Met Asp Val Val Leu Gln Gln His Asn Lys Ala
1               5                   10                  15

His Gly Arg Ser
            20

<210> SEQ ID NO 250
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 250

Gln Leu Ile Pro Cys Met Asp Val Val Leu Gln Gln His Asn Leu Ala
1               5                   10                  15

His Gly Arg Ser
            20

<210> SEQ ID NO 251
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 251

Gln Leu Ile Pro Cys Met Asp Val Val Leu Gln Gln His Asn Ile Val
1               5                   10                  15

His Gly Arg Ser
            20

<210> SEQ ID NO 252
<211> LENGTH: 20
<212> TYPE: PRT
<213> ORGANISM: Artificial Sequence

```
<220> FEATURE:
<223> OTHER INFORMATION: Description of Artificial Sequence: Synthetic
      wheat gliadin peptide

<400> SEQUENCE: 252

Gln Leu Thr Pro Cys Met Asp Val Val Leu Gln Gln His Asn Ile Ala
1               5                   10                  15

Arg Gly Arg Ser
            20

<210> SEQ ID NO 253
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 253

Gln Leu Ile Pro Cys Met Asp Val Val Leu Gln Gln His Asn Ile Val
1               5                   10                  15

His Gly Lys Ser
            20

<210> SEQ ID NO 254
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 254

Gln Leu Ile Pro Cys Arg Asp Val Val Leu Gln Gln His Ser Ile Ala
1               5                   10                  15

Tyr Gly Ser Ser
            20

<210> SEQ ID NO 255
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 255

Gln Leu Ile Pro Cys Arg Asp Val Val Leu Gln Gln His Ser Ile Ala
1               5                   10                  15

His Gly Ser Ser
            20

<210> SEQ ID NO 256
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 256

Gln Leu Ile Pro Cys Arg Asp Val Val Leu Gln Gln His Asn Ile Ala
1               5                   10                  15

His Gly Ser Ser
            20
```

<210> SEQ ID NO 257
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 257

Gln Leu Ile Pro Cys Arg Asp Val Val Leu Gln Gln His Asn Ile Ala
1               5                   10                  15

His Ala Arg Ser
            20

<210> SEQ ID NO 258
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 258

Gln Leu Ile Pro Cys Arg Asp Val Val Leu Gln Gln His Asn Ile Ala
1               5                   10                  15

His Ala Ser Ser
            20

<210> SEQ ID NO 259
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 259

Val Leu Gln Gln His Asn Ile Ala His Gly Arg Ser Gln Val Leu Gln
1               5                   10                  15

Gln Ser Thr Tyr
            20

<210> SEQ ID NO 260
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 260

Val Leu Gln Gln His Asn Lys Ala His Gly Arg Ser Gln Val Leu Gln
1               5                   10                  15

Gln Ser Thr Tyr
            20

<210> SEQ ID NO 261
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 261

```
Val Leu Gln Gln His Asn Leu Ala His Gly Arg Ser Gln Val Leu Gln
1               5                   10                  15

Gln Ser Th

<213> ORGANISM: Artificial Sequence
<220> FEATURE:
<223> OTHER INFORMATION: Description of Artificial Sequence: Synthetic
      wheat gliadin peptide

<400> SEQUENCE: 266

Val Leu Gln Gln His Ser Ile Ala His Gly Ser Ser Gln Val Leu Gln
1               5                   10                  15

Gln Ser Thr Tyr
            20

<210> SEQ ID NO 267
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 267

Val Leu Gln Gln His Asn Ile Ala His Gly Ser Ser Gln Val Leu Gln
1               5                   10                  15

Glu Ser Thr Tyr
            20

<210> SEQ ID NO 268
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 268

Val Leu Gln Gln His Asn Ile Ala His Ala Arg Ser Gln Val Leu Gln
1               5                   10                  15

Gln Ser Thr Tyr
            20

<210> SEQ ID NO 269
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 269

Val Leu Gln Gln His Asn Ile Ala His Ala Ser Ser Gln Val Leu Gln
1               5                   10                  15

Gln Ser Thr Tyr
            20

<210> SEQ ID NO 270
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 270

Val Leu Gln Gln His Asn Ile Ala His Ala Ser Ser Gln Val Leu Gln
1               5                   10                  15

Gln Ser Ser Tyr

20

<210> SEQ ID NO 271
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 271

His Gly Arg Ser Gln Val Leu Gln Gln Ser Thr Tyr Gln Leu Leu Gln
1               5                   10                  15

Glu Leu Cys Cys
            20

<210> SEQ ID NO 272
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 272

His Gly Arg Ser Gln Val Leu Gln Gln Ser Thr Tyr Gln Leu Leu Arg
1               5                   10                  15

Glu Leu Cys Cys
            20

<210> SEQ ID NO 273
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 273

His Gly Arg Ser Gln Val Leu Gln Gln Ser Thr Tyr Gln Leu Leu Arg
1               5                   10                  15

Glu Leu Cys Cys
            20

<210> SEQ ID NO 274
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 274

His Gly Lys Ser Gln Val Leu Gln Gln Ser Thr Tyr Gln Leu Leu Gln
1               5                   10                  15

Glu Leu Cys Cys
            20

<210> SEQ ID NO 275
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 275

Tyr Gly Ser Ser Gln Val Leu Gln Gln Ser Thr Tyr Gln Leu Val Gln
1               5                   10                  15

Gln Leu Cys Cys
            20

<210> SEQ ID NO 276
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 276

His Gly Ser Ser Gln Val Leu Gln Gln Ser Thr Tyr Gln Leu Val Gln
1               5                   10                  15

Gln Phe Cys Cys
            20

<210> SEQ ID NO 277
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 277

His Gly Ser Ser Gln Val Leu Gln Glu Ser Thr Tyr Gln Leu Val Gln
1               5                   10                  15

Gln Leu Cys Cys
            20

<210> SEQ ID NO 278
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 278

His Ala Arg Ser Gln Val Leu Gln Gln Ser Thr Tyr Gln Pro Leu Gln
1               5                   10                  15

Gln Leu Cys Cys
            20

<210> SEQ ID NO 279
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 279

His Ala Ser Ser Gln Val Leu Gln Gln Ser Thr Tyr Gln Leu Leu Gln
1               5                   10                  15

Gln Leu Cys Cys
            20

<210> SEQ ID NO 280
<211> LENGTH: 20

```
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 280

His Ala Ser Ser Gln Val Leu Gln Gln Ser Ser Tyr Gln Gln Leu Gln
1               5                   10                  15

Gln Leu Cys Cys
        20

<210> SEQ ID NO 281
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 281

Gln Ser Thr Tyr Gln Leu Leu Gln Glu Leu Cys Cys Gln His Leu Trp
1               5                   10                  15

Gln Ile Pro Glu
        20

<210> SEQ ID NO 282
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 282

Gln Ser Thr Tyr Gln Leu Leu Arg Glu Leu Cys Cys Gln His Leu Trp
1               5                   10                  15

Gln Ile Pro Glu
        20

<210> SEQ ID NO 283
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 283

Gln Ser Thr Tyr Gln Leu Leu Arg Glu Leu Cys Cys Gln His Leu Trp
1               5                   10                  15

Gln Ile Pro Glu
        20

<210> SEQ ID NO 284
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 284

Gln Ser Thr Tyr Gln Leu Val Gln Gln Leu Cys Cys Gln Gln Leu Trp
1               5                   10                  15
```

Gln Ile Pro Glu
            20

<210> SEQ ID NO 285
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 285

Gln Ser Thr Tyr Gln Leu Val Gln Gln Phe Cys Cys Gln Gln Leu Trp
1               5                   10                  15

Gln Ile Pro Glu
            20

<210> SEQ ID NO 286
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 286

Gln Ser Thr Tyr Gln Pro Leu Gln Gln Leu Cys Cys Gln Gln Leu Trp
1               5                   10                  15

Gln Ile Pro Glu
            20

<210> SEQ ID NO 287
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 287

Gln Ser Thr Tyr Gln Leu Leu Gln Gln Leu Cys Cys Gln Gln Leu Leu
1               5                   10                  15

Gln Ile Pro Glu
            20

<210> SEQ ID NO 288
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 288

Gln Ser Ser Tyr Gln Gln Leu Gln Gln Leu Cys Cys Gln Gln Leu Phe
1               5                   10                  15

Gln Ile Pro Glu
            20

<210> SEQ ID NO 289
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

```
<400> SEQUENCE: 289

Glu Leu Cys Cys Gln His Leu Trp Gln Ile Pro Glu Gln Ser Gln Cys
1               5                   10                  15

Gln Ala Ile His
            20

<210> SEQ ID NO 290
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 290

Glu Leu Cys Cys Gln His Leu Trp Gln Ile Leu Glu Gln Ser Gln Cys
1               5                   10                  15

Gln Ala Ile His
            20

<210> SEQ ID NO 291
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 291

Glu Leu Cys Cys Gln His Leu Trp Gln Ile Pro Glu Lys Leu Gln Cys
1               5                   10                  15

Gln Ala Ile His
            20

<210> SEQ ID NO 292
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 292

Gln Leu Cys Cys Gln Gln Leu Trp Gln Ile Pro Glu Gln Ser Arg Cys
1               5                   10                  15

Gln Ala Ile His
            20

<210> SEQ ID NO 293
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 293

Gln Phe Cys Cys Gln Gln Leu Trp Gln Ile Pro Glu Gln Ser Arg Cys
1               5                   10                  15

Gln Ala Ile His
            20

<210> SEQ ID NO 294
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 294

Gln Leu Cys Cys Gln Gln Leu Leu Gln Ile Pro Glu Gln Ser Arg Cys
1               5                   10                  15

Gln Ala Ile His
            20

<210> SEQ ID NO 295
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 295

Gly Leu Cys Cys Gln Gln Leu Leu Gln Ile Pro Glu Gln Ser Gln Cys
1               5                   10                  15

Gln Ala Ile His
            20

<210> SEQ ID NO 296
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 296

Gln Leu Cys Cys Gln Gln Leu Phe Gln Ile Pro Glu Gln Ser Arg Cys
1               5                   10                  15

Gln Ala Ile His
            20

<210> SEQ ID NO 297
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 297

Gln Ile Pro Glu Gln Ser Gln Cys Gln Ala Ile His Asn Val Val His
1               5                   10                  15

Ala Ile Ile Leu
            20

<210> SEQ ID NO 298
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 298

Gln Ile Pro Glu Gln Ser Gln Cys Gln Ala Ile Gln Asn Val Val His
1               5                   10                  15
```

Ala Ile Ile Leu
        20

<210> SEQ ID NO 299
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 299

Gln Ile Leu Glu Gln Ser Gln Cys Gln Ala Ile His Asn Val Val His
1               5                   10                  15

Ala Ile Ile Leu
        20

<210> SEQ ID NO 300
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 300

Gln Ile Pro Glu Gln Ser Gln Cys Gln Ala Ile His Lys Val Val His
1               5                   10                  15

Ala Ile Ile Leu
        20

<210> SEQ ID NO 301
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 301

Gln Ile Pro Glu Lys Leu Gln Cys Gln Ala Ile His Asn Val Val His
1               5                   10                  15

Ala Ile Ile Leu
        20

<210> SEQ ID NO 302
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 302

Gln Ile Pro Glu Gln Ser Arg Cys Gln Ala Ile His Asn Val Val His
1               5                   10                  15

Ala Ile Ile Leu
        20

<210> SEQ ID NO 303
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 303

Gln Ile Pro Glu Gln Ser Gln Cys Gln Ala Ile His Asn Val Ala His
1               5                   10                  15

Ala Ile Ile Met
            20

<210> SEQ ID NO 304
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 304

Gln Ile Pro Glu Gln Ser Arg Cys Gln Ala Ile His Asn Val Val His
1               5                   10                  15

Ala Ile Ile Leu
            20

<210> SEQ ID NO 305
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 305

Gln Ala Ile His Asn Val Val His Ala Ile Ile Leu His Gln Gln Gln
1               5                   10                  15

Lys Gln Gln Gln
            20

<210> SEQ ID NO 306
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 306

Gln Ala Ile His Asn Val Val His Ala Ile Ile Leu His Gln Gln Gln
1               5                   10                  15

Gln Lys Gln Gln
            20

<210> SEQ ID NO 307
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 307

Gln Ala Ile Gln Asn Val Val His Ala Ile Ile Leu His Gln Gln Gln
1               5                   10                  15

Lys Gln Gln Gln
            20

```
<210> SEQ ID NO 308
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 308

Gln Ala Ile His Lys Val Val His Ala Ile Ile Leu His Gln Gln Gln
1               5                   10                  15

Lys Gln Gln Gln
            20

<210> SEQ ID NO 309
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 309

Gln Ala Ile His Asn Val Val His Ala Ile Ile Leu His Gln Gln Gln
1               5                   10                  15

Gln Gln Gln Gln
            20

<210> SEQ ID NO 310
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 310

Gln Ala Ile His Asn Val Val His Ala Ile Ile Leu His Gln Gln His
1               5                   10                  15

His His Gln
            20

<210> SEQ ID NO 311
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 311

Gln Ala Ile His Asn Val Val His Ala Ile Ile Leu His Gln Gln Gln
1               5                   10                  15

Arg Gln Gln Gln
            20

<210> SEQ ID NO 312
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 312

Gln Ala Ile His Asn Val Val His Ala Ile Ile Met His Gln Gln Glu
```

```
                  1               5                  10                  15

Gln Gln Gln Gln
            20

<210> SEQ ID NO 313
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 313

Gln Ala Ile His Asn Val Ala His Ala Ile Ile Met His Gln Gln Gln
1               5                  10                  15

Gln Gln Gln Gln
            20

<210> SEQ ID NO 314
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 314

Gln Ala Ile His Asn Val Val His Ala Ile Ile Leu His His His Gln
1               5                  10                  15

Gln Gln Gln Gln
            20

<210> SEQ ID NO 315
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 315

Ala Ile Ile Leu His Gln Gln Gln Lys Gln Gln Gln Gln Pro Ser Ser
1               5                  10                  15

Gln Val Ser Phe
            20

<210> SEQ ID NO 316
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 316

Ala Ile Ile Leu His Gln Gln Gln Gln Lys Gln Gln Gln Gln Pro Ser
1               5                  10                  15

Ser Gln Phe Ser
            20

<210> SEQ ID NO 317
<211> LENGTH: 20
<212> TYPE: PRT
<213> ORGANISM: Artificial Sequence
<220> FEATURE:
```

```
<223> OTHER INFORMATION: Description of Artificial Sequence: Synthetic
      wheat gliadin peptide

<400> SEQUENCE: 317

Ala Ile Ile Leu His Gln Gln Gln Lys Gln Gln Gln Gln Leu Ser Ser
1               5                   10                  15

Gln Val Ser Phe
            20

<210> SEQ ID NO 318
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 318

Ala Ile Ile Leu His Gln Gln Gln Lys Gln Gln Gln Pro Ser Ser Gln
1               5                   10                  15

Val Ser Phe Gln
            20

<210> SEQ ID NO 319
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 319

Ala Ile Ile Leu His Gln Gln Gln Gln Gln Gln Gln Glu Gln Lys Gln
1               5                   10                  15

Gln Leu Gln Gln
            20

<210> SEQ ID NO 320
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 320

Ala Ile Ile Leu His Gln Gln Gln Gln Gln Gln Gln Gln Gln Gln Gln
1               5                   10                  15

Gln Pro Leu Ser
            20

<210> SEQ ID NO 321
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 321

Ala Ile Ile Leu His Gln Gln His His His His Gln Gln Gln Gln Gln
1               5                   10                  15

Gln Gln Gln Gln
            20
```

<210> SEQ ID NO 322
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 322

Ala Ile Ile Leu His Gln Gln His His His Gln Glu Gln Lys Gln
1               5                   10                  15

Gln Leu Gln Gln
            20

<210> SEQ ID NO 323
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 323

Ala Ile Ile Leu His Gln Gln Gln Arg Gln Gln Gln Pro Ser Ser Gln
1               5                   10                  15

Val Ser Leu Gln
            20

<210> SEQ ID NO 324
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 324

Ala Ile Ile Met His Gln Gln Glu Gln Gln Gln Gln Leu Gln Gln Gln
1               5                   10                  15

Gln Gln Gln Gln
            20

<210> SEQ ID NO 325
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 325

Ala Ile Ile Met His Gln Gln Gln Gln Gln Gln Glu Gln Lys Gln
1               5                   10                  15

Gln Leu Gln Gln
            20

<210> SEQ ID NO 326
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 326

Ala Ile Ile Leu His His His Gln Gln Gln Gln Gln Gln Pro Ser Ser
1               5                   10                  15

Gln Val Ser Tyr
            20

<210> SEQ ID NO 327
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 327

Lys Gln Gln Gln Gln Pro Ser Ser Gln Val Ser Phe Gln Gln Pro Leu
1               5                   10                  15

Gln Gln Tyr Pro
            20

<210> SEQ ID NO 328
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 328

Lys Gln Gln Gln Gln Pro Ser Ser Gln Phe Ser Phe Gln Gln Pro Leu
1               5                   10                  15

Gln Gln Tyr Pro
            20

<210> SEQ ID NO 329
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 329

Lys Gln Gln Gln Gln Leu Ser Ser Gln Val Ser Phe Gln Gln Pro Gln
1               5                   10                  15

Gln Gln Tyr Pro
            20

<210> SEQ ID NO 330
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 330

Lys Gln Gln Gln Pro Ser Ser Gln Val Ser Phe Gln Gln Pro Gln Gln
1               5                   10                  15

Gln Tyr Pro Leu
            20

<210> SEQ ID NO 331
<211> LENGTH: 20
<212> TYPE: PRT
<213> ORGANISM: Artificial Sequence

```
<220> FEATURE:
<223> OTHER INFORMATION: Description of Artificial Sequence: Synthetic
      wheat gliadin peptide

<400> SEQUENCE: 331

Gln Gln Gln Gln Glu Gln Lys Gln Gln Leu Gln Gln Gln Gln Gln
1               5                   10                  15

Gln Gln Gln Leu
            20

<210> SEQ ID NO 332
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 332

His His His Gln Glu Gln Lys Gln Gln Leu Gln Gln Gln Gln Gln
1               5                   10                  15

Gln Gln Gln Leu
            20

<210> SEQ ID NO 333
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 333

Arg Gln Gln Gln Pro Ser Ser Gln Val Ser Leu Gln Gln Pro Gln Gln
1               5                   10                  15

Gln Tyr Pro Ser
            20

<210> SEQ ID NO 334
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 334

Gln Gln Gln Gln Leu Gln Gln Gln Gln Gln Gln Leu Gln Gln Gln
1               5                   10                  15

Gln Gln Gln Gln
            20

<210> SEQ ID NO 335
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 335

Gln Gln Gln Gln Gln Pro Ser Ser Gln Val Ser Tyr Gln Gln Pro Gln
1               5                   10                  15

Glu Gln Tyr Pro
            20
```

<210> SEQ ID NO 336
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 336

Gln Leu Gln Gln Gln Gln Gln Gln Gln Gln Leu Gln Gln Gln Gln
1               5                   10                  15

Gln Lys Gln Gln
            20

<210> SEQ ID NO 337
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 337

Gln Gln Gln Leu Gln Gln Gln Gln Lys Gln Gln Gln Gln Pro Ser
1               5                   10                  15

Ser Gln Val Ser
            20

<210> SEQ ID NO 338
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 338

Gln Gln Gln Gln Gln Gln Gln Gln Gln Pro Leu Ser Gln Val Ser Phe
1               5                   10                  15

Gln Gln Pro Gln
            20

<210> SEQ ID NO 339
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 339

Gln Gln Gln Gln Gln Gln Gln Gln Gln Pro Leu Ser Gln Val Cys Phe
1               5                   10                  15

Gln Gln Ser Gln
            20

<210> SEQ ID NO 340
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 340

His His His Gln Gln Gln Gln Gln Gln Gln Gln Pro Leu Ser
1               5                   10                  15

Gln Val Ser Phe
            20

<210> SEQ ID NO 341
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 341

Gln Gln Gln Gln Gln Gln Gln Gln Gln Pro Ser Ser Gln Val Ser Phe
1               5                   10                  15

Gln Gln Pro Gln
            20

<210> SEQ ID NO 342
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 342

Gln Pro Leu Ser Gln Val Ser Phe Gln Gln Pro Gln Gln Gln Tyr Pro
1               5                   10                  15

Ser Gly Gln Gly
            20

<210> SEQ ID NO 343
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 343

Gln Pro Leu Ser Gln Val Cys Phe Gln Gln Ser Gln Gln Gln Tyr Pro
1               5                   10                  15

Ser Gly Gln Gly
            20

<210> SEQ ID NO 344
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 344

Gln Pro Ser Ser Gln Val Ser Phe Gln Gln Pro Gln Gln Gln Tyr Pro
1               5                   10                  15

Ser Ser Gln Val
            20

<210> SEQ ID NO 345
<211> LENGTH: 20
<212> TYPE: PRT

<213> ORGANISM: Artificial Sequence
<220> FEATURE:
<223> OTHER INFORMATION: Description of Artificial Sequence: Synthetic wheat gliadin peptide

<400> SEQUENCE: 345

Gln Val Ser Phe Gln Gln Pro Leu Gln Gln Tyr Pro Leu Gly Gln Gly
1               5                   10                  15

Ser Phe Arg Pro
            20

<210> SEQ ID NO 346
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 346

Gln Phe Ser Phe Gln Gln Pro Leu Gln Gln Tyr Pro Leu Gly Gln Gly
1               5                   10                  15

Ser Phe Arg Pro
            20

<210> SEQ ID NO 347
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 347

Gln Val Ser Phe Gln Gln Pro Gln Gln Gln Tyr Pro Leu Gly Gln Gly
1               5                   10                  15

Ser Phe Arg Pro
            20

<210> SEQ ID NO 348
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 348

Gln Val Ser Phe Gln Gln Pro Gln Gln Gln Tyr Pro Ser Gly Gln Gly
1               5                   10                  15

Ser Phe Gln Pro
            20

<210> SEQ ID NO 349
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 349

Gln Val Cys Phe Gln Gln Ser Gln Gln Gln Tyr Pro Ser Gly Gln Gly
1               5                   10                  15

Ser Phe Gln Pro

20

<210> SEQ ID NO 350
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 350

Gln Val Ser Phe Gln Gln Pro Gln Gln Gln Tyr Pro Ser Gly Gln Gly
1               5                   10                  15

Phe Phe Gln Pro
            20

<210> SEQ ID NO 351
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 351

Gln Val Ser Phe Gln Gln Pro Gln Gln Gln Tyr Pro Ser Gly Gln Gly
1               5                   10                  15

Phe Phe Gln Pro
            20

<210> SEQ ID NO 352
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 352

Gln Val Ser Leu Gln Gln Pro Gln Gln Gln Tyr Pro Ser Gly Gln Gly
1               5                   10                  15

Phe Phe Gln Pro
            20

<210> SEQ ID NO 353
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 353

Gln Val Ser Phe Gln Gln Pro Gln Gln Gln Tyr Pro Ser Ser Gln Val
1               5                   10                  15

Ser Phe Gln Pro
            20

<210> SEQ ID NO 354
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

```
<400> SEQUENCE: 354

Gln Val Ser Phe Gln Gln Pro Gln Gln Gln Tyr Pro Ser Ser Gln Gly
1               5                   10                  15

Ser Phe Gln Pro
            20

<210> SEQ ID NO 355
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 355

Gln Val Ser Tyr Gln Gln Pro Gln Glu Gln Tyr Pro Ser Gly Gln Val
1               5                   10                  15

Ser Phe Gln Ser
            20

<210> SEQ ID NO 356
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 356

Gln Gln Tyr Pro Leu Gly Gln Gly Ser Phe Arg Pro Ser Gln Gln Asn
1               5                   10                  15

Pro Gln Ala Gln
            20

<210> SEQ ID NO 357
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 357

Gln Gln Tyr Pro Leu Gly Gln Gly Ser Phe Arg Pro Ser Gln Gln Asn
1               5                   10                  15

Ser Gln Ala Gln
            20

<210> SEQ ID NO 358
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 358

Gln Gln Tyr Pro Ser Gly Gln Gly Ser Phe Gln Pro Ser Gln Gln Asn
1               5                   10                  15

Pro Gln Ala Gln
            20

<210> SEQ ID NO 359
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 359

Gln Gln Tyr Pro Ser Gly Gln Gly Phe Phe Gln Pro Ser Gln Gln Asn
1               5                   10                  15

Pro Gln Ala Gln
            20

<210> SEQ ID NO 360
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 360

Gln Gln Tyr Pro Ser Gly Gln Gly Phe Phe Gln Pro Phe Gln Gln Asn
1               5                   10                  15

Pro Gln Ala Gln
            20

<210> SEQ ID NO 361
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 361

Gln Gln Tyr Pro Ser Gly Gln Gly Phe Phe Gln Pro Ser Gln Gln Asn
1               5                   10                  15

Pro Gln Ala Gln
            20

<210> SEQ ID NO 362
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 362

Gln Gln Tyr Pro Ser Ser Gln Val Ser Phe Gln Pro Ser Gln Leu Asn
1               5                   10                  15

Pro Gln Ala Gln
            20

<210> SEQ ID NO 363
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 363

Gln Gln Tyr Pro Ser Ser Gln Gly Ser Phe Gln Pro Ser Gln Gln Asn
1               5                   10                  15
```

Pro Gln Ala Gln
        20

<210> SEQ ID NO 364
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 364

Glu Gln Tyr Pro Ser Gly Gln Val Ser Phe Gln Ser Ser Gln Gln Asn
1               5                   10                  15

Pro Gln Ala Gln
        20

<210> SEQ ID NO 365
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 365

Ser Phe Arg Pro Ser Gln Gln Asn Pro Leu Ala Gln Gly Ser Val Gln
1               5                   10                  15

Pro Gln Gln Leu
        20

<210> SEQ ID NO 366
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 366

Ser Phe Arg Pro Ser Gln Gln Asn Pro Gln Ala Gln Gly Ser Val Gln
1               5                   10                  15

Pro Gln Gln Leu
        20

<210> SEQ ID NO 367
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 367

Ser Phe Arg Pro Ser Gln Gln Asn Pro Gln Thr Gln Gly Ser Val Gln
1               5                   10                  15

Pro Gln Gln Leu
        20

<210> SEQ ID NO 368
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

```
<400> SEQUENCE: 368

Ser Phe Arg Pro Ser Gln Gln Asn Ser Gln Ala Gln Gly Ser Val Gln
1               5                   10                  15

Pro Gln Gln Leu
            20

<210> SEQ ID NO 369
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 369

Ser Phe Arg Pro Ser Gln Gln Asn Pro Gln Asp Gln Gly Ser Val Gln
1               5                   10                  15

Pro Gln Gln Leu
            20

<210> SEQ ID NO 370
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 370

Ser Phe Arg Pro Ser Gln Gln Asn Pro Arg Ala Gln Gly Ser Val Gln
1               5                   10                  15

Pro Gln Gln Leu
            20

<210> SEQ ID NO 371
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 371

Ser Phe Gln Pro Ser Gln Gln Asn Pro Gln Ala Gln Gly Ser Val Gln
1               5                   10                  15

Pro Gln Gln Leu
            20

<210> SEQ ID NO 372
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 372

Phe Phe Gln Pro Ser Gln Gln Asn Pro Gln Ala Gln Gly Ser Phe Gln
1               5                   10                  15

Pro Gln Gln Leu
            20

<210> SEQ ID NO 373
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 373

Phe Phe Gln Pro Phe Gln Gln Asn Pro Gln Ala Gln Gly Ser Phe Gln
1               5                   10                  15

Pro Gln Gln Leu
            20

<210> SEQ ID NO 374
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 374

Phe Phe Gln Pro Ser Gln Gln Asn Pro Gln Ala Gln Gly Ser Val Gln
1               5                   10                  15

Pro Gln Gln Leu
            20

<210> SEQ ID NO 375
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 375

Ser Phe Gln Pro Ser Gln Leu Asn Pro Gln Ala Gln Gly Ser Val Gln
1               5                   10                  15

Pro Gln Gln Leu
            20

<210> SEQ ID NO 376
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 376

Ser Phe Gln Pro Ser Gln Leu Asn Pro Gln Ala Gln Gly Ser Val Gln
1               5                   10                  15

Pro Gln Gln Leu
            20

<210> SEQ ID NO 377
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 377

Ser Phe Gln Pro Ser Gln Gln Asn Pro Gln Ala Gln Gly Ser Val Gln
1               5                   10                  15
```

Pro Gln Gln Leu
            20

<210> SEQ ID NO 378
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 378

Ser Phe Gln Ser Ser Gln Gln Asn Pro Gln Ala Gln Gly Ser Val Gln
1               5                   10                  15

Pro Gln Gln Leu
            20

<210> SEQ ID NO 379
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 379

Pro Gln Ala Gln Gly Ser Val Gln Pro Gln Gln Leu Pro Gln Phe Glu
1               5                   10                  15

Glu Ile Arg Asn
            20

<210> SEQ ID NO 380
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 380

Pro Gln Thr Gln Gly Ser Val Gln Pro Gln Gln Leu Pro Gln Phe Glu
1               5                   10                  15

Glu Ile Arg Asn
            20

<210> SEQ ID NO 381
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 381

Pro Gln Ala Gln Gly Ser Val Gln Pro Gln Gln Leu Pro Gln Phe Glu
1               5                   10                  15

Ile Arg Asn Leu
            20

<210> SEQ ID NO 382
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 382

Pro Leu Ala Gln Gly Ser Val Gln Pro Gln Gln Leu Pro Gln Phe Glu
1               5                   10                  15

Glu Ile Arg Asn
            20

<210> SEQ ID NO 383
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 383

Pro Gln Asp Gln Gly Ser Val Gln Pro Gln Gln Leu Pro Gln Phe Glu
1               5                   10                  15

Glu Ile Arg Asn
            20

<210> SEQ ID NO 384
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 384

Pro Arg Ala Gln Gly Ser Val Gln Pro Gln Gln Leu Pro Gln Phe Glu
1               5                   10                  15

Glu Ile Arg Asn
            20

<210> SEQ ID NO 385
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 385

Pro Gln Ala Gln Gly Ser Phe Gln Pro Gln Gln Leu Pro Gln Phe Glu
1               5                   10                  15

Glu Ile Arg Asn
            20

<210> SEQ ID NO 386
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 386

Pro Gln Ala Gln Gly Ser Phe Gln Pro Gln Gln Leu Pro Gln Phe Glu
1               5                   10                  15

Ala Ile Arg Asn
            20

-continued

```
<210> SEQ ID NO 387
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 387

Pro Gln Ala Gln Gly Ser Val Gln Pro Gln Gln Leu Pro Gln Phe Ala
1               5                   10                  15

Glu Ile Arg Asn
            20

<210> SEQ ID NO 388
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 388

Pro Gln Ala Gln Gly Ser Val Gln Pro Gln Gln Leu Pro Gln Phe Gln
1               5                   10                  15

Glu Ile Arg Asn
            20

<210> SEQ ID NO 389
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 389

Pro Gln Gln Leu Pro Gln Phe Glu Glu Ile Arg Asn Leu Ala Leu Gln
1               5                   10                  15

Thr Leu Pro Ala
            20

<210> SEQ ID NO 390
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 390

Pro Gln Gln Leu Pro Gln Phe Glu Ile Arg Asn Leu Ala Leu Gln Thr
1               5                   10                  15

Leu Pro Ala Met
            20

<210> SEQ ID NO 391
<211> LENGTH: 16
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 391

Pro Gln Gln Leu Pro Gln Phe Glu Glu Ile Arg Asn Leu Ala Arg Lys
```

<210> SEQ ID NO 392
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 392

Pro Gln Gln Leu Pro Gln Phe Glu Glu Ile Arg Asn Leu Ala Leu Glu
1               5                   10                  15

Thr Leu Pro Ala
            20

<210> SEQ ID NO 393
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 393

Pro Gln Gln Leu Pro Gln Phe Glu Ala Ile Arg Asn Leu Ala Leu Gln
1               5                   10                  15

Thr Leu Pro Ala
            20

<210> SEQ ID NO 394
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 394

Pro Gln Gln Leu Pro Gln Phe Ala Glu Ile Arg Asn Leu Ala Leu Gln
1               5                   10                  15

Thr Leu Pro Ala
            20

<210> SEQ ID NO 395
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 395

Pro Gln Gln Leu Pro Gln Phe Gln Glu Ile Arg Asn Leu Ala Leu Gln
1               5                   10                  15

Thr Leu Pro Ala
            20

<210> SEQ ID NO 396
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

```
<400> SEQUENCE: 396

Glu Ile Arg Asn Leu Ala Leu Gln Thr Leu Pro Ala Met Cys Asn Val
1               5                   10                  15

Tyr Ile Pro Pro
            20

<210> SEQ ID NO 397
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 397

Glu Ile Arg Asn Leu Ala Leu Gln Thr Leu Pro Ser Met Cys Asn Val
1               5                   10                  15

Tyr Ile Pro Pro
            20

<210> SEQ ID NO 398
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 398

Glu Ile Arg Asn Leu Ala Leu Glu Thr Leu Pro Ala Met Cys Asn Val
1               5                   10                  15

Tyr Ile Pro Pro
            20

<210> SEQ ID NO 399
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 399

Glu Ile Arg Asn Leu Ala Leu Gln Thr Leu Pro Arg Met Cys Asn Val
1               5                   10                  15

Tyr Ile Pro Pro
            20

<210> SEQ ID NO 400
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 400

Thr Leu Pro Ala Met Cys Asn Val Tyr Ile Pro Pro Tyr Cys Thr Ile
1               5                   10                  15

Ala Pro Phe Gly
            20

<210> SEQ ID NO 401
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 401

Thr Leu Pro Ser Met Cys Asn Val Tyr Ile Pro Pro Tyr Cys Thr Ile
1               5                   10                  15

Ala Pro Phe Gly
            20

<210> SEQ ID NO 402
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 402

Thr Leu Pro Ala Met Cys Asn Val Tyr Ile Pro Pro Tyr Cys Thr Ile
1               5                   10                  15

Val Pro Phe Gly
            20

<210> SEQ ID NO 403
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 403

Thr Leu Pro Ala Met Cys Asn Val Tyr Ile Pro Pro Tyr Cys Ala Met
1               5                   10                  15

Ala Pro Phe Gly
            20

<210> SEQ ID NO 404
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 404

Thr Leu Pro Ala Met Cys Asn Val Tyr Ile Pro Pro Tyr Cys Thr Ile
1               5                   10                  15

Thr Pro Phe Gly
            20

<210> SEQ ID NO 405
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 405

Thr Leu Pro Ala Met Cys Asn Val Tyr Ile Pro Pro Tyr Cys Thr Ile
1               5                   10                  15
```

Ala Pro Val Gly
            20

<210> SEQ ID NO 406
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 406

Thr Leu Pro Ala Met Cys Asn Val Tyr Ile Pro Pro Tyr Cys Ser Thr
1               5                   10                  15

Thr Ile Ala Pro
            20

<210> SEQ ID NO 407
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 407

Thr Leu Pro Arg Met Cys Asn Val Tyr Ile Pro Pro Tyr Cys Ser Thr
1               5                   10                  15

Thr Ile Ala Pro
            20

<210> SEQ ID NO 408
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 408

Thr Leu Pro Arg Met Cys Asn Val Tyr Ile Pro Pro Tyr Cys Ser Thr
1               5                   10                  15

Thr Thr Ala Pro
            20

<210> SEQ ID NO 409
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 409

Thr Leu Pro Ala Met Cys Asn Val Tyr Ile Pro Pro His Cys Ser Thr
1               5                   10                  15

Thr Ile Ala Pro
            20

<210> SEQ ID NO 410
<211> LENGTH: 19
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 410

Tyr Ile Pro Pro Tyr Cys Thr Ile Ala Pro Phe Gly Ile Phe Gly Thr
1               5                   10                  15

Asn Tyr Arg

<210> SEQ ID NO 411
<211> LENGTH: 19
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 411

Tyr Ile Pro Pro Tyr Cys Thr Ile Val Pro Phe Gly Ile Phe Gly Thr
1               5                   10                  15

Asn Tyr Arg

<210> SEQ ID NO 412
<211> LENGTH: 19
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 412

Tyr Ile Pro Pro Tyr Cys Ala Met Ala Pro Phe Gly Ile Phe Gly Thr
1               5                   10                  15

Asn Tyr Arg

<210> SEQ ID NO 413
<211> LENGTH: 19
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 413

Tyr Ile Pro Pro Tyr Cys Thr Met Ala Pro Phe Gly Ile Phe Gly Thr
1               5                   10                  15

Asn Tyr Arg

<210> SEQ ID NO 414
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 414

Tyr Ile Pro Pro Tyr Cys Thr Ile Thr Pro Phe Gly Ile Phe Gly Thr
1               5                   10                  15

Asn

<210> SEQ ID NO 415
<211> LENGTH: 19
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 415

Tyr Ile Pro Pro Tyr Cys Thr Ile Ala Pro Val Gly Ile Phe Gly Thr
1               5                   10                  15

Asn Tyr Arg

<210> SEQ ID NO 416
<211> LENGTH: 19
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 416

Tyr Ile Pro Pro Tyr Cys Ser Thr Thr Ile Ala Pro Val Gly Ile Phe
1               5                   10                  15

Gly Thr Asn

<210> SEQ ID NO 417
<211> LENGTH: 19
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 417

Tyr Ile Pro Pro Tyr Cys Ser Thr Thr Thr Ala Pro Phe Gly Ile Phe
1               5                   10                  15

Gly Thr Asn

<210> SEQ ID NO 418
<211> LENGTH: 19
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 418

Tyr Ile Pro Pro His Cys Ser Thr Thr Ile Ala Pro Phe Gly Ile Phe
1               5                   10                  15

Gly Thr Asn

<210> SEQ ID NO 419
<211> LENGTH: 19
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 419

Tyr Ile Pro Pro His Cys Ser Thr Thr Ile Ala Pro Phe Gly Ile Ser
1               5                   10                  15

Gly Thr Asn

<210> SEQ ID NO 420
<211> LENGTH: 20
<212> TYPE: PRT
<213> ORGANISM: Artificial Sequence
<220> FEATURE:

<223> OTHER INFORMATION: Description of Artificial Sequence: Synthetic
      wheat gliadin peptide

<400> SEQUENCE: 420

Ile Pro Pro Tyr Cys Ser Thr Thr Ile Ala Pro Phe Gly Ile Phe Gly
1               5                   10                  15

Thr Asn Tyr Arg
            20

<210> SEQ ID NO 421
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 421

Gly Thr Ala Asn Met Gln Val Asp Pro Ser Ser Gln Val Gln Trp Pro
1               5                   10                  15

Gln Gln Gln Pro
            20

<210> SEQ ID NO 422
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 422

Gly Thr Ala Asn Ile Gln Val Asp Pro Ser Gly Gln Val Gln Trp Leu
1               5                   10                  15

Gln Gln Gln Leu
            20

<210> SEQ ID NO 423
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 423

Ala Thr Ala Asn Met Gln Val Asp Pro Ser Gly Gln Val Pro Trp Pro
1               5                   10                  15

Gln Gln Gln Pro
            20

<210> SEQ ID NO 424
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 424

Met Asn Ile Gln Val Asp Pro Ser Gly Gln Val Pro Trp Pro Gln Gln
1               5                   10                  15

Gln Pro Phe Pro
            20

<210> SEQ ID NO 425
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 425

Ala Thr Ala Asn Met Gln Ala Asp Pro Ser Gly Gln Val Gln Trp Pro
1               5                   10                  15

Gln Gln Gln Pro
            20

<210> SEQ ID NO 426
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 426

Thr Thr Ala Asn Ile Gln Val Asp Pro Ser Gly Gln Val Gln Trp Pro
1               5                   10                  15

Gln Gln Gln Gln
            20

<210> SEQ ID NO 427
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 427

Ala Thr Ala Asn Met Gln Val Asp Pro Ser Gly Gln Val Gln Trp Pro
1               5                   10                  15

Gln Gln Gln Pro
            20

<210> SEQ ID NO 428
<211> LENGTH: 19
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 428

Gln Ile Val Phe Pro Ser Gly Gln Val Gln Trp Pro Gln Gln Gln Gln
1               5                   10                  15

Pro Phe Pro

<210> SEQ ID NO 429
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 429

Pro Ser Ser Gln Val Gln Trp Pro Gln Gln Gln Pro Val Pro Gln Pro

```
                 1               5                  10                 15

His Gln Pro Phe
            20

<210> SEQ ID NO 430
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 430

Pro Ser Gly Gln Val Gln Trp Leu Gln Gln Leu Val Pro Gln Leu
1               5                  10                 15

Gln Gln Pro Leu
            20

<210> SEQ ID NO 431
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 431

Pro Ser Gly Gln Val Pro Trp Pro Gln Gln Pro Phe Pro Gln Pro
1               5                  10                 15

His Gln Pro Phe
            20

<210> SEQ ID NO 432
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 432

Pro Ser Gly Gln Val Gln Trp Pro Gln Gln Pro Phe Leu Gln Pro
1               5                  10                 15

His Gln Pro Phe
            20

<210> SEQ ID NO 433
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 433

Pro Ser Gly Gln Val Gln Trp Pro Gln Gln Gln Pro Phe Pro Gln
1               5                  10                 15

Pro Gln Gln Pro
            20

<210> SEQ ID NO 434
<211> LENGTH: 20
<212> TYPE: PRT
<213> ORGANISM: Artificial Sequence
<220> FEATURE:
```

<223> OTHER INFORMATION: Description of Artificial Sequence: Synthetic
      wheat gliadin peptide

<400> SEQUENCE: 434

Pro Ser Gly Gln Val Gln Trp Pro Gln Gln Pro Phe Arg Gln Pro
1               5                   10                  15

Gln Gln Pro Phe
            20

<210> SEQ ID NO 435
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 435

Pro Ser Gly Gln Val Gln Trp Pro Gln Gln Pro Phe Pro Gln Pro
1               5                   10                  15

Gln Gln Pro Phe
            20

<210> SEQ ID NO 436
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 436

Gln Gln Gln Pro Val Pro Gln Pro His Gln Pro Phe Ser Gln Pro
1               5                   10                  15

Gln Gln Thr Phe
            20

<210> SEQ ID NO 437
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 437

Gln Gln Gln Leu Val Pro Gln Leu Gln Gln Pro Leu Ser Gln Pro
1               5                   10                  15

Gln Gln Thr Phe
            20

<210> SEQ ID NO 438
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 438

Gln Gln Gln Pro Phe Pro Gln Pro His Gln Pro Phe Ser Gln Pro
1               5                   10                  15

Gln Gln Thr Phe
            20

<210> SEQ ID NO 439
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 439

Gln Gln Gln Pro Phe Leu Gln Pro His Gln Pro Phe Ser Gln Gln Pro
1               5                   10                  15

Gln Gln Ile Phe
            20

<210> SEQ ID NO 440
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 440

Gln Gln Gln Gln Pro Phe Pro Gln Pro Gln Gln Pro Phe Ser Gln Gln
1               5                   10                  15

Pro Gln Gln Ile
            20

<210> SEQ ID NO 441
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 441

Gln Gln Gln Gln Pro Phe Pro Gln Pro Gln Gln Pro Gln Gln Pro Phe
1               5                   10                  15

Pro Gln Pro Gln
            20

<210> SEQ ID NO 442
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 442

Gln Gln Gln Pro Phe Arg Gln Pro Gln Gln Pro Phe Tyr Gln Gln Pro
1               5                   10                  15

Gln His Thr Phe
            20

<210> SEQ ID NO 443
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 443

Gln Gln Gln Pro Phe Pro Gln Pro Gln Gln Pro Phe Cys Gln Gln Pro
1               5                   10                  15

Gln Arg Thr Ile
            20

<210> SEQ ID NO 444
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 444

Gln Gln Gln Pro Phe Pro Gln Pro Gln Gln Pro Phe Cys Glu Gln Pro
1               5                   10                  15

Gln Arg Thr Ile
            20

<210> SEQ ID NO 445
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 445

His Gln Pro Phe Ser Gln Gln Pro Gln Gln Thr Phe Pro Gln Pro Gln
1               5                   10                  15

Gln Thr Phe Pro
            20

<210> SEQ ID NO 446
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 446

Gln Gln Pro Leu Ser Gln Gln Pro Gln Gln Thr Phe Pro Gln Pro Gln
1               5                   10                  15

Gln Thr Phe Pro
            20

<210> SEQ ID NO 447
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 447

His Gln Pro Phe Ser Gln Gln Pro Gln Gln Ile Phe Pro Gln Pro Gln
1               5                   10                  15

Gln Thr Phe Pro
            20

<210> SEQ ID NO 448
<211> LENGTH: 20
<212> TYPE: PRT
<213> ORGANISM: Artificial Sequence

```
<220> FEATURE:
<223> OTHER INFORMATION: Description of Artificial Sequence: Synthetic
      wheat gliadin peptide

<400> SEQUENCE: 448

Gln Gln Pro Phe Ser Gln Gln Pro Gln Gln Ile Phe Pro Gln Pro Gln
1               5                   10                  15

Gln Thr Phe Pro
            20

<210> SEQ ID NO 449
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 449

Gln Gln Pro Gln Gln Pro Phe Pro Gln Pro Gln Gln Pro Gln Leu Pro
1               5                   10                  15

Phe Pro Gln Gln
            20

<210> SEQ ID NO 450
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 450

Gln Gln Pro Phe Tyr Gln Gln Pro Gln His Thr Phe Pro Gln Pro Gln
1               5                   10                  15

Gln Thr Cys Pro
            20

<210> SEQ ID NO 451
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 451

Gln Gln Pro Phe Cys Gln Gln Pro Gln Arg Thr Ile Pro Gln Pro His
1               5                   10                  15

Gln Thr Phe His
            20

<210> SEQ ID NO 452
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 452

Gln Gln Pro Phe Cys Gln Gln Pro Gln Gln Thr Ile Pro Gln Pro His
1               5                   10                  15

Gln Thr Phe His
            20
```

<210> SEQ ID NO 453
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 453

Gln Gln Pro Phe Cys Glu Gln Pro Gln Arg Thr Ile Pro Gln Pro His
1               5                   10                  15

Gln Thr Phe His
            20

<210> SEQ ID NO 454
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 454

Gln Gln Thr Phe Pro Gln Pro Gln Gln Thr Phe Pro His Gln Pro Gln
1               5                   10                  15

Gln Gln Phe Pro
            20

<210> SEQ ID NO 455
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 455

Gln Gln Ile Phe Pro Gln Pro Gln Gln Thr Phe Pro His Gln Pro Gln
1               5                   10                  15

Gln Gln Phe Pro
            20

<210> SEQ ID NO 456
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 456

Gln Gln Ile Phe Pro Gln Pro Gln Gln Thr Phe Pro His Gln Pro Gln
1               5                   10                  15

Gln Ala Phe Pro
            20

<210> SEQ ID NO 457
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 457

```
Gln Arg Thr Ile Pro Gln Pro His Gln Thr Phe His His Gln Pro Gln
1               5                   10                  15

Gln Thr Phe Pro
            20

<210> SEQ ID NO 458
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 458

Gln Thr Phe Pro His Gln Pro Gln Gln Ala Phe Pro Gln Pro Gln Gln
1               5                   10                  15

Thr Phe Pro His
            20

<210> SEQ ID NO 459
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 459

Gln Thr Phe His His Gln Pro Gln Gln Thr Phe Pro Gln Pro Gln Gln
1               5                   10                  15

Thr Tyr Pro His
            20

<210> SEQ ID NO 460
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 460

Gln Thr Phe His His Gln Pro Gln Gln Thr Phe Pro Gln Pro Glu Gln
1               5                   10                  15

Thr Tyr Pro His
            20

<210> SEQ ID NO 461
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 461

Gln Ala Phe Pro Gln Pro Gln Gln Thr Phe Pro His Gln Pro Gln Gln
1               5                   10                  15

Gln Phe Pro Gln
            20

<210> SEQ ID NO 462
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      wheat gliadin peptide

<400> SEQUENCE: 462

Gln His Thr Phe Pro Gln Pro Gln Gln Thr Cys Pro His Gln Pro Gln
1               5                   10                  15

Gln Gln Phe Pro
            20

<210> SEQ ID NO 463
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 463

Gln Thr Phe Pro Gln Pro Gln Gln Thr Tyr Pro His Gln Pro Gln Gln
1               5                   10                  15

Gln Phe Pro Gln
            20

<210> SEQ ID NO 464
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 464

Gln Thr Phe Pro Gln Pro Glu Gln Thr Tyr Pro His Gln Pro Gln Gln
1               5                   10                  15

Gln Phe Pro Gln
            20

<210> SEQ ID NO 465
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 465

Gln Thr Phe Pro His Gln Pro Gln Gln Phe Pro Gln Pro Gln Gln
1               5                   10                  15

Pro Gln Gln Gln
            20

<210> SEQ ID NO 466
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 466

Gln Thr Phe Pro His Gln Pro Gln Gln Val Pro Gln Pro Gln Gln
1               5                   10                  15

Pro Gln Gln Pro
```

20

<210> SEQ ID NO 467
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 467

Gln Thr Phe Pro His Gln Pro Gln Gln Gln Phe Ser Gln Pro Gln Gln
1               5                   10                  15

Pro Gln Gln Gln
            20

<210> SEQ ID NO 468
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 468

Gln Thr Cys Pro His Gln Pro Gln Gln Gln Phe Pro Gln Pro Gln Gln
1               5                   10                  15

Pro Gln Gln Pro
            20

<210> SEQ ID NO 469
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 469

Gln Thr Tyr Pro His Gln Pro Gln Gln Gln Phe Pro Gln Thr Gln Gln
1               5                   10                  15

Pro Gln Gln Pro
            20

<210> SEQ ID NO 470
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 470

Gln Gln Phe Pro Gln Pro Gln Gln Pro Gln Gln Phe Leu Gln Pro
1               5                   10                  15

Gln Gln Pro Phe
            20

<210> SEQ ID NO 471
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 471

Gln Gln Val Pro Gln Pro Gln Gln Pro Gln Gln Pro Phe Leu Gln Pro
1               5                   10                  15

Gln Gln Pro Phe
            20

<210> SEQ ID NO 472
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 472

Gln Gln Phe Ser Gln Pro Gln Gln Pro Gln Gln Phe Ile Gln Pro
1               5                   10                  15

Gln Gln Pro Phe
            20

<210> SEQ ID NO 473
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 473

Gln Gln Phe Pro Gln Pro Gln Gln Pro Gln Gln Phe Leu Gln Pro
1               5                   10                  15

Arg Gln Pro Phe
            20

<210> SEQ ID NO 474
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 474

Gln Gln Phe Pro Gln Pro Gln Gln Pro Gln Pro Phe Pro Gln Gln
1               5                   10                  15

Pro Gln Gln Gln
            20

<210> SEQ ID NO 475
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 475

Gln Gln Phe Pro Gln Thr Gln Pro Gln Gln Pro Phe Pro Gln Pro
1               5                   10                  15

Gln Gln Thr Phe
            20

<210> SEQ ID NO 476
<211> LENGTH: 20

```
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 476

Pro Gln Gln Gln Phe Leu Gln Pro Gln Gln Pro Phe Pro Gln Gln Pro
1               5                   10                  15

Gln Gln Pro Tyr
            20

<210> SEQ ID NO 477
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 477

Pro Gln Gln Gln Phe Ile Gln Pro Gln Gln Pro Phe Pro Gln Gln Pro
1               5                   10                  15

Gln Gln Thr Tyr
            20

<210> SEQ ID NO 478
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 478

Pro Gln Gln Gln Phe Ile Gln Pro Gln Gln Pro Gln Gln Thr Tyr Pro
1               5                   10                  15

Gln Arg Pro Gln
            20

<210> SEQ ID NO 479
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 479

Pro Gln Gln Gln Phe Leu Gln Pro Arg Gln Pro Phe Pro Gln Gln Pro
1               5                   10                  15

Gln Gln Pro Tyr
            20

<210> SEQ ID NO 480
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 480

Pro Gln Gln Pro Phe Pro Gln Gln Pro Gln Gln Phe Pro Gln Pro
1               5                   10                  15
```

```
Gln Gln Pro Gln
            20

<210> SEQ ID NO 481
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 481

Pro Gln Pro Phe Pro Gln Pro Gln Gln Pro Gln Gln Pro Phe Pro
1               5                   10                  15

Gln Pro Gln Gln
            20

<210> SEQ ID NO 482
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 482

Pro Gln Gln Pro Phe Pro Gln Pro Gln Gln Thr Phe Pro Gln Pro
1               5                   10                  15

Gln Leu Pro Phe
            20

<210> SEQ ID NO 483
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 483

Pro Gln Gln Phe Pro Gln Pro Gln Gln Pro Gln Gln Pro Phe Pro
1               5                   10                  15

Gln Gln Pro Gln
            20

<210> SEQ ID NO 484
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 484

Gln Gln Pro Gln Gln Pro Phe Pro Gln Gln Pro Gln Gln Phe Pro
1               5                   10                  15

Gln Pro Gln Gln
            20

<210> SEQ ID NO 485
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide
```

<400> SEQUENCE: 485

Gln Gln Pro Gln Gln Gln Phe Pro Gln Pro Gln Gln Pro Gln Gln Pro
1               5                   10                  15

Phe Pro Gln Pro
            20

<210> SEQ ID NO 486
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 486

Gln Pro Gln Gln Pro Gln Gln Pro Phe Pro Gln Pro Gln Gln Pro Gln
1               5                   10                  15

Leu Pro Phe Pro
            20

<210> SEQ ID NO 487
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 487

Gln Gln Pro Phe Pro Gln Gln Pro Gln Gln Pro Tyr Pro Gln Gln Pro
1               5                   10                  15

Gln Gln Pro Phe
            20

<210> SEQ ID NO 488
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 488

Gln Gln Pro Phe Pro Gln Gln Pro Gln Gln Pro Phe Pro Gln Thr Gln
1               5                   10                  15

Gln Pro Gln Gln
            20

<210> SEQ ID NO 489
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 489

Gln Gln Pro Phe Pro Gln Gln Pro Gln Gln Thr Tyr Pro Gln Arg Pro
1               5                   10                  15

Gln Gln Pro Phe
            20

<210> SEQ ID NO 490

```
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 490

Arg Gln Pro Phe Pro Gln Gln Pro Gln Gln Pro Tyr Pro Gln Gln Pro
1               5                   10                  15

Gln Gln Pro Phe
            20

<210> SEQ ID NO 491
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 491

Gln Gln Pro Phe Pro Gln Pro Gln Gln Pro Gln Leu Pro Phe Pro Gln
1               5                   10                  15

Gln Pro Gln Gln
            20

<210> SEQ ID NO 492
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 492

Gln Gln Pro Phe Pro Gln Pro Gln Gln Ala Gln Leu Pro Phe Pro Gln
1               5                   10                  15

Gln Pro Gln Gln
            20

<210> SEQ ID NO 493
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 493

Gln Gln Thr Phe Pro Gln Gln Pro Gln Leu Pro Phe Pro Gln Gln Pro
1               5                   10                  15

Gln Gln Pro Phe
            20

<210> SEQ ID NO 494
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 494

Gln Gln Pro Tyr Pro Gln Gln Pro Gln Gln Pro Phe Pro Gln Thr Gln
1               5                   10                  15
```

Gln Pro Gln Gln
        20

<210> SEQ ID NO 495
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 495

Gln Gln Pro Phe Pro Gln Thr Gln Gln Pro Gln Gln Pro Phe Pro Gln
1               5                   10                  15

Gln Pro Gln Gln
        20

<210> SEQ ID NO 496
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 496

Gln Gln Thr Tyr Pro Gln Arg Pro Gln Gln Pro Phe Pro Gln Thr Gln
1               5                   10                  15

Gln Pro Gln Gln
        20

<210> SEQ ID NO 497
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 497

Gln Pro Gln Leu Pro Phe Pro Gln Gln Pro Gln Gln Pro Gln Gln
1               5                   10                  15

Pro Phe Pro Gln
        20

<210> SEQ ID NO 498
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 498

Gln Ala Gln Leu Pro Phe Pro Gln Gln Pro Gln Pro Leu Pro Gln
1               5                   10                  15

Pro Gln Gln Pro
        20

<210> SEQ ID NO 499
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 499

Gln Leu Pro Phe Pro Gln Gln Pro Gln Gln Pro Phe Pro Gln Pro Gln
1               5                   10                  15

Gln Pro Gln Gln
            20

<210> SEQ ID NO 500
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 500

Gln Pro Gln Gln Pro Phe Pro Gln Gln Pro Gln Gln Pro Phe Pro Gln
1               5                   10                  15

Thr Gln Gln Pro
            20

<210> SEQ ID NO 501
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 501

Gln Pro Gln Gln Pro Phe Pro Gln Thr Gln Gln Pro Gln Gln Pro Phe
1               5                   10                  15

Pro Gln Gln Pro
            20

<210> SEQ ID NO 502
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 502

Thr Gln Gln Pro Gln Gln Pro Phe Pro Gln Gln Pro Gln Gln Pro Phe
1               5                   10                  15

Pro Gln Thr Gln
            20

<210> SEQ ID NO 503
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 503

Pro Gln Gln Pro Gln Gln Pro Phe Pro Gln Thr Gln Gln Pro Gln Gln
1               5                   10                  15

Pro Phe Pro Gln
            20

```
<210> SEQ ID NO 504
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 504

Gln Gln Pro Phe Pro Gln Thr Gln Gln Pro Gln Gln Leu Phe Pro Gln
1               5                   10                  15

Ser Gln Gln Pro
            20

<210> SEQ ID NO 505
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 505

Gln Gln Pro Phe Pro Gln Thr Gln Gln Pro Gln Gln Pro Phe Pro Gln
1               5                   10                  15

Leu Gln Gln Pro
            20

<210> SEQ ID NO 506
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 506

Gln Gln Pro Phe Pro Gln Thr Gln Gln Pro Gln Gln Pro Phe Pro Gln
1               5                   10                  15

Ser Gln Gln Pro
            20

<210> SEQ ID NO 507
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 507

Gln Gln Pro Phe Pro Gln Thr Gln Gln Pro Gln Gln Pro Phe Pro Gln
1               5                   10                  15

Ser Lys Gln Pro
            20

<210> SEQ ID NO 508
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 508

Gln Gln Pro Phe Pro Gln Pro Gln Gln Pro Gln Gln Pro Phe Pro Gln
```

```
                1               5                  10                  15

Leu Gln Gln Pro
            20

<210> SEQ ID NO 509
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 509

Gln Gln Pro Leu Pro Gln Pro Gln Gln Pro Gln Gln Pro Phe Pro Gln
1               5                  10                  15

Ser Gln Gln Pro
            20

<210> SEQ ID NO 510
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 510

Gln Gln Pro Phe Pro Gln Pro Gln Gln Pro Gln Gln Pro Phe Pro Gln
1               5                  10                  15

Ser Gln Gln Pro
            20

<210> SEQ ID NO 511
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 511

Gln Pro Gln Gln Leu Phe Pro Gln Ser Gln Gln Pro Gln Gln Gln Phe
1               5                  10                  15

Ser Gln Pro Gln
            20

<210> SEQ ID NO 512
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 512

Gln Pro Gln Gln Pro Phe Pro Gln Leu Gln Gln Pro Gln Gln Pro Phe
1               5                  10                  15

Pro Gln Pro Gln
            20

<210> SEQ ID NO 513
<211> LENGTH: 20
<212> TYPE: PRT
<213> ORGANISM: Artificial Sequence
<220> FEATURE:
```

-continued

<223> OTHER INFORMATION: Description of Artificial Sequence: Synthetic
      wheat gliadin peptide

<400> SEQUENCE: 513

Gln Pro Gln Gln Pro Phe Pro Gln Ser Gln Gln Pro Gln Gln Pro Phe
1               5                   10                  15

Pro Gln Pro Gln
            20

<210> SEQ ID NO 514
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 514

Gln Pro Gln Gln Pro Phe Pro Gln Ser Lys Gln Pro Gln Gln Pro Phe
1               5                   10                  15

Pro Gln Pro Gln
            20

<210> SEQ ID NO 515
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 515

Gln Pro Gln Gln Pro Phe Pro Gln Leu Gln Gln Pro Gln Gln Pro Leu
1               5                   10                  15

Pro Gln Pro Gln
            20

<210> SEQ ID NO 516
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 516

Ser Gln Gln Pro Gln Gln Gln Phe Ser Gln Pro Gln Gln Gln Phe Pro
1               5                   10                  15

Gln Pro Gln Gln
            20

<210> SEQ ID NO 517
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 517

Leu Gln Gln Pro Gln Gln Pro Phe Pro Gln Pro Gln Gln Gln Leu Pro
1               5                   10                  15

Gln Pro Gln Gln
            20

<210> SEQ ID NO 518
<211> LENGTH: 20
<212> TYPE: PRT
<213> ORGANISM: Artificial Sequence
<220> FEATURE:
<223> OTHER INFORMATION: Description of Artificial Sequence: Synthetic
    wheat gliadin peptide

<400> SEQUENCE: 518

Ser Gln Gln Pro Gln Gln Pro Phe Pro Gln Pro Gln Gln Phe Pro
1               5                   10                  15

Gln Pro Gln Gln
            20

<210> SEQ ID NO 519
<211> LENGTH: 20
<212> TYPE: PRT
<213> ORGANISM: Artificial Sequence
<220> FEATURE:
<223> OTHER INFORMATION: Description of Artificial Sequence: Synthetic
    wheat gliadin peptide

<400> SEQUENCE: 519

Ser Lys Gln Pro Gln Gln Pro Phe Pro Gln Pro Gln Gln Pro Gln Gln
1               5                   10                  15

Ser Phe Pro Gln
            20

<210> SEQ ID NO 520
<211> LENGTH: 20
<212> TYPE: PRT
<213> ORGANISM: Artificial Sequence
<220> FEATURE:
<223> OTHER INFORMATION: Description of Artificial Sequence: Synthetic
    wheat gliadin peptide

<400> SEQUENCE: 520

Leu Gln Gln Pro Gln Gln Pro Leu Pro Gln Pro Gln Gln Pro Gln Gln
1               5                   10                  15

Pro Phe Pro Gln
            20

<210> SEQ ID NO 521
<211> LENGTH: 20
<212> TYPE: PRT
<213> ORGANISM: Artificial Sequence
<220> FEATURE:
<223> OTHER INFORMATION: Description of Artificial Sequence: Synthetic
    wheat gliadin peptide

<400> SEQUENCE: 521

Ser Gln Gln Pro Gln Gln Pro Phe Pro Gln Pro Gln Gln Pro Gln Gln
1               5                   10                  15

Ser Phe Pro Gln
            20

<210> SEQ ID NO 522
<211> LENGTH: 20
<212> TYPE: PRT
<213> ORGANISM: Artificial Sequence
<220> FEATURE:
<223> OTHER INFORMATION: Description of Artificial Sequence: Synthetic
    wheat gliadin peptide

<400> SEQUENCE: 522

```
Ser Gln Pro Gln Gln Gln Phe Pro Gln Pro Gln Gln Pro Gln Gln Ser
1               5                   10                  15

Phe Pro Gln Gln
            20

<210> SEQ ID NO 523
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 523

Pro Gln Pro Gln Gln Gln Leu Pro Gln Pro Gln Gln Pro Gln Gln Ser
1               5                   10                  15

Phe Pro Gln Gln
            20

<210> SEQ ID NO 524
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 524

Pro Gln Pro Gln Gln Gln Phe Pro Gln Pro Gln Gln Pro Gln Gln Ser
1               5                   10                  15

Phe Pro Gln Gln
            20

<210> SEQ ID NO 525
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 525

Pro Gln Pro Gln Gln Pro Gln Gln Ser Phe Pro Gln Gln Gln Pro Ser
1               5                   10                  15

Leu Ile Gln Gln
            20

<210> SEQ ID NO 526
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 526

Pro Gln Pro Gln Gln Pro Gln Gln Pro Phe Pro Gln Gln Gln Gln Pro
1               5                   10                  15

Leu Ile Gln Pro
            20

<210> SEQ ID NO 527
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      wheat gliadin peptide

<400> SEQUENCE: 527

Pro Gln Pro Gln Gln Pro Gln Gln Ser Phe Pro Gln Gln Gln Gln Pro
1               5                   10                  15

Leu Ile Gln Pro
            20

<210> SEQ ID NO 528
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 528

Gln Pro Gln Gln Pro Gln Gln Ser Phe Pro Gln Gln Gln Pro Pro Phe
1               5                   10                  15

Ile Gln Pro Ser
            20

<210> SEQ ID NO 529
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 529

Gln Pro Gln Gln Pro Gln Gln Ser Phe Pro Gln Gln Gln Arg Pro Phe
1               5                   10                  15

Ile Gln Pro Ser
            20

<210> SEQ ID NO 530
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 530

Gln Pro Gln Gln Pro Gln Gln Ser Phe Pro Gln Gln Gln Pro Ser Leu
1               5                   10                  15

Ile Gln Gln Ser
            20

<210> SEQ ID NO 531
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 531

Phe Pro Gln Gln Gln Pro Pro Phe Ile Gln Pro Ser Leu Gln Gln Gln
1               5                   10                  15

Val Asn Pro Cys
            20
```

```
<210> SEQ ID NO 532
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 532

Phe Pro Gln Gln Gln Arg Pro Phe Ile Gln Pro Ser Leu Gln Gln Gln
1               5                   10                  15

Leu Asn Pro Cys
        20

<210> SEQ ID NO 533
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 533

Phe Pro Gln Gln Gln Pro Ser Leu Ile Gln Gln Ser Leu Gln Gln Gln
1               5                   10                  15

Leu Asn Pro Cys
        20

<210> SEQ ID NO 534
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 534

Phe Pro Gln Gln Gln Gln Pro Leu Ile Gln Pro Tyr Leu Gln Gln Gln
1               5                   10                  15

Met Asn Pro Cys
        20

<210> SEQ ID NO 535
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 535

Phe Pro Gln Gln Gln Gln Pro Ala Ile Gln Ser Phe Leu Gln Gln Gln
1               5                   10                  15

Met Asn Pro Cys
        20

<210> SEQ ID NO 536
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 536
```

```
Ile Gln Pro Ser Leu Gln Gln Gln Val Asn Pro Cys Lys Asn Phe Leu
1               5                   10                  15

Leu Gln Gln Cys
            20

<210> SEQ ID NO 537
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 537

Ile Gln Pro Ser Leu Gln Gln Gln Leu Asn Pro Cys Lys Asn Ile Leu
1               5                   10                  15

Leu Gln Gln Ser
            20

<210> SEQ ID NO 538
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 538

Ile Gln Ser Leu Gln Gln Gln Leu Asn Pro Cys Lys Asn Phe Leu
1               5                   10                  15

Leu Gln Gln Cys
            20

<210> SEQ ID NO 539
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 539

Ile Gln Pro Tyr Leu Gln Gln Gln Met Asn Pro Cys Lys Asn Tyr Leu
1               5                   10                  15

Leu Gln Gln Cys
            20

<210> SEQ ID NO 540
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 540

Ile Gln Ser Phe Leu Gln Gln Gln Met Asn Pro Cys Lys Asn Phe Leu
1               5                   10                  15

Leu Gln Gln Cys
            20

<210> SEQ ID NO 541
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      wheat gliadin peptide

<400> SEQUENCE: 541

Val Asn Pro Cys Lys Asn Phe Leu Leu Gln Gln Cys Lys Pro Val Ser
1               5                   10                  15

Leu Val Ser Ser
            20

<210> SEQ ID NO 542
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 542

Leu Asn Pro Cys Lys Asn Ile Leu Leu Gln Gln Ser Lys Pro Ala Ser
1               5                   10                  15

Leu Val Ser Ser
            20

<210> SEQ ID NO 543
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 543

Leu Asn Pro Cys Lys Asn Phe Leu Leu Gln Gln Cys Lys Pro Val Ser
1               5                   10                  15

Leu Val Ser Ser
            20

<210> SEQ ID NO 544
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 544

Met Asn Pro Cys Lys Asn Tyr Leu Leu Gln Gln Cys Asn Pro Val Ser
1               5                   10                  15

Leu Val Ser Ser
            20

<210> SEQ ID NO 545
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 545

Met Asn Pro Cys Lys Asn Phe Leu Leu Gln Gln Cys Asn His Val Ser
1               5                   10                  15

Leu Val Ser Ser
```

```
<210> SEQ ID NO 546
<211> LENGTH: 20
<212> TYPE: PRT
<213> ORGANISM: Artificial Sequence
<220> F

<400> SEQUENCE: 550

Leu Gln Gln Cys Asn His Val Ser Leu Val Ser Ser Leu Val Ser Ile
1               5                   10                  15

Ile Leu Pro Arg
            20

<210> SEQ ID NO 551
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 551

Leu Val Ser Ser Leu Trp Ser Met Ile Trp Pro Gln Ser Asp Cys Gln
1               5                   10                  15

Val Met Arg Gln
            20

<210> SEQ ID NO 552
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 552

Leu Val Ser Ser Leu Trp Ser Ile Ile Trp Pro Gln Ser Asp Cys Gln
1               5                   10                  15

Val Met Arg Gln
            20

<210> SEQ ID NO 553
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 553

Leu Val Ser Ser Leu Trp Ser Met Ile Leu Pro Arg Ser Asp Cys Gln
1               5                   10                  15

Val Met Arg Gln
            20

<210> SEQ ID NO 554
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 554

Leu Val Ser Ser Leu Trp Ser Ile Ile Leu Pro Pro Ser Asp Cys Gln
1               5                   10                  15

Val Met Arg Gln
            20

<210> SEQ ID NO 555
<211> LENGTH: 20

```
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 555

Leu Val Ser Ser Leu Val Ser Met Ile Leu Pro Arg Ser Asp Cys Lys
1               5                   10                  15

Val Met Arg Gln
            20

<210> SEQ ID NO 556
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 556

Leu Val Ser Ser Leu Val Ser Met Ile Leu Pro Arg Ser Asp Cys Gln
1               5                   10                  15

Val Met Gln Gln
            20

<210> SEQ ID NO 557
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 557

Leu Val Ser Ser Leu Val Ser Ile Ile Leu Pro Arg Ser Asp Cys Gln
1               5                   10                  15

Val Met Gln Gln
            20

<210> SEQ ID NO 558
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 558

Ile Trp Pro Gln Ser Asp Cys Gln Val Met Arg Gln Gln Cys Cys Gln
1               5                   10                  15

Gln Leu Ala Gln
            20

<210> SEQ ID NO 559
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 559

Ile Leu Pro Arg Ser Asp Cys Gln Val Met Arg Gln Gln Cys Cys Gln
1               5                   10                  15
```

Gln Leu Ala Gln
        20

<210> SEQ ID NO 560
<211> LENGTH: 20
<212> TYPE: PRT
<213> ORGANISM: Artificial Sequence
<220> FEATURE:
<223> OTHER INFORMATION: Description of Artificial Sequence: Synthetic
     wheat gliadin peptide

<400> SEQUENCE: 560

Ile Leu Pro Pro Ser Asp Cys Gln Val Met Arg Gln Gln Cys Cys Gln
1             5                 10               15

Gln Leu Ala Gln
        20

<210> SEQ ID NO 561
<211> LENGTH: 20
<212> TYPE: PRT
<213> ORGANISM: Artificial Sequence
<220> FEATURE:
<223> OTHER INFORMATION: Description of Artificial Sequence: Synthetic
     wheat gliadin peptide

<400> SEQUENCE: 561

Ile Leu Pro Arg Ser Asp Cys Lys Val Met Arg Gln Gln Cys Cys Gln
1             5                 10               15

Gln Leu Ala Arg
        20

<210> SEQ ID NO 562
<211> LENGTH: 20
<212> TYPE: PRT
<213> ORGANISM: Artificial Sequence
<220> FEATURE:
<223> OTHER INFORMATION: Description of Artificial Sequence: Synthetic
     wheat gliadin peptide

<400> SEQUENCE: 562

Ile Leu Pro Arg Ser Asp Cys Gln Val Met Gln Gln Gln Cys Cys Gln
1             5                 10               15

Gln Leu Ala Gln
        20

<210> SEQ ID NO 563
<211> LENGTH: 20
<212> TYPE: PRT
<213> ORGANISM: Artificial Sequence
<220> FEATURE:
<223> OTHER INFORMATION: Description of Artificial Sequence: Synthetic
     wheat gliadin peptide

<400> SEQUENCE: 563

Val Met Arg Gln Gln Cys Cys Gln Gln Leu Ala Gln Ile Pro Gln Gln
1             5                 10               15

Leu Gln Cys Ala
        20

<210> SEQ ID NO 564
<211> LENGTH: 20
<212> TYPE: PRT
<213> ORGANISM: Artificial Sequence
<220> FEATURE:
<223> OTHER INFORMATION: Description of Artificial Sequence: Synthetic
     wheat gliadin peptide

<400> SEQUENCE: 564

Val Met Arg Gln Gln Cys Cys Gln Gln Leu Ala Arg Ile Pro Gln Gln
1               5                   10                  15

Leu Gln Cys Ala
            20

<210> SEQ ID NO 565
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 565

Val Met Gln Gln Gln Cys Cys Gln Gln Leu Ala Gln Ile Pro Arg Gln
1               5                   10                  15

Leu Gln Cys Ala
            20

<210> SEQ ID NO 566
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 566

Val Met Gln Gln Gln Cys Cys Gln Gln Leu Ala Gln Ile Pro Gln Gln
1               5                   10                  15

Leu Gln Cys Ala
            20

<210> SEQ ID NO 567
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 567

Gln Leu Ala Gln Ile Pro Gln Gln Leu Gln Cys Ala Ala Ile His Thr
1               5                   10                  15

Ile Ile His Ser
            20

<210> SEQ ID NO 568
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 568

Gln Leu Ala Gln Ile Pro Gln Gln Leu Gln Cys Ala Ala Ile His Thr
1               5                   10                  15

Val Ile His Ser
            20

<210> SEQ ID NO 569

```
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 569

Gln Leu Ala Gln Ile Pro Gln Gln Leu Gln Cys Ala Ala Ile His Ser
1               5                  10                  15

Val Val His Ser
            20

<210> SEQ ID NO 570
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 570

Gln Leu Ala Gln Ile Pro Gln Gln Leu Gln Cys Ala Ala Ile His Ser
1               5                  10                  15

Ile Val His Ser
            20

<210> SEQ ID NO 571
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 571

Gln Leu Ala Arg Ile Pro Gln Gln Leu Gln Cys Ala Ala Ile His Gly
1               5                  10                  15

Ile Val His Ser
            20

<210> SEQ ID NO 572
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 572

Gln Leu Ala Gln Ile Pro Arg Gln Leu Gln Cys Ala Ala Ile His Ser
1               5                  10                  15

Val Val His Ser
            20

<210> SEQ ID NO 573
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 573

Gln Leu Ala Gln Ile Pro Gln Gln Leu Gln Cys Ala Ala Ile His Ser
1               5                  10                  15
```

Val Ala His Ser
            20

<210> SEQ ID NO 574
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 574

Leu Gln Cys Ala Ala Ile His Thr Ile Ile His Ser Ile Ile Met Gln
1               5                   10                  15

Gln Glu Gln Gln
            20

<210> SEQ ID NO 575
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 575

Leu Gln Cys Ala Ala Ile His Thr Val Ile His Ser Ile Ile Met Gln
1               5                   10                  15

Gln Glu Gln Gln
            20

<210> SEQ ID NO 576
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 576

Leu Gln Cys Ala Ala Ile His Ser Val Val His Ser Ile Ile Met Gln
1               5                   10                  15

Gln Gln Gln Gln
            20

<210> SEQ ID NO 577
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 577

Leu Gln Cys Ala Ala Ile His Ser Ile Val His Ser Ile Ile Met Gln
1               5                   10                  15

Gln Glu Gln Gln
            20

<210> SEQ ID NO 578
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 578

Leu Gln Cys Ala Ala Ile His Ser Val Val His Ser Ile Ile Met Gln
1               5                   10                  15

Gln Glu Gln Gln
            20

<210> SEQ ID NO 579
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 579

Leu Gln Cys Ala Ala Ile His Gly Ile Val His Ser Ile Ile Met Gln
1               5                   10                  15

Gln Glu Gln Gln
            20

<210> SEQ ID NO 580
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 580

Leu Gln Cys Ala Ala Ile His Ser Val Ala His Ser Ile Ile Met Gln
1               5                   10                  15

Gln Glu Gln Gln
            20

<210> SEQ ID NO 581
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 581

Ile Ile His Ser Ile Ile Met Gln Gln Glu Gln Gln Glu Gln Gln Gln
1               5                   10                  15

Gly Met His Ile
            20

<210> SEQ ID NO 582
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 582

Val Ile His Ser Ile Ile Met Gln Gln Glu Gln Gln Gln Gly Met His
1               5                   10                  15

Ile Leu Leu Pro
            20

```
<210> SEQ ID NO 583
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 583

Val Val His Ser Ile Ile Met Gln Gln Gln Gln Gln Gln Gln Gln
1               5                   10                  15

Gln Gly Ile Asp
            20

<210> SEQ ID NO 584
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 584

Ile Val His Ser Ile Ile Met Gln Gln Glu Gln Gln Glu Gln Arg Gln
1               5                   10                  15

Gly Val Gln Ile
            20

<210> SEQ ID NO 585
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 585

Val Val His Ser Ile Ile Met Gln Gln Glu Gln Gln Glu Gln Leu Gln
1               5                   10                  15

Gly Val Gln Ile
            20

<210> SEQ ID NO 586
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 586

Ile Val His Ser Ile Ile Met Gln Gln Glu Gln Gln Gln Gln Gln
1               5                   10                  15

Gln Gln Gln Gln
            20

<210> SEQ ID NO 587
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 587

Val Val His Ser Ile Val Met Gln Gln Glu Gln Gln Gln Gly Ile Gln
```

<210> SEQ ID NO 588
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 588

Val Ala His Ser Ile Ile Met Gln Gln Glu Gln Gln Gln Gly Val Pro
1               5                   10                  15
Ile Leu Arg Pro
            20

<210> SEQ ID NO 589
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 589

Gln Glu Gln Gln Glu Gln Gln Gln Gly Met His Ile Leu Leu Pro Leu
1               5                   10                  15
Tyr Gln Gln Gln
            20

<210> SEQ ID NO 590
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 590

Gln Gln Gln Gln Gln Gln Gln Gln Gly Ile Asp Ile Phe Leu Pro
1               5                   10                  15
Leu Ser Gln His
            20

<210> SEQ ID NO 591
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 591

Gln Gln Gln Gln Gln Gln Gln Gln Gly Met His Ile Phe Leu Pro
1               5                   10                  15
Leu Ser Gln Gln
            20

<210> SEQ ID NO 592
<211> LENGTH: 20
<212> TYPE: PRT
<213> ORGANISM: Artificial Sequence
<220> FEATURE:

<223> OTHER INFORMATION: Description of Artificial Sequence: Synthetic
      wheat gliadin peptide

<400> SEQUENCE: 592

Gln Glu Gln Gln Glu Gln Arg Gln Gly Val Gln Ile Leu Val Pro Leu
1               5                   10                  15

Ser Gln Gln Gln
            20

<210> SEQ ID NO 593
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 593

Gln Glu Gln Gln Glu Gln Leu Gln Gly Val Gln Ile Leu Val Pro Leu
1               5                   10                  15

Ser Gln Gln Gln
            20

<210> SEQ ID NO 594
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 594

Gln Glu Gln Gln Gln Gln Gln Gln Gln Gln Gln Gln Gln Gln Gln Gly
1               5                   10                  15

Ile Gln Ile Met
            20

<210> SEQ ID NO 595
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 595

Gln Glu Gln Gln Gln Gly Ile Gln Ile Leu Arg Pro Leu Phe Gln Leu
1               5                   10                  15

Val Gln Gly Gln
            20

<210> SEQ ID NO 596
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 596

Gln Glu Gln Gln Gln Gly Val Pro Ile Leu Arg Pro Leu Phe Gln Leu
1               5                   10                  15

Ala Gln Gly Leu
            20

<210> SEQ ID NO 597
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 597

Gln Gln Gln Gln Gln Gln Gln Gly Ile Gln Ile Met Arg Pro Leu Phe
1               5                   10                  15

Gln Leu Val Gln
            20

<210> SEQ ID NO 598
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 598

Gly Met His Ile Leu Leu Pro Leu Tyr Gln Gln Gln Gln Val Gly Gln
1               5                   10                  15

Gly Thr Leu Val
            20

<210> SEQ ID NO 599
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 599

Gly Ile Asp Ile Phe Leu Pro Leu Ser Gln His Glu Gln Val Gly Gln
1               5                   10                  15

Gly Ser Leu Val
            20

<210> SEQ ID NO 600
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 600

Gly Met His Ile Phe Leu Pro Leu Ser Gln Gln Gln Gln Val Gly Gln
1               5                   10                  15

Gly Ser Leu Val
            20

<210> SEQ ID NO 601
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 601

```
Gly Val Gln Ile Leu Val Pro Leu Ser Gln Gln Gln Val Gly Gln
1               5                  10                 15

Gly Thr Leu Val
            20

<210> SEQ ID NO 602
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 602

Gly Val Gln Ile Leu Val Pro Leu Ser Gln Gln Gln Val Gly Gln
1               5                  10                 15

Gly Ile Leu Val
            20

<210> SEQ ID NO 603
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 603

Gly Ile Gln Ile Met Arg Pro Leu Phe Gln Leu Val Gln Gly Gln Gly
1               5                  10                 15

Ile Ile Gln Pro
            20

<210> SEQ ID NO 604
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 604

Gly Ile Gln Ile Leu Arg Pro Leu Phe Gln Leu Val Gln Gly Gln Gly
1               5                  10                 15

Ile Ile Gln Pro
            20

<210> SEQ ID NO 605
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 605

Gly Val Pro Ile Leu Arg Pro Leu Phe Gln Leu Ala Gln Gly Leu Gly
1               5                  10                 15

Ile Ile Gln Pro
            20

<210> SEQ ID NO 606
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      wheat gliadin peptide

<400> SEQUENCE: 606

Tyr Gln Gln Gln Gln Val Gly Gln Gly Thr Leu Val Gln Gly Gln Gly
1               5                   10                  15

Ile Ile Gln Pro
            20

<210> SEQ ID NO 607
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 607

Ser Gln His Glu Gln Val Gly Gln Gly Ser Leu Val Gln Gly Gln Gly
1               5                   10                  15

Ile Ile Gln Pro
            20

<210> SEQ ID NO 608
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 608

Ser Gln Gln Gln Gln Val Gly Gln Gly Ser Leu Val Gln Gly Gln Gly
1               5                   10                  15

Ile Ile Gln Pro
            20

<210> SEQ ID NO 609
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 609

Ser Gln Gln Gln Gln Val Gly Gln Gly Thr Leu Val Gln Gly Gln Gly
1               5                   10                  15

Ile Ile Gln Pro
            20

<210> SEQ ID NO 610
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 610

Ser Gln Gln Gln Gln Val Gly Gln Gly Ile Leu Val Gln Gly Gln Gly
1               5                   10                  15

Ile Ile Gln Pro
            20
```

<210> SEQ ID NO 611
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 611

Gly Thr Leu Val Gln Gly Gln Gly Ile Ile Gln Pro Gln Gln Pro Ala
1               5                   10                  15

Gln Leu Glu Ala
            20

<210> SEQ ID NO 612
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 612

Gly Ser Leu Val Gln Gly Gln Gly Ile Ile Gln Pro Gln Gln Pro Ala
1               5                   10                  15

Gln Leu Glu Ala
            20

<210> SEQ ID NO 613
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 613

Phe Gln Leu Val Gln Gly Gln Gly Ile Ile Gln Pro Gln Gln Pro Ala
1               5                   10                  15

Gln Leu Glu Val
            20

<210> SEQ ID NO 614
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 614

Phe Gln Leu Ala Gln Gly Leu Gly Ile Ile Gln Pro Gln Gln Pro Ala
1               5                   10                  15

Gln Leu Glu Gly
            20

<210> SEQ ID NO 615
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 615

Ile Ile Gln Pro Gln Gln Pro Ala Gln Leu Glu Ala Ile Arg Ser Leu
1               5                   10                  15

Val Leu Gln Thr
            20

<210> SEQ ID NO 616
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 616

Ile Ile Gln Pro Gln Gln Pro Ala Gln Leu Glu Val Ile Arg Ser Leu
1               5                   10                  15

Val Leu Gln Thr
            20

<210> SEQ ID NO 617
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 617

Ile Ile Gln Pro Gln Gln Pro Ala Gln Leu Glu Val Ile Arg Ser Ser
1               5                   10                  15

Val Leu Gln Thr
            20

<210> SEQ ID NO 618
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 618

Ile Ile Gln Pro Gln Gln Pro Ala Gln Tyr Glu Val Ile Arg Ser Leu
1               5                   10                  15

Val Leu Arg Thr
            20

<210> SEQ ID NO 619
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 619

Ile Ile Gln Pro Gln Gln Pro Ala Gln Leu Glu Gly Ile Arg Ser Leu
1               5                   10                  15

Val Leu Lys Thr
            20

<210> SEQ ID NO 620
<211> LENGTH: 20
<212> TYPE: PRT

<213> ORGANISM: Artificial Sequence
<220> FEATURE:
<223> OTHER INFORMATION: Description of Artificial Sequence: Synthetic
      wheat gliadin peptide

<400> SEQUENCE: 620

```
Gln Leu Glu Ala Ile Arg Ser Leu Val Leu Gln Thr Leu Pro Thr Met
1               5                   10                  15

Cys Asn Val Tyr
            20
```

<210> SEQ ID NO 621
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 621

```
Gln Leu Glu Ala Ile Arg Ser Leu Val Leu Gln Thr Leu Pro Ser Met
1               5                   10                  15

Cys Asn Val Tyr
            20
```

<210> SEQ ID NO 622
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 622

```
Gln Leu Glu Val Ile Arg Ser Leu Val Leu Gln Thr Leu Ala Thr Met
1               5                   10                  15

Cys Asn Val Tyr
            20
```

<210> SEQ ID NO 623
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 623

```
Gln Leu Glu Val Ile Arg Ser Ser Val Leu Gln Thr Leu Ala Thr Met
1               5                   10                  15

Cys Asn Val Tyr
            20
```

<210> SEQ ID NO 624
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 624

```
Gln Leu Glu Val Ile Arg Ser Leu Val Leu Gly Thr Leu Pro Thr Met
1               5                   10                  15

Cys Asn Val Phe
```

20

<210> SEQ ID NO 625
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 625

Gln Tyr Glu Val Ile Arg Ser Leu Val Leu Arg Thr Leu Pro Asn Met
1               5                   10                  15

Cys Asn Val Tyr
            20

<210> SEQ ID NO 626
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 626

Gln Leu Glu Gly Ile Arg Ser Leu Val Leu Lys Thr Leu Pro Thr Met
1               5                   10                  15

Cys Asn Val Tyr
            20

<210> SEQ ID NO 627
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 627

Val Leu Gln Thr Leu Pro Thr Met Cys Asn Val Tyr Val Pro Pro Glu
1               5                   10                  15

Cys Ser Ile Ile
            20

<210> SEQ ID NO 628
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 628

Val Leu Gln Thr Leu Pro Ser Met Cys Asn Val Tyr Val Pro Pro Glu
1               5                   10                  15

Cys Ser Ile Met
            20

<210> SEQ ID NO 629
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

```
<400> SEQUENCE: 629

Val Leu Gln Thr Leu Ala Thr Met Cys Asn Val Tyr Val Pro Pro Tyr
1               5                   10                  15

Cys Ser Thr Ile
            20

<210> SEQ ID NO 630
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 630

Val Leu Gly Thr Leu Pro Thr Met Cys Asn Val Phe Val Pro Pro Glu
1               5                   10                  15

Cys Ser Thr Thr
            20

<210> SEQ ID NO 631
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 631

Val Leu Arg Thr Leu Pro Asn Met Cys Asn Val Tyr Val Arg Pro Asp
1               5                   10                  15

Cys Ser Thr Ile
            20

<210> SEQ ID NO 632
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 632

Val Leu Lys Thr Leu Pro Thr Met Cys Asn Val Tyr Val Pro Pro Asp
1               5                   10                  15

Cys Ser Thr Ile
            20

<210> SEQ ID NO 633
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 633

Cys Asn Val Tyr Val Pro Pro Glu Cys Ser Ile Ile Lys Ala Pro Phe
1               5                   10                  15

Ser Ser Val Val
            20

<210> SEQ ID NO 634
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 634

Cys Asn Val Tyr Val Pro Pro Glu Cys Ser Ile Met Arg Ala Pro Phe
1               5                   10                  15

Ala Ser Ile Val
            20

<210> SEQ ID NO 635
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 635

Cys Asn Val Tyr Val Pro Pro Tyr Cys Ser Thr Ile Arg Ala Pro Phe
1               5                   10                  15

Ala Ser Ile Val
            20

<210> SEQ ID NO 636
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 636

Cys Asn Val Phe Val Pro Pro Glu Cys Ser Thr Thr Lys Ala Pro Phe
1               5                   10                  15

Ala Ser Ile Val
            20

<210> SEQ ID NO 637
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 637

Cys Asn Val Tyr Val Arg Pro Asp Cys Ser Thr Ile Asn Ala Pro Phe
1               5                   10                  15

Ala Ser Ile Val
            20

<210> SEQ ID NO 638
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 638

Cys Asn Val Tyr Val Pro Pro Asp Cys Ser Thr Ile Asn Val Pro Tyr
1               5                   10                  15
```

Ala Asn Ile Asp
            20

<210> SEQ ID NO 639
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 639

Cys Ser Ile Ile Lys Ala Pro Phe Ser Ser Val Val Ala Gly Ile Gly
1               5                   10                  15

Gly Gln

<210> SEQ ID NO 640
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 640

Cys Ser Ile Met Arg Ala Pro Phe Ala Ser Ile Val Ala Gly Ile Gly
1               5                   10                  15

Gly Gln

<210> SEQ ID NO 641
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 641

Cys Ser Thr Ile Arg Ala Pro Phe Ala Ser Ile Val Ala Gly Ile Gly
1               5                   10                  15

Gly Gln Tyr Arg
            20

<210> SEQ ID NO 642
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 642

Cys Ser Thr Ile Arg Ala Pro Phe Ala Ser Ile Val Ala Ser Ile Gly
1               5                   10                  15

Gly Gln

<210> SEQ ID NO 643
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 643

Cys Ser Thr Thr Lys Ala Pro Phe Ala Ser Ile Val Ala Asp Ile Gly
1               5                   10                  15

Gly Gln

<210> SEQ ID NO 644
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 644

Cys Ser Thr Ile Asn Ala Pro Phe Ala Ser Ile Val Ala Gly Ile Ser
1               5                   10                  15

Gly Gln

<210> SEQ ID NO 645
<211> LENGTH: 18
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 645

Cys Ser Thr Ile Asn Val Pro Tyr Ala Asn Ile Asp Ala Gly Ile Gly
1               5                   10                  15

Gly Gln

<210> SEQ ID NO 646
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 646

Pro Gln Gln Pro Phe Pro Leu Gln Pro Gln Gln Ser Phe Leu Trp Gln
1               5                   10                  15

Ser Gln Gln Pro
            20

<210> SEQ ID NO 647
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 647

Pro Gln Gln Ser Phe Leu Trp Gln Ser Gln Gln Pro Phe Leu Gln Gln
1               5                   10                  15

Pro Gln Gln Pro
            20

<210> SEQ ID NO 648
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

```
<400> SEQUENCE: 648

Ser Gln Gln Pro Phe Leu Gln Gln Pro Gln Gln Pro Ser Pro Gln Pro
1               5                   10                  15

Gln Gln Val Val
            20

<210> SEQ ID NO 649
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 649

Pro Gln Gln Pro Ser Pro Gln Pro Gln Gln Val Val Gln Ile Ile Ser
1               5                   10                  15

Pro Ala Thr Pro
            20

<210> SEQ ID NO 650
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 650

Gln Gln Val Val Gln Ile Ile Ser Pro Ala Thr Pro Thr Thr Ile Pro
1               5                   10                  15

Ser Ala Gly Lys
            20

<210> SEQ ID NO 651
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 651

Pro Ala Thr Pro Thr Thr Ile Pro Ser Ala Gly Lys Pro Thr Ser Ala
1               5                   10                  15

Pro Phe Pro Gln
            20

<210> SEQ ID NO 652
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 652

Ser Ala Gly Lys Pro Thr Ser Ala Pro Phe Pro Gln Gln Gln Gln Gln
1               5                   10                  15

His Gln Gln Leu
            20

<210> SEQ ID NO 653
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 653

Pro Phe Pro Gln Gln Gln Gln His Gln Gln Leu Ala Gln Gln
1               5                   10                  15

Ile Pro Val Val
            20

<210> SEQ ID NO 654
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 654

His Gln Gln Leu Ala Gln Gln Ile Pro Val Val Gln Pro Ser Ile
1               5                   10                  15

Leu Gln Gln Leu
            20

<210> SEQ ID NO 655
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 655

Ile Pro Val Val Gln Pro Ser Ile Leu Gln Gln Leu Asn Pro Cys Lys
1               5                   10                  15

Val Phe Leu Gln
            20

<210> SEQ ID NO 656
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 656

Leu Gln Gln Leu Asn Pro Cys Lys Val Phe Leu Gln Gln Gln Cys Ser
1               5                   10                  15

Pro Val Ala Met
            20

<210> SEQ ID NO 657
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 657

Val Phe Leu Gln Gln Gln Cys Ser Pro Val Ala Met Pro Gln Arg Leu
1               5                   10                  15
```

Ala Arg Ser Gln
        20

<210> SEQ ID NO 658
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 658

Pro Val Ala Met Pro Gln Arg Leu Ala Arg Ser Gln Met Leu Gln Gln
1               5                   10                  15

Ser Ser Cys His
        20

<210> SEQ ID NO 659
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 659

Ala Arg Ser Gln Met Leu Gln Gln Ser Ser Cys His Val Met Gln Gln
1               5                   10                  15

Gln Cys Cys Gln
        20

<210> SEQ ID NO 660
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 660

Ser Ser Cys His Val Met Gln Gln Gln Cys Cys Gln Gln Leu Pro Gln
1               5                   10                  15

Ile Pro Gln Gln
        20

<210> SEQ ID NO 661
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 661

Gln Cys Cys Gln Gln Leu Pro Gln Ile Pro Gln Gln Ser Arg Tyr Gln
1               5                   10                  15

Ala Ile Arg Ala
        20

<210> SEQ ID NO 662
<211> LENGTH: 20
<212> TYPE: PRT
<213> ORGANISM: Artificial Sequence
<220> FEATURE:
<223> OTHER INFORMATION: Description of Artificial Sequence: Synthetic wheat gliadin peptide

<400> SEQUENCE: 662

Pro Gln Ile Pro Gln Gln Ser Arg Tyr Glu Ala Ile Arg Ala Ile Ile
1               5                   10                  15

Tyr Ser Ile Ile
            20

<210> SEQ ID NO 663
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 663

Ile Pro Gln Gln Ser Arg Tyr Gln Ala Ile Arg Ala Ile Ile Tyr Ser
1               5                   10                  15

Ile Ile Leu Gln
            20

<210> SEQ ID NO 664
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 664

Ala Ile Arg Ala Ile Ile Tyr Ser Ile Ile Leu Gln Glu Gln Gln Gln
1               5                   10                  15

Val Gln Gly Ser
            20

<210> SEQ ID NO 665
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 665

Ile Ile Leu Gln Glu Gln Gln Gln Val Gln Gly Ser Ile Gln Ser Gln
1               5                   10                  15

Gln Gln Gln Pro
            20

<210> SEQ ID NO 666
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 666

Val Gln Gly Ser Ile Gln Ser Gln Gln Gln Pro Gln Gln Leu Gly
1               5                   10                  15

Gln Cys Val Ser
            20

```
<210> SEQ ID NO 667
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 667

Gln Gln Gln Pro Gln Gln Leu Gly Gln Cys Val Ser Gln Pro Gln Gln
1               5                   10                  15

Gln Ser Gln Gln
            20

<210> SEQ ID NO 668
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 668

Gln Cys Val Ser Gln Pro Gln Gln Ser Gln Gln Gln Leu Gly Gln
1               5                   10                  15

Gln Pro Gln Gln
            20

<210> SEQ ID NO 669
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 669

Gln Ser Gln Gln Gln Leu Gly Gln Gln Pro Gln Gln Gln Gln Leu Ala
1               5                   10                  15

Gln Gly Thr Phe
            20

<210> SEQ ID NO 670
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 670

Gln Pro Gln Gln Gln Gln Leu Ala Gln Gly Thr Phe Leu Gln Pro His
1               5                   10                  15

Gln Ile Ala Gln
            20

<210> SEQ ID NO 671
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 671

Gln Gly Thr Phe Leu Gln Pro His Gln Ile Ala Gln Leu Glu Val Met
```

```
                1               5                  10                  15

Thr Ser Ile Ala
            20

<210> SEQ ID NO 672
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 672

Gln Ile Ala Gln Leu Glu Val Met Thr Ser Ile Ala Leu Arg Ile Leu
1               5                   10                  15

Pro Thr Met Cys
            20

<210> SEQ ID NO 673
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 673

Thr Ser Ile Ala Leu Arg Ile Leu Pro Thr Met Cys Ser Val Asn Val
1               5                   10                  15

Pro Leu Tyr Arg
            20

<210> SEQ ID NO 674
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 674

Pro Thr Met Cys Ser Val Asn Val Pro Leu Tyr Arg Thr Thr Thr Ser
1               5                   10                  15

Val Pro Phe Gly
            20

<210> SEQ ID NO 675
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 675

Pro Leu Tyr Arg Thr Thr Thr Ser Val Pro Phe Gly Val Gly Thr Gly
1               5                   10                  15

Val Gly Ala Tyr
            20

<210> SEQ ID NO 676
<211> LENGTH: 20
<212> TYPE: PRT
<213> ORGANISM: Artificial Sequence
<220> FEATURE:
```

<223> OTHER INFORMATION: Description of Artificial Sequence: Synthetic
      wheat gliadin peptide

<400> SEQUENCE: 676

Thr Ile Thr Arg Thr Phe Pro Ile Pro Thr Ile Ser Ser Asn Asn Asn
1               5                   10                  15

His His Phe Arg
            20

<210> SEQ ID NO 677
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 677

Pro Thr Ile Ser Ser Asn Asn Asn His His Phe Arg Ser Asn Ser Asn
1               5                   10                  15

His His Phe His
            20

<210> SEQ ID NO 678
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 678

His His Phe Arg Ser Asn Ser Asn His His Phe His Ser Asn Asn Asn
1               5                   10                  15

Gln Phe Tyr Arg
            20

<210> SEQ ID NO 679
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 679

His His Phe His Ser Asn Asn Asn Gln Phe Tyr Arg Asn Asn Asn Ser
1               5                   10                  15

Pro Gly His Asn
            20

<210> SEQ ID NO 680
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 680

Gln Phe Tyr Arg Asn Asn Asn Ser Pro Gly His Asn Asn Pro Leu Asn
1               5                   10                  15

Asn Asn Asn Ser
            20

<210> SEQ ID NO 681
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 681

Pro Gly His Asn Asn Pro Leu Asn Asn Asn Asn Ser Pro Asn Asn
1               5                   10                  15

Ser Pro Ser Asn
            20

<210> SEQ ID NO 682
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 682

Asn Asn Asn Ser Pro Asn Asn Asn Ser Pro Ser Asn His His Asn Asn
1               5                   10                  15

Ser Pro Asn Asn
            20

<210> SEQ ID NO 683
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 683

Ser Pro Ser Asn His His Asn Asn Ser Pro Asn Asn Asn Phe Gln Tyr
1               5                   10                  15

His Thr His Pro
            20

<210> SEQ ID NO 684
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 684

Ser Pro Asn Asn Asn Phe Gln Tyr His Thr His Pro Ser Asn His Lys
1               5                   10                  15

Asn Leu Pro His
            20

<210> SEQ ID NO 685
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 685

His Thr His Pro Ser Asn His Lys Asn Leu Pro His Thr Asn Asn Ile
1               5                   10                  15

Gln Gln Gln Gln
            20

<210> SEQ ID NO 686
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 686

Asn Leu Pro His Thr Asn Asn Ile Gln Gln Gln Gln Pro Pro Phe Ser
1               5                   10                  15

Gln Gln Gln Gln
            20

<210> SEQ ID NO 687
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 687

Gln Gln Gln Gln Pro Pro Phe Ser Gln Gln Gln Pro Pro Phe Ser
1               5                   10                  15

Gln Gln Gln Gln
            20

<210> SEQ ID NO 688
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 688

Gln Gln Gln Gln Pro Pro Phe Ser Gln Gln Gln Gln Pro Val Leu Pro
1               5                   10                  15

Gln Gln Ser Pro
            20

<210> SEQ ID NO 689
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 689

Gln Gln Gln Gln Pro Val Leu Pro Gln Gln Ser Pro Phe Ser Gln Gln
1               5                   10                  15

Gln Gln Leu Val
            20

<210> SEQ ID NO 690
<211> LENGTH: 20
<212> TYPE: PRT
<213> ORGANISM: Artificial Sequence

```
<220> FEATURE:
<223> OTHER INFORMATION: Description of Artificial Sequence: Synthetic
      wheat gliadin peptide

<400> SEQUENCE: 690

Gln Gln Ser Pro Phe Ser Gln Gln Gln Leu Val Leu Pro Pro Gln
1               5                   10                  15

Gln Gln Gln Gln
            20

<210> SEQ ID NO 691
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 691

Gln Gln Leu Val Leu Pro Pro Gln Gln Gln Gln Gln Leu Val Gln
1               5                   10                  15

Gln Gln Ile Pro
            20

<210> SEQ ID NO 692
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 692

Gln Gln Gln Gln Gln Leu Val Gln Gln Gln Ile Pro Ile Val Gln Pro
1               5                   10                  15

Ser Val Leu Gln
            20

<210> SEQ ID NO 693
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 693

Gln Gln Ile Pro Ile Val Gln Pro Ser Val Leu Gln Gln Leu Asn Pro
1               5                   10                  15

Cys Lys Val Phe
            20

<210> SEQ ID NO 694
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 694

Ser Val Leu Gln Gln Leu Asn Pro Cys Lys Val Phe Leu Gln Gln Gln
1               5                   10                  15

Cys Ser Pro Val
            20
```

<210> SEQ ID NO 695
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 695

Cys Lys Val Phe Leu Gln Gln Gln Cys Ser Pro Val Ala Met Pro Gln
1               5                   10                  15

Arg Leu Ala Arg
            20

<210> SEQ ID NO 696
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 696

Cys Ser Pro Val Ala Met Pro Gln Arg Leu Ala Arg Ser Gln Met Trp
1               5                   10                  15

Gln Gln Ser Ser
            20

<210> SEQ ID NO 697
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 697

Arg Leu Ala Arg Ser Gln Met Trp Gln Gln Ser Ser Cys His Val Met
1               5                   10                  15

Gln Gln Gln Cys
            20

<210> SEQ ID NO 698
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 698

Gln Gln Ser Ser Cys His Val Met Gln Gln Gln Cys Cys Gln Gln Leu
1               5                   10                  15

Gln Gln Ile Pro
            20

<210> SEQ ID NO 699
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 699

-continued

Gln Gln Gln Cys Cys Gln Gln Leu Gln Gln Ile Pro Glu Gln Ser Arg
1               5                   10                  15

Tyr Glu Ala Ile
            20

<210> SEQ ID NO 700
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 700

Gln Gln Ile Pro Glu Gln Ser Arg Tyr Glu Ala Ile Arg Ala Ile Ile
1               5                   10                  15

Tyr Ser Ile Ile
            20

<210> SEQ ID NO 701
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 701

Tyr Glu Ala Ile Arg Ala Ile Ile Tyr Ser Ile Ile Leu Gln Glu Gln
1               5                   10                  15

Gln Gln Gly Phe
            20

<210> SEQ ID NO 702
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 702

Tyr Ser Ile Ile Leu Gln Glu Gln Gln Gln Gly Phe Val Gln Pro Gln
1               5                   10                  15

Gln Gln Gln Pro
            20

<210> SEQ ID NO 703
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 703

Gln Gln Gly Phe Val Gln Pro Gln Gln Gln Pro Gln Gln Ser Gly
1               5                   10                  15

Gln Gly Val Ser
            20

<210> SEQ ID NO 704
<211> LENGTH: 20
<212> TYPE: PRT

<213> ORGANISM: Artificial Sequence
<220> FEATURE:
<223> OTHER INFORMATION: Description of Artificial Sequence: Synthetic
      wheat gliadin peptide

<400> SEQUENCE: 704

Gln Gln Gln Pro Gln Gln Ser Gly Gln Gly Val Ser Gln Ser Gln Gln
1               5                   10                  15

Gln Ser Gln Gln
            20

<210> SEQ ID NO 705
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 705

Gln Gly Val Ser Gln Ser Gln Gln Gln Ser Gln Gln Leu Gly Gln
1               5                   10                  15

Cys Ser Phe Gln
            20

<210> SEQ ID NO 706
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 706

Gln Ser Gln Gln Gln Leu Gly Gln Cys Ser Phe Gln Gln Pro Gln Gln
1               5                   10                  15

Gln Leu Gly Gln
            20

<210> SEQ ID NO 707
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 707

Cys Ser Phe Gln Gln Pro Gln Gln Gln Leu Gly Gln Gln Pro Gln Gln
1               5                   10                  15

Gln Gln Gln Gln
            20

<210> SEQ ID NO 708
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 708

Gln Leu Gly Gln Gln Pro Gln Gln Gln Gln Gln Gln Val Leu Gln
1               5                   10                  15

Gly Thr Phe Leu

20

<210> SEQ ID NO 709
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 709

Gln Gln Gln Gln Gln Val Leu Gln Gly Thr Phe Leu Gln Pro His Gln
1               5                   10                  15

Ile Ala His Leu
            20

<210> SEQ ID NO 710
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 710

Gly Thr Phe Leu Gln Pro His Gln Ile Ala His Leu Glu Ala Val Thr
1               5                   10                  15

Ser Ile Ala Leu
            20

<210> SEQ ID NO 711
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 711

Ile Ala His Leu Glu Ala Val Thr Ser Ile Ala Leu Arg Thr Leu Pro
1               5                   10                  15

Thr Met Cys Ser
            20

<210> SEQ ID NO 712
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 712

Ser Ile Ala Leu Arg Thr Leu Pro Thr Met Cys Ser Val Asn Val Pro
1               5                   10                  15

Leu Tyr Ser Ala
            20

<210> SEQ ID NO 713
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 713

Thr Met Cys Ser Val Asn Val Pro Leu Tyr Ser Ala Thr Thr Ser Val
1               5                   10                  15

Pro Phe Gly Val
            20

<210> SEQ ID NO 714
<211> LENGTH: 19
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 714

Leu Tyr Ser Ala Thr Thr Ser Val Pro Phe Gly Val Gly Thr Gly Val
1               5                   10                  15

Gly Ala Tyr

<210> SEQ ID NO 715
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 715

Ser Cys Ile Ser Gly Leu Glu Arg Pro Trp Gln Gln Gln Pro Leu Pro
1               5                   10                  15

Pro Gln Gln Ser
            20

<210> SEQ ID NO 716
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 716

Pro Trp Gln Gln Gln Pro Leu Pro Pro Gln Gln Ser Phe Ser Gln Gln
1               5                   10                  15

Pro Pro Phe Ser
            20

<210> SEQ ID NO 717
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 717

Pro Gln Gln Ser Phe Ser Gln Gln Pro Pro Phe Ser Gln Gln Gln Gln
1               5                   10                  15

Gln Pro Leu Pro
            20

<210> SEQ ID NO 718
<211> LENGTH: 20
<212> TYPE: PRT

```
<213> ORGANISM: Artificial Sequence
<220> FEATURE:
<223> OTHER INFORMATION: Description of Artificial Sequence: Synthetic
      wheat gliadin peptide

<400> SEQUENCE: 718

Pro Pro Phe Ser Gln Gln Gln Gln Pro Leu Pro Gln Gln Pro Ser
1               5                  10                  15

Phe Ser Gln Gln
            20

<210> SEQ ID NO 719
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 719

Gln Pro Leu Pro Gln Gln Pro Ser Phe Ser Gln Gln Pro Pro Phe
1               5                  10                  15

Ser Gln Gln Gln
            20

<210> SEQ ID NO 720
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 720

Phe Ser Gln Gln Gln Pro Pro Phe Ser Gln Gln Gln Pro Ile Leu Ser
1               5                  10                  15

Gln Gln Pro Pro
            20

<210> SEQ ID NO 721
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 721

Ser Gln Gln Gln Pro Ile Leu Ser Gln Gln Pro Pro Phe Ser Gln Gln
1               5                  10                  15

Gln Gln Pro Val
            20

<210> SEQ ID NO 722
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 722

Ala Thr Ala Ala Arg Glu Leu Asn Pro Ser Asn Lys Glu Leu Gln Ser
1               5                  10                  15

Pro Gln Gln Ser
```

```
                    20

<210> SEQ ID NO 723
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 723

Pro Ser Asn Lys Glu Leu Gln Ser Pro Gln Gln Ser Phe Ser Tyr Gln
1               5                   10                  15

Gln Gln Pro Phe
            20

<210> SEQ ID NO 724
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 724

Pro Gln Gln Ser Phe Ser Tyr Gln Gln Gln Pro Phe Pro Gln Gln Pro
1               5                   10                  15

Tyr Pro Gln Gln
            20

<210> SEQ ID NO 725
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 725

Gln Gln Pro Phe Pro Gln Gln Pro Tyr Pro Gln Gln Pro Tyr Pro Ser
1               5                   10                  15

Gln Gln Pro Tyr
            20

<210> SEQ ID NO 726
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 726

Tyr Pro Gln Gln Pro Tyr Pro Ser Gln Gln Pro Tyr Pro Ser Gln Gln
1               5                   10                  15

Pro Phe Pro Thr
            20

<210> SEQ ID NO 727
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide
```

```
<400> SEQUENCE: 727

Gln Gln Pro Tyr Pro Ser Gln Gln Pro Phe Pro Thr Pro Gln Gln
1               5                   10                  15

Phe Pro Glu Gln
            20

<210> SEQ ID NO 728
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 728

Pro Phe Pro Thr Pro Gln Gln Gln Phe Pro Glu Gln Ser Gln Gln Pro
1               5                   10                  15

Phe Thr Gln Pro
            20

<210> SEQ ID NO 729
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 729

Phe Pro Glu Gln Ser Gln Gln Pro Phe Thr Gln Pro Gln Gln Pro Thr
1               5                   10                  15

Pro Ile Gln Pro
            20

<210> SEQ ID NO 730
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 730

Phe Thr Gln Pro Gln Gln Pro Thr Pro Ile Gln Pro Gln Gln Pro Phe
1               5                   10                  15

Pro Gln Gln Pro
            20

<210> SEQ ID NO 731
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 731

Pro Ile Gln Pro Gln Gln Pro Phe Pro Gln Gln Pro Gln Gln Pro Gln
1               5                   10                  15

Gln Pro Phe Pro
            20

<210> SEQ ID NO 732
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 732

Pro Gln Gln Pro Gln Gln Pro Gln Gln Pro Phe Pro Gln Pro Gln Gln
1               5                  10                  15

Pro Phe Pro Trp
            20

<210> SEQ ID NO 733
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 733

Gln Pro Phe Pro Gln Pro Gln Gln Pro Phe Pro Trp Gln Pro Gln Gln
1               5                  10                  15

Pro Phe Pro Gln
            20

<210> SEQ ID NO 734
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 734

Pro Phe Pro Trp Gln Pro Gln Gln Pro Phe Pro Gln Thr Gln Gln Ser
1               5                  10                  15

Phe Pro Leu Gln
            20

<210> SEQ ID NO 735
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 735

Pro Phe Pro Gln Thr Gln Gln Ser Phe Pro Leu Gln Pro Gln Gln Pro
1               5                  10                  15

Phe Pro Gln Gln
            20

<210> SEQ ID NO 736
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 736

Phe Pro Leu Gln Pro Gln Gln Pro Phe Pro Gln Gln Pro Gln Gln Pro
1               5                  10                  15
```

Phe Pro Gln Pro
            20

<210> SEQ ID NO 737
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 737

Phe Pro Gln Gln Pro Gln Gln Pro Phe Pro Gln Pro Gln Leu Pro Phe
1               5                   10                  15

Pro Gln Gln Ser
            20

<210> SEQ ID NO 738
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 738

Phe Pro Gln Pro Gln Leu Pro Phe Pro Gln Gln Ser Glu Gln Ile Ile
1               5                   10                  15

Pro Gln Gln Leu
            20

<210> SEQ ID NO 739
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 739

Pro Gln Gln Ser Glu Gln Ile Ile Pro Gln Gln Leu Gln Gln Pro Phe
1               5                   10                  15

Pro Leu Gln Pro
            20

<210> SEQ ID NO 740
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 740

Pro Gln Gln Leu Gln Gln Pro Phe Pro Leu Gln Pro Gln Gln Pro Phe
1               5                   10                  15

Pro Gln Gln Pro
            20

<210> SEQ ID NO 741
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 741

Pro Leu Gln Pro Gln Gln Pro Phe Pro Gln Gln Pro Gln Gln Pro Phe
1               5                   10                  15

Pro Gln Pro Gln
            20

<210> SEQ ID NO 742
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 742

Pro Gln Gln Pro Gln Gln Pro Phe Pro Gln Pro Gln Gln Pro Ile Pro
1               5                   10                  15

Val Gln Pro Gln
            20

<210> SEQ ID NO 743
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 743

Pro Gln Pro Gln Gln Pro Ile Pro Val Gln Pro Gln Gln Ser Phe Pro
1               5                   10                  15

Gln Gln Ser Gln
            20

<210> SEQ ID NO 744
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 744

Val Gln Pro Gln Gln Ser Phe Pro Gln Gln Ser Gln Gln Ser Gln Gln
1               5                   10                  15

Pro Phe Ala Gln
            20

<210> SEQ ID NO 745
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 745

Gln Gln Ser Gln Gln Ser Gln Gln Pro Phe Ala Gln Pro Gln Gln Leu
1               5                   10                  15

Phe Pro Glu Leu
            20

<210> SEQ ID NO 746

```
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 746

Pro Phe Ala Gln Pro Gln Gln Leu Phe Pro Glu Leu Gln Gln Pro Ile
1               5                   10                  15

Pro Gln Gln Pro
            20

<210> SEQ ID NO 747
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 747

Phe Pro Glu Leu Gln Gln Pro Ile Pro Gln Gln Pro Gln Gln Pro Phe
1               5                   10                  15

Pro Leu Gln Pro
            20

<210> SEQ ID NO 748
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 748

Pro Gln Gln Pro Gln Gln Pro Phe Pro Leu Gln Pro Gln Gln Pro Phe
1               5                   10                  15

Pro Gln Gln Pro
            20

<210> SEQ ID NO 749
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 749

Pro Leu Gln Pro Gln Gln Pro Phe Pro Gln Gln Pro Gln Gln Pro Phe
1               5                   10                  15

Pro Gln Gln Pro
            20

<210> SEQ ID NO 750
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 750

Pro Gln Gln Pro Gln Gln Pro Phe Pro Gln Gln Pro Gln Gln Ser Phe
1               5                   10                  15
```

```
Pro Gln Gln Pro
        20

<210> SEQ ID NO 751
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 751

Pro Gln Gln Pro Gln Gln Ser Phe Pro Gln Gln Pro Gln Gln Pro Tyr
1               5                   10                  15

Pro Gln Gln Gln
        20

<210> SEQ ID NO 752
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 752

Pro Gln Gln Pro Gln Gln Pro Tyr Pro Gln Gln Pro Tyr Gly Ser
1               5                   10                  15

Ser Leu Thr Ser
        20

<210> SEQ ID NO 753
<211> LENGTH: 16
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 753

Pro Gln Gln Gln Pro Tyr Gly Ser Ser Leu Thr Ser Ile Gly Gly Gln
1               5                   10                  15

<210> SEQ ID NO 754
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 754

Ala Arg Gln Leu Asn Pro Ser Asp Gln Glu Leu Gln Ser Pro Gln Gln
1               5                   10                  15

Leu Tyr Pro Gln
        20

<210> SEQ ID NO 755
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 755
```

-continued

```
Gln Glu Leu Gln Ser Pro Gln Leu Tyr Pro Gln Gln Pro Tyr Pro
1               5                   10                  15

Gln Gln Pro Tyr
            20

<210> SEQ ID NO 756
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 756

Ser Arg Leu Leu Ser Pro Arg Gly Lys Glu Leu His Thr Pro Gln Glu
1               5                   10                  15

Gln Phe Pro Gln
            20

<210> SEQ ID NO 757
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 757

Lys Glu Leu His Thr Pro Gln Glu Gln Phe Pro Gln Gln Gln Gln Phe
1               5                   10                  15

Pro Gln Pro Gln
            20

<210> SEQ ID NO 758
<211> LENGTH: 16
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 758

Gln Phe Pro Gln Gln Gln Gln Phe Pro Gln Pro Gln Gln Phe Pro Gln
1               5                   10                  15

<210> SEQ ID NO 759
<211> LENGTH: 5
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 759

Pro Glu Leu Pro Tyr
1               5

<210> SEQ ID NO 760
<211> LENGTH: 4
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 760
```

Pro Gln Leu Pro
1

<210> SEQ ID NO 761
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 761

Pro Gln Gln Pro Phe Pro Gln Pro Gln Leu Pro Phe Pro Gln Gln Ser
1               5                   10                  15

Glu

<210> SEQ ID NO 762
<211> LENGTH: 17
<212> TYPE: PRT
<213> ORGANISM: Artificial Sequence
<220> FEATURE:
<223> OTHER INFORMATION: Description of Artificial Sequence: Synthetic
      Barley Hordein peptide

<400> SEQUENCE: 762

Gln Gln Pro Phe Pro Leu Gln Pro Gln Leu Pro Phe Pro Gln Pro Gln
1               5                   10                  15

Gln

<210> SEQ ID NO 763
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 763

Gln Gln Thr Phe Pro Gln Gln Pro Gln Leu Pro Phe Pro Gln Gln Pro
1               5                   10                  15

Gln

<210> SEQ ID NO 764
<211> LENGTH: 17
<212> TYPE: PRT
<213> ORGANISM: Artificial Sequence
<220> FEATURE:
<223> OTHER INFORMATION: Description of Artificial Sequence: Synthetic
      Rye secalin peptide

<400> SEQUENCE: 764

Gln Gln Pro Ser Pro Gln Gln Pro Gln Leu Pro Phe Pro Gln Pro Gln
1               5                   10                  15

Gln

<210> SEQ ID NO 765
<211> LENGTH: 17
<212> TYPE: PRT
<213> ORGANISM: Artificial Sequence
<220> FEATURE:
<223> OTHER INFORMATION: Description of Artificial Sequence: Synthetic
      Barley Hordein peptide

<400> SEQUENCE: 765

```
Gln Gln Pro Phe Pro Gln Gln Pro Gln Leu Pro His Gln His Gln Phe
1               5                   10                  15
Pro
```

<210> SEQ ID NO 766
<211> LENGTH: 17
<212> TYPE: PRT
<213> ORGANISM: Artificial Sequence
<220> FEATURE:
<223> OTHER INFORMATION: Description of Artificial Sequence: Synthetic
      Wheat glutenin peptide

<400> SEQUENCE: 766

```
Leu Gln Gln Gln Pro Ile Leu Pro Gln Leu Pro Phe Ser Gln Gln Gln
1               5                   10                  15
Gln
```

<210> SEQ ID NO 767
<211> LENGTH: 17
<212> TYPE: PRT
<213> ORGANISM: Artificial Sequence
<220> FEATURE:
<223> OTHER INFORMATION: Description of Artificial Sequence: Synthetic
      Wheat glutenin peptide

<400> SEQUENCE: 767

```
His Gly Tyr Tyr Pro Thr Ser Pro Gln Leu Ser Gly Gln Gly Gln Arg
1               5                   10                  15
Pro
```

<210> SEQ ID NO 768
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 768

```
Gln Gln Cys Cys Gln Gln Leu Pro Gln Ile Pro Gln Gln Ser Arg Tyr
1               5                   10                  15
Gln
```

<210> SEQ ID NO 769
<211> LENGTH: 17
<212> TYPE: PRT
<213> ORGANISM: Artificial Sequence
<220> FEATURE:
<223> OTHER INFORMATION: Description of Artificial Sequence: Synthetic
      Wheat glutenin peptide

<400> SEQUENCE: 769

```
Gln Gln Cys Cys Gln Gln Leu Pro Gln Ile Pro Gln Gln Ser Arg Tyr
1               5                   10                  15
Glu
```

<210> SEQ ID NO 770
<211> LENGTH: 17
<212> TYPE: PRT
<213> ORGANISM: Artificial Sequence
<220> FEATURE:
<223> OTHER INFORMATION: Description of Artificial Sequence: Synthetic
      Wheat glutenin peptide

<400> SEQUENCE: 770

Gln Gln Cys Cys Arg Gln Leu Pro Gln Ile Pro Glu Gln Ser Arg Tyr
1               5                   10                  15

Asp

<210> SEQ ID NO 771
<211> LENGTH: 17
<212> TYPE: PRT
<213> ORGANISM: Artificial Sequence
<220> FEATURE:
<223> OTHER INFORMATION: Description of Artificial Sequence: Synthetic
      Barley Hordein peptide

<400> SEQUENCE: 771

Gln Gln Cys Cys Gln Gln Leu Pro Gln Ile Pro Glu Gln Phe Arg His
1               5                   10                  15

Glu

<210> SEQ ID NO 772
<211> LENGTH: 17
<212> TYPE: PRT
<213> ORGANISM: Artificial Sequence
<220> FEATURE:
<223> OTHER INFORMATION: Description of Artificial Sequence: Synthetic
      Barley Hordein peptide

<400> SEQUENCE: 772

Gln Gln Cys Cys Gln Gln Leu Pro Gln Ile Ser Glu Gln Phe Arg His
1               5                   10                  15

Glu

<210> SEQ ID NO 773
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 773

Pro Gln Gln Pro Gln Gln Pro Gln Gln Pro Phe Pro Gln Pro Gln
1               5                   10                  15

<210> SEQ ID NO 774
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 774

Gln Gln Pro Gln Gln Pro Gln Gln Pro Phe Pro Gln Pro Gln Gln
1               5                   10                  15

<210> SEQ ID NO 775
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 775

Gln Pro Gln Gln Pro Gln Gln Pro Phe Pro Gln Pro Gln Gln Pro
1               5                   10                  15

<210> SEQ ID NO 776
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 776

Pro Gln Gln Pro Gln Gln Pro Phe Pro Gln Pro Gln Gln Pro Phe
1               5                   10                  15

<210> SEQ ID NO 777
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 777

Gln Gln Pro Gln Gln Pro Phe Pro Gln Pro Gln Gln Pro Phe Pro
1               5                   10                  15

<210> SEQ ID NO 778
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 778

Pro Gln Gln Pro Phe Pro Gln Pro Gln Gln Pro Phe Pro Trp Gln
1               5                   10                  15

<210> SEQ ID NO 779
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 779

Gln Gln Pro Phe Pro Gln Pro Gln Gln Pro Phe Pro Trp Gln Pro
1               5                   10                  15

<210> SEQ ID NO 780
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 780

Gln Leu Gln Pro Phe Pro Gln Pro Pro Leu Pro Tyr Pro Gln Pro Gln
1               5                   10                  15

Ser

<210> SEQ ID NO 781
<211> LENGTH: 17
<212> TYPE: PRT
<213> ORGANISM: Artificial Sequence
<220> FEATURE:

<223> OTHER INFORMATION: Description of Artificial Sequence: Synthetic
      wheat gliadin peptide

<400> SEQUENCE: 781

Pro Gln Pro Gln Pro Phe Leu Pro Glu Leu Pro Tyr Pro Gln Pro Gln
1               5                   10                  15
Ser

<210> SEQ ID NO 782
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 782

Gln Leu Gln Pro Phe Pro Gln Pro Glu Leu Pro Tyr Leu Gln Pro Gln
1               5                   10                  15
Pro

<210> SEQ ID NO 783
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 783

Gln Leu Gln Pro Phe Pro Arg Pro Glu Leu Pro Tyr Leu Gln Pro Gln
1               5                   10                  15
Pro

<210> SEQ ID NO 784
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 784

Gln Leu Gln Pro Phe Pro Gln Pro Glu Leu Pro Tyr Ser Gln Pro Gln
1               5                   10                  15
Pro

<210> SEQ ID NO 785
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 785

Gln Leu Gln Pro Leu Pro Gln Pro Glu Leu Pro Tyr Ser Gln Pro Gln
1               5                   10                  15
Pro

<210> SEQ ID NO 786
<211> LENGTH: 17
<212> TYPE: PRT
<213> ORGANISM: Artificial Sequence

```
<220> FEATURE:
<223> OTHER INFORMATION: Description of Artificial Sequence: Synthetic
      wheat gliadin peptide

<400> SEQUENCE: 786

Gln Leu Gln Pro Ser Pro Gln Pro Glu Leu Pro Tyr Ser Gln Pro Gln
1               5                   10                  15

Pro

<210> SEQ ID NO 787
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 787

Gln Leu Gln Pro Phe Pro Gln Pro Glu Leu Ser Tyr Ser Gln Pro Gln
1               5                   10                  15

Pro

<210> SEQ ID NO 788
<211> LENGTH: 17
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 788

Pro Gln Pro Gln Pro Phe Pro Pro Glu Leu Pro Tyr Pro Gln Pro Gln
1               5                   10                  15

Ser

<210> SEQ ID NO 789
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 789

Pro Gln Gln Pro Glu Gln Pro Gln Gln Pro Phe Pro Gln Pro Gln Gln
1               5                   10                  15

Pro Phe Pro Trp
            20

<210> SEQ ID NO 790
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 790

Pro Gln Gln Pro Gln Gln Pro Glu Gln Pro Phe Pro Gln Pro Gln Gln
1               5                   10                  15

Pro Phe Pro Trp
            20

<210> SEQ ID NO 791
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 791

Pro Gln Gln Pro Gln Gln Pro Gln Gln Pro Phe Pro Gln Pro Glu Gln
1               5                   10                  15

Pro Phe Pro Trp
            20

<210> SEQ ID NO 792
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 792

Pro Gln Gln Pro Arg Gln Pro Gln Gln Pro Phe Pro Gln Pro Gln Gln
1               5                   10                  15

Pro Phe Pro Trp
            20

<210> SEQ ID NO 793
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 793

Pro Gln Gln Pro Gln Gln Pro Arg Gln Pro Phe Pro Gln Pro Gln Gln
1               5                   10                  15

Pro Phe Pro Trp
            20

<210> SEQ ID NO 794
<211> LENGTH: 20
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 794

Pro Gln Gln Pro Gln Gln Pro Gln Gln Pro Phe Pro Gln Pro Arg Gln
1               5                   10                  15

Pro Phe Pro Trp
            20

<210> SEQ ID NO 795
<211> LENGTH: 15
<212> TYPE: PRT
<213> ORGANISM: Artificial Sequence
<220> FEATURE:
<223> OTHER INFORMATION: Description of Artificial Sequence: Synthetic
      wheat gliadin peptide

<400> SEQUENCE: 795

Glu Gln Pro Phe Pro Gln Pro Glu Gln Pro Phe Pro Trp Gln Pro
1               5                   10                  15
```

```
<210> SEQ ID NO 796
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 796

Gln Leu Gln Pro Ser Pro Gln Pro Gln Leu Pro Tyr Pro Gln Pro Gln
1               5                   10                  15

<210> SEQ ID NO 797
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 797

Gln Leu Gln Pro Phe Pro Gln Pro Glu Leu Pro Val Pro Gln Pro Gln
1               5                   10                  15

Ser

<210> SEQ ID NO 798
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 798

Gln Leu Gln Pro Phe Pro Gln Pro Gln Leu Phe Val Phe Gln Pro Gln
1               5                   10                  15

Leu

<210> SEQ ID NO 799
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(7)
<223> OTHER INFORMATION: Any amino acid
<220> FEATURE:
<221> NAME/KEY: MOD_RES
<222> LOCATION: (13)..(17)
<223> OTHER INFORMATION: Any amino acid

<400> SEQUENCE: 799

Xaa Xaa Xaa Xaa Xaa Xaa Xaa Pro Gln Leu Pro Tyr Xaa Xaa Xaa Xaa
1               5                   10                  15

Xaa

<210> SEQ ID NO 800
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)..(5)
<223> OTHER INFORMATION: Tyr or Phe

<400> SEQUENCE: 800

Pro Gln Leu Pro Xaa
1               5

<210> SEQ ID NO 801
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 801

Phe Pro Gln Pro Gln Gln Thr Phe Pro His Gln Pro Gln Gln Gln Phe
1               5                   10                  15

Pro

<210> SEQ ID NO 802
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 802

Gln Gln Pro Phe Pro Gln Pro Gln Gln Pro Gln Leu Pro Phe Pro Gln
1               5                   10                  15

<210> SEQ ID NO 803
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 803

Gln Leu Gln Pro Phe Leu Gln Pro Glu Leu Pro Tyr Ser Gln Pro Gln
1               5                   10                  15

Pro

<210> SEQ ID NO 804
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 804

Gln Pro Gln Pro Phe Pro Pro Pro Glu Leu Pro Tyr Pro Gln Thr Gln
1               5                   10                  15

Pro

<210> SEQ ID NO 805
<211> LENGTH: 17
<212> TYPE: PRT
<213> ORGANISM: Artificial Sequence
<220> FEATURE:
<223> OTHER INFORMATION: Description of Artificial Sequence: Synthetic
```

```
                                  peptide

<400> SEQUENCE: 805

Pro Gln Pro Gln Pro Phe Pro Pro Glu Leu Pro Tyr Pro Gln Thr Gln
1               5                   10                  15

Pro

<210> SEQ ID NO 806
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 806

Gln Leu Gln Pro Phe Pro Gln Pro Glu Leu Ser Tyr Ser Gln Pro Gln
1               5                   10                  15

Pro

<210> SEQ ID NO 807
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 807

Pro Gln Pro Gln Pro Phe Leu Pro Glu Leu Pro Tyr Pro Gln Pro Gln
1               5                   10                  15

Ser

<210> SEQ ID NO 808
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 808

Pro Gln Pro Gln Pro Phe Pro Pro Glu Leu Pro Tyr Pro Gln Pro Pro
1               5                   10                  15

Pro
```

THERAPEUTIC EPITOPES AND USES THEREOF

CROSS REFERENCE TO RELATED APPLICATIONS

This application is a National Stage Entry of PCT/GB03/02450 filed Jun. 5, 2003, which claims benefit of priority of UK Application No. 0212885.8, filed Jun. 5, 2002.

SEQUENCE LISTING

The instant application contains a Sequence Listing which has been submitted electronically in ASCII format and is hereby incorporated by reference in its entirety. Said ASCII copy, created on Aug. 12, 2016, is named 07588_0148-00_SL.txt and is 270,169 bytes in size.

The invention relates to epitopes useful in the diagnosis and therapy of coeliac disease, including diagnostics, therapeutics, kits, and methods of using the foregoing.

An immune reaction to gliadin (a component of gluten) in the diet causes coeliac disease. It is known that immune responses in the intestinal tissue preferentially respond to gliadin which has been modified by an intestinal transglutaminase. Coeliac disease is diagnosed by detection of anti-endomysial antibodies, but this requires confirmation by the finding of a lymphocytic inflammation in intestinal biopsies. The taking of such a biopsy is inconvenient for the patient.

Investigators have previously assumed that only intestinal T cell responses provide an accurate indication of the immune response against gliadins. Therefore they have concentrated on the investigation of T cell responses in intestinal tissue[1]. Gliadin epitopes which require transglutaminase modification (before they are recognised by the immune system) are known[2].

The inventors have found the immunodominant T cell A-gliadin epitope recognised by the immune system in coeliac disease, and have shown that this is recognised by T cells in the peripheral blood of individuals with coeliac disease (see WO 01/25793). Such T cells were found to be present at high enough frequencies to be detectable without restimulation (i.e. a 'fresh response' detection system could be used). The epitope was identified using a non-T cell cloning based method which provided a more accurate reflection of the epitopes being recognised. The immunodominant epitope requires transglutaminase modification (causing substitution of a particular glutamine to glutamate) before immune system recognition.

Based on this work the inventors have developed a test which can be used to diagnose coeliac disease at an early stage. The test may be carried out on a sample from peripheral blood and therefore an intestinal biopsy is not required. The test is more sensitive than the antibody tests which are currently being used.

The invention thus provides a method of diagnosing coeliac disease, or susceptibility to coeliac disease, in an individual comprising:

(a) contacting a sample from the host with an agent selected from (i) the epitope comprising sequence which is: SEQ ID NO:1 (PQPELPY) or SEQ ID NO:2 (QLQPFPQPELPYPQPQS), or an equivalent sequence from a naturally occurring homologue of the gliadin represented by SEQ ID NO:3, (ii) an epitope comprising sequence comprising: SEQ ID NO:1, or an equivalent sequence from a naturally occurring homologue of the gliadin represented by SEQ ID NO:3 (shown in Table 1), which epitope is an isolated oligopeptide derived from a gliadin protein, (iii) an analogue of (i) or (ii) which is capable of being recognised by a T cell receptor that recognises (i) or (ii), which in the case of a peptide analogue is not more than 50 amino acids in length, or (iv) a product comprising two or more agents as defined in (i), (ii) or (iii), and (b) determining in vitro whether T cells in the sample recognise the agent, recognition by the T cells indicating that the individual has, or is susceptible to, coeliac disease.

Through comprehensive mapping of wheat gliadin T cell epitopes (see Example 13), the inventors have also found epitopes bioactive in coeliac disease in HLA-DQ2+ patients in other wheat gliadins, having similar core sequences (e.g., SEQ ID NOS:18-22) and similar full length sequences (e.g., SEQ ID NOS:31-36), as well as in rye secalins and barley hordeins (e.g., SEQ ID NOS:39-41); see also Tables 20 and 21. Additionally, several epitopes bioactive in coeliac disease in HLA-DQ8+ patients have been identified (e.g., SEQ ID NOS:42-44, 46). This comprehensive mapping thus provides the dominant epitopes recognized by T cells in coeliac patients. Thus, the above-described method and other methods of the invention described herein may be performed using any of these additional identified epitopes, and analogues and equivalents thereof; (i) and (ii) herein include these additional epitopes. That is, the agents of the invention also include these novel epitopes.

The invention also provides use of the agent for the preparation of a diagnostic means for use in a method of diagnosing coeliac disease, or susceptibility to coeliac disease, in an individual, said method comprising determining whether T cells of the individual recognise the agent, recognition by the T cells indicating that the individual has, or is susceptible to, coeliac disease.

The finding of an immunodominant epitope which is modified by transglutaminase (as well as the additional other epitopes defined herein) also allows diagnosis of coeliac disease based on determining whether other types of immune response to this epitope are present. Thus the invention also provides a method of diagnosing coeliac disease, or susceptibility to coeliac disease, in an individual comprising determining the presence of an antibody that binds to the epitope in a sample from the individual, the presence of the antibody indicating that the individual has, or is susceptible to, coeliac disease.

The invention additionally provides the agent, optionally in association with a carrier, for use in a method of treating or preventing coeliac disease by tolerising T cells which recognise the agent. Also provided is an antagonist of a cell which has a T cell receptor that recognises (i) or (ii), optionally in association with a carrier, for use in a method of treating or preventing coeliac disease by antagonising such T cells. Additionally provided is the agent or an analogue that binds an antibody (that binds the agent) for use in a method of treating or preventing coeliac disease in an individual by tolerising the individual to prevent the production of such an antibody.

The invention provides a method of determining whether a composition is capable of causing coeliac disease comprising determining whether a protein capable of being modified by a transglutaminase to an oligopeptide sequence as defined above is present in the composition, the presence of the protein indicating that the composition is capable of causing coeliac disease.

The invention also provides a mutant gliadin protein whose wild-type sequence can be modified by a transglutaminase to a sequence that comprises an epitope comprising sequence as defined above, but which mutant gliadin protein has been modified in such a way that it does not contain sequence which can be modified by a transglutaminase to a sequence that comprises such an epitope comprising sequence; or a fragment of such a mutant gliadin protein which is at least 15 amino acids long and which comprises sequence which has been modified in said way.

The invention also provides a protein that comprises a sequence which is able to bind to a T cell receptor, which T cell receptor recognises the agent, and which sequence is able to cause antagonism of a T cell that carries such a T cell receptor.

Additionally the invention provides a food that comprises the proteins defined above.

SUMMARY OF THE INVENTION

The present invention provides methods of preventing or treating coeliac disease comprising administering to an individual at least one agent selected from: a) a peptide comprising at least one epitope comprising a sequence selected from the group consisting of SEQ ID NOs:18-22, 31-36, 39-44, and 46, and equivalents thereof; and b) an analogue of a) which is capable of being recognised by a T cell receptor that recognises the peptide of a) and which is not more than 50 amino acids in length; and c) optionally, in addition to the agent selected from a) and b), a peptide comprising at least one epitope comprising a sequence selected from SEQ ID NO:1 and SEQ ID NO:2. In some embodiments, the agent is HLA-DQ2-restricted, HLA-DQ8-restricted or one agent is HLA-DQ2-restricted and a second agent is HLA-DQ8-restricted. In some embodiments, the agent comprises a wheat epitope, a rye epitope, a barley epitope or any combination thereof either as a single agent or as multiple agents.

The present invention also provides methods of preventing or treating coeliac disease comprising administering to an individual a pharmaceutical composition comprising an agent above and pharmaceutically acceptable carrier or diluent.

The present invention also provides methods of preventing or treating coeliac disease comprising administering to an individual a pharmaceutical composition comprising an antagonist of a T cell which has a T cell receptor as defined above, and a pharmaceutically acceptable carrier or diluent. The present invention also provides methods of preventing or treating coeliac disease comprising administering to an individual a composition for tolerising an individual to a gliadin protein to suppress the production of a T cell or antibody response to an agent as defined above, which composition comprises an agent as defined above.

The present invention also provides methods of preventing or treating coeliac disease by 1) diagnosing coeliac disease in an individual by either: a) contacting a sample from the host with at least one agent selected from: i) a peptide comprising at least one epitope comprising a sequence selected from the group consisting of: SEQ ID NOS:18-22, 31-36, 39-44, and 46, and equivalents thereof; and ii) an analogue of i) which is capable of being recognised by a T cell receptor that recognises i) and which is not more than 50 amino acids in length; and iii) optionally, in addition to the agent selected from i) and ii), a peptide comprising at least one epitope comprising a sequence selected from SEQ ID NOS:1 and 2; and determining in vitro whether T cells in the sample recognise the agent; recognition by the T cells indicating that the individual has, or is susceptible to, coeliac disease; or b) administering an agent as defined above and determining in vivo whether T cells in the individual recognise the agent, recognition of the agent indicating that the individual has or is susceptible to coeliac disease; and 2) administering to an individual diagnosed as having, or being susceptible to, coeliac disease a therapeutic agent for preventing or treating coeliac disease.

The present invention also provides agents as defined above, optionally in association with a carrier, for use in a method of treating or preventing coeliac disease by tolerising T cells which recognise the agent.

The present invention also provides antagonists of a T cell which has a T cell receptor as defined above, optionally in association with a carrier, for use in a method of treating or preventing coeliac disease by antagonising such T cells.

The present invention also provides proteins that comprises a sequence which is able to bind to a T cell receptor, which T cell receptor recognises an agent as defined above, and which sequence is able to cause antagonism of a T cell that carries such a T cell receptor.

The present invention also provides pharmaceutical compositions comprising an agent or antagonist as defined and a pharmaceutically acceptable carrier or diluent.

The present invention also provides compositions for tolerising an individual to a gliadin protein to suppress the production of a T cell or antibody response to an agent as defined above, which composition comprises an agent as defined above.

The present invention also provides compositions for antagonising a T cell response to an agent as defined above, which composition comprises an antagonist as defined above.

The present invention also provides mutant gliadin proteins whose wild-type sequence can be modified by a transglutaminase to a sequence which is an agent as defined in claim 1, which mutant gliadin protein comprises a mutation which prevents its modification by a transglutaminase to a sequence which is an agent as defined above; or a fragment of such a mutant gliadin protein which is at least 15 amino acids long and which comprises the mutation.

The present invention also provides polynucleotides that comprises a coding sequence that encodes a protein or fragment as defined above.

The present invention also provides cells comprising a polynucleotide as defined above or which has been transformed with such a polynucleotide.

The present invention also provides mammals that expresses a T cell receptor as defined above.

The present invention also provides methods of diagnosing coeliac disease, or susceptibility to coeliac disease, in an individual comprising: a) contacting a sample from the host with at least one agent selected from i) a peptide comprising at least one epitope comprising a sequence selected from the group consisting of: SEQ ID NOS:18-22, 31-36, 39-44, and 46, and equivalents thereof; and ii) an analogue of i) which is capable of being recognised by a T cell receptor that recognises i) and which is not more than 50 amino acids in length; and iii) optionally, in addition to the agent selected from i) and ii), a peptide comprising at least one epitope comprising a sequence selected from SEQ ID NOS:1 and 2; and b) determining in vitro whether T cells in the sample recognise the agent; recognition by the T cells indicating that the individual has, or is susceptible to, coeliac disease.

The present invention also provides methods of determining whether a composition is capable of causing coeliac disease comprising determining whether a protein capable of being modified by a transglutaminase to an oligopeptide sequence is present in the composition, the presence of the protein indicating that the composition is capable of causing coeliac disease.

The present invention also provides methods of identifying an antagonist of a T cell, which T cell recognises an agent as defined above, comprising contacting a candidate substance with the T cell and detecting whether the substance causes a decrease in the ability of the T cell to undergo an antigen specific response, the detecting of any such decrease in said ability indicating that the substance is an antagonist.

The present invention also provides kits for carrying out any of the method described above comprising an agent as defined above and a means to detect the recognition of the peptide by the T cell.

The present invention also provides methods of identifying a product which is therapeutic for coeliac disease comprising administering a candidate substance to a mammal as defined above which has, or which is susceptible to, coeliac disease and determining whether substance prevents or treats coeliac disease in the mammal, the prevention or treatment of coeliac disease indicating to that the substance is a therapeutic product.

The present invention also provides processes for the production of a protein encoded by a coding sequence as defined above which process comprises: a) cultivating a cell described above under conditions that allow the expression of the protein; and optionally b) recovering the expressed protein.

The present invention also provides methods of obtaining a transgenic plant cell comprising transforming a plant cell with a vector as described above to give a transgenic plant cell.

The present invention also provides methods of obtaining a first-generation transgenic plant comprising regenerating a transgenic plant cell transformed with a vector as described above to give a transgenic plant.

The present invention also provides methods of obtaining a transgenic plant seed comprising obtaining a transgenic seed from a transgenic plant obtainable as described above.

The present invention also provides methods of obtaining a transgenic progeny plant comprising obtaining a second-generation transgenic progeny plant from a first-generation transgenic plant obtainable by a method as described above, and optionally obtaining transgenic plants of one or more further generations from the second-generation progeny plant thus obtained.

The present invention also provides transgenic plant cells, plants, plant seeds or progeny plants obtainable by any of the methods described above.

The present invention also provides transgenic plants or plant seeds comprising plant cells as described above.

The present invention also provides transgenic plant cell calluses comprising plant cells as described above obtainable from a transgenic plant cell, first-generation plant, plant seed or progeny as defined above.

The present invention also provides methods of obtaining a crop product comprising harvesting a crop product from a plant according to any method described above and optionally further processing the harvested product.

The present invention also provides food that comprises a protein as defined above.

BRIEF DESCRIPTION OF THE DRAWINGS

The patent or application file contains at least one drawing executed in color. Copies of this patent or patent application with color drawing(s) will be provided by the Office upon request and payment of the necessary fee.

The invention is illustrated by the accompanying drawings in which:

FIG. 4 shows how the minimal structure of the dominant A-gliadin epitope was mapped using tTG-treated 7-17mer A-gliadin peptides (0.1 µM) including the sequence, PQP QLPY (SEQ ID NO:4) (A-gliadin 62-68) (a), and the same peptides without tTG treatment but with the substitution Q→E65 (b). Each line represents PBMC IFNγ ELISPOT responses in each of three Coeliac disease subjects on day 6 or 7 after bread was ingested on days 1-3. (In individual subjects, ELISPOT responses were calculated as a % of the response elicited by the 17mer, A-gliadin 57-73 (SEQ ID NO:10).)

FIG. 7 shows that tTG treated A-gliadin 56-75 (SEQ ID NO:5) (0.1 µM) elicited IFN-g ELISPOT responses in (a) CD4 and CD8 magnetic bead depleted PBMC. (Bars represent CD4 depleted PBMC responses as a % of CD8 depleted PBMC responses; spot forming cells per million CD8 depleted PBMC were: Subject 4: 29, and Subject 6: 535). (b) PBMC IFNγ ELISPOT responses (spot forming cells/million PBMC) after incubation with monoclonal antibodies to HLA-DR (L243), -DQ (L2) and -DP (B7.21) (10 µg/ml) 1 h prior to tTG-treated 56-75 (0.1 µM) in two coeliac disease subjects homozygous for HLA-DQ a1*0501, b1*0201.

FIG. 10 shows CD8, CD4, β$_7$, and α$^E$-specific immunomagnetic bead depletion of peripheral blood mononuclear cells from two coeliac subjects 6 days after commencing gluten challenge followed by interferon gamma ELISpot. A-gliadin 57-73 QE65 (SEQ ID NO:2) (25 mcg/ml), tTG-treated chymotrypsin-digested gliadin (100 mcg/ml) or PPD (10 mcg/ml) were used as antigen.

FIGS. 17 to 27 show the agonist activity of A-gliadin 57-73 QE65 (SEQ ID NO: 2) variants. On Sheets 25 through 35 of 47, FIGS. 17 through 27 disclose the amino acid sequence SEQ ID NO:2.

FIG. 29 shows bioactivity of prolamin homologues of A-gliadin 57-73 (SEQ ID NO:10).

FIG. 30 shows, for healthy HLA-DQ2 subjects, the change in IFNgamma ELISpot responses to tTG-deamidated gliadin peptide pools.

FIG. 31 shows, for coeliac HLA-DQ2 subjects, the change in IFNgamma ELISpot responses to tTG-deamidated gliadin peptide pools.

FIG. 32 shows individual peptide contributions to "summed" gliadin peptide response.

FIG. 33 shows, for coeliac HLA-DQ2/8 subject C08, gluten challenge induced IFNγ ELISpot responses to tTG-deamidated gliadin peptide pools.

FIG. 34 shows, for coeliac HLA-DQ2/8 subject C07, gluten challenge induced IFNγ ELISpot responses to tTG-deamidated gliadin peptide pools.

FIG. 35 shows, for coeliac HLA-DQ8/7 subject C12, gluten challenge induced IFNγ ELISpot responses to tTG-deamidated gliadin peptide pools.

FIG. 36 shows, for coeliac HLA-DQ6/8 subject C11, gluten challenge induced IFNγ ELISpot responses to tTG-deamidated gliadin peptide pools.

DETAILED DESCRIPTION OF THE INVENTION

Figure 1B:
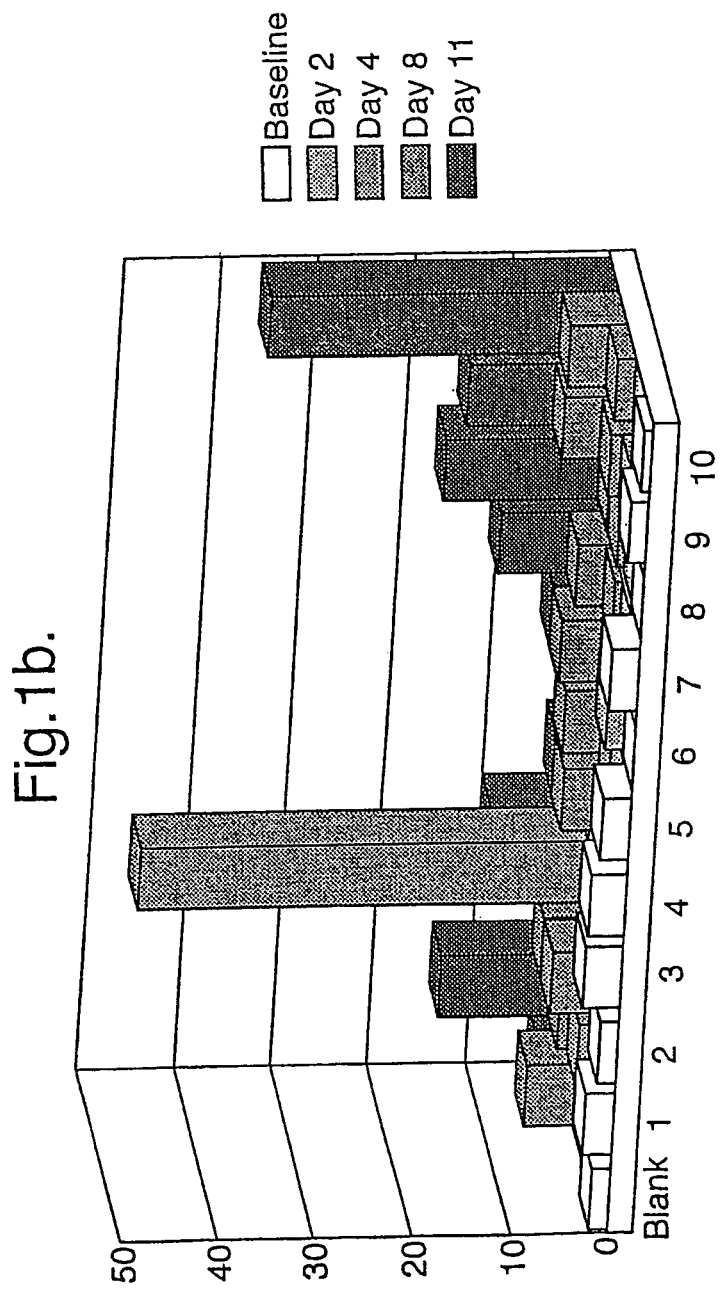
FIG. 1 shows freshly isolated PBMC (peripheral blood mononuclear cell) IFNγ ELISPOT responses (vertical axis shows spot forming cells per $10^6$ PBMC) to transglutaminase (tTG)-treated and untreated peptide pool 3 (each peptide 10 µg/ml) including five overlapping 15mers spanning A-gliadin 51-85 (see Table 1) and a-chymotrypsin-digested gliadin (40 µg/ml) in coeliac disease Subject 1, initially in remission following a gluten free diet then challenged with 200 g bread daily for three days from day 1 (a). PBMC IFNγ ELISPOT responses by Subject 2 to tTG-treated A-gliadin peptide pools 1-10 spanning the complete A-gliadin protein during ten day bread challenge (b). The horizontal axis shows days after commencing bread.

The term "coeliac disease" encompasses a spectrum of conditions caused by varying degrees of gluten sensitivity, including a severe form characterised by a flat small intestinal mucosa (hyperplastic villous atrophy) and other forms characterised by milder symptoms.

The individual mentioned above (in the context of diagnosis or therapy) is human. They may have coeliac disease (symptomatic or asymptomatic) or be suspected of having it. They may be on a gluten free diet. They may be in an acute phase response (for example they may have coeliac disease, but have only ingested gluten in the last 24 hours before which they had been on a gluten free diet for 14 to 28 days).

The individual may be susceptible to coeliac disease, such as a genetic susceptibility (determined for example by the individual having relatives with coeliac disease or possessing genes which cause predisposition to coeliac disease).

The Agent

The agent is typically a peptide, for example of length 7 to 50 amino acids, such as 10 to 40, or 15 to 30 amino acids in length.

SEQ ID NO:1 is PQPELPY. SEQ ID NO:2 is QLQP-FPQPELPYPQPQS. SEQ ID NO:3 is shown in Table 1 and is the sequence of a whole A-gliadin. The glutamate at position 4 of SEQ ID NO:1 (equivalent to position 9 of SEQ ID NO:2) is generated by transglutaminase treatment of A-gliadin.

The agent may be the peptide represented by SEQ ID NO:1 or 2 or an epitope comprising sequence that comprises SEQ ID NO:1 which is an isolated oligopeptide derived from a gliadin protein; or an equivalent of these sequences from a naturally occurring gliadin protein which is a homologue of SEQ ID NO:3. Thus the epitope may be a derivative of the protein represented by SEQ ID NO:3. Such a derivative is typically a fragment of the gliadin, or a mutated derivative of the whole protein or fragment. Therefore the epitope of the invention does not include this naturally occurring whole gliadin protein, and does not include other whole naturally occurring gliadins.

The epitope may thus be a fragment of A-gliadin (e.g. SEQ ID NO:3), which comprises the sequence of SEQ ID NO:1, obtainable by treating (fully or partially) with transglutaminase, i.e. with 1, 2, 3 or more glutamines substituted to glutamates (including the substitution within SEQ ID NO:1).

Such fragments may be or may include the sequences represented by positions 55 to 70, 58 to 73, 61 to 77 of SEQ ID NO:3 shown in Table 1. Typically such fragments will be recognised by T cells to at least the same extent that the peptides represented by SEQ ID NO:1 or 2 are recognised in any of the assays described herein using samples from coeliac disease patients.

Additionally, the agent may be the peptide represented by any of SEQ ID NOS:18-22, 31-36, 39-44, and 46 or a protein comprising a sequence corresponding to any of SEQ ID NOS:18-22, 31-36, 39-44, and 46 (such as fragments of a gliadin comprising any of SEQ ID NOS:18-22, 31-36, 39-44, and 46, for example after the gliadin has been treated with transglutaminase). Bioactive fragments of such sequences are also agents of the invention. Sequences equivalent to any of SEQ ID NOS:18-22, 31-36, 39-44, and 46 or analogues of these sequences are also agents of the invention.

In the case where the epitope comprises a sequence equivalent to the above epitopes (including fragments) from another gliadin protein (e.g. any of the gliadin proteins mentioned herein or any gliadins which cause coeliac disease), such equivalent sequences will correspond to a fragment of a gliadin protein typically treated (partially or fully) with transglutaminase. Such equivalent peptides can be determined by aligning the sequences of other gliadin proteins with the gliadin from which the original epitope derives, such as with SEQ ID NO:3 (for example using any of the programs mentioned herein). Transglutaminase is commercially available (e.g. Sigma T-5398). Table 4 provides a few examples of suitable equivalent sequences.

The agent which is an analogue is capable of being recognised by a TCR which recognises (i) or (ii). Therefore generally when the analogue is added to T cells in the presence of (i) or (ii), typically also in the presence of an antigen presenting cell (APC) (such as any of the APCs mentioned herein), the analogue inhibits the recognition of (i) or (ii), i.e. the analogue is able to compete with (i) or (ii) in such a system.

The analogue may be one which is capable of binding the TCR which recognises (i) or (ii). Such binding can be tested by standard techniques. Such TCRs can be isolated from T cells which have been shown to recognise (i) or (ii) (e.g. using the method of the invention). Demonstration of the binding of the analogue to the TCRs can then shown by determining whether the TCRs inhibit the binding of the analogue to a substance that binds the analogue, e.g. an antibody to the analogue. Typically the analogue is bound to a class II MHC molecule (e.g. HLA-DQ2) in such an inhibition of binding assay.

Typically the analogue inhibits the binding of (i) or (ii) to a TCR. In this case the amount of (i) or (ii) which can bind the TCR in the presence of the analogue is decreased. This is because the analogue is able to bind the TCR and therefore competes with (i) or (ii) for binding to the TCR.

T cells for use in the above binding experiments can be isolated from patients with coeliac disease, for example with the aid of the method of the invention. Other binding characteristics of the analogue may also be the same as (i) or (ii), and thus typically the analogue binds to the same MHC class II molecule to which the peptide binds (HLA-DQ2 or -DQ8). The analogue typically binds to antibodies specific for (i) or (ii), and thus inhibits binding of (i) or (ii) to such antibodies.

The analogue is typically a peptide. It may have homology with (i) or (ii), typically at least 70% homology, preferably at least 80, 90%, 95%, 97% or 99% homology with (i) or (ii), for example over a region of at least 15 more (such as the entire length of the analogue and/or (i) or (ii), or across the region which contacts the TCR or binds the MHC molecule) contiguous amino acids. Methods of measuring protein homology are well known in the art and it will be understood by those of skill in the art that in the present context, homology is calculated on the basis of amino acid identity (sometimes referred to as "hard homology").

For example the UWGCG Package provides the BEST-FIT program which can be used to calculate homology (for example used on its default settings) (Devereux et al (1984) *Nucleic Acids Research* 12, p 387-395). The PILEUP and BLAST algorithms can be used to calculate homology or line up sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information on the world wide web through the internet at, for example, "www.ncbi.nlm.nih.govl". This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous peptide analogues typically differ from (i) or (ii) by 1, 2, 3, 4, 5, 6, 7, 8 or more mutations (which may be substitutions, deletions or insertions). These mutations may be measured across any of the regions mentioned above in relation to calculating homology. The substitutions are preferably 'conservative'. These are defined according to the following Table. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Typically the amino acids in the analogue at the equivalent positions to amino acids in (i) or (ii) that contribute to binding the MHC molecule or are responsible for the recognition by the TCR, are the same or are conserved.

Typically the analogue peptide comprises one or more modifications, which may be natural post-translation modifications or artificial modifications. The modification may provide a chemical moiety (typically by substitution of a hydrogen, e.g. of a C—H bond), such as an amino, acetyl, hydroxy or halogen (e.g. fluorine) group or carbohydrate group. Typically the modification is present on the N or C terminus.

The analogue may comprise one or more non-natural amino acids, for example amino acids with a side chain different from natural amino acids. Generally, the non-natural amino acid will have an N terminus and/or a C terminus. The non-natural amino acid may be an L- or a D-amino acid.

The analogue typically has a shape, size, flexibility or electronic configuration that is substantially similar to (i) or (ii). It is typically a derivative of (i) or (ii). In one embodiment the analogue is a fusion protein comprising the sequence of SEQ ID NO:1 or 2, or any of the other peptides mentioned herein; and non-gliadin sequence.

In one embodiment the analogue is or mimics (i) or (ii) bound to a MHC class II molecule. 2, 3, 4 or more of such complexes may be associated or bound to each other, for example using a biotin/streptavidin based system, in which typically 2, 3 or 4 biotin labelled MHC molecules bind to a streptavidin moiety.

This analogue typically inhibits the binding of the (i) or (ii)/MHC Class II complex to a TCR or antibody which is specific for the complex.

The analogue is typically an antibody or a fragment of an antibody, such as a Fab or (Fab)$_2$ fragment. The analogue may be immobilised on a solid support, particularly an analogue that mimics peptide bound to a MHC molecule.

The analogue is typically designed by computational means and then synthesised using methods known in the art. Alternatively the analogue can be selected from a library of compounds. The library may be a combinatorial library or a display library, such as a phage display library. The library of compounds may be expressed in the display library in the form of being bound to a MHC class II molecule, such as HLA-DQ2 or -DQ8. Analogues are generally selected from the library based on their ability to mimic the binding characteristics (i) or (ii). Thus they may be selected based on ability to bind a TCR or antibody which recognises (i) or (ii).

Typically analogues will be recognised by T cells to at least the same extent as any of the agents (i) or (ii), for example at least to the same extent as the equivalent epitope and preferably to the same extent as the peptide represented by SEQ ID NO:2, is recognised in any of the assays described herein, typically using T cells from coeliac disease patients. Analogues may be recognised to these extents in vivo and thus may be able to induce coeliac disease symptoms to at least the same extent as any of the agents mentioned herein (e.g. in a human patient or animal model).

Analogues may be identified in a method comprising determining whether a candidate substance is recognised by a T cell receptor that recognises an epitope of the invention, recognition of the substance indicating that the substance is an analogue. Such TCRs may be any of the TCRs mentioned herein, and may be present on T cells. Any suitable assay mentioned herein can be used to identify the analogue. In one embodiment this method is carried out in vivo. As mentioned above preferred analogues are recognised to at least the same extent as the peptide SEQ ID NO:2, and so the method may be used to identify analogues which are recognised to this extent.

In one embodiment the method comprises determining whether a candidate substance is able to inhibit the recognition of an epitope of the invention, inhibition of recognition indicating that the substance is an analogue.

The agent may be a product comprising at least 2, 5, 10 or 20 agents as defined by (i), (ii) or (iii). Typically the composition comprises epitopes of the invention (or equivalent analogues) from different gliadins, such as any of the species or variety of or types of gliadin mentioned herein. Preferred compositions comprise at least one epitope of the invention, or equivalent analogue, from all of the gliadins present in any of the species or variety mentioned herein, or from 2, 3, 4 or more of the species mentioned herein (such as from the panel of species consisting of wheat, rye, barley, oats and triticale). Thus, the agent may be monovalent or multivalent.

Diagnosis

As mentioned above the method of diagnosis of the invention may be based on the detection of T cells that bind the agent or on the detection of antibodies that recognise the agent.

The T cells that recognise the agent in the method (which includes the use mentioned above) are generally T cells that have been pre-sensitised in vivo to gliadin. As mentioned above such antigen-experienced T cells have been found to be present in the peripheral blood.

In the method the T cells can be contacted with the agent in vitro or in vivo, and determining whether the T cells recognise the agent can be performed in vitro or in vivo. Thus the invention provides the agent for use in a method of diagnosis practiced on the human body. Different agents are provided for simultaneous, separate or sequential use in such a method.

The in vitro method is typically carried out in aqueous solution into which the agent is added. The solution will also comprise the T cells (and in certain embodiments the APCs discussed below). The term 'contacting' as used herein includes adding the particular substance to the solution.

Determination of whether the T cells recognise the agent is generally accomplished by detecting a change in the state of the T cells in the presence of the agent or determining whether the T cells bind the agent. The change in state is generally caused by antigen specific functional activity of the T cell after the TCR binds the agent. The change of state may be measured inside (e.g. change in intracellular expression of proteins) or outside (e.g. detection of secreted substances) the T cells.

The change in state of the T cell may be the start of or increase in secretion of a substance from the T cell, such as a cytokine, especially IFN-γ, IL-2 or TNF-α. Determination of IFN-γ secretion is particularly preferred. The substance can typically be detected by allowing it to bind to a specific binding agent and then measuring the presence of the specific binding agent/substance complex. The specific binding agent is typically an antibody, such as polyclonal or monoclonal antibodies. Antibodies to cytokines are commercially available, or can be made using standard techniques.

Typically the specific binding agent is immobilised on a solid support. After the substance is allowed to bind the solid support can optionally be washed to remove material which is not specifically bound to the agent. The agent/substance complex may be detected by using a second binding agent that will bind the complex. Typically the second agent binds the substance at a site which is different from the site which binds the first agent. The second agent is preferably an antibody and is labelled directly or indirectly by a detectable label.

Thus the second agent may be detected by a third agent that is typically labelled directly or indirectly by a detectable label. For example the second agent may comprise a biotin moiety, allowing detection by a third agent which comprises a streptavidin moiety and typically alkaline phosphatase as a detectable label.

In one embodiment the detection system which is used is the ex-vivo ELISPOT assay described in WO 98/23960. In that assay IFN-γ secreted from the T cell is bound by a first IFN-γ specific antibody that is immobilised on a solid support. The bound IFN-γ is then detected using a second IFN-γ specific antibody which is labelled with a detectable label. Such a labelled antibody can be obtained from MABTECH (Stockholm, Sweden). Other detectable labels which can be used are discussed below.

The change in state of the T cell that can be measured may be the increase in the uptake of substances by the T cell, such as the uptake of thymidine. The change in state may be an increase in the size of the T cells, or proliferation of the T cells, or a change in cell surface markers on the T cell.

In one embodiment the change of state is detected by measuring the change in the intracellular expression of proteins, for example the increase in intracellular expression of any of the cytokines mentioned above. Such intracellular changes may be detected by contacting the inside of the T cell with a moiety that binds the expressed proteins in a specific manner and which allows sorting of the T cells by flow cytometry.

In one embodiment when binding the TCR the agent is bound to an MHC class II molecule (typically HLA-DQ2 or -DQ8), which is typically present on the surface of an antigen presenting cell (APC). However as mentioned herein other agents can bind a TCR without the need to also bind an MHC molecule.

Generally the T cells which are contacted in the method are taken from the individual in a blood sample, although other types of samples which contain T cells can be used. The sample may be added directly to the assay or may be processed first. Typically the processing may comprise diluting of the sample, for example with water or buffer. Typically the sample is diluted from 1.5 to 100 fold, for example 2 to 50 or 5 to 10 fold.

The processing may comprise separation of components of the sample. Typically mononuclear cells (MCs) are separated from the samples. The MCs will comprise the T cells and APCs. Thus in the method the APCs present in the separated MCs can present the peptide to the T cells. In another embodiment only T cells, such as only CD4 T cells, can be purified from the sample. PBMCs, MCs and T cells can be separated from the sample using techniques known in the art, as those described in Lalvani et al (1997) *J. Exp. Med.* 186, p 859-865.

In one embodiment, the T cells used in the assay are in the form of unprocessed or diluted samples, or are freshly isolated T cells (such as in the form of freshly isolated MCs or PBMCs) which are used directly ex vivo, i.e. they are not cultured before being used in the method. Thus the T cells have not been restimulated in an antigen specific manner in vitro. However the T cells can be cultured before use, for example in the presence of one or more of the agents, and generally also exogenous growth promoting cytokines. During culturing the agent(s) are typically present on the surface of APCs, such as the APC used in the method. Pre-culturing of the T cells may lead to an increase in the sensitivity of the method. Thus the T cells can be converted into cell lines, such as short term cell lines (for example as described in Ota et al (1990) *Nature* 346, p 183-187).

The APC that is typically present in the method may be from the same individual as the T cell or from a different host. The APC may be a naturally occurring APC or an artificial APC. The APC is a cell that is capable of presenting the peptide to a T cell. It is typically a B cell, dendritic cell or macrophage. It is typically separated from the same sample as the T cell and is typically co-purified with the T cell. Thus the APC may be present in MCs or PBMCs. The APC is typically a freshly isolated ex vivo cell or a cultured cell. It may be in the form of a cell line, such as a short term or immortalised cell line. The APC may express empty MHC class II molecules on its surface.

In the method one or more (different) agents may be used. Typically the T cells derived from the sample can be placed into an assay with all the agents which it is intended to test or the T cells can be divided and placed into separate assays each of which contain one or more of the agents.

The invention also provides the agents such as two or more of any of the agents mentioned herein (e.g. the combinations of agents which are present in the composition agent discussed above) for simultaneous separate or sequential use (eg. for in vivo use).

In one embodiment agent per se is added directly to an assay comprising T cells and APCs. As discussed above the T cells and APCs in such an assay could be in the form of MCs. When agents that can be recognised by the T cell without the need for presentation by APCs are used then APCs are not required. Analogues which mimic the original (i) or (ii) bound to a MHC molecule are an example of such an agent.

In one embodiment the agent is provided to the APC in the absence of the T cell. The APC is then provided to the T cell, typically after being allowed to present the agent on its surface. The peptide may have been taken up inside the APC and presented, or simply be taken up onto the surface without entering inside the APC.

The duration for which the agent is contacted with the T cells will vary depending on the method used for determining recognition of the peptide. Typically $10^5$ to $10^7$, preferably 5×10⁵ to 10⁶ PBMCs are added to each assay. In the case where agent is added directly to the assay its concentration is from $10^{-1}$ to $10^3$ µg/ml, preferably 0.5 to 50 µg/ml or 1 to 10 µg/ml.

Typically the length of time for which the T cells are incubated with the agent is from 4 to 24 hours, preferably 6 to 16 hours. When using ex vivo PBMCs it has been found that 0.3×10⁶ PBMCs can be incubated in 10 µg/ml of peptide for 12 hours at 37° C.

The determination of the recognition of the agent by the T cells may be done by measuring the binding of the agent to the T cells (this can be carried out using any suitable binding assay format discussed herein). Typically T cells which bind the agent can be sorted based on this binding, for example using a FACS machine. The presence of T cells that recognise the agent will be deemed to occur if the frequency of cells sorted using the agent is above a "control" value. The frequency of antigen-experienced T cells is generally 1 in $10^6$ to 1 in $10^3$, and therefore whether or not the sorted cells are antigen-experienced T cells can be determined.

The determination of the recognition of the agent by the T cells may be measured in vivo. Typically the agent is administered to the host and then a response which indicates recognition of the agent may be measured. The agent is typically administered intradermally or epidermally. The agent is typically administered by contacting with the outside of the skin, and may be retained at the site with the aid of a plaster or dressing. Alternatively the agent may be administered by needle, such as by injection, but can also be administered by other methods such as ballistics (e.g. the ballistics techniques which have been used to deliver nucleic acids). EP-A-0693119 describes techniques that can typically be used to administer the agent. Typically from 0.001 to 1000 µg, for example from 0.01 to 100 µg or 0.1 to 10 µg of agent is administered.

In one embodiment a product can be administered which is capable of providing the agent in vivo. Thus a polynucleotide capable of expressing the agent can be administered, typically in any of the ways described above for the administration of the agent. The polynucleotide typically has any of the characteristics of the polynucleotide provided by the invention which is discussed below. The agent is expressed from the polynucleotide in vivo. Typically from 0.001 to 1000 µg, for example from 0.01 to 100 µg or 0.1 to 10 µg of polynucleotide is administered.

Recognition of the agent administered to the skin is typically indicated by the occurrence of inflammation (e.g. induration, erythema or oedema) at the site of administration. This is generally measured by visual examination of the site.

The method of diagnosis based on the detection of an antibody that binds the agent is typically carried out by contacting a sample from the individual (such as any of the samples mentioned here, optionally processed in any manner mentioned herein) with the agent and determining whether an antibody in the sample binds the agent, such a binding indicating that the individual has, or is susceptible to coeliac disease. Any suitable format of binding assay may be used, such as any such format mentioned herein.

Therapy

The identification of the immunodominant epitope and other epitopes described herein allows therapeutic products to be made which target the T cells which recognise this epitope (such T cells being ones which participate in the immune response against gliadin). These findings also allow the prevention or treatment of coeliac disease by suppressing (by tolerisation) an antibody or T cell response to the epitope(s).

Certain agents of the invention bind the TCR that recognises the epitope of the invention (as measured using any of the binding assays discussed above) and cause tolerisation of the T cell that carries the TCR. Such agents, optionally in association with a carrier, can therefore be used to prevent or treat coeliac disease.

Generally tolerisation can be caused by the same peptides which can (after being recognised by the TCR) cause antigen specific functional activity of the T cell (such as any such activity mentioned herein, e.g. secretion of cytokines). Such agents cause tolerisation when they are presented to the immune system in a 'tolerising' context.

Tolerisation leads to a decrease in the recognition of a T cell or antibody epitope by the immune system. In the case of a T cell epitope this can be caused by the deletion or anergising of T cells that recognise the epitope. Thus T cell activity (for example as measured in suitable assays mentioned herein) in response to the epitope is decreased. Tolerisation of an antibody response means that a decreased amount of specific antibody to the epitope is produced when the epitope is administered.

Methods of presenting antigens to the immune system in such a context are known and are described for example in Yoshida et al. Clin. Immunol. Immunopathol. 82, 207-215 (1997), Thurau et al. Clin. Exp. Immunol. 109, 370-6 (1997), and Weiner et al. Res. Immunol. 148, 528-33 (1997). In particular certain routes of administration can cause tolerisation, such as oral, nasal or intraperitoneal. Particular products which cause tolerisation may be administered (e.g. in a composition that also comprises the agent) to the individual. Such products include cytokines, such as cytokines that favour a Th2 response (e.g. IL-4, TGF-β or IL-10). Products or agent may be administered at a dose that causes tolerisation.

The invention provides a protein that comprises a sequence able to act as an antagonist of the T cell (which T cell recognises the agent). Such proteins and such antagonists can also be used to prevent or treat coeliac disease. The antagonist will cause a decrease in the T cell response. In one embodiment, the antagonist binds the TCR of the T cell (generally in the form of a complex with HLA-DQ2 or -DQ8) but instead of causing normal functional activation causing an abnormal signal to be passed through the TCR intracellular signalling cascade, which causes the T cell to have decreased function activity (e.g. in response to recognition of an epitope, typically as measured by any suitable assay mentioned herein).

In one embodiment the antagonist competes with epitope to bind a component of MHC processing and presentation pathway, such as an MHC molecule (typically HLA-DQ2 or -DQ8). Thus the antagonist may bind HLA-DQ2 or -DQ8 (and thus be a peptide presented by this MHC molecule), such as peptide TP (Table 10) or a homologue thereof.

Methods of causing antagonism are known in the art. In one embodiment the antagonist is a homologue of the epitopes mentioned above and may have any of the sequence, binding or other properties of the agent (particularly analogues). The antagonists typically differ from any of the above epitopes (which are capable of causing a normal antigen specific function in the T cell) by 1, 2, 3, 4 or more mutations (each of which may be a substitution, insertion or deletion). Such antagonists are termed "altered peptide ligands" or "APL" in the art. The mutations are typically at the amino acid positions that contact the TCR.

The antagonist may differ from the epitope by a substitution within the sequence that is equivalent to the sequence represented by amino acids 65 to 67 of A-gliadin (such antagonists are shown in Table 9). Thus preferably the antagonist has a substitution at the equivalent of position 64, 65 or 67. Preferably the substitution is 64W, 67W, 67M or 65T.

Since the T cell immune response to the epitope of the invention in an individual is polyclonal, more than one antagonist may need to be administered to cause antagonism of T cells of the response which have different TCRs. Therefore the antagonists may be administered in a composition which comprises at least 2, 4, 6 or more different antagonists, which each antagonise different T cells.

The invention also provides a method of identifying an antagonist of a T cell (which recognises the agent), comprising contacting a candidate substance with the T cell and detecting whether the substance causes a decrease in the ability of the T cell to undergo an antigen specific response (e.g. using any suitable assay mentioned herein), the detecting of any such decrease in said ability indicating that the substance is an antagonist.

In one embodiment, the antagonists (including combinations of antagonists to a particular epitope) or tolerising (T cell and antibody tolerising) agents are present in a composition comprising at least 2, 4, 6 or more antagonists or agents which antagonise or tolerise to different epitopes of the invention, for example to the combinations of epitopes discussed above in relation to the agents which are a product comprising more than one substance.

Testing Whether a Composition is Capable of Causing Coeliac Disease

As mentioned above the invention provides a method of determining whether a composition is capable of causing coeliac disease comprising detecting the presence of a protein sequence which is capable of being modified by a transglutaminase to as sequence comprising the agent or epitope of the invention (such transglutaminase activity may be a human intestinal transglutaminase activity). Typically this is performed by using a binding assay in which a moiety which binds to the sequence in a specific manner is contacted with the composition and the formation of sequence/moiety complex is detected and used to ascertain the presence of the agent. Such a moiety may be any suitable substance (or type of substance) mentioned herein, and is typically a specific antibody. Any suitable format of binding assay can be used (such as those mentioned herein).

In one embodiment, the composition is contacted with at least 2, 5, 10 or more antibodies which are specific for epitopes of the invention from different gliadins, for example a panel of antibodies capable of recognising the combinations of epitopes discussed above in relation to agents of the invention which are a product comprising more than one substance.

The composition typically comprises material from a plant that expresses a gliadin which is capable of causing coeliac disease (for example any of the gliadins or plants mentioned herein). Such material may be a plant part, such as a harvested product (e.g. seed). The material may be processed products of the plant material (e.g. any such product mentioned herein), such as a flour or food that comprises the gliadin. The processing of food material and testing in suitable binding assays is routine, for example as mentioned in Kricka J. Biolumin. Chemilumin. 13, 189-93 (1998).

Binding Assays

The determination of binding between any two substances mentioned herein may be done by measuring a characteristic of either or both substances that changes upon binding, such as a spectroscopic change.

The binding assay format may be a 'band shift' system. This involves determining whether the presence of one substance (such as a candidate substance) advances or retards the progress of the other substance during gel electrophoresis.

The format may be a competitive binding method which determines whether the one substance is able to inhibit the binding of the other substance to an agent which is known to bind the other substance, such as a specific antibody.

Mutant Gliadin Proteins

The invention provides a gliadin protein in which an epitope sequence of the invention, or sequence which can be modified by a transglutaminase to provide such a sequence has been mutated so that it no longer causes, or is recognised by, a T cell response that recognises the epitope. In this context the term recognition refers to the TCR binding the epitope in such a way that normal (not antagonistic) antigen-specific functional activity of the T cell occurs.

Methods of identifying equivalent epitopes in other gliadins are discussed above. The wild type of the mutated gliadin is one which causes coeliac disease. Such a gliadin may have homology with SEQ ID NO:3, for example to the degree mentioned above (in relation to the analogue) across all of SEQ ID NO:3 or across 15, 30, 60, 100 or 200 contiguous amino acids of SEQ ID NO:3. Likewise, for other non-A-gliadins, homology will be present between the mutant and the native form of that gliadin. The sequences of other natural gliadin proteins are known in the art.

The mutated gliadin will not cause coeliac disease or will cause decreased symptoms of coeliac disease. Typically the mutation decreases the ability of the epitope to induce a T cell response. The mutated epitope may have a decreased binding to HLA-DQ2 or -DQ8, a decreased ability to be presented by an APC or a decreased ability to bind to or to be recognised (i.e. cause antigen-specific functional activity) by T cells that recognise the agent. The mutated gliadin or epitope will therefore show no or reduced recognition in any of the assays mentioned herein in relation to the diagnostic aspects of the invention.

The mutation may be one or more deletions, additions or substitutions of length 1 to 3, 4 to 6, 6 to 10, 11 to 15 or more in the epitope, for example across sequence SEQ ID NO:2 or across any of SEQ ID NOS: 18-22, 31-36, 39-44, and 46; or across equivalents thereof. Preferably the mutant gliadin has at least one mutation in the sequence SEQ ID NO:1. A preferred mutation is at position 65 in A-gliadin (or in an equivalent position in other gliadins). Typically the naturally occurring glutamine at this position is substituted to any of the amino acids shown in Table 3, preferably to histidine, tyrosine, tryptophan, lysine, proline, or arginine.

The invention thus also provides use of a mutation (such any of the mutations in any of the sequences discussed herein) in an epitope of a gliadin protein, which epitope is an epitope of the invention, to decrease the ability of the gliadin protein to cause coeliac disease.

In one embodiment the mutated sequence is able to act as an antagonist. Thus the invention provides a protein that comprises a sequence which is able to bind to a T cell receptor, which T cell receptor recognises an agent of the invention, and which sequence is able to cause antagonism of a T cell that carries such a T cell receptor.

The invention also provides proteins which are fragments of the above mutant gliadin proteins, which are at least 15 amino acids long (e.g. at least 30, 60, 100, 150, 200, or 250 amino acids long) and which comprise the mutations discussed above which decrease the ability of the gliadin to be recognised. Any of the mutant proteins (including fragments) mentioned herein may also be present in the form of fusion proteins, for example with other gliadins or with non-gliadin proteins.

The equivalent wild type protein to the mutated gliadin protein is typically from a graminaceous monocotyledon, such as a plant of genus *Triticum*, e.g. wheat, rye, barley, oats or triticale. The protein is typically an α, αβ, β, γ or ω gliadin. The gliadin may be an A-gliadin.

Kits

The invention also provides a kit for carrying out the method comprising one or more agents and optionally a means to detect the recognition of the agent by the T cell. Typically the different agents are provided for simultaneous, separate or sequential use. Typically the means to detect recognition allows or aids detection based on the techniques discussed above.

Thus the means may allow detection of a substance secreted by the T cells after recognition. The kit may thus additionally include a specific binding moiety for the substance, such as an antibody. The moiety is typically specific for IFN-γ. The moiety is typically immobilised on a solid support. This means that after binding the moiety the substance will remain in the vicinity of the T cell which secreted it. Thus "spots" of substance/moiety complex are formed on the support, each spot representing a T cell which is secreting the substance. Quantifying the spots, and typically comparing against a control, allows determination of recognition of the agent.

The kit may also comprise a means to detect the substance/moiety complex. A detectable change may occur in the moiety itself after binding the substance, such as a colour change. Alternatively a second moiety directly or indirectly labelled for detection may be allowed to bind the substance/moiety complex to allow the determination of the spots. As discussed above the second moiety may be specific for the substance, but binds a different site on the substance than the first moiety.

The immobilised support may be a plate with wells, such as a microtitre plate. Each assay can therefore be carried out in a separate well in the plate.

The kit may additionally comprise medium for the T cells, detection moieties or washing buffers to be used in the detection steps. The kit may additionally comprise reagents suitable for the separation from the sample, such as the separation of PBMCs or T cells from the sample. The kit may be designed to allow detection of the T cells directly in the sample without requiring any separation of the components of the sample.

The kit may comprise an instrument which allows administration of the agent, such as intradermal or epidermal administration. Typically such an instrument comprises plaster, dressing or one or more needles. The instrument may allow ballistic delivery of the agent. The agent in the kit may be in the form of a pharmaceutical composition.

The kit may also comprise controls, such as positive or negative controls. The positive control may allow the detection system to be tested. Thus the positive control typically mimics recognition of the agent in any of the above methods. Typically in the kits designed to determine recognition in vitro the positive control is a cytokine. In the kit designed to detect in vivo recognition of the agent the positive control may be antigen to which most individuals should response.

The kit may also comprise a means to take a sample containing T cells from the host, such as a blood sample. The kit may comprise a means to separate mononuclear cells or T cells from a sample from the host.

Polynucleotides, Cells, Transgenic Mammals and Antibodies

The invention also provides a polynucleotide which is capable of expression to provide the agent or mutant gliadin proteins. Typically the polynucleotide is DNA or RNA, and is single or double stranded. The polynucleotide will preferably comprise at least 50 bases or base pairs, for example 50 to 100, 100 to 500, 500 to 1000 or 1000 to 2000 or more bases or base pairs. The polynucleotide therefore comprises a sequence which encodes the sequence of SEQ ID NO: 1 or 2 or any of the other agents mentioned herein. To the 5' and 3' of this coding sequence the polynucleotide of the invention has sequence or codons which are different from the sequence or codons 5' and 3' to these sequences in the corresponding gliadin gene.

5' and/or 3' to the sequence encoding the peptide the polynucleotide has coding or non-coding sequence. Sequence 5' and/or 3' to the coding sequence may comprise sequences which aid expression, such as transcription and/or translation, of the sequence encoding the agent. The polynucleotide may be capable of expressing the agent prokaryotic or eukaryotic cell. In one embodiment the polynucleotide is capable of expressing the agent in a mammalian cell, such as a human, primate or rodent (e.g. mouse or rat) cell.

A polynucleotide of the invention may hybridise selectively to a polynucleotide that encodes SEQ ID NO:3 at a level significantly above background. Selective hybridisation is typically achieved using conditions of medium to high stringency (for example 0.03M sodium chloride and 0.03M sodium citrate at from about 50° C. to about 60° C.). However, such hybridisation may be carried out under any suitable conditions known in the art (see Sambrook et al (1989), Molecular Cloning: A Laboratory Manual). For example, if high stringency is required, suitable conditions include 0.2×SSC at 60° C. If lower stringency is required, suitable conditions include 2×SSC at 60° C.

Agents or proteins of the invention may be encoded by the polynucleotides described herein.

The polynucleotide may form or be incorporated into a replicable vector. Such a vector is able to replicate in a suitable cell. The vector may be an expression vector. In such a vector the polynucleotide of the invention is operably linked to a control sequence which is capable of providing for the expression of the polynucleotide. The vector may contain a selectable marker, such as the ampicillin resistance gene.

The polynucleotide or vector may be present in a cell. Such a cell may have been transformed by the polynucleotide or vector. The cell may express the agent. The cell will be chosen to be compatible with the said vector and may for example be a prokaryotic (bacterial), yeast, insect or mammalian cell. The polynucleotide or vector may be introduced into host cells using conventional techniques including calcium phosphate precipitation, DEAE-dextran transfection, or electroporation.

The invention provides processes for the production of the proteins of the invention by recombinant means. This may comprise (a) cultivating a transformed cell as defined above under conditions that allow the expression of the protein; and preferably (b) recovering the expressed polypeptide.

Optionally, the polypeptide may be isolated and/or purified, by techniques known in the art.

The invention also provides TCRs which recognise (or bind) the agent, or fragments thereof which are capable of such recognition (or binding). These can be present in the any form mentioned herein (e.g. purity) discussed herein in relation to the protein of the invention. The invention also provides T cells which express such TCRs which can be present in any form (e.g. purity) discussed herein for the cells of the invention.

The invention also provides monoclonal or polyclonal antibodies which specifically recognise the agents (such as any of the epitopes of the invention) and which recognise the mutant gliadin proteins (and typically which do not recognise the equivalent wild-type gliadins) of the invention, and methods of making such antibodies. Antibodies of the invention bind specifically to these substances of the invention.

For the purposes of this invention, the term "antibody" includes antibody fragments such as Fv, F(ab) and F(ab)$_2$ fragments, as well as single-chain antibodies.

A method for producing a polyclonal antibody comprises immunising a suitable host animal, for example an experimental animal, with the immunogen and isolating immunoglobulins from the serum. The animal may therefore be inoculated with the immunogen, blood subsequently removed from the animal and the IgG fraction purified. A method for producing a monoclonal antibody comprises immortalising cells which produce the desired antibody. Hybridoma cells may be produced by fusing spleen cells from an inoculated experimental animal with tumour cells (Kohler and Milstein (1975) *Nature* 256, 495-497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat or mouse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified. The polynucleotide, agent, protein or antibody of the invention, may carry a detectable label. Detectable labels which allow detection of the secreted substance by visual inspection, optionally with the aid of an optical magnifying means, are preferred. Such a system is typically based on an enzyme label which causes colour change in a substrate, for example alkaline phosphatase causing a colour change in a substrate. Such substrates are commercially available, e.g. from BioRad. Other suitable labels include other enzymes such as peroxidase, or protein labels, such as biotin; or radioisotopes, such as $^{32}$P or $^{35}$S. The above labels may be detected using known techniques.

Polynucleotides, agents, proteins, antibodies or cells of the invention may be in substantially purified form. They may be in substantially isolated form, in which case they will generally comprise at least 80% e.g. at least 90, 95, 97 or 99% of the polynucleotide, peptide, antibody, cells or dry mass in the preparation. The polynucleotide, agent, protein or antibody is typically substantially free of other cellular components. The polynucleotide, agent, protein or antibody may be used in such a substantially isolated, purified or free form in the method or be present in such forms in the kit.

The invention also provides a transgenic non-human mammal which expresses a TCR of the invention. This may be any of the mammals discussed herein (e.g. in relation to the production of the antibody). Preferably the mammal has, or is susceptible, to coeliac disease. The mammal may also express HLA-DQ2 or -DQ8 or HLA-DR3-DQ2 and/or may be given a diet comprising a gliadin which cause coeliac disease (e.g. any of the gliadin proteins mentioned herein). Thus the mammal may act as an animal model for coeliac disease.

The invention also provides a method of identifying a product which is therapeutic for coeliac disease comprising administering a candidate substance to a mammal of the invention which has, or which is susceptible to, coeliac disease and determining whether substance prevents or treats coeliac disease in the mammal, the prevention or treatment of coeliac disease indicating that the substance is a therapeutic product. Such a product may be used to treat or prevent coeliac disease.

The invention provides therapeutic (including prophylactic) agents or diagnostic substances (the agents, proteins and polynucleotides of the invention). These substances are formulated for clinical administration by mixing them with a pharmaceutically acceptable carrier or diluent. For example they can be formulated for topical, parenteral, intravenous, intramuscular, subcutaneous, intraocular, intradermal, epidermal or transdermal administration. The substances may be mixed with any vehicle which is pharmaceutically acceptable and appropriate for the desired route of administration. The pharmaceutically carrier or diluent for injection may be, for example, a sterile or isotonic solution such as Water for Injection or physiological saline, or a carrier particle for ballistic delivery.

The dose of the substances may be adjusted according to various parameters, especially according to the agent used; the age, weight and condition of the patient to be treated; the mode of administration used; the severity of the condition to be treated; and the required clinical regimen. As a guide, the amount of substance administered by injection is suitably from 0.01 mg/kg to 30 mg/kg, preferably from 0.1 mg/kg to 10 mg/kg.

The routes of administration and dosages described are intended only as a guide since a skilled practitioner will be able to determine readily the optimum route of administration and dosage for any particular patient and condition.

The substances of the invention may thus be used in a method of treatment of the human or animal body, or in a diagnostic method practised on the human body. In particular they may be used in a method of treating or preventing coeliac disease. The invention also provide the agents for use in a method of manufacture of a medicament for treating or preventing coeliac disease. Thus the invention provides a method of preventing or treating coeliac disease comprising administering to a human in need thereof a substance of the invention (typically a non-toxic effective amount thereof).

The agent of the invention can be made using standard synthetic chemistry techniques, such as by use of an automated synthesizer. The agent may be made from a longer polypeptide e.g. a fusion protein, which polypeptide typically comprises the sequence of the peptide. The peptide may be derived from the polypeptide by for example hydrolysing the polypeptide, such as using a protease; or by physically breaking the polypeptide. The polynucleotide of the invention can be made using standard techniques, such as by using a synthesiser.

Plant Cells and Plants that Express Mutant Gliadin Proteins or Express Proteins Comprising Sequences which can Act as Antagonists The cell of the invention may be a plant cell, such as a cell of a graminaceous monocotyledonous species. The species may be one whose wild-type form expresses gliadins, such as any of the gliadin proteins mentioned herein (including gliadins with any degree of homology to SEQ ID NO:3 mentioned herein). Such a gliadin may cause coeliac disease in humans. The cell may be of wheat, maize, oats, rye, rice, barley, triticale, sorghum, or sugar cane. Typically the cell is of the *Triticum* genus, such as *aestivum, spelta, polonicum* or *monococcum*.

The plant cell of the invention is typically one which does not express a wild-type gliadin (such as any of the gliadins mentioned herein which may cause coeliac disease), or one which does not express a gliadin comprising a sequence that can be recognised by a T cell that recognises the agent. Thus if the wild-type plant cell did express such a gliadin then it may be engineered to prevent or reduce the expression of such a gliadin or to change the amino acid sequence of the gliadin so that it no longer causes coeliac disease (typically by no longer expressing the epitope of the invention).

This can be done for example by introducing mutations into 1, 2, 3 or more or all of such gliadin genes in the cell, for example into coding or non-coding (e.g. promoter regions). Such mutations can be any of the type or length of mutations discussed herein (e.g., in relation to homologous proteins). The mutations can be introduced in a directed manner (e.g., using site directed mutagenesis or homologous recombination techniques) or in a random manner (e.g. using a mutagen, and then typically selecting for mutagenised cells which no longer express the gliadin (or a gliadin sequence which causes coeliac disease)).

In the case of plants or plant cells that express a protein that comprises a sequence able to act as an antagonist such a plant or plant cell may express a wild-type gliadin protein (e.g. one which causes coeliac disease). Preferably though the presence of the antagonist sequence will cause reduced coeliac disease symptoms (such as no symptoms) in an individual who ingests a food comprising protein from the plant or plant cell.

The polynucleotide which is present in (or which was transformed into) the plant cell will generally comprise promoter capable of expressing the mutant gliadin protein the plant cell. Depending on the pattern of expression desired, the promoter may be constitutive, tissue- or stage-specific; and/or inducible. For example, strong constitutive expression in plants can be obtained with the CAMV 35S, Rubisco ssu, or histone promoters. Also, tissue-specific or stage-specific promoters may be used to target expression of protein of the invention to particular tissues in a transgenic plant or to particular stages in its development. Thus, for example seed-specific, root-specific, leaf-specific, flower-specific etc promoters may be used. Seed-specific promoters include those described by Dalta et al (Biotechnology Ann. Rev. (1997), 3, pp. 269-296). Particular examples of seed-specific promoters are napin promoters (EP-A-0 255, 378), phaseolin promoters, glutenine promoters, helianthenine promoters (WO92/17580), albumin promoters (WO98/45460), oleosin promoters (WO98/45461) and ATS1 and ATS3 promoters (PCT/US98/06798).

The cell may be in any form. For example, it may be an isolated cell, e.g. a protoplast, or it may be part of a plant tissue, e.g. a callus, or a tissue excised from a plant, or it may be part of a whole plant. The cell may be of any type (e.g. of any type of plant part). For example, an undifferentiated cell, such as a callus cell; or a differentiated cell, such as a cell of a type found in embryos, pollen, roots, shoots or leaves. Plant parts include roots; shoots; leaves; and parts involved in reproduction, such as pollen, ova, stamens, anthers, petals, sepals and other flower parts.

The invention provides a method of obtaining a transgenic plant cell comprising transforming a plant cell with a polynucleotide or vector of the invention to give a transgenic plant cell. Any suitable transformation method may be used (in the case of wheat the techniques disclosed in Vasil V et al, Biotechnology 10, 667-674 (1992) may be used). Preferred transformation techniques include electroporation of plant protoplasts and particle bombardment. Transformation may thus give rise to a chimeric tissue or plant in which some cells are transgenic and some are not.

The cell of the invention or thus obtained cell may be regenerated into a transgenic plant by techniques known in the art. These may involve the use of plant growth substances such as auxins, giberellins and/or cytokinins to stimulate the growth and/or division of the transgenic cell. Similarly, techniques such as somatic embryogenesis and meristem culture may be used. Regeneration techniques are well known in the art and examples can be found in, e.g. U.S. Pat. No. 4,459,355, U.S. Pat. No. 4,536,475, U.S. Pat. No. 5,464,763, U.S. Pat. No. 5,177,010, U.S. Pat. No. 5,187,073, EP 267,159, EP 604, 662, EP 672, 752, U.S. Pat. No. 4,945,050, U.S. Pat. No. 5,036,006, U.S. Pat. No. 5,100,792, U.S. Pat. No. 5,371,014, U.S. Pat. No. 5,478,744, U.S. Pat. No. 5,179,022, U.S. Pat. No. 5,565,346, U.S. Pat. No. 5,484,956, U.S. Pat. No. 5,508,468, U.S. Pat. No. 5,538,877, U.S. Pat. No. 5,554,798, U.S. Pat. No. 5,489,520, U.S. Pat. No. 5,510,318, U.S. Pat. No. 5,204,253, U.S. Pat. No. 5,405,765, EP 442,174, EP 486,233, EP 486,234, EP 539,563, EP 674,725, WO91/02071 and WO 95/06128.

In many such techniques, one step is the formation of a callus, i.e. a plant tissue comprising expanding and/or dividing cells. Such calli are a further aspect of the invention as are other types of plant cell cultures and plant parts. Thus, for example, the invention provides transgenic plant tissues and parts, including embryos, meristems, seeds, shoots, roots, stems, leaves and flower parts. These may be chimeric in the sense that some of their cells are cells of the invention and some are not. Transgenic plant parts and tissues, plants and seeds of the invention may be of any of the plant species mentioned herein.

Regeneration procedures will typically involve the selection of transformed cells by means of marker genes.

The regeneration step gives rise to a first generation transgenic plant. The invention also provides methods of obtaining transgenic plants of further generations from this first generation plant. These are known as progeny transgenic plants. Progeny plants of second, third, fourth, fifth, sixth and further generations may be obtained from the first generation transgenic plant by any means known in the art.

Thus, the invention provides a method of obtaining a transgenic progeny plant comprising obtaining a second-generation transgenic progeny plant from a first-generation transgenic plant of the invention, and optionally obtaining transgenic plants of one or more further generations from the second-generation progeny plant thus obtained.

Progeny plants may be produced from their predecessors of earlier generations by any known technique. In particular, progeny plants may be produced by:

obtaining a transgenic seed from a transgenic plant of the invention belonging to a previous generation, then obtaining a transgenic progeny plant of the invention belonging to a new generation by growing up the transgenic seed; and/or propagating clonally a transgenic plant of the invention belonging to a previous generation to give a transgenic progeny plant of the invention belonging to a new generation; and/or crossing a first-generation transgenic plant of the invention belonging to a previous generation with another compatible plant to give a transgenic progeny plant of the invention belonging to a new generation; and optionally obtaining transgenic progeny plants of one or more further generations from the progeny plant thus obtained.

These techniques may be used in any combination. For example, clonal propagation and sexual propagation may be used at different points in a process that gives rise to a transgenic plant suitable for cultivation. In particular, repetitive back-crossing with a plant taxon with agronomically desirable characteristics may be undertaken. Further steps of removing cells from a plant and regenerating new plants therefrom may also be carried out.

Also, further desirable characteristics may be introduced by transforming the cells, plant tissues, plants or seeds, at any suitable stage in the above process, to introduce desirable coding sequences other than the polynucleotides of the invention. This may be carried out by the techniques described herein for the introduction of polynucleotides of the invention.

For example, further transgenes may be selected from those coding for other herbicide resistance traits, e.g. tolerance to: Glyphosate (e.g. using an EPSP synthase gene (e.g. EP-A-0 293,358) or a glyphosate oxidoreductase (WO 92/000377) gene); or tolerance to fosametin; a dihalobenzonitrile; glufosinate, e.g. using a phosphinothrycin acetyl transferase (PAT) or glutamine synthase gene (cf. EP-A-0 242,236); asulam, e.g. using a dihydropteroate synthase gene (EP-A-0 369,367); or a sulphonylurea, e.g. using an ALS gene); diphenyl ethers such as acifluorfen or oxyfluorfen, e.g. using a protoporphyrogen oxidase gene); an oxadiazole such as oxadiazon; a cyclic imide such as chlorophthalim; a phenyl pyrazole such as TNP, or a phenopylate or carbamate analogue thereof.

Similarly, genes for beneficial properties other than herbicide tolerance may be introduced. For example, genes for insect resistance may be introduced, notably genes encoding *Bacillus thuringiensis* (BI) toxins. Likewise, genes for disease resistance may be introduced, e.g. as in WO91/02701 or WO95/06128.

Typically, a protein of the invention is expressed in a plant of the invention. Depending on the promoter used, this expression may be constitutive or inducible. Similarly, it may be tissue- or stage-specific, i.e. directed towards a particular plant tissue (such as any of the tissues mentioned herein) or stage in plant development.

The invention also provides methods of obtaining crop products by harvesting, and optionally processing further, transgenic plants of the invention. By crop product is meant any useful product obtainable from a crop plant.

Products that Contain Mutant Gliadin Proteins or Proteins that Comprise Sequence Capable of Acting as an Antagonist The invention provides a product that comprises the mutant gliadin proteins or protein that comprises sequence capable of acting as an antagonist. This is typically derived from or comprise plant parts from plants mentioned herein which express such proteins. Such a product may be obtainable directly by harvesting or indirectly, by harvesting and further processing the plant of the invention. Directly obtainable products include grains. Alternatively, such a product may be obtainable indirectly, by harvesting and further processing. Examples of products obtainable by further processing are flour or distilled alcoholic beverages; food products made from directly obtained or further processed material, e.g. baked products (e.g. bread) made from flour. Typically such food products, which are ingestible and digestible (i.e. non-toxic and of nutrient value) by human individuals.

In the case of food products that comprise the protein which comprises an antagonist sequence the food product may also comprise wild-type gliadin, but preferably the antagonist is able to cause a reduction (e.g. completely) in the coeliac disease symptoms after such food is ingested.

The invention is illustrated by the following nonlimiting Examples:

Example 1

We carried out epitope mapping in Coeliac disease by using a set of 51 synthetic 15-mer peptides that span the complete sequence of a fully characterized a-gliadin, "A-gliadin" (see Table 1). A-Gliadin peptides were also individually treated with tTG to generate products that might mimic those produced in vivo[3]. We also sought to study Coeliac disease patients at the point of initiation of disease relapse to avoid the possibility that epitope "spreading" or "exhaustion" may have occurred, as described in experimental infectious and autoimmune diseases.

Clinical and A-Gliadin Specific T Cell Responses with 3 and 10 Day Bread Challenge In a pilot study, two subjects with Coeliac disease in remission, defined by absence of serum anti-endomysial antibody (EMA), on a gluten free diet were fed four slices of standard gluten-containing white bread daily in addition to their usual gluten free diet. Subject 1 ceased bread because of abdominal pain, mouth ulcers and mild diarrhoea after three days, but Subject 2 continued for 10 days with only mild nausea at one week. The EMA became positive in Subject 2 one week after the bread challenge, indicating the bread used had caused a relapse of Coeliac disease. But in Subject 1, EMA remained negative up to two months after bread challenge. In both subjects, symptoms that appeared with bread challenge resolved within two days after returning to gluten free diet.

PBMC responses in IFNγ ELISPOT assays to A-gliadin peptides were not found before or during bread challenge. But from the day after bread withdrawal (Day 4) in Subject 1 a single pool of 5 overlapping peptides spanning A-gliadin 51-85 (Pool 3) treated with tTG showed potent IFNγ responses (see FIG. 1a). In Subject 1, the PBMC IFNγ response to A-gliadin peptide remained targeted to Pool 3 alone and was maximal on Day 8. The dynamics and magnitude of the response to Pool 3 was similar to that elicited by α-chymotrypsin digested gliadin. PBMC IFNγ responses to tTG-treated Pool 3 were consistently 5 to 12-fold greater than Pool 3 not treated with tTG, and responses to α-chymotrypsin digested gliadin were 3 to 10-fold greater if treated with tTG. In Subject 2, Pool 3 treated with tTG was also the only immunogenic set of A-gliadin peptides on Day 8, but this response was weaker than Subject 1, was not seen on Day 4 and by Day 11 the response to Pool 3 had diminished and other tTG-treated pools of A-gliadin peptides elicited stronger IFNα responses (see FIG. 1b).

The pilot study indicated that the initial T cell response in these Coeliac disease subjects was against a single tTG-treated A-gliadin pool of five peptides and was readily measured in peripheral blood. But if antigen exposure is continued for ten days instead of three, T cell responses to other A-gliadin peptides appear, consistent with epitope spreading.

Coeliac Disease-Specific IFN-g Induction by ITG-Treated A-Gliadin Peptides

Figure 2A:
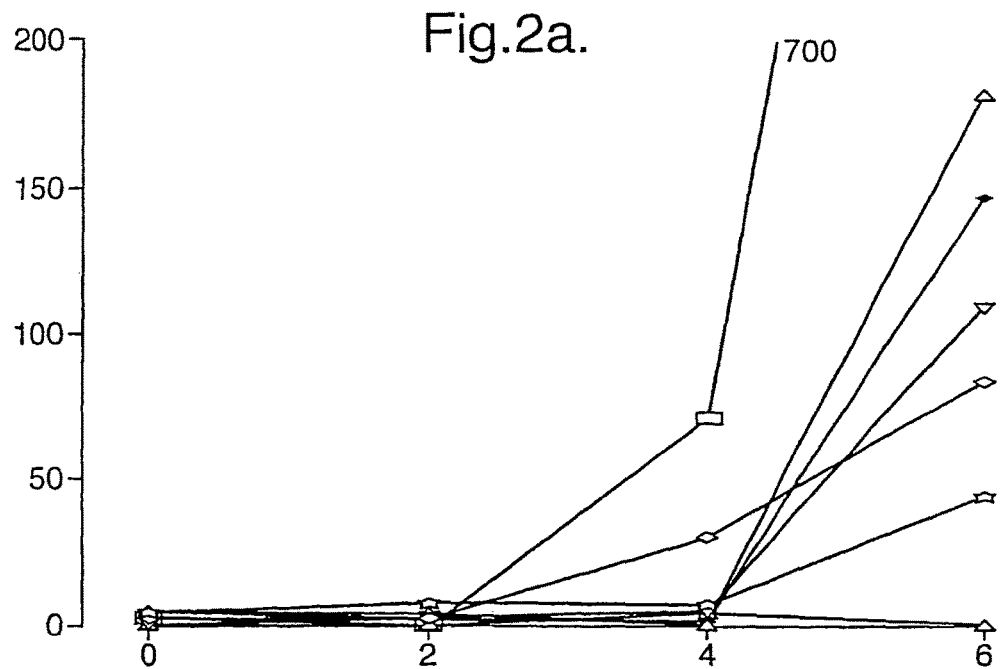
FIG. 2 shows PBMC IFNγ ELISPOT responses to tTG-treated peptide pool 3 (spanning A-gliadin 51-85) in 7 individual coeliac disease subjects (vertical axis shows spot forming cells per $10^6$ PBMC), initially in remission on gluten free diet, challenged with bread for three days (days 1 to 3). The horizontal axis shows days after commencing bread. (a). PBMC IFNγ Elispot responses to tTG-treated overlapping 15mer peptides included in pool 3; bars represent the mean (±SEM) response to individual peptides (10 µg/ml) in 6 Coeliac disease subjects on day 6 or 7(b). (In individual subjects, ELISPOT responses to peptides were calculated as a % of response elicited by peptide 12—as shown by the vertical axis.)
Figure 2B:
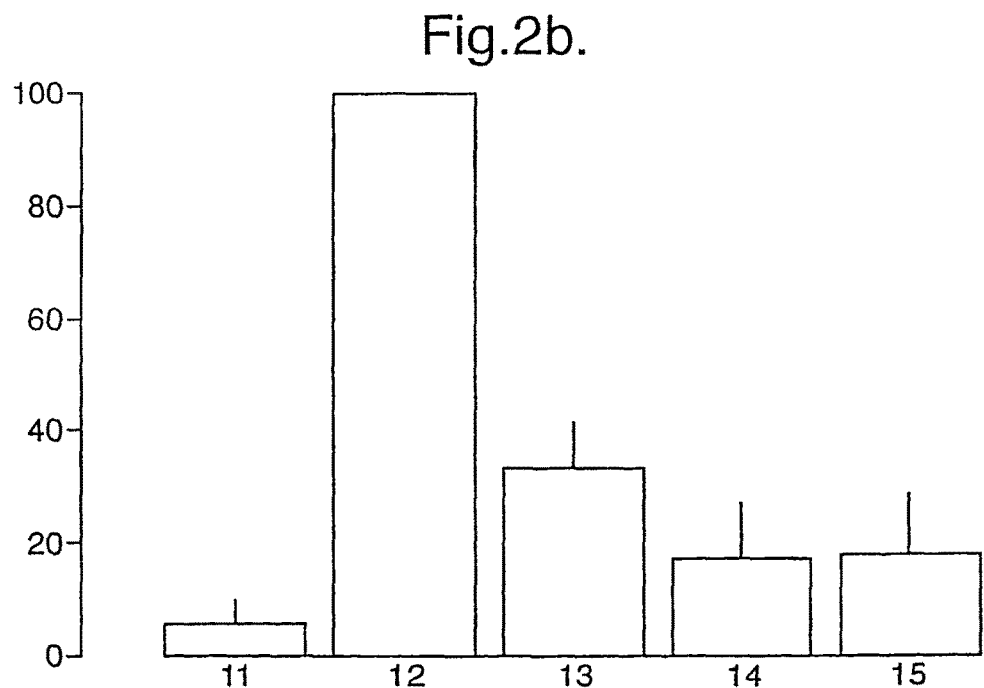

In five out of six further Coeliac disease subjects on gluten free diet (see Table 1), bread challenge for three days identified tTG-treated peptides in Pool 3, and in particular, peptides corresponding to 56-70 (12) and 60-75 (13) as the sole A-gliadin components eliciting IFNγ from PBMC (see FIG. 2). IL-10 ELISPOT assays run in parallel to IFNγ ELISPOT showed no IL-10 response to tTG-treated peptides 12 or 13. In one subject, there were no IFNγ responses to any A-gliadin peptide or α-chymotrypsin digested gliadin before, during or up to four days after bread challenge. In none of these Coeliac disease subjects did EMA status change from baseline when measured for up to two months after bread challenge.

PBMC from four healthy, EMA-negative subjects with the HLA-DQ alleles α1*0501, β1*0201 (ages 28-52, 2 females) who had been challenged for three days with bread after following a gluten free diet for one month, showed no IFNγ responses above the negative control to any of the A-gliadin peptides with or without tTG treatment. Thus, induction of IFNγ in PBMC to tTG-treated Pool 3 and A-gliadin peptides 56-70 (12) and 60-75 (13) were Coeliac disease specific (7/8 vs. 0/4, p<0.01 by Chi-squared analysis).

Figure 3:
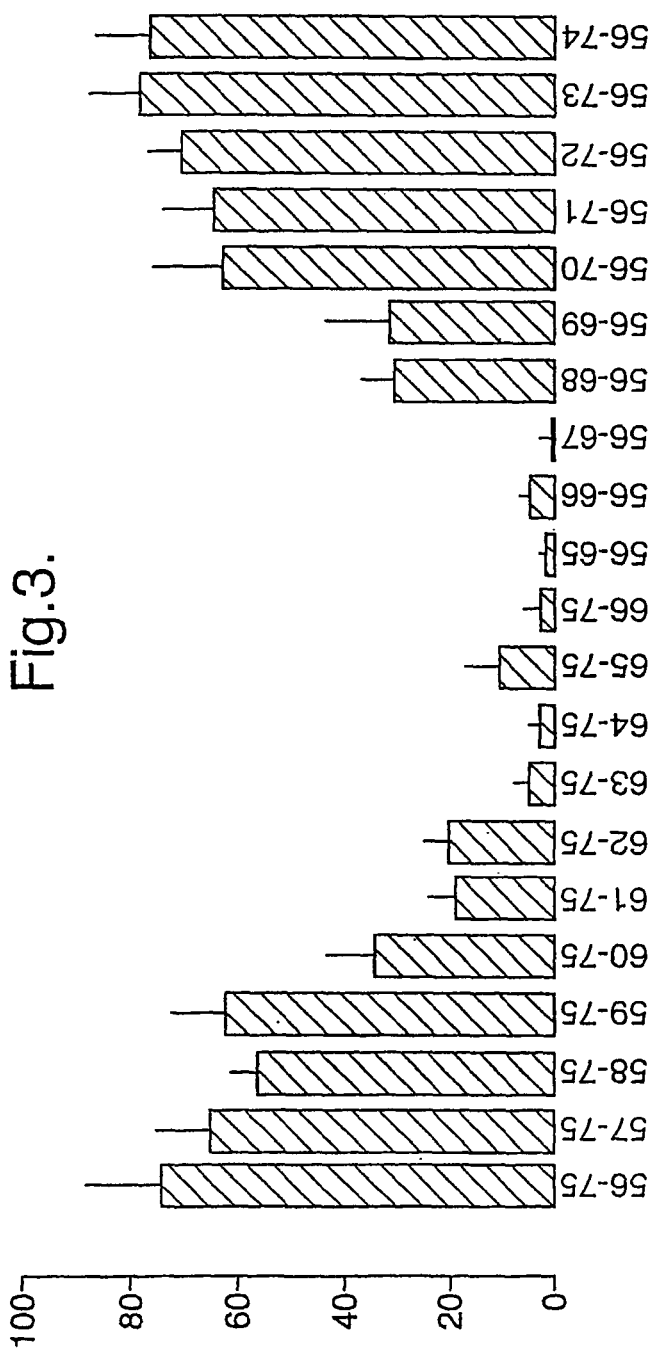
FIG. 3 shows PBMC IFNγ ELISPOT responses to tTG-treated truncations of A-gliadin 56-75 (SEQ ID NO:5) (0.1 µM). Bars represent the mean (±SEM) in 5 Coeliac disease subjects. (In individual subjects, responses were calculated as the % of the maximal response elicited by any of the peptides tested.)

Fine Mapping of the Minimal A-Gliadin T Cell Epitope tTG-treated peptides representing truncations of A-gliadin 56-75 (SEQ ID NO:5) revealed that the same core peptide sequence QPQLP (SEQ ID NO:9) was essential for antigenicity in all of the five Coeliac disease subjects assessed (see FIG. 3). PBMC IFNγ responses to tTG-treated peptides spanning this core sequence beginning with the 7-mer PQPQLPY (SEQ ID NO:4) and increasing in length, indicated that the tTG-treated 17-mer QLQPFPQPQLPYPQPQS (SEQ ID NO:10) (A-gliadin 57-73) possessed optimal activity in the IFNγ ELISPOT (see FIG. 4).

Figure 5:
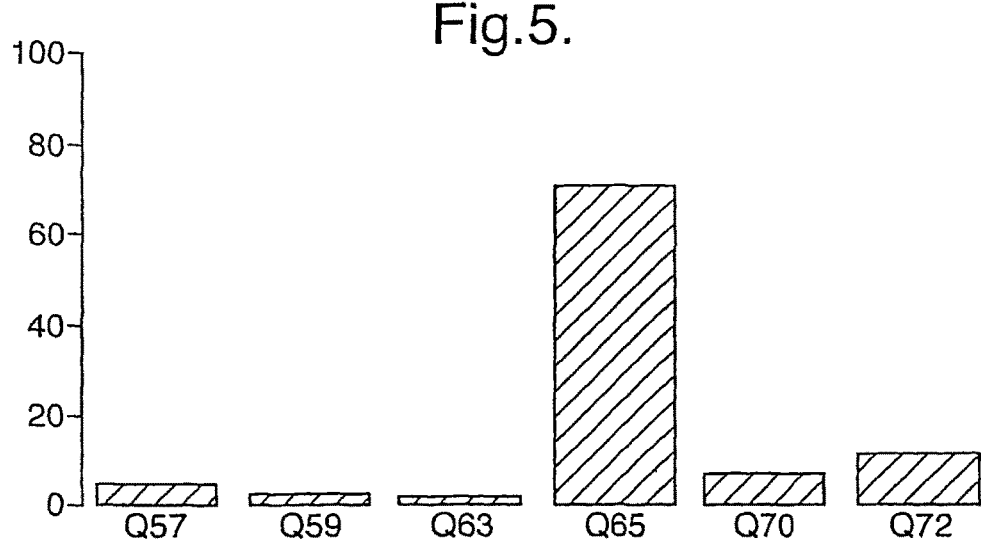
FIG. 5 shows the amino acids that were deamidated by tTG. A-gliadin 56-75 LQLQPFPQPQLPYPQPQSFP (SEQ ID NO:5) (0.1 µM) was incubated with tTG (50 µg/ml) at 37° C. for 2 hours. A single product was identified and purified by reverse phase HPLC. Amino acid analysis allowed % deamidation (Q→E) of each Gln residue in A-gliadin 56-75 (SEQ ID NO:5) attributable to tTG to be calculated (vertical axis).
Figure 6:
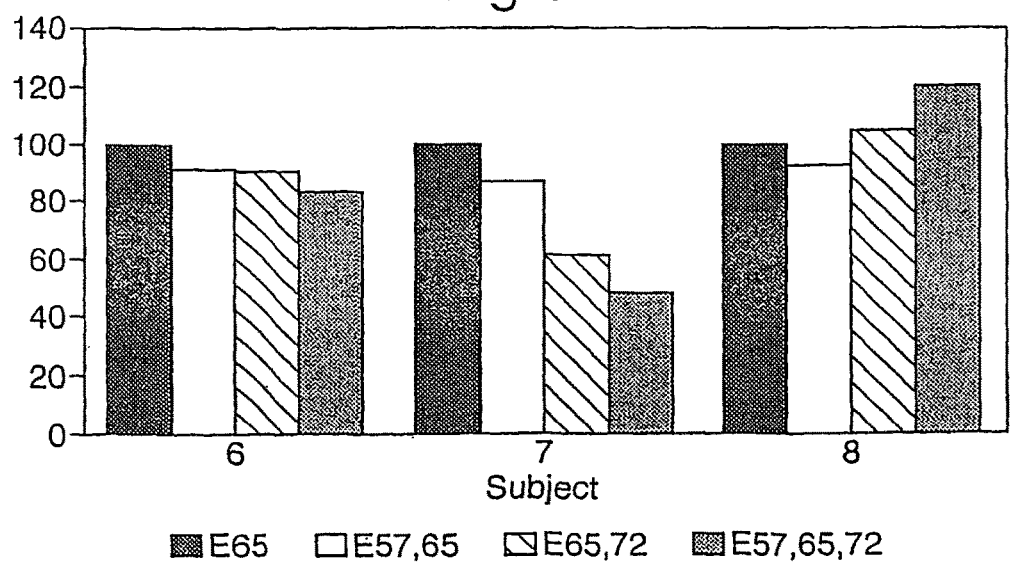
FIG. 6 shows the effect of substituting Q→E in A-gliadin 57-73 (SEQ ID NO:10) at other positions in addition to Q65 using the 17mers: ELQPFPQPELPYPQPQS (SEQ ID NO:6) (E57,65), QLQPFPQPELPYPQPES (SEQ ID NO:7) (E65,72), ELQPFPQPELPYPQPES (SEQ ID NO:8) (E57, 65, 72), and QLQPFPQPELPYPQPQS (SEQ ID NO:2) (E65) in three Coeliac disease subjects on day 6 or 7 after bread was ingested on days 1-3. Vertical axis shows % of the E65 response.

Deamidation of Q65 by tTG Generates the Immunodominant T Cell Epitope in A-Gliadin HPLC analysis demonstrated that tTG treatment of A-gliadin 56-75 (SEQ ID NO:5) generated a single product that eluted marginally later than the parent peptide. Amino acid sequencing indicated that out of the six glutamine (Q) residues contained in A-gliadin 56-75, Q65 (SEQ ID NO:5) was preferentially deamidated by tTG (see FIG. 5). Bioactivity of peptides corresponding to serial expansions from the core A-gliadin 62-68 sequence in which glutamate (E) replaced Q65, was equivalent to the same peptides with Q65 after tTG-treatment (see FIG. 4a). Replacement of Q57 and Q72 by E together or alone, with E65 did not enhance antigenicity of the 17-mer in the three Coeliac disease subjects studied (see FIG. 6). Q57 and Q72 were investigated because glutamine residues followed by proline in gliadin peptides are not deamidated by tTG in vitro (W. Vader et al, Proceedings 8th International Symposium Coeliac Disease). Therefore, the immunodominant T cell epitope was defined as QLQPFPQPELPYPQPQS (SEQ ID NO:2).

Immunodominant T Cell Epitope Response is DQ2-Restricted and CD4 Dependent

In two Coeliac disease subjects homozygous for HLA-DQ α1*0501, β1*0201, anti-DQ monoclonal antibody blocked the ELISPOT IFNγ response to tTG-treated A-gliadin 56-75 (SEQ ID NO:5), but anti-DP and -DR antibody did not (see FIG. 7). Anti-CD4 and anti-CD8 magnetic bead depletion of PBMC from two Coeliac disease subjects indicated the IFNγ response to tTG-treated A-gliadin 56-75 (SEQ ID NO:5) is CD4 T cell-mediated.

Discussion

In this study we describe a rather simple dietary antigen challenge using standard white bread to elicit a transient population of CD4 T cells in peripheral blood of Coeliac disease subjects responsive to a tTG-treated A-gliadin 17-mer with the sequence: QLQPFPQPELPYPQPQS (SEQ ID NO:2) (residues 57-73). The immune response to A-gliadin 56-75 (Q→E65) (SEQ ID NO:11) is restricted to the Coeliac disease-associated HLA allele, DQ a 1*0501, 01*0201. Tissue transglutaminase action in vitro selectively deamidates Q65. Elicited peripheral blood IFNg responses to synthetic A-gliadin peptides with the substitution Q→E65 is equivalent to tTG-treated Q65 A-gliadin peptides; both stimulate up to 10-fold more T cells in the IFNg ELISPOT than unmodified Q65 A-gliadin peptides.

We have deliberately defined this Coeliac disease-specific T cell epitope using in vivo antigen challenge and short-term ex vivo immune assays to avoid the possibility of methodological artifacts that may occur with the use of T cell clones in epitope mapping. Our findings indicate that peripheral blood T cell responses to ingestion of gluten are rapid but short-lived and can be utilized for epitope mapping. In vivo antigen challenge has also shown there is a temporal hierarchy of immune responses to A-gliadin peptides; A-gliadin 57-73 (SEQ ID NO:10) modified by tTG not only elicits the strongest IFNg response in PBMC but it is also the first IFNg response to appear.

Because we have assessed only peptides spanning A-gliadin, there may be other epitopes in other gliadins of equal or greater importance in the pathogenesis of Coeliac disease. Indeed, the peptide sequence at the core of the epitope in A-gliadin that we have identified PQPQLPY (SEQ ID NO:4) is shared by several other gliadins (SwissProt and Trembl accession numbers: P02863, Q41528, Q41531, Q41533, Q9ZP09, P04722, P04724, P18573). However, A-gliadin peptides that have previously been shown to possess bioactivity in biopsy challenge and in vivo studies (for example: 31-43, 44-55, and 206-217)[4,5] did not elicit IFNg responses in PBMC following three day bread challenge in Coeliac disease subjects. These peptides may be "secondary" T cell epitopes that arise with spreading of the immune response.

Example 2

The Effect on T Cell Recognition of Substitutions in the Immunodominant Epitope

Figure 8:
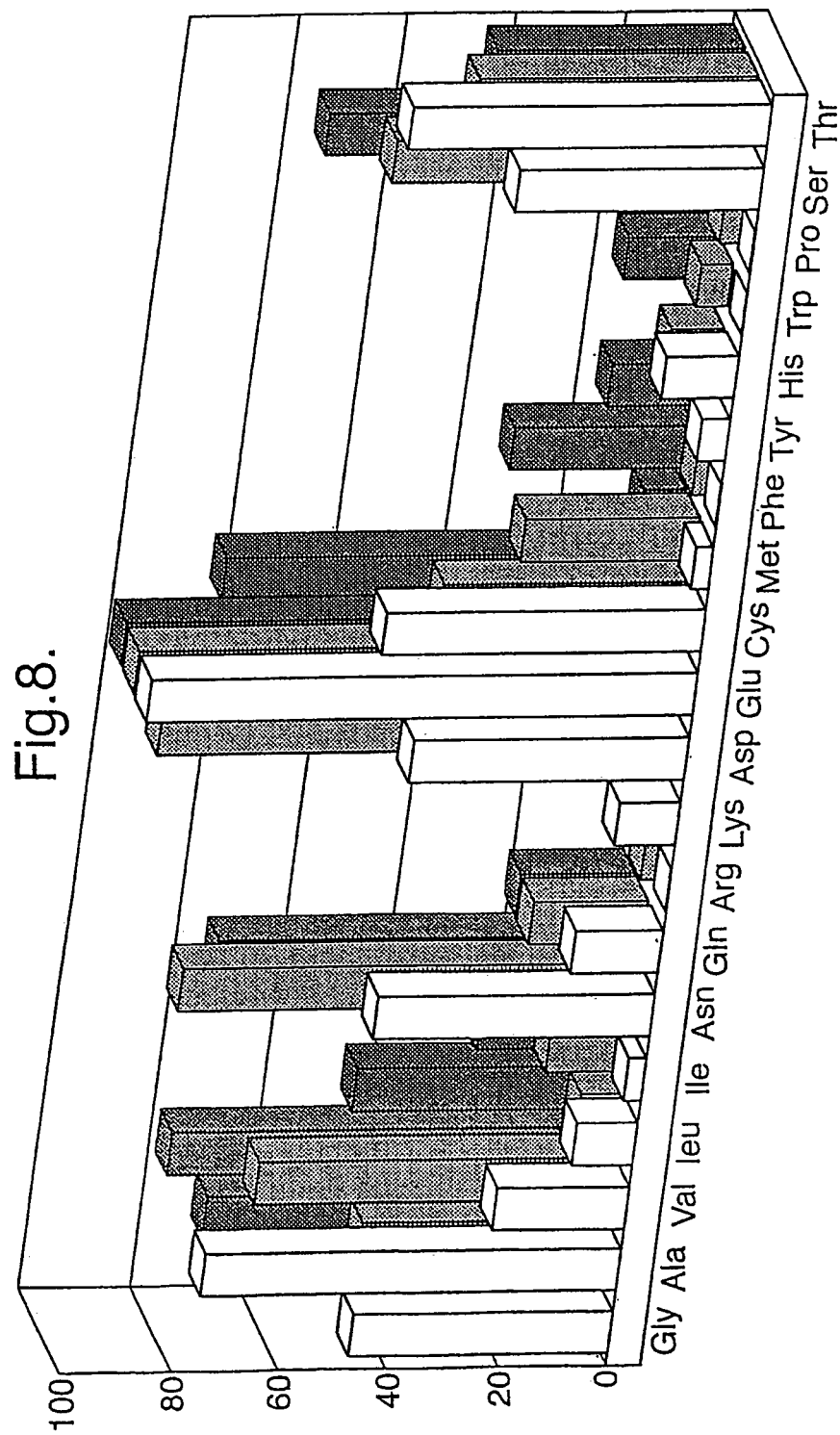
FIG. 8 shows the effect of substituting Glu at position 65 for other amino acids in the immunodominant epitope. The vertical axis shows the % response in the 3 subjects in relation to the immunodominant epitope.

The effect of substituting the glutamate at position 65 in the 57-73 A-gliadin epitope was determined by measuring peripheral blood responses against the substituted epitopes in an IFNγ ELISPOT assay using synthetic peptides (at 50 μg/ml). The responses were measured in 3 Coeliac disease subjects 6 days after commencing gluten challenge (4 slices bread daily for 3 days). Results are shown in table 3 and FIG. 8. As can be seen substitution of the glutamate to histidine, tyrosine, tryptophan, lysine, proline or arginine stimulated a response whose magnitude was less than 10% of the magnitude of the response to the immunodominant epitope. Thus mutation of A-gliadin at this position could be used to produce a mutant gliadin with reduce or absent immunoreactivity.

Example 3

Figure 9:
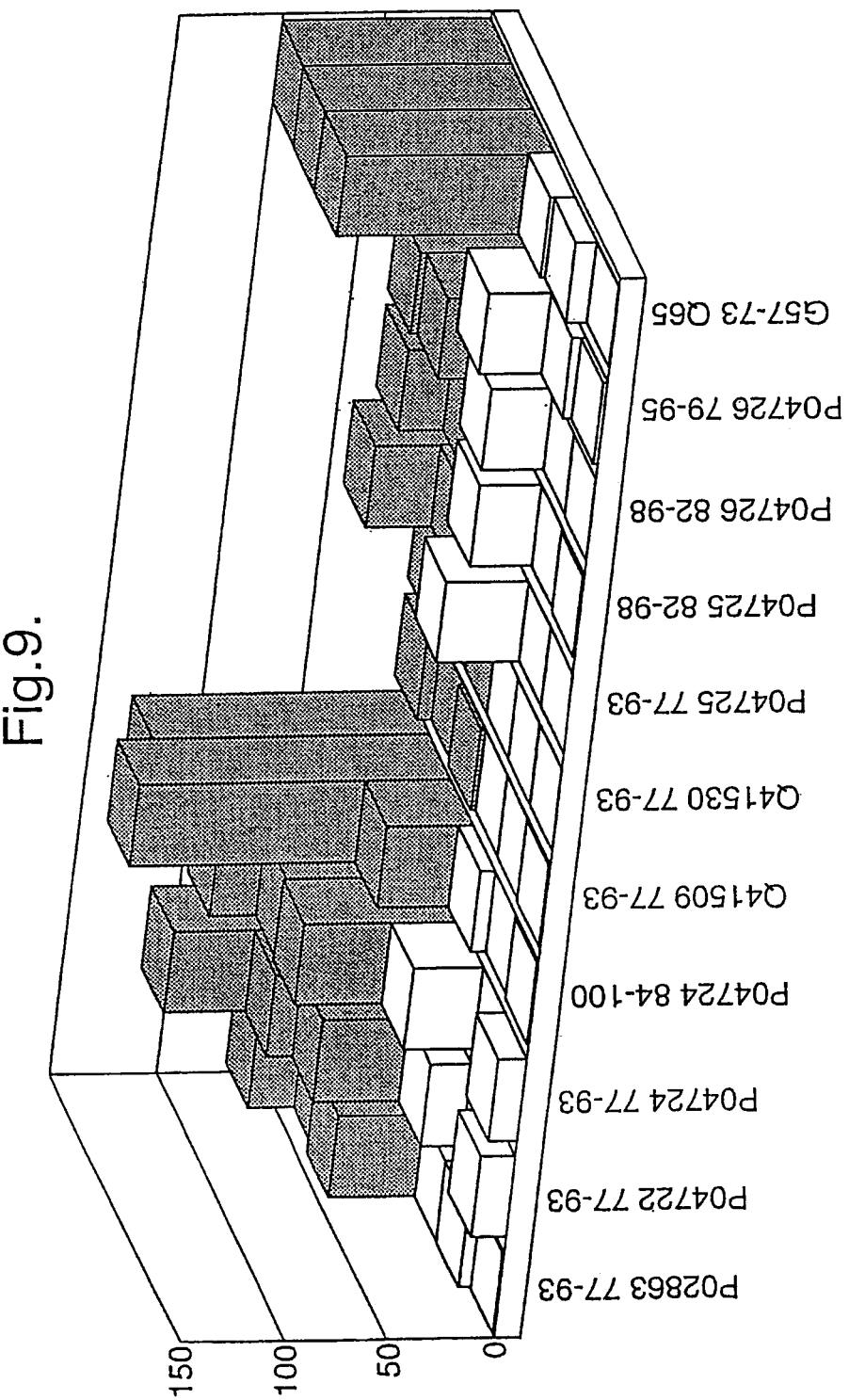
FIG. 9 shows the immunoreactivity of naturally occurring gliadin peptides (measuring responses from 3 subjects) which contain the sequence PQLPY (SEQ ID NO:12) with (shaded) and without (clear) transglutaminase treatment.

Testing the Immunoreactivity of Equivalent Peptides from Other Naturally Occurring Gliadins The immunoreactivity of equivalent peptides form other naturally occurring wheat gliadins was assessed using synthetic peptides corresponding to the naturally occurring sequences which were then treated with transglutaminase. These peptides were tested in an ELISPOT in the same manner and with PBMCs from the same subjects as described in Example 2. At least five of the peptides show immunoreactivity comparable to the A-gliadin 57-73 E65 (SEQ ID NO:2) peptide (after transglutaminase treatment) indicating that other gliadin proteins in wheat are also likely to induce this Coeliac disease-specific immune response (Table 4 and FIG. 9).

Methods

Subjects: Patients used in the study attended a Coeliac Clinic in Oxford, United Kingdom. Coeliac disease was diagnosed on the basis of typical small intestinal histology, and normalization of symptoms and small intestinal histology with gluten free diet.

Tissue Typing:

Tissue typing was performed using DNA extracted from EDTA-anticoagulated peripheral blood. HLA-DQA and DQB genotyping was performed by PCR using sequence-specific primer mixes[6-8].

Anti-Endomysial Antibody Assay:

EMA were detected by indirect immunofluorescence using patient serum diluted 1:5 with monkey oesophagus, followed by FITC-conjugated goat anti-human IgA. IgA was quantitated prior to EMA, none of the subjects were IgA deficient.

Antigen Challenge:

Coeliac disease subjects following a gluten free diet, consumed 4 slices of gluten-containing bread (50 g/slice, Sainsbury's "standard white sandwich bread") daily for 3 or 10 days. EMA was assessed the week before and up to two months after commencing the bread challenge. Healthy subjects who had followed a gluten free diet for four weeks, consumed their usual diet including four slices of gluten-containing bread for three days, then returned to gluten free diet for a further six days.

IFNγ and IL-10 ELISPOT:

PBMC were prepared from 50-100 ml of venous blood by Ficoll-Hypaque density centrifugation. After three washes, PBMC were resuspended in complete RPMI containing 10% heat inactivated human AB serum. ELISPOT assays for single cell secretion of IFNγ and IL-10 were performed using commercial kits (Mabtech; Stockholm, Sweden) with 96-well plates (MAIP-S-45; Millipore, Bedford, Mass.) according to the manufacturers instructions (as described elsewhere[9]) with $2-5\times10^5$ (IFNγ) or $0.4-1\times10^5$ (IL-10) PBMC in each well. Peptides were assessed in duplicate wells, and *Mycobacterium tuberculosis* purified protein derivative (PPD RT49) (Serum Institute; Copenhagen, Denmark) (20 µg/ml) was included as a positive control in all assays.

Peptides:

Synthetic peptides were purchased from Research Genetics (Huntsville, Ala.) Mass-spectroscopy and HPLC verified peptides' authenticity and >70% purity. Digestion of gliadin (Sigma; G-3375) (100 mg/ml) with α-chymotrypsin (Sigma; C-3142) 200:1 (w/w) was performed at room temperature in 0.1 M $NH_4HCO_3$ with 2M urea and was halted after 24 h by heating to 98° C. for 10 minutes. After centrifugation (13,000 g, 10 minutes), the gliadin digest supernatant was filter-sterilized (0.2 mm). Digestion of gliadin was verified by SDS-PAGE and protein concentration assessed. α-Chymotrypsin-digested gliadin (640 µg/ml) and synthetic gliadin peptides (15-mers: 160 µg/ml, other peptides: 0.1 mM) were individually treated with tTG (Sigma; T-5398) (50 Mimi) in $PBS+CaCl_2$ 1 mM for 2 h at 37° C. Peptides and peptide pools were aliquotted into sterile 96-well plates and stored frozen at −20° C. until use.

Amino Acid Sequencing of Peptides:

Reverse phase HPLC was used to purify the peptide resulting from tTG treatment of A-gliadin 56-75 (SEQ ID NO:5). A single product was identified and subjected to amino acid sequencing (automated sequencer Model 494A, Applied Biosystems, Foster City, Calif.). The sequence of unmodified G56-75 was confirmed as: LQLQPFPQPQLPYPQPQSFP (SEQ ID NO:5), and tTG treated G56-75 was identified as: LQLQPFPQPELPYPQPQSFP (SEQ ID NO:11). Deamidation of glutamyl residues was defined as the amount (pmol) of glutamate recovered expressed as a percent of the combined amount of glutamine and glutamate recovered in cycles 2, 4, 8, 10, 15 and 17 of the amino acid sequencing. Deamidation attributable to tTG was defined as (% deamidation of glutamine in the tTG treated peptide−% deamidation in the untreated peptide)/(100−% deamidation in the untreated peptide).

CD4/CD8 and HLA Class II Restriction:

Anti-CD4 or anti-CD8 coated magnetic beads (Dynal, Oslo, Norway) were washed four times with RPMI then incubated with PBMC in complete RPMI containing 10% heat inactivated human AB serum ($5\times10^6$ cells/trip for 30 minutes on ice. Beads were removed using a magnet and cells remaining counted. In vivo HLA-class II restriction of the immune response to tTG-treated 56-75 (SEQ ID NO:5) was established by incubating PBMC ($5\times10^6$ cells/ml) with anti-HLA-DR (L243), -DQ (L2), and -DP (B7.21) monoclonal antibodies (10 µg/ml) at room temperature for one hour prior to the addition of peptide.

Example 4

Mucosal Integrin Expression by Gliadin-Specific Peripheral Blood Lymphocytes

Interaction between endothelial and lymphocyte adressins facilitates homing of organ-specific lymphocytes. Many adressins are known. The heterodimer $\alpha_4\beta_7$ is specific for lamina propria gut and other mucosal lymphocytes, and $\alpha^E\beta_7$ is specific for intra-epithelial lymphocytes in the gut and skin. Approximately 30% of peripheral blood CD4 T cells express $\alpha_4\beta_7$ and are presumed to be in transit to a mucosal site, while 5% of peripheral blood T cells express $\alpha^E\beta_7$. Immunomagnetic beads coated with antibody specific for $\alpha^E$ or $\beta_7$ deplete PBMC of cells expressing $\alpha^E\beta_7$ or $\alpha^E\beta_7$ and $\alpha_4\beta_7$, respectively. In combination with ELISpot assay, immunomagnetic bead depletion allows determination of gliadin-specific T cell addressin expression that may identify these cells as homing to a mucosal surface. Interestingly, gluten challenge in vivo is associated with rapid influx of CD4 T cells to the small intestinal lamina propria (not intra-epithelial sites), where over 90% lymphocytes express $\alpha_4\beta_7$.

Immunomagnetic beads were prepared and used to deplete PBMC from coeliac subjects on day 6 or 7 after commencing 3 day gluten challenge. FACS analysis demonstrated $\alpha^E$ beads depleted approximately 50% of positive CD4 T cells, while $\beta_7$ beads depleted all $\beta_7$ positive CD4 T cells. Depletion of PBMC using CD4- or $\beta_7$-beads, but not CD8- or $\alpha^E$-beads, abolished responses in the interferon gamma ELISpot. tTG gliadin and PPD responses were abolished by CD4 depletion, but consistently affected by integrin-specific bead depletion.

Thus A-gliadin 57-73 QE65 (SEQ ID NO:2)-specific T cells induced after gluten challenge in coeliac disease express the integrin, $\alpha_4\beta_7$, present on lamina propria CD4 T cells in the small intestine.

Example 5

Optimal T Cell Epitope Length

Previous data testing peptides from 7 to 17 amino acids in length spanning the core of the dominant T cell epitope in A-gliadin indicated that the 17mer, A-gliadin 57-73 QE65 (SEQ ID NO:2) induced maximal responses in the interferon gamma Elispot using peripheral blood mononuclear cells (PBMC) from coeliac volunteers 6 days after commencing a 3-day gluten challenge.

Peptides representing expansions form the core sequence of the dominant T cell epitope in A-gliadin were assessed in the IFN gamma ELISPOT using peripheral blood mononuclear cells (PBMC) from coeliac volunteers in 6 days after commencing a 3-day gluten challenge (n=4). Peptide 13: A-gliadin 59-71 QE65 (13mer), peptide 15: 58-72 QE65 (15mer), . . . , peptide 27: 52-78 SE65 (27mer).

Figure 11:
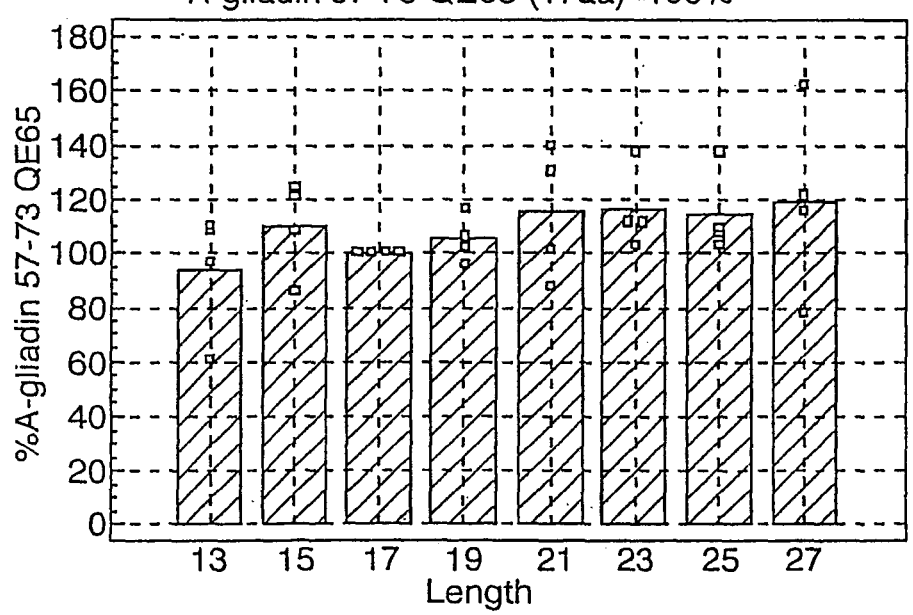
FIG. 11 shows the optimal T cell epitope length.
Figure 12A:
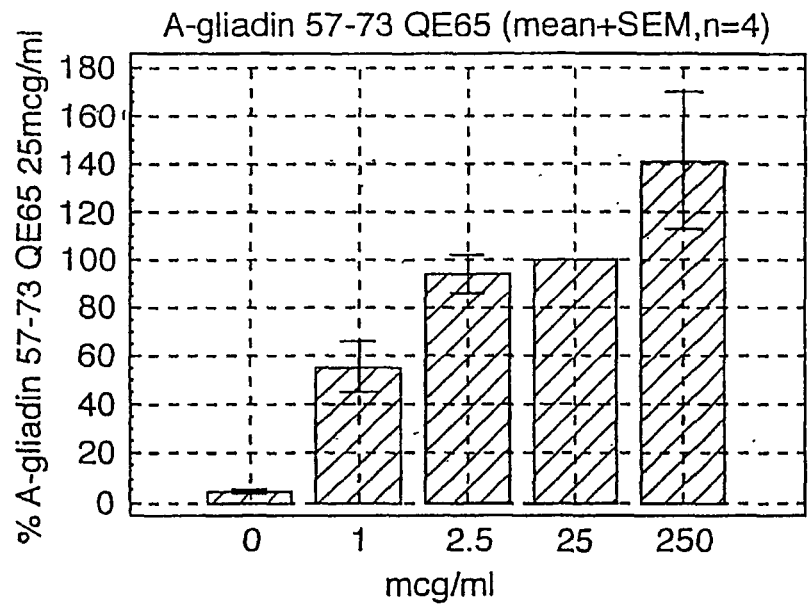
FIG. 12 shows a comparison of A-gliadin 57-73 QE65 (SEQ ID NO:2) with other peptides in a dose response study. On Sheet 12 of 47, FIG. 12(a) discloses the amino acid sequence A-gliadin 57-73 QE65 (SEQ ID NO:2). On Sheet 12 of 47, FIG. 12(b) discloses the amino acid sequence GDA4_WHEAT P04724 84-100 QE92 (SEQ ID NO:101). On Sheet 13 of 47, FIG. 12(c) discloses the amino acid sequence A-gliadin 57-73 (SEQ ID NO:10). On Sheet 13 of 47, FIG. 12(d) discloses the amino acid sequence GDA4_WHEAT P04724 84-100 (SEQ ID NO:72). On Sheet 14 of 47, FIG. 12(e) discloses the amino acid sequence A-gliadin 57-68 QE65 (labelled E65) (SEQ ID NO:13) and amino acid sequence A-gliadin 57-68: (labelled Q65) (SEQ ID NO:53). On Sheet 15 of 47, FIG. 12(f) discloses the amino acid sequence a-2 62-75 QE65 & QE72: (SEQ ID NO:47) (labelled E65) and amino acid sequence a-2 62-75 Q65 (SEQ ID NO:102) (labelled Q65). On Sheet 16 of 47, FIG. 12(g) discloses the amino acid sequence GDA9 202-219: QE208 &216 (SEQ ID NO:99) (labelled E) and amino acid sequence GDA9 202-219 (SEQ ID NO:44) (labelled Q). On Sheet 17 of 47, FIG. 12(h) discloses the amino acid sequence GDB2 134-153 OE140, 148,150 (SEQ ID NO:48) (labelled E) and amino acid sequence GDB2 134-153 SEQ ID NO:103 (labelled Q).
Figure 12B:
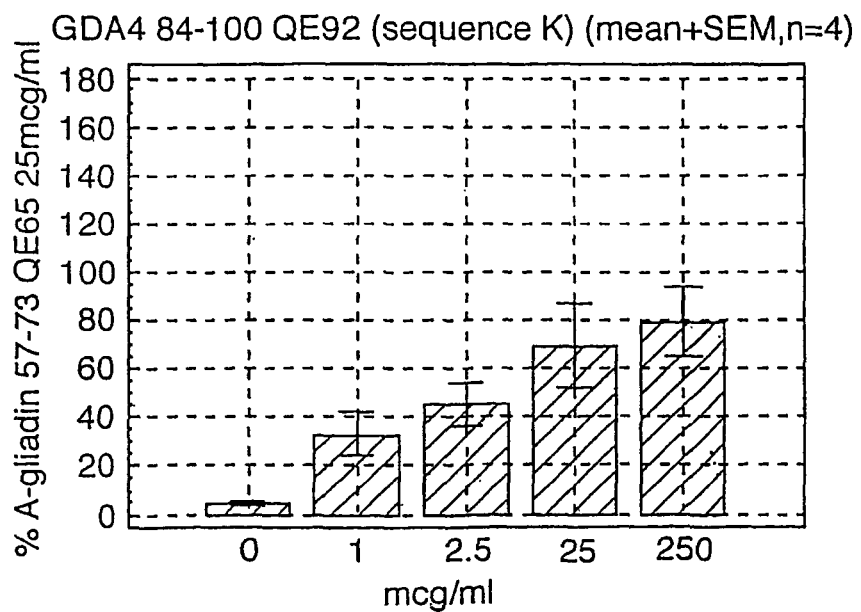
Figure 12C:
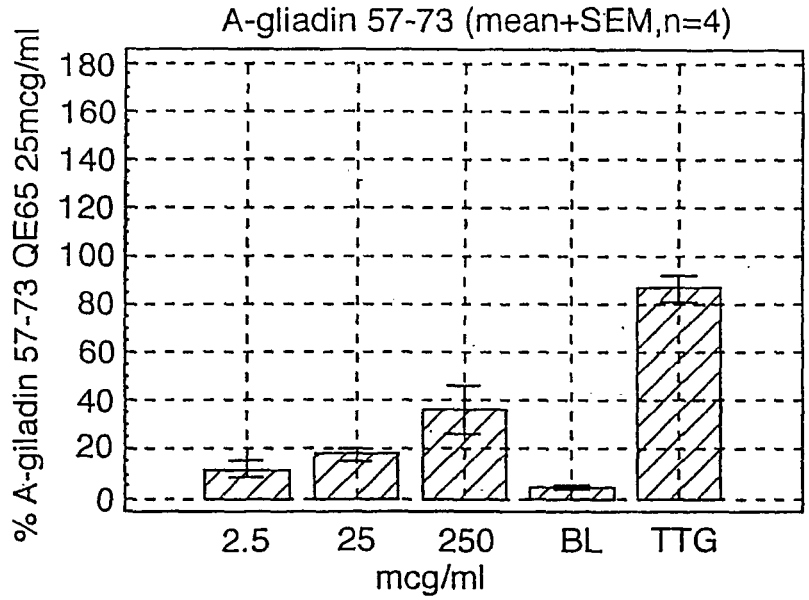
Figure 12D:
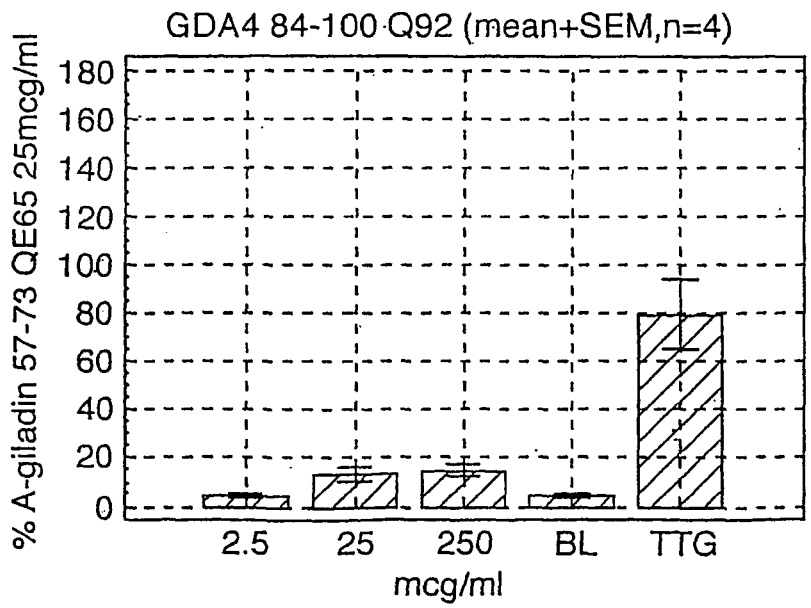
Figure 12E:
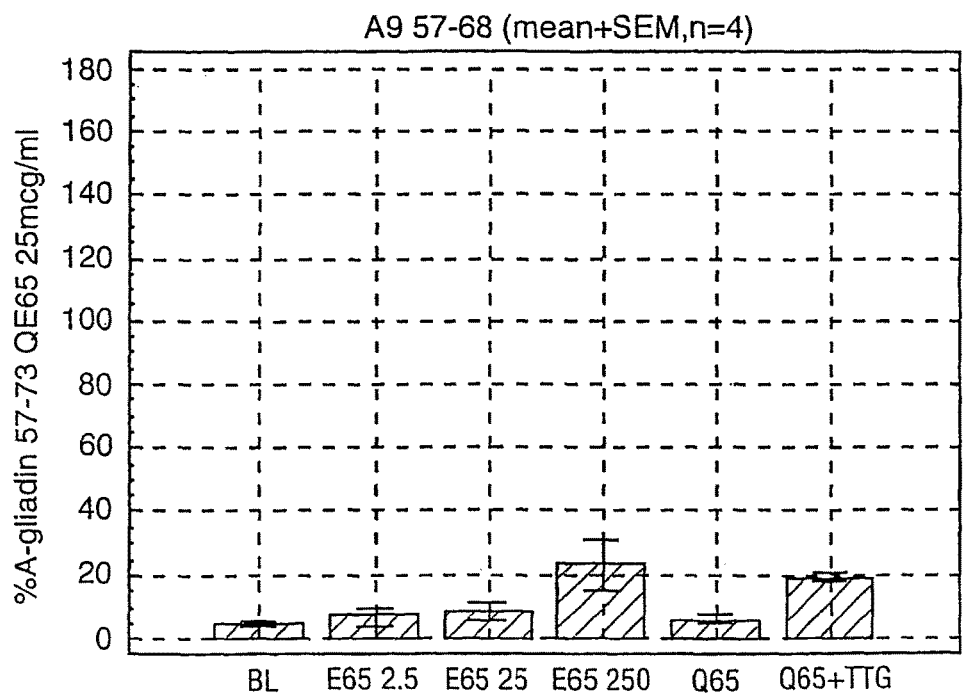
Figure 12F:
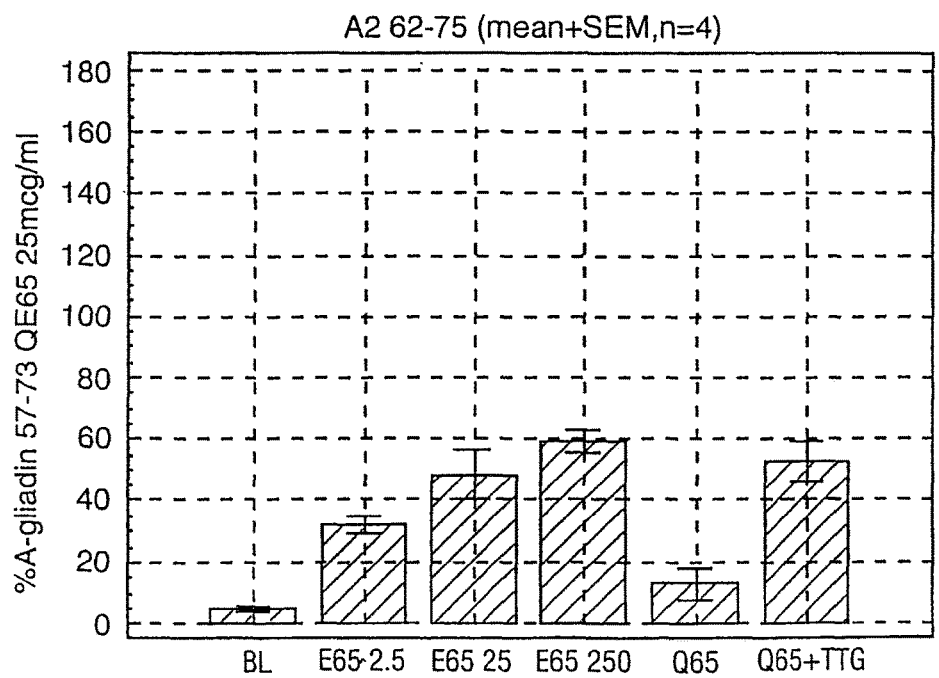
Figure 12G:
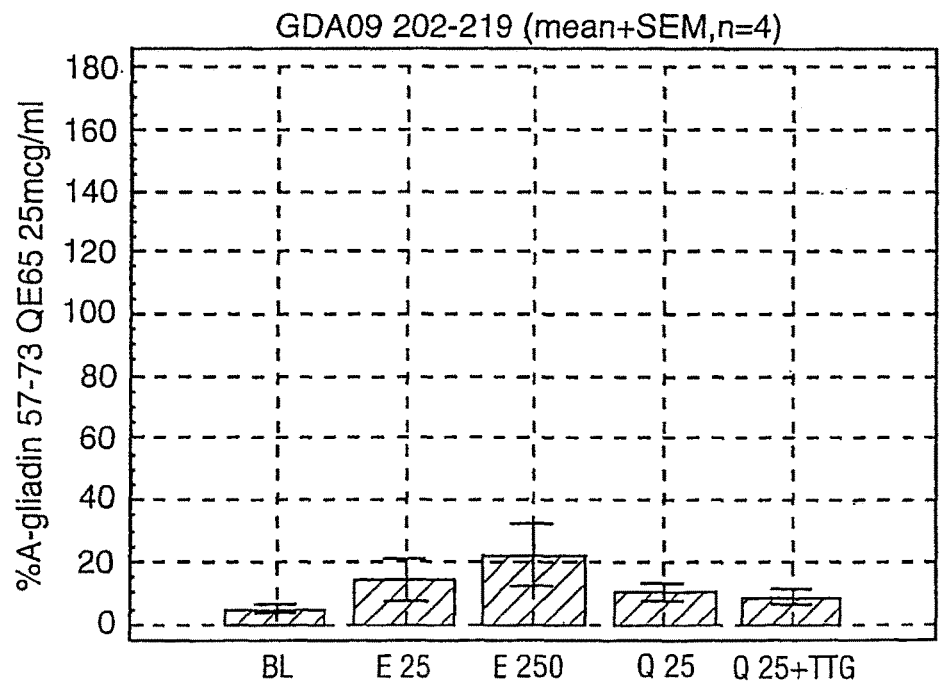
Figure 12H:
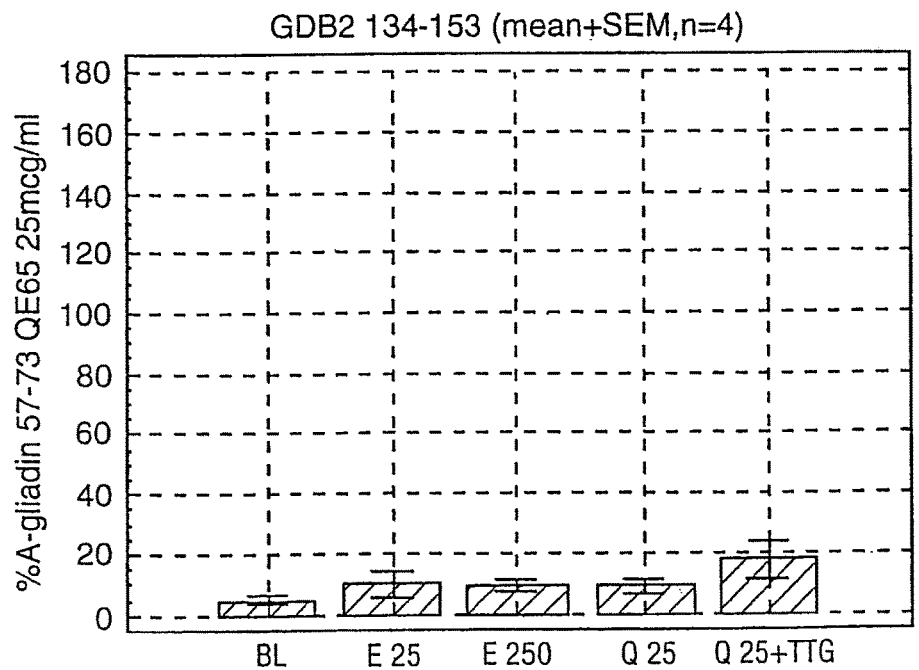

As shown in FIG. 11 expansion of the A-gliadin 57-73 QE65 (SEQ ID NO:2) sequence does not substantially enhance response in the IFNgamma Elispot. Subsequent Examples characterise the agonist and antagonist activity of A-gliadin 57-73 QE65 (SEQ ID NO:2) using 17mer peptides.

Example 6

Comparison of A-Gliadin 57-73 QE65 (SEQ ID NO: 2) with Other DQ2-Restricted T Cell Epitopes in Coeliac Disease Dose response studies were performed using peptides corresponding to unmodified and transglutaminase-treated peptides corresponding to T cell epitopes of gluten-specific T cell clones and lines from intestinal biopsies of coeliac subjects. Responses to peptides were expressed as percent of response to A-gliadin 57-73 QE65 (SEQ ID NO:2). AU subjects were HLA-DQ2+(none were DQ8+).

The studies indicate that A-gliadin 57-73 QE65 (SEQ ID NO:2) is the most potent gliadin peptide for induction of interferon gamma in the ELISpot assay using coeliac PBMC after gluten challenge (see FIG. 12a-h, and Tables 5 and 6). The second and third epitopes are suboptimal fragments of larger peptides i.e. A-gliadin 57-73 QE65 (SEQ ID NO:2) and GDA4_WHEAT P04724-84-100 QE92. The epitope is only modestly bioactive (approximately $\frac{1}{20}^{th}$ as active as A-gliadin 57-73 QE65 (SEQ ID NO:2) after blank is subtracted).

A-gliadin 57-73 QE65 (SEQ ID NO:2) is more potent than other known T cell epitopes in coeliac disease. There are 16 polymorphisms of A-gliadin 57-73 (SEQ ID NO:10) (including the sequence PQLPY (SEQ ID NO:12)) amongst sequenced gliadin genes, their bioactivity is assessed next.

Example 7

Comparison of Gliadin- and A-Gliadin 57-73 QE65 (SEQ ID NO:2)-Specific Responses in Peripheral Blood The relative contribution of the dominant epitope, A-gliadin 57-73 QE65, (SEQ ID NO:2) to the total T cell response to gliadin in coeliac disease is a critical issue. Pepsin-trypsin and chymotrypsin-digested gliadin have been traditionally used as antigen for development of T cell lines and clones in coeliac disease. However, it is possible that these proteases may cleave through certain peptide epitopes. Indeed, chymotrypsin digestion of recombinant a9-gliadin generates the peptide QLQPFPQPELPY (SEQ ID NO:13), that is a truncation of the optimal epitope sequence QLQPFPQPELPYPQPQS (SEQ ID NO:2) (see above). Transglutaminase-treatment substantially increases the potency of chymotrypsin-digested gliadin in proliferation assays of gliadin-specific T cell clones and lines. Hence, transglutaminase-treated chymotrypsin-digested gliadin (tTG gliadin) may not be an ideal antigen, but responses against this mixture may approximate the "total" number of peripheral blood lymphocyte specific for gliadin. Comparison of responses against A-gliadin 57-73 QE65 (SEQ ID NO:2) and tTG gliadin in the ELISpot assay gives an indication of the contribution of this dominant epitope to the overall immune response to gliadin in coeliac disease, and also be a measure of epitope spreading.

Figure 13A:
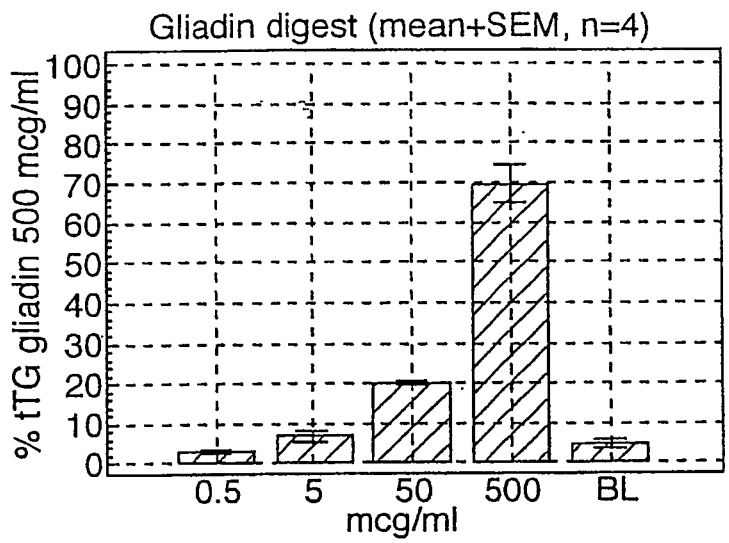
FIG. 13 shows a comparison of gliadin and A-gliadin 57-73 QE65 (SEQ ID NO:2) specific responses.
Figure 13B:
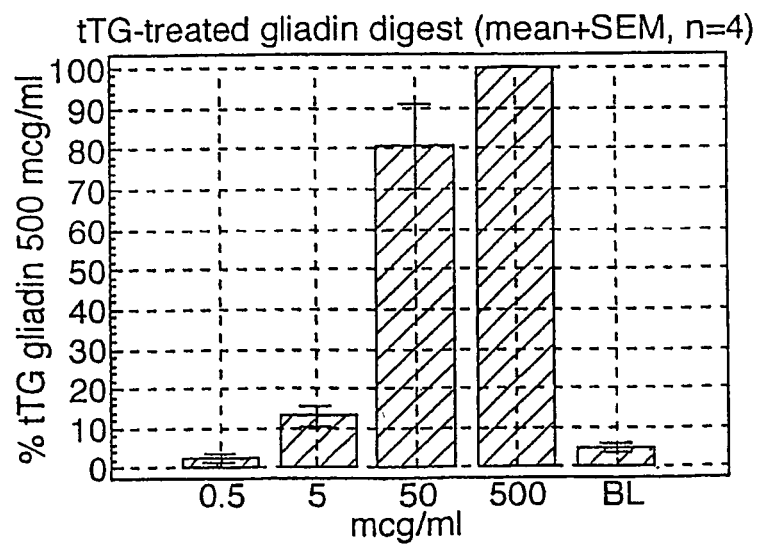
Figure 13C:
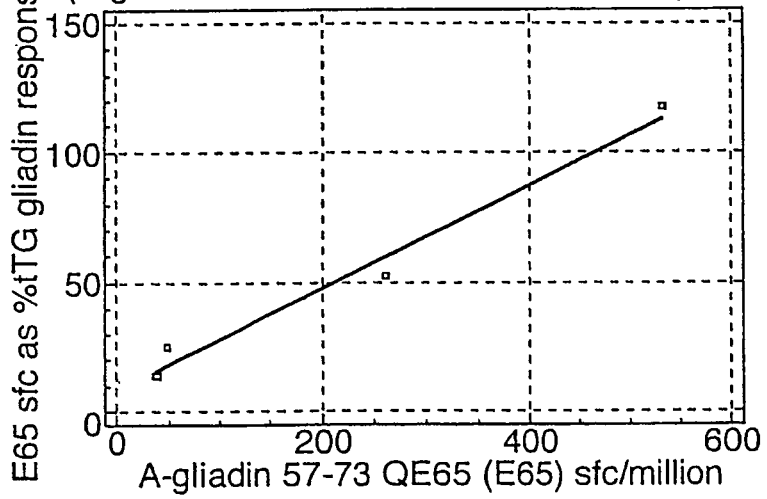

PBMC collected on day 6 or 7 after commencing gluten challenge in 4 coeliac subjects were assessed in dose response studies using chymotrypsin-digested gliadin+/− tTG treatment and compared with ELISpot responses to an optimal concentration of A-gliadin 57-73 QE65 (SEQ ID NO:2) (25 mcg/ml). TTG treatment of gliadin enhanced PBMC responses in the ELISpot approximately 10-fold (tTG was comparable to blank when assessed alone) (see FIG. 13a-c). In the four coeliac subjects studied, A-gliadin 57-73 QE65 (SEQ ID NO:2) (25 mcg/ml) elicited responses between 14 and 115% those of tTG gliadin (500 mcg/ml), and the greater the response to A-gliadin 57-73 QE65 (SEQ ID NO:2) the greater proportion it represented of the tTG gliadin response.

Relatively limited data suggest that A-gliadin 57-73 QE65 (SEQ ID NO:2) responses are comparable to tTG gliadin in some subjects. Epitope spreading associated with more evolved anti-gliadin T cell responses may account for the smaller contribution of A-gliadin 57-73 QE65 (SEQ ID NO:2) to "total" gliadin responses in peripheral blood in some individuals. Epitope spreading may be maintained in individuals with less strictly gluten free diets.

Example 8

Definition of Gliadin Peptides Bioactive in Coeliac Disease: Polymorphisms of A-Gliadin 57-73 (SEQ ID NO:10).

Overlapping 15mer peptides spanning the complete sequence of A-gliadin were assessed in order to identify the immunodominant sequence in coeliac disease. A-gliadin was the first fully sequenced alpha gliadin protein and gene, but is one of approximately 30-50 related alpha gliadin proteins in wheat. Twenty five distinct alpha-gliadin genes have been identified by searching protein data bases, Swiss-Prot and TREMBL describing a further 8 alpha-gliadins. Contained within these 25 alpha-gliadins, there are 16 distinct polymorphisms of the sequence corresponding to A-gliadin 57-73 (SEQ ID NO:10) (see Table 7).

Figure 14B:
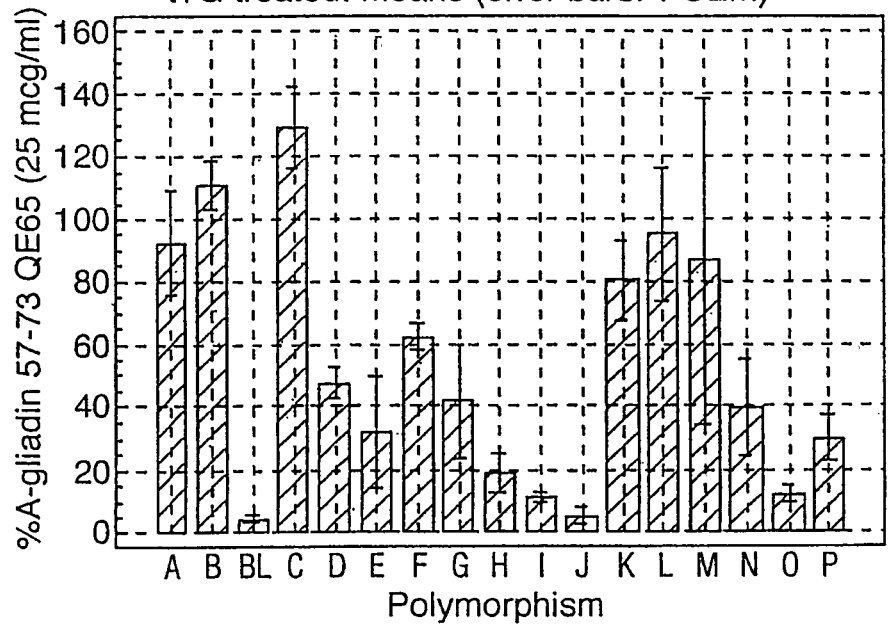
FIG. 14 shows the bioactivity of gliadin polymorphisms in coeliac subjects. On Sheets 20 through 23 of 47, sixteen amino acids are identified (A-P) in the legend of each figure. The amino acid sequences A through P correspond to the following sequence identifiers:
  A—SEQ ID NO: 10
  B—SEQ ID NO: 26
  C—SEQ ID NO: 51
  D—SEQ ID NO: 104
  E—SEQ ID NO: 68
  F—SEQ ID NO:28
  G—SEQ ID NO: 69
  H—SEQ ID NO:70
  I—SEQ ID NO:71
  J—SEQ ID NO:105
  K—SEQ ID NO:72
  L—SEQ ID NO:73
  M—SEQ ID NO:74
  N—SEQ ID NO:75
  O—SEQ ID NO:97
  P—SEQ ID NO:77
Figure 14C:
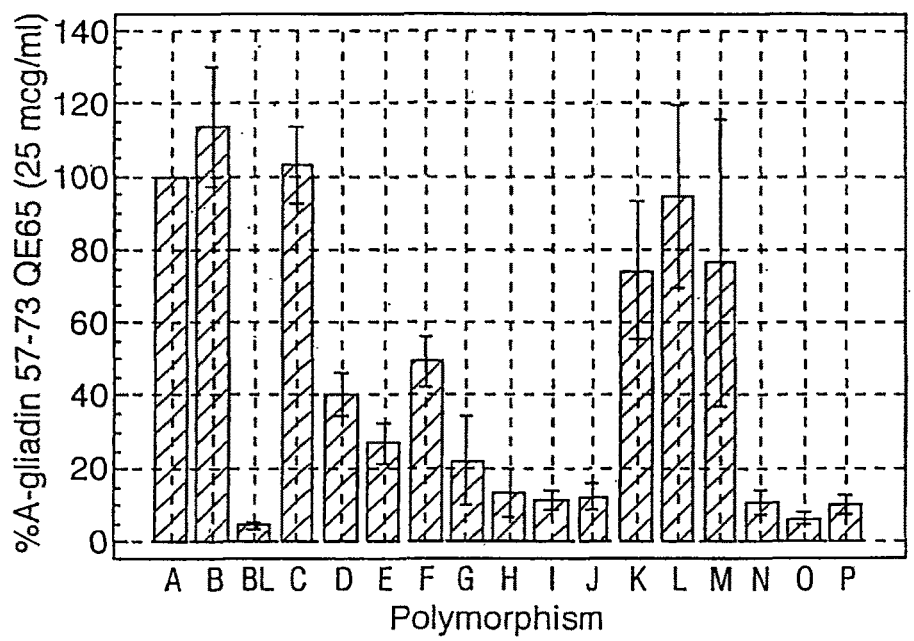

Synthetic peptides corresponding to these 16 polymorphisms, in an unmodified form, after treatment with transglutaminase in vitro, as well as with glutamate substituted at position 10 (equivalent to QE65 in A-gliadin 57-73 (SEQ ID NO:10)) were assessed using PBMC from coeliac subjects, normally following a gluten free diet, day 6 or 7 after gluten challenge in interferon gamma ELISpot assays. Glutamate-substituted peptides were compared at three concentrations (2.5, 25 and 250 mcg/ml), unmodified peptide and transglutaminase-treated peptides were assessed at 25 mcg/ml only. Bioactivity was expressed as % of response associated with A-gliadin 57-73 QE65 (SEQ ID NO:2) 25 mcg/ml in individual subjects (n=4). (See FIG. 14).

Bioactivity of "wild-type" peptides was substantially increased (>5-fold) by treatment with transglutaminase. Transglutaminase treatment of wild-type peptides resulted in bioactivity similar to that of the same peptides substituted with glutamate at position 10. Bioactivities of five glutamate-substituted peptides (B, C, K, L, M), were >70% that of A-gliadin 57-73 QE65 (SEQ ID NO:2) (A), but none was significantly more bioactive than A-gliadin 57-73 QE65 (SEQ ID NO:2). PBMC responses to glutamate-substituted peptides at concentrations of 2.5 and 250 mcg/ml were comparable to those at 25 mcg/ml. Six glutamate-substituted gliadin peptides (H, I, J, N, O, P) were <15% as bioactive as A-gliadin 57-73 QE65 (SEQ ID NO:2). Other peptides were intermediate in bioactivity.

At least six gliadin-derived peptides are equivalent in potency to A-gliadin 57-73 QE65 (SEQ ID NO:2) after modification by transglutaminase. Relatively non-bioactive polymorphisms of A-gliadin 57-73 (SEQ ID NO:10) also exist. These data indicate that transglutaminase modification of peptides from several gliadins of *Triticum aestivum, T. uariu* and *T. spelta* may be capable of generating the immunodominant T cell epitope in coeliac disease.

Genetic modification of wheat to generate non-coeliac-toxic wheat may likely require removal or modification of multiple gliadin genes. Generation of wheat containing gliadins or other proteins or peptides incorporating sequences defining altered peptide ligand antagonists of A-gliadin 57-73 (SEQ ID NO:10) is an alternative strategy to generate genetically modified wheat that is therapeutic rather than "non-toxic" in coeliac disease.

Example 9

Definition of Core Epitope Sequence:

Comparison of peptides corresponding to truncations of A-gliadin 56-75 (SEQ ID NO:5) from the N- and C-terminal indicated that the core sequence of the T cell epitope is PELPY (A-gliadin 64-68—SEQ ID NO:759). Attempts to define non-agonists and antagonists will focus on variants of A-gliadin that are substituted at residues that substantially contribute to its bioactivity.

Figure 15:
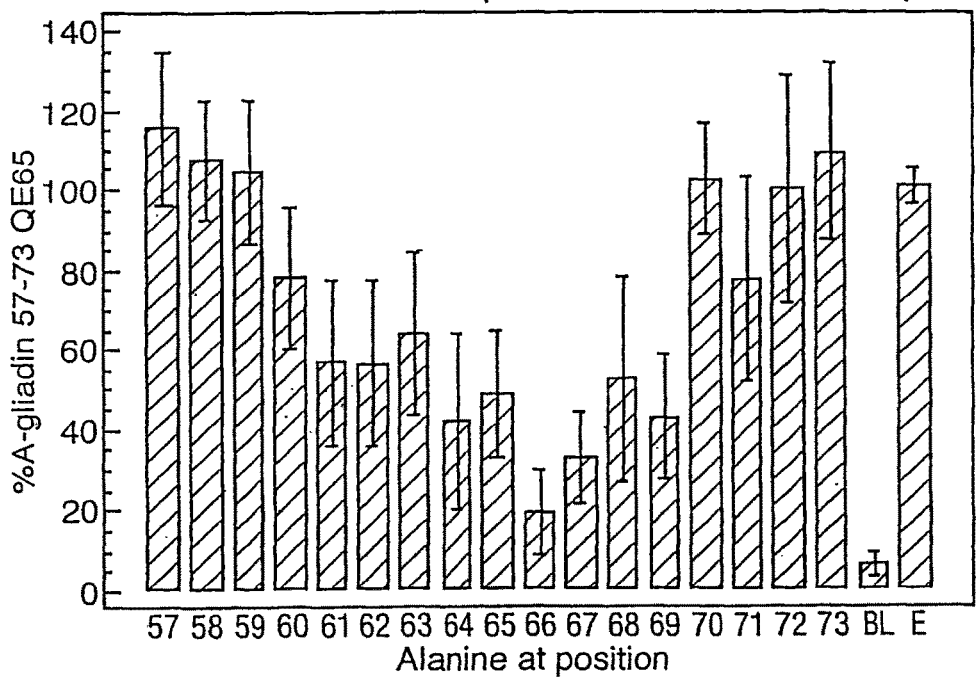
FIGS. 15 and 16 show the defining of the core epitope sequence.
Figure 16:
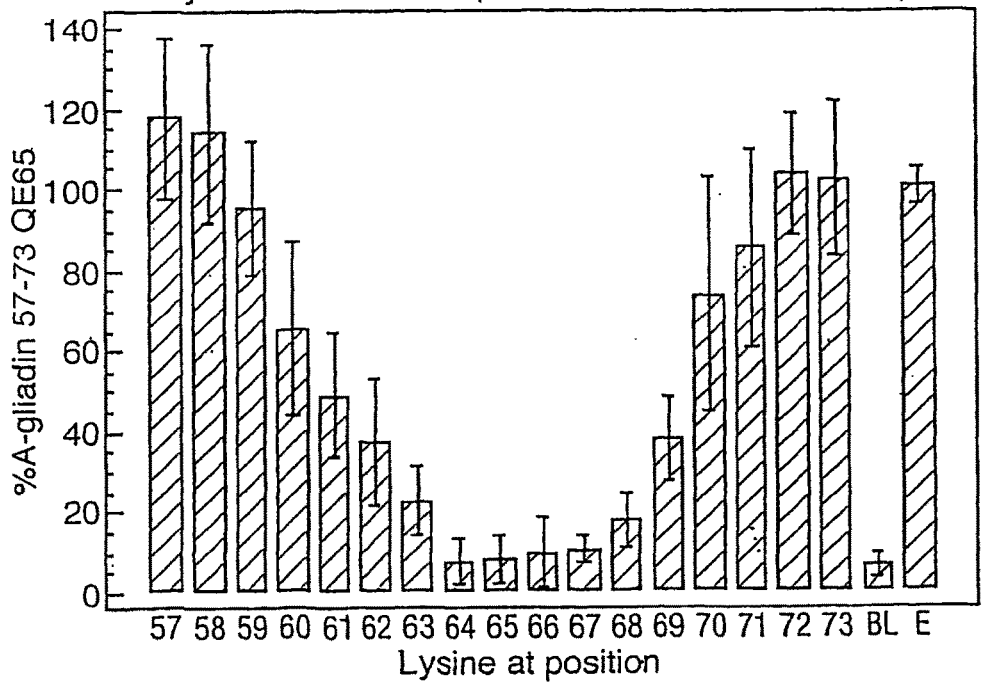
Figure 17:
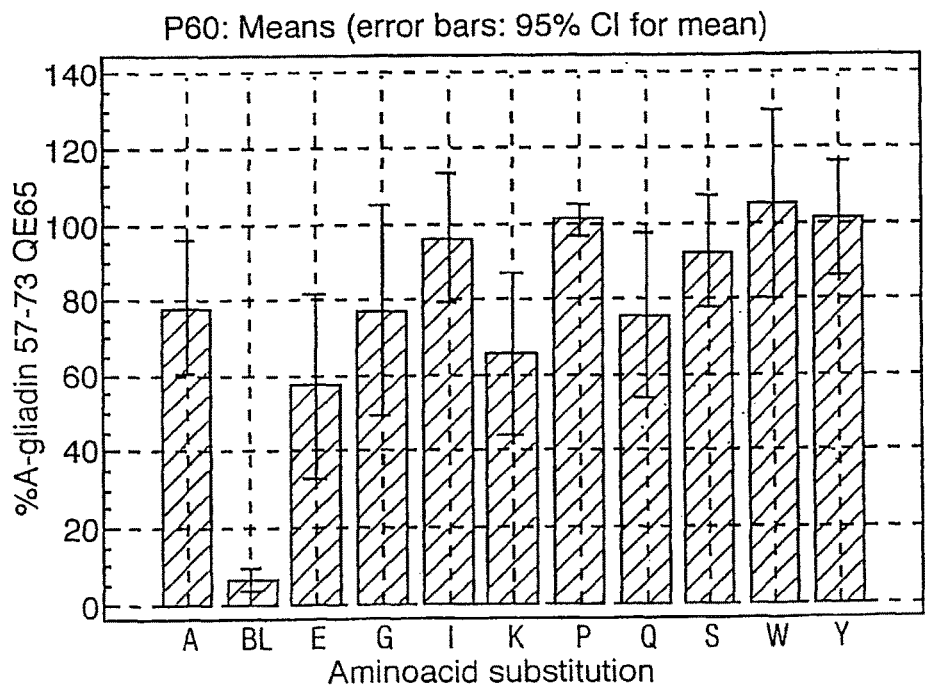
Figure 19:
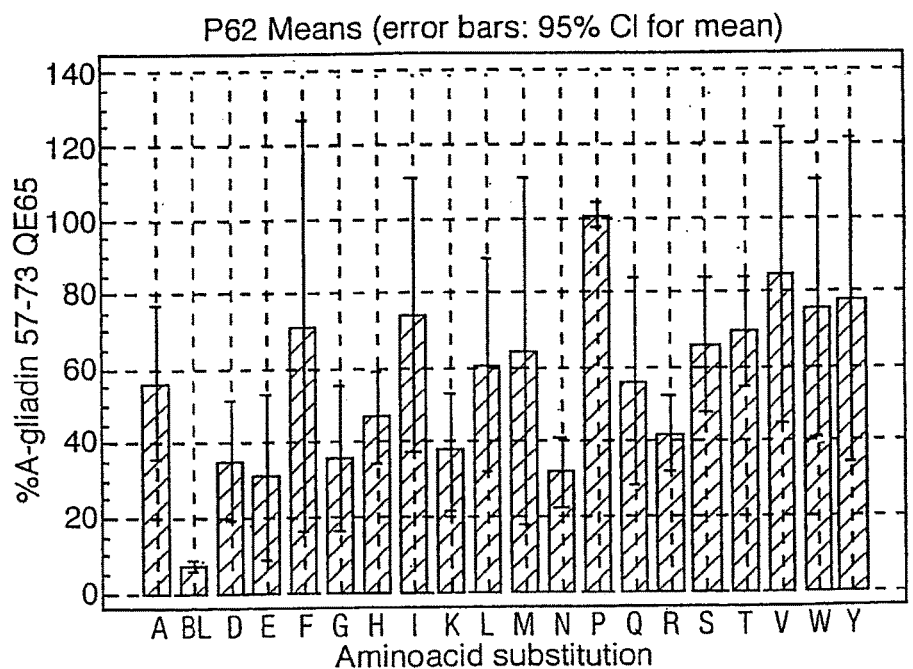
Figure 22:
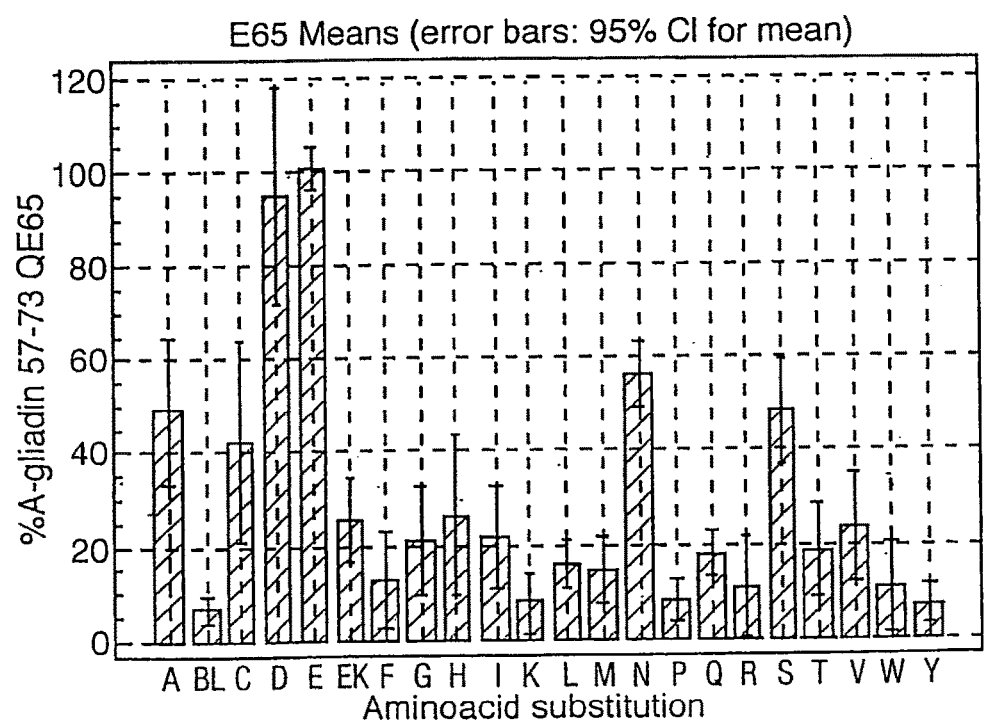
Figure 23:
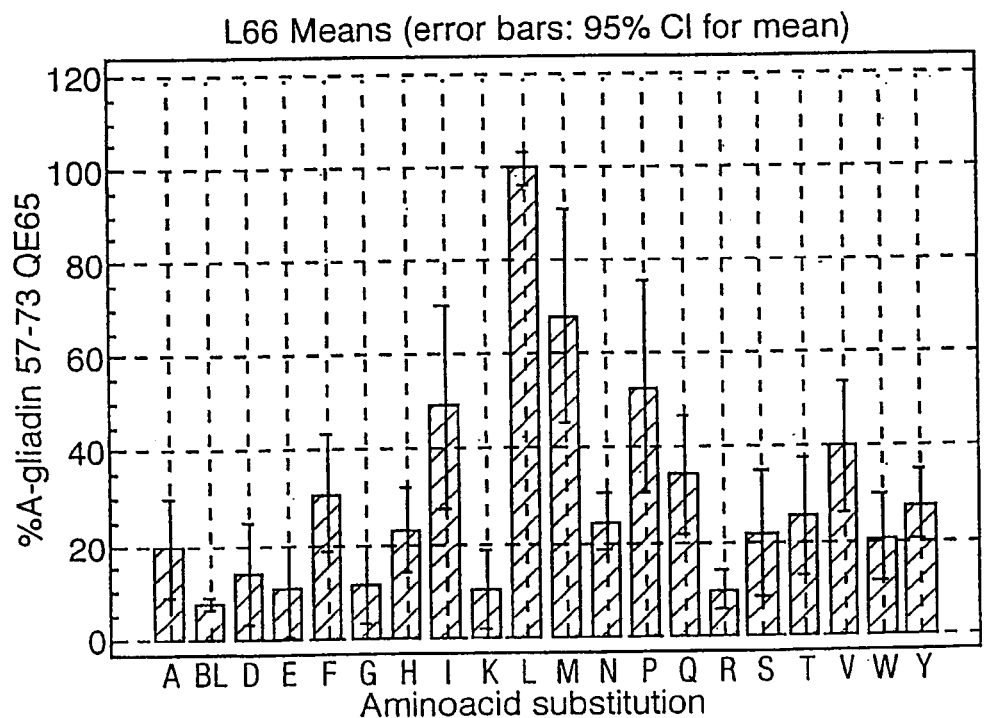
Figure 24:
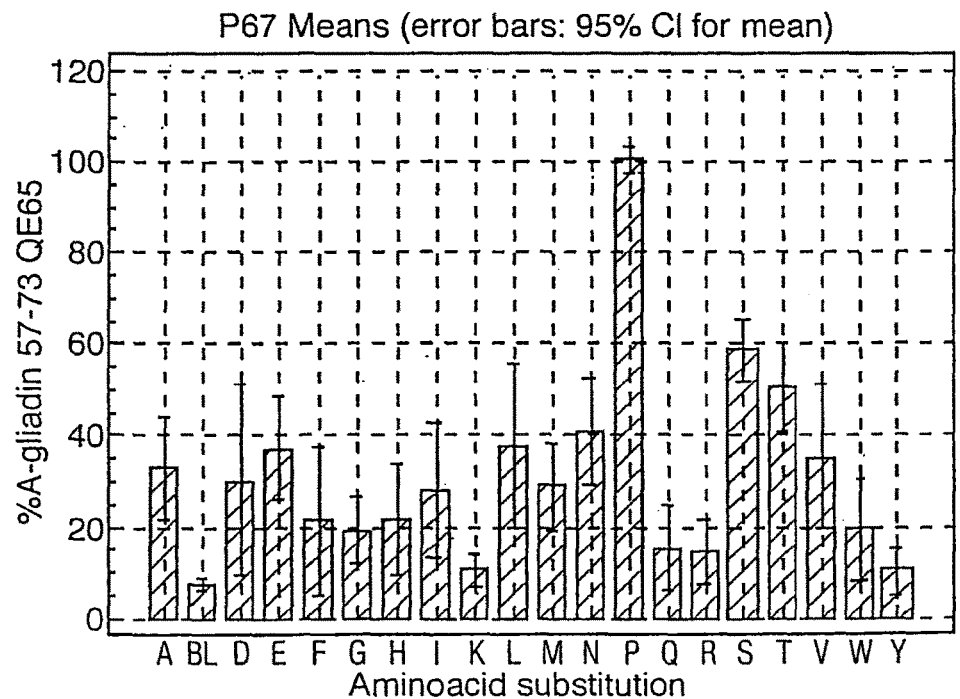
Figure 28B:
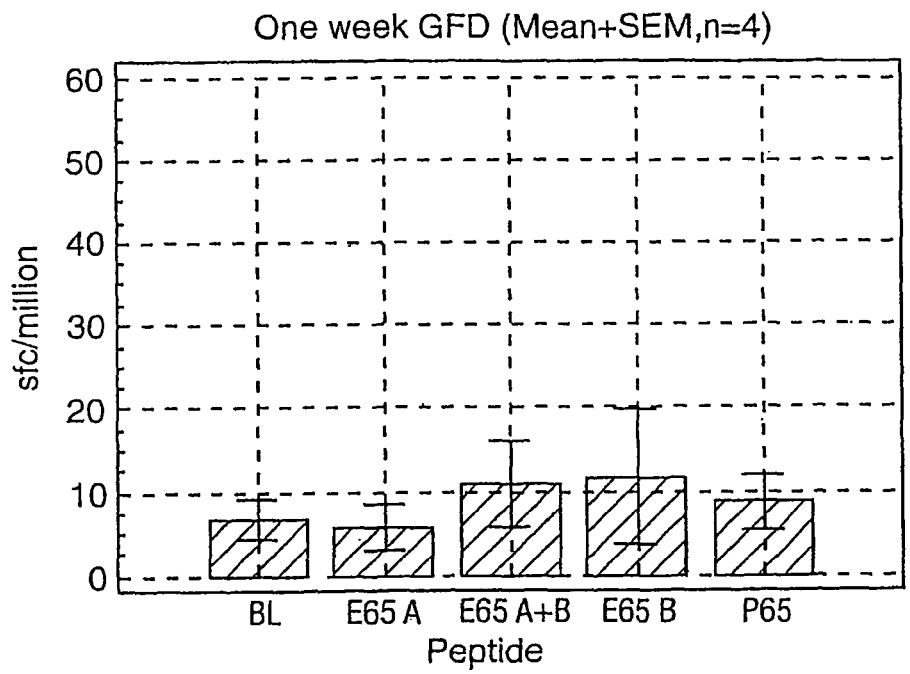
FIG. 28 shows responses in different patient groups.
Figure 28C:
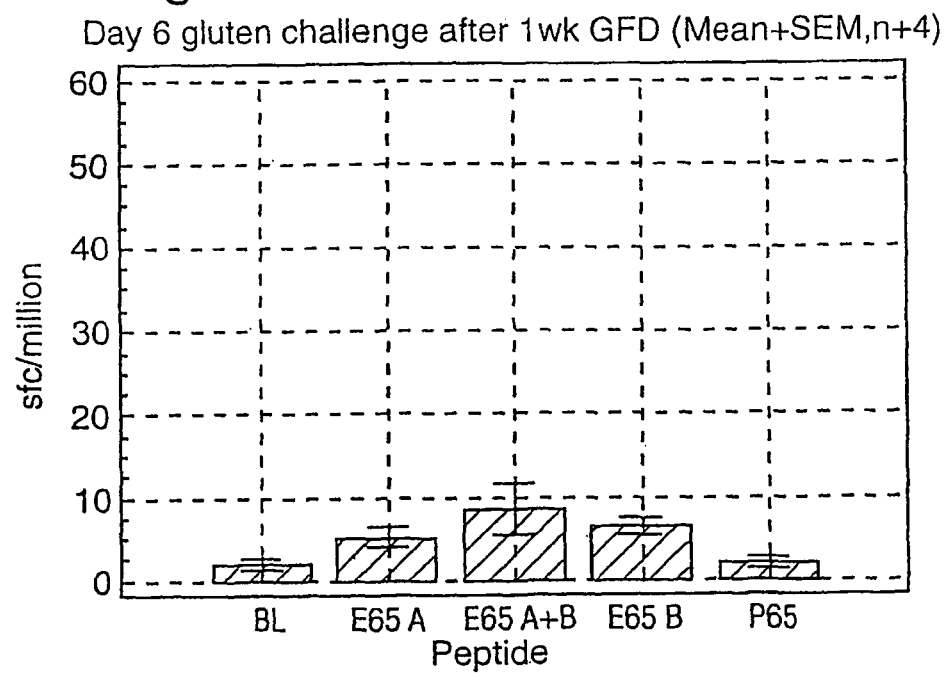
Figure 28D:
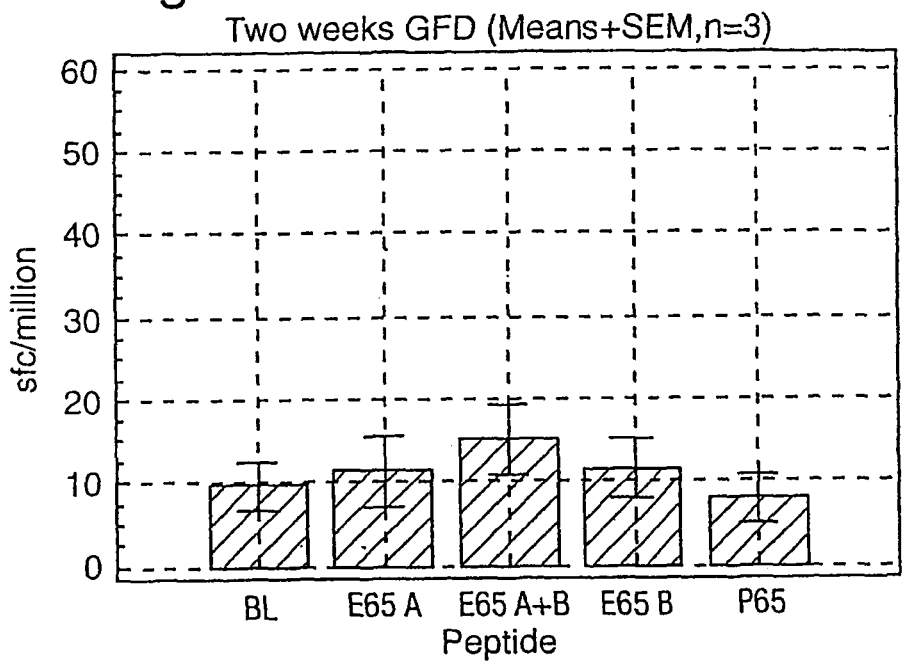
Figure 28E:
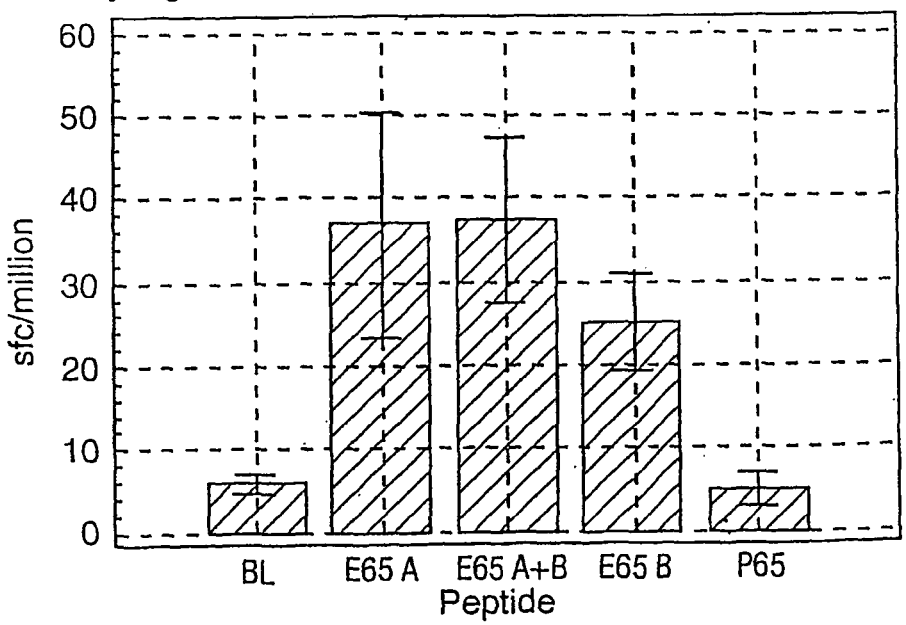
Figure 28F:
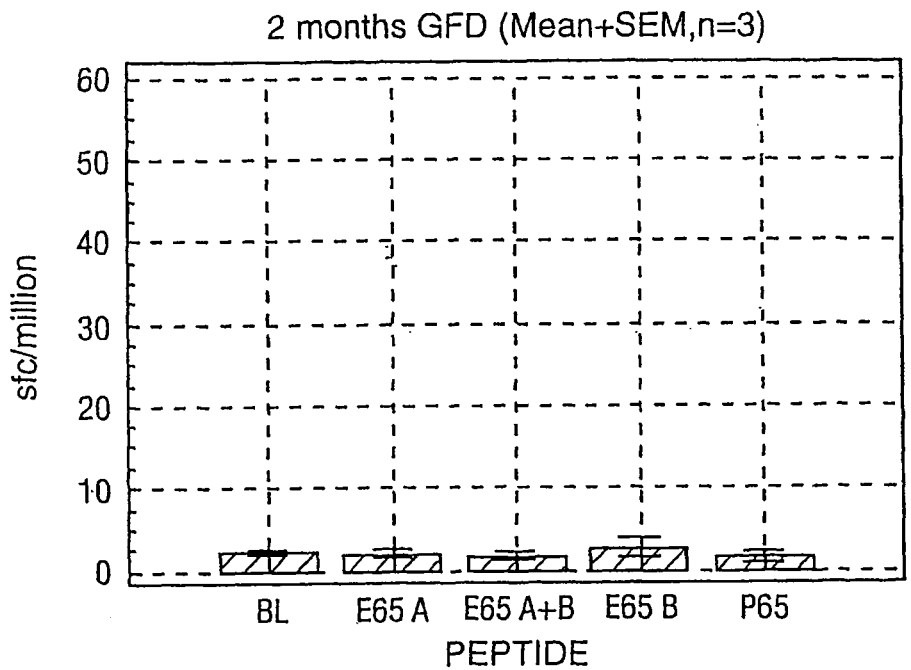
Figure 28G:
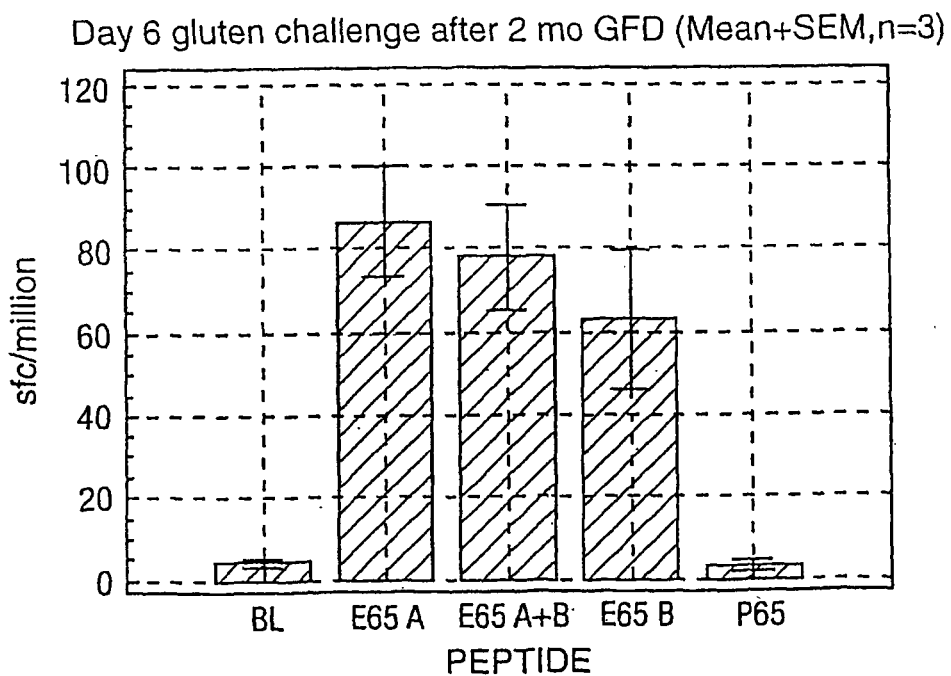
Figure 37:
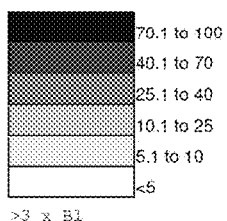

Peptides corresponding to A-gliadin 57-73 QE65 (SEQ ID NO:2) with alanine (FIG. 15) or lysine (FIG. 16) substituted for residues 57 to 73 were compared in the IFN gamma ELISPOT using peripheral blood mononuclear cells (PBMC) from coeliac volunteers 6 days after commencing a 3-day gluten challenge (n=8). (BL is blank, E is A-gliadin 57-73 QE65: QLQPFPQPELPYPQPQS (SEQ ID NO:2)).

It was found that residues corresponding to A-gliadin 60-70 QE65 (PFPQPELPYPQ (SEQ ID NO:14)) contribute substantially to the bioactivity in A-gliadin 57-73 QE65 (SEQ ID NO:2). Variants of A-gliadin 57-73 QE65 (SEQ ID NO:2) substituted at positions 60-70 are assessed in a 2-step procedure. Initially, A-gliadin 57-73 QE65 (SEQ ID NO:2) substituted at positions 60-70 using 10 different amino acids with contrasting properties are assessed. A second group of A-gliadin 57-73 QE65 (SEQ ID NO:2) variants (substituted with all other naturally occurring amino acids except cysteine at positions that prove are sensitive to modification) are assessed in a second round.

Example 10

Agonist Activity of Substituted Variants Op-Gliadin 57-73 QE65 (SEQ ID NO:2)

A-gliadin 60-70 QE65 is the core sequence of the dominant T cell epitope in A-gliadin. Antagonist and non-agonist peptide variants of this epitope are most likely generated by modification of this core sequence. Initially, A-gliadin 57-73 QE65 (SEQ ID NO:2) substituted at positions 60-70 using 10 different amino acids with contrasting properties will be assessed in the IFNgamma ELISPOT using PBMC from coeliac subjects 6 days after starting 3 day gluten challenge. A second group of A-gliadin 57-73 QE65 (SEQ ID NO:2) variants (substituted with all other naturally occurring amino acids except cysteine) at positions 61-70 were also assessed. Both groups of peptides (all at 50 mcg/ml, in duplicate) were assessed using PBMC from 8 subjects and compared to the unmodified peptide (20 replicates per assay). Previous studies indicate that the optimal concentration for A-gliadin 57-73 QE65 (SEQ ID NO:2) in this assay is between 10 and 100 mcg/ml.

Results are expressed as mean response in spot forming cells (95% confidence interval) as % A-G 57-73 QE65 mean response in each individual. Unpaired t-tests will be used to compare ELISPOT responses of modified peptides with A-G 57-73 QE65. Super-agonists were defined as having a greater response than A-G 57-73 QE65 at a level of significance of $p<0.01$; partial agonists as having a response less than A-G 57-73 QE65 at a level of significance of $p<0.01$, and non-agonists as being not significantly different ($p>0.01$) from blank (buffer without peptide). Peptides with agonist activity 30% or less that of A-gliadin 57-73 QE65 (SEQ ID NO:2) were considered "suitable" partial or non-agonists to assess for antagonistic activity (see Table 8 and FIGS. 17-27).

The IFNgamma ELISPOT response of PBMC to A-gliadin 57-73 QE65 (SEQ ID NO:2) is highly specific at a molecular level. Proline at position 64 (P64), glutamate at 65 (E65) and leucine at position 66 (L66), and to a lesser extent Q63, P67, Y68 and P69 are particularly sensitive to modification. The substitutions Y61 and Y70 both generate super-agonists with 30% greater bioactivity than the parent peptide, probably by enhancing binding to HLA-DQ2 since the motif for this HLA molecule indicates a preference for bulky hydrophobic resides at positions 1 and 9. Eighteen non-agonist peptides were identified. Bioactivities of the variants (50 mcg/ml): P65, K64, K65 and Y65 (bioactivity 7-8%) were comparable to blank (7%). In total, 57 mutated variants of A-gliadin 57-73 QE65 (SEQ ID NO:2) were 30% or less bioactive than A-gliadin 57-73 QE65 (SEQ ID NO:2).

The molecular specificity of the peripheral blood lymphocyte (PBL) T cell response to the dominant epitope, A-gliadin 57-73 QE65 (SEQ ID NO:2), is consistently reproducible amongst HLA-DQ2+ coeliac subjects, and is highly specific to a restricted number of amino acids in the core 7 amino acids. Certain single-amino acid variants of A-gliadin 57-73 QE65 (SEQ ID NO:2) are consistently non-agonists in all HLA-DQ2+ coeliac subjects.

Example 11

Antagonist Activity of Substituted Variants

The homogeneity of the PBL T cell response to A-gliadin 57-73 QE65 (SEQ ID NO:2) in HLA-DQ2+ coeliac disease suggests that altered peptide ligands (APL) capable of antagonism in PBMC ex vivo may exist, even though the PBL T cell response is likely to be poly- or oligo-clonal. APL antagonists are generally weak agonists. Fifty-seven single amino acid-substituted variants of A-gliadin 57-73 QE65 (SEQ ID NO:2) with agonist activity 30% or less have been identified and are suitable candidates as APL antagonists. In addition, certain weakly bioactive naturally occurring polymorphisms of A-gliadin 57-73 QE65 (SEQ ID NO:2) have also been identified (see below) and may be "naturally occurring" APL antagonists. It has also been suggested that competition for binding MHC may also antagonise antigen-specific T cell immune. Hence, non-gliadin peptides that do not induce IFNgamma responses in coeliac PBMC after gluten challenge but are known to bind to HLA-DQ2 may be capable of reducing T cell responses elicited by A-gliadin 57-73 QE65 (SEQ ID NO:2). Two peptides that bind avidly to HLA-DQ2 are HLA class 1 α 46-60 (HLA 1a) (PRAPWIEQEGPEYW (SEQ ID NO:15)) and thyroid peroxidase (tp) 632-645Y (IDVWLGGLLAE-NFLPY (SEQ ID NO:16)).

Simultaneous addition of peptide (50 µg/ml) or buffer and A-gliadin 57-73 QE65 (SEQ ID NO:2) (10 µg/ml) in IFNgamma ELISPOT using PBMC from coeliac volunteers 6 days after commencing 3 day gluten challenge (n=5). Results were expressed as response with peptide plus A-G 57-73 QE65 (mean of duplicates) as % response with buffer plus A-G 57-73 QE65 (mean of 20 replicates). (See Table 9).

Four single amino acid-substituted variants of A-gliadin 57-73 QE65 (SEQ ID NO:2) reduce the interferon gamma PBMC ELISPOT response to A-gliadin 57-73 QE65 (SEQ ID NO:2) ($p<0.01$) by between 25% and 28%, 13 other peptide variants reduce the ELISPOT response by between 18% and 24% ($p<0.06$). The HLA-DQ2 binder, thyroid peroxidase (tp) 632-645Y reduces PBMC interferon gamma responses to A-gliadin 57-73 QE65 (SEQ ID NO:2) by 31% ($p<0.0001$) but the other HLA-DQ2 binder, HLA class 1 α 46-60, does not alter responses (see Tables 9 and 10). The peptide corresponding to a transglutaminase-modified polymorphism of A-gliadin 57-73 (SEQ ID NO: 10), SwissProt accession no.: P04725 82-98 QE90 (PQPQPFP-PELPYPQPQS (SEQ ID NO:17)) reduces responses to A-gliadin 57-73 QE65 (SEQ ID NO:2) by 19% ($p<0.009$) (see Table 11).

Interferon gamma responses of PBMC to A-gliadin 57-73 QE65 (SEQ ID NO:2) in ELISPOT assays are reduced by co-administration of certain single-amino acid A-gliadin 57-73 QE65 (SEQ ID NO:2) variants, a polymorphism of A-gliadin 57-73 QE65 (SEQ ID NO:2), and an unrelated peptide known to bind HLA-DQ2 in five-fold excess. These finding suggest that altered peptide ligand antagonists of A-gliadin 57-73 QE65 (SEQ ID NO:2) exist. Not only putative APL antagonists but also certain peptides that bind HLA-DQ2 effectively reduce PBL T cell responses to A-gliadin 57-73 QE65 (SEQ ID NO:2).

These findings support two strategies to interrupt the T cell response to the dominant A-gliadin epitope in HLA-DQ2+ coeliac disease.
1. Optimisation of APL antagonists by substituting amino acids at more than one position (64-67) for use as "traditional" peptide pharmaceuticals or for specific genetic modification of gliadin genes in wheat.
2. Use of high affinity HLA-DQ2 binding peptides to competitively inhibit presentation of A-gliadin 57-73 QE65 (SEQ ID NO:2) in association with HLA-DQ2.

These two approaches may be mutually compatible. Super-agonists were generated by replacing F61 and Q70 with tyrosine residues. It is likely these super-agonists resulted from improved binding to HLA-DQ2 rather than enhanced contact with the T cell receptor. By combining these modifications with other substitutions that generate modestly effective APL antagonists might substantially enhance the inhibitory effect of substituted A-gliadin 57-73 QE65 (SEQ ID NO:2) variants.

Example 12

Development of Interferon Gamma ELISpot Using PBMC and A-Gliadin 57-73 QE65 (SEQ ID NO:2) and P04724 84-100 QE92 (SEQ ID NO:101) as a Diagnostic for Coeliac Disease: Definition of Immune-Responsiveness in Newly Diagnosed Coeliac Disease Induction of responsiveness to the dominant A-gliadin T cell epitope in PBMC measured in the interferon gamma ELISpot follows gluten challenge in almost all DQ2+ coeliac subjects following a long term strict gluten free diet (GFD) but not in healthy DQ2+ subjects after 4 weeks following a strict GFD. A-gliadin 57-73 QE65 (SEQ ID NO:2) responses are not measurable in PBMC of coeliac subjects before gluten challenge and pilot data have suggested these responses could not be measured in PBMC of untreated coeliacs. These data suggest that in coeliac disease immune-responsiveness to A-gliadin 57-73 QE65 (SEQ ID NO:2) is restored following antigen exclusion (GFD). If a diagnostic test is to be developed using the ELISpot assay and PBMC, it is desirable to define the duration of GFD required before gluten challenge is capable of inducing responses to A-gliadin 57-73 QE65 (SEQ ID NO:2) and other immunoreactive gliadin peptides in blood.

Newly diagnosed DQ2 I coeliac subjects were recruited from the gastroenterology outpatient service. PBMC were prepared and tested in interferon gamma ELISpot assays before subjects commenced GFD, and at one or two weeks after commencing GFD. In addition, gluten challenge (3 days consuming 4 slices standard white bread, 200 g/day) was performed at one or two weeks after starting GFD. PBMC were prepared and assayed on day six are after commencing gluten challenge. A-gliadin 57-73 QE65 (SEQ ID NO:2) (A), P04724 84-100 QE92 (SEQ ID NO:101) (B) (alone and combined) and A-gliadin 57-73 QP65 (SEQ ID NO: 780) (P65) (non-bioactive variant, see above) (all 25 mcg/ml) were assessed.

All but one newly diagnosed coeliac patient was DQ2+ (one was DQ8+) (n=11). PBMC from newly diagnosed coeliacs that were untreated, or after 1 or 2 weeks following GFD did not show responses to A-gliadin 57-73 QE65 (SEQ ID NO:2) and P04724 84-100 QE92 (SEQ ID NO:101) (alone or combined) that were not significantly different from blank or A-gliadin 57-73 QP65 (SEQ ID NO:780) (n=9) (see FIG. 28). Gluten challenge in coeliacs who had followed GFD for only one week did not substantially enhance responses to A-gliadin 57-73 QE65 (SEQ ID NO:2) or P04724 84-100 QE92 (SEQ ID NO:101) (alone or combined). But gluten challenge 2 weeks after commencing GFD did induce responses to A-gliadin 57-73 QE65 (SEQ ID NO:2) and P04724 84-100 QE92 (SEQ ID NO:101) (alone or combined) that were significantly greater than the non-bioactive variant A-gliadin 57-73 QP65 (SEQ ID NO:780) and blank. Although these responses after gluten challenge at 2 weeks were substantial they appear to be less than in subjects>2 months after commencing GFD. Responses to A-gliadin 57-73 QE65 (SEQ ID NO:2) alone were equivalent or greater than responses to P04724 84-100 QE92 (SEQ ID NO:101) alone or when mixed with A-gliadin 57-73 QE65 (SEQ ID NO:2). None of the subjects experienced troubling symptoms with gluten challenge.

Immune responsiveness (as measured in PBMC after gluten challenge) to A-gliadin is partially restored 2 weeks after commencing GFD, implying that "immune unresponsiveness" to this dominant T cell epitope prevails in untreated coeliac disease and for at least one week after starting GFD. The optimal timing of a diagnostic test for coeliac disease using gluten challenge and measurement of responses to A-gliadin 57-73 QE65 (SEQ ID NO:2) in the ELISpot assay is at least 2 weeks after commencing a GFD.

Interferon gamma-secreting T cells specific to A-gliadin 57-73 QE65 (SEQ ID NO:2) cannot be measured in the peripheral blood in untreated coeliacs, and can only be induced by gluten challenge after at least 2 weeks GFD (antigen exclusion). Therefore, timing of a diagnostic test using this methodology is crucial and further studies are needed for its optimization. These finding are consistent with functional anergy of T cells specific for the dominant epitope, A-gliadin 57-73 QE65 (SEQ ID NO:2), reversed by antigen exclusion (GFD). This phenomenon has not been previously demonstrated in a human disease, and supports the possibility that T cell anergy may be inducible with peptide therapy in coeliac disease.

Example 13

Comprehensive Mapping of Wheat Gliadin T Cell Epitopes

Antigen challenge induces antigen-specific T cells in peripheral blood. In coeliac disease, gluten is the antigen that maintains this immune-mediated disease. Gluten challenge in coeliac disease being treated with a gluten free diet leads to the appearance of gluten-specific T cells in peripheral blood, so enabling determination of the molecular specificity of gluten T cell epitopes. As described above, we have identified a single dominant T cell epitope in a model gluten protein, A-gliadin (57-73 deamidated at Q65) (SEQ ID NO:2). In this Example, gluten challenge in coeliac patients was used to test all potential 12 amino acid sequences in every known wheat gliadin protein derived from 111 entries in Genbank. In total, 652 20mer peptides were tested in HLA-DQ2 and HLA-DQ8 associated coeliac disease. Seven of the 9 coeliac subjects with the classical HLA-DQ2 complex (HLA-DQA1*05, HLA-DQB1*02) present in over 90% of coeliacs had an inducible A-gliadin 57-73 QE65 (SEQ ID NO:2)- and gliadin-specific T cell response in peripheral blood. A-gliadin 57-73 (SEQ ID NO:10) was the only significant α-gliadin T cell epitope, as well as the most potent gliadin T cell epitope, in HLA-DQ2-associated coeliac disease. In addition, there were as many as 5 families of structurally related peptides that were between 10 and 70% as potent as A-gliadin 57-73 (SEQ ID NO:10) in the interferon-γ ELISpot assay. These new T cell epitopes were derived from γ- and ω-gliadins and included common sequences that were structurally very similar, but not identical to the core sequence of A-gliadin 57-73 (SEQ ID NO:10) (core sequence: FPQPQLPYP (SEQ ID NO:18)), for example: FPQPQQPFP (SEQ ID NO:19) and PQQPQQPFP (SEQ ID NO:20). Although no homologues of A-gliadin 57-73 (SEQ ID NO:10) have been found in rye or barley, the other two cereals toxic in coeliac disease, the newly defined T cell epitopes in γ- and ω-gliadins have exact matches in rye and barley storage proteins (secalins and hordeins, respectively).

Coeliac disease not associated with HLA-DQ2 is almost always associated with HLA-DQ8. None of the seven HLA-DQ8+ coeliac subjects had inducible A-gliadin 57-73-specific T cell responses following gluten challenge, unless they also possessed the complete HLA-DQ2 complex. Two of 4 HLA-DQ8+ coeliac subjects who did not possess the complete HLA-DQ2 complex, had inducible gliadin peptide-specific T cell responses following gluten challenge. In one HLA-DQ8 subject, a novel dominant T cell epitope was identified with the core sequence LQPQNPSQQQPQ (SEQ ID NO:21). The transglutaminase-deamidated version of this peptide was more potent than the non-deamidated peptide. Previous studies suggest that the transglutaminase-deamidated peptide would have the sequence LQPENPSQEQPE (SEQ ID NO:22); but further studies are required to confirm this sequence. Amongst the healthy HLA-DQ2 (10) and HLA-DQ8 (1) subjects who followed a gluten free diet for a month, gliadin peptide-specific T cell responses were uncommon, seldom changed with gluten challenge, and were never potent T cell epitopes revealed with gluten challenge in coeliac subjects. In conclusion, there are unlikely to be more than six important T cell epitopes in HLA-DQ2-associated coeliac disease, of which A-gliadin 57-73 (SEQ ID NO:10) is the most potent. HLA-DQ2- and HLA-DQ8-associated coeliac disease do not share the same T cell specificity.

We have shown that short-term gluten challenge of individuals with coeliac disease following a gluten free diet induces gliadin-specific T cells in peripheral blood. The frequency of these T cells is maximal in peripheral blood on day 6 and then rapidly wanes over the following week. Peripheral blood gliadin-specific T cells express the integrin α4β7 that is associated with homing to the gut lamina propria. We exploited this human antigen-challenge design to map T cell epitopes relevant to coeliac disease in the archetypal gluten α-gliadin protein, A-gliadin. Using 15mer peptides overlapping by 10 amino acids with and without deamidation by transglutaminase (tTG), we demonstrated that T cells induced in peripheral blood initially target only one A-gliadin peptide, residues 57-73 (SEQ ID NO:10) in which glutamine at position 65 is deamidated (SEQ ID NO:2). The epitope is HLA-DQ2-restricted, consistent with the intimate association of coeliac disease with HLA-DQ2.

Coeliac disease is reactivated by wheat, rye and barley exposure. The α/β-gliadin fraction of wheat gluten is consistently toxic in coeliac disease, and most studies have focused on these proteins. The gene cluster coding for α/β-gliadins is located on wheat chromosome 6C. There are no homologues of α/β-gliadins in rye or barley. However, all three of the wheat gliadin subtypes (α/β, γ, and ω) are toxic in coeliac disease. The γ- and ω-gliadin genes are located on chromosome 1A in wheat, and are homologous to the secalins and hordeins in rye and barley.

There are now genes identified for 61 α-gliadins in wheat (*Triticum aestivum*). The α-gliadin sequences are closely homologous, but the dominant epitope in A-gliadin derives from the most polymorphic region in the α-gliadin sequence. Anderson et al (1997) have estimated that there are a total of about 150 distinct α-gliadin genes in *T. aestivum*, but many are psuedogenes. Hence, it is to unlikely that T-cell epitopes relevant to coeliac disease are not included within known α-gliadin sequences.

Our work has identified a group of deamidated α-gliadin peptides almost identical to A-gliadin 57-73 (SEQ ID NO:10) as potent T cell epitopes specific to coeliac disease. Over 90% of coeliac patients are HLA-DQ2+, and so far, we have only assessed HLA-DQ2+ coeliac subjects after gluten challenge. However, coeliac patients who do not express HLA-DQ2 nearly all carry HLA-DQ8. Hence, it is critical to know whether A-gliadin 57-73 (SEQ ID NO:10) and its homologues in other wheat, rye and barley gluten proteins are the only T-cell epitopes recognized by T cells induced by gluten challenge in both HLA-DQ2+ and HLA-DQ8+ coeliac disease. If this were the case, design of peptide therapeutics for coeliac disease might only require one peptide.

Homologues of A-Gliadin 57-73 (SEQ ID NO:10) as T-Cell Epitopes

Initial searches of SwissProt and Trembl gene databases for cereal genes coding for the core sequence of A-gliadin 57-73 (PQLPY <SEQ ID NO:12>) only revealed α/β-gliadins. However, our fine-mapping studies of the A-gliadin 57-73 QE65 (SEQ ID NO:2) epitope revealed a limited number of permissive point substitutions in the core region (PQLP—SEQ ID NO:760) (note Q65 is actually deamidated in the epitope). Hence, we extended our search to genes in SwissProt or Trembl databases encoding for peptides with the sequence XXXXXXXPQ[ILMP][PST]XXXXXX (SEQ ID NO:23). Homologues were identified amongst γ-gliadins, glutenins, hordeins and secalins (see Table 12). A further homologue was identified in co-gliadin by visual search of the three co-gliadin entries in Genbank.

These homologues of A-gliadin 57-73 (SEQ ID NO:10) were assessed after deamidation by tTG (or synthesis of the glutamate (QE)-substituted variant in four close homologues) using the IFNγ ELISpot assay with peripheral blood mononuclear cells after gluten challenge in coeliac subjects. The co-gliadin sequence (AAG17702 141-157—SEQ ID NO:761) was the only bioactive peptide, approximately half as potent as A-gliadin 57-73 (SEQ ID NO: 10)(see Table 12, and FIG. 29). Hence, searches for homologues of the dominant A-gliadin epitope failed to account for the toxicity of γ-gliadin, secalins, and hordeins.

Methods

Design of a Set of Peptides Spanning all Possible Wheat Gliadin T-Cell Epitopes

In order to identify all possible T cell epitopes coded by the known wheat (*Triticum aestivum*) gliadin genes or gene fragments (61 α/β-, 47 γ-, and 3 ω-gliadin entries in Genbank), gene-derived protein sequences were aligned using the CustalW software (MegAlign) and arranged into phylogenetic groupings (see Table 22). Many entries represented truncations of longer sequences, and many gene segments were identical except for the length of polyglutamine repeats or rare substitutions. Hence, it was possible to rationalize all potential unique 12 amino acid sequences encoded by known wheat genes to be included in a set of 652 20mer peptides. (Signal peptide sequences were not included). Peptide sequences are listed in Table 23.

Comprehensive Epitope Mapping

Healthy controls (HLA-DQ2+n=10, and HLA-DQ8+n=1) who had followed a gluten free diet for 4 weeks, and coeliac subjects (six HLA-DQ2, four complex heterozygotes HLA-DQ2/8, and three HLA-DQ8/X) (see Table 13) following long-term gluten free diet were studied before and on day 6 and 7 after 3-day gluten challenge (four 50 g slices of standard white bread—Sainsbury's sandwich bread, each day). Peripheral blood (a total of 300 ml over seven days) was collected and peripheral blood mononuclear cells (PBMC) were separated by Lymphoprep density gradient. PBMC were incubated with pools of 6 or 8 20mer peptides, or single peptides with or without deamidation by tTG in overnight interferon gamma (IFNγ) ELISpot assays.

Peptides were synthesized in batches of 96 as Pepsets (Mimotopes Inc., Melbourne Australia). Approximately 0.6 micromole of each of 652 20mers was provided. Two marker 20mer peptides were included in each set of 96 (VLQQHNIAHGSSQVLQESTY—peptide 161 (SEQ ID NO:24), and IKDFHVYFRESRDALWKGPG (SEQ ID NO:25)) and were characterized by reverse phase-HPLC and amino acid sequence analysis. Average purities of these marker peptides were 50% and 19%, respectively. Peptides were initially dissolved in acetonitrile (10%) and Hepes 100 mM to 10 mg/ml.

The final concentration of individual peptides in pools (or alone) incubated with PBMC for the IFNγ ELISpot assays was 20 µg/ml. Five-times concentrated solutions of peptides and pools in PBS with calcium chloride 1 mM were aliquotted and stored in 96-well plates according to the template later used in ELISpot assays. Deamidated peptides and pools of peptides were prepared by incubation with guinea pig tissue tTG (Sigma T5398) in the ratio 100:32 µg/ml for two hours at 37° C. Peptides solutions were stored at –20° C. and freshly thawed prior to use.

Gliadin (Sigma G3375) (100 mg/ml) in endotoxin-free water and 2M urea was boiled for 10 minutes, cooled to room temperature and incubated with filter (0.2 µm)-sterilised pepsin (Sigma P6887) (2 mg/ml) in HCl 0.02M or chymotrypsin (C3142) (4 mg/ml) in ammonium bicarbonate (0.2M). After incubation for 4 hours, pepsin-digested gliadin was neutralized with sodium hydroxide, and then both pepsin- and chymotrypsin-digested gliadin were boiled for 15 minutes. Identical incubations with protease in which gliadin was omitted were also performed. Samples were centrifuged at 15 000 g, then protein concentrations were estimated in supernatants by the BCA method (Pierce, USA). Before final use in IFNγ ELISpot assays, aliquots of gliadin-protease were incubated with tTG in the ratio 2500: 64 µg/ml.

IFNγ ELISpot assays (Mabtech, Sweden) were performed in 96-well plates (MAIP S-45, Millipore) in which each well contained 25 µl of peptide solution and 100 µl of PBMC ($2-8 \times 10^5$/well) in RPMI containing 10% heat inactivated human AB serum. Deamidated peptide pools were assessed in one 96-well ELISpot plate, and peptides pools without deamidation in a second plate (with an identical layout) on both day 0 and day 6. All wells in the plate containing deamidated peptides included tTG (64 µg/ml). In each ELISpot plate there were 83 wells with peptide pools (one unique pool in each well), and a series of wells for "control" peptides (peptides all>90% purity, characterized by MS and HPLC, Research Genetics): P04722 77-93 (QLQP-FPQPQLPYPQPQP (SEQ ID NO:26)), P04722 77-93 QE85 (in duplicate) (QLQPFPQPELPYPQPQP (SEQ ID NO:27)), P02863 77-93 (QLQPFPQPQLPYSQPQP (SEQ ID NO:28)), P02863 77-93 QE85 (QLQPFPQPELPYSQPQP (SEQ ID NO:29)), and chymotrypsin-digested gliadin (500 µg/ml), pepsin-digested gliadin (500 µg/ml), chymotrypsin (20 µg/ml) alone, pepsin (10 µg/ml) alone, and blank (PBS+/-tTG) (in triplicate).

After development and drying, IFNγ ELISpot plates were assessed using the MAIP automated ELISpot plate counter. In HLA-DQ2 healthy and coeliac subjects, induction of spot forming cells (sfc) by peptide pools in the IFNγ ELISpot assay was tested using a one-tailed Wilcoxon Matched-Pairs Signed-Ranks test (using SPSS software) applied to spot forming cells (sfc) per million PBMC minus blank on day 6 versus day 0 ("net response"). Significant induction of an IFNγ response to peptide pools in PBMC by in vivo gluten challenge was defined as a median "net response" of at least 10 sfc/million PBMC and p<0.05 level of significance. Significant response to a particular pool of peptides on day 6 was followed by assessment of individual peptides within each pool using PBMC drawn the same day or on day 7.

For IFNγ ELISpot assays of individual peptides, bioactivity was expressed as a percent of response to P04722 77-93 QE85 (SEQ ID NO:27) assessed in the same ELISpot plate. Median response to blank (PBS alone) was 0.2 (range 0-5) sfc per well, and the positive control (P04722 77-93 QE85—SEQ ID NO:27) 76.5 (range: 25-282) sfc per well using a median of 0.36 million (range: 0.3-0.72) PBMC. Hence, median response to blank expressed as a percentage of P04722 77-93 QE65 (SEQ ID NO:27) was 0.2% (range: 0-6.7). Individual peptides with mean bioactivity greater than 10% that of P04722 QE85 (SEQ ID NO:27) were analyzed for common structural motifs.

Results

Healthy HLA-DQ2 Subjects

None of the healthy HLA-DQ2+ subjects following a gluten free diet for a month had IFNγ ELISpot responses to homologues of A-gliadin 57-73 before or after gluten challenge. However, in 9/10 healthy subjects, gluten challenge was associated with a significant increase in IFNγ responses to both peptic- and chymotryptic-digests of gliadin, from a median of 0-4 sfc/million on day 0 to a median of 16-29 sfc/million (see Table 14). Gliadin responses in healthy subjects were unaffected by deamidation (see Table 15). Amongst healthy subjects, there was no consistent induction of IFNγ responses to specific gliadin peptide pools with gluten challenge (see FIG. 30, and Table 16). IFNγ ELISpot responses were occasionally found, but these were weak, and not altered by deamidation. Many of the strongest responses to pools were also present on day 0 (see Table 17, subjects H2, H8 and H9). Four healthy subjects did show definite responses to pool 50, and the two with strongest responses on day 6 also had responses on day 0. In both subjects, the post-challenge responses to pool 50 responses were due to peptide 390 (QQTYPQRPQQPFPQTQQPQQ (SEQ ID NO:30)).

HLA-DQ2 Coeliac Subjects

Following gluten challenge in HLA-DQ2+ coeliac subjects, median IFNγ ELISpot responses to P04722 77-93 E85 (SEQ ID NO:29) rose from a median of 0 to 133 sfc/million (see Table 4). One of the six coeliac subjects (C06) did not respond to P04722 77-93 QE85 (SEQ ID NO:27) (2 sfc/million) and had only weak responses to gliadin peptide pools (maximum: Pool 50+tTG 27 sfc/million). Consistent with earlier work, bioactivity of wild-type P04722 increased 6.5 times with deamidation by tTG (see Table 15). Interferon-gamma responses to gliadin-digests were present at baseline, but were substantially increased by gluten challenge from a median of 20 up to 92 sfc/million for chymotryptic-gliadin, and from 44 up to 176 sfc/million for peptide-gliadin. Deamidation of gliadin increased bioactivity by a median of 3.2 times for chymotryptic-gliadin and 1.9 times for peptic-gliadin (see Table 15). (Note that the acidity required for digestion by pepsin is likely to result in partial deamidation of gliadin.)

In contrast to healthy subjects, gluten challenge induced IFNγ ELISpot responses to 22 of the 83 tTG-treated pools including peptides from α-, γ- and ω-gliadins (see FIG. 31, and Table 17). Bioactivity of pools was highly consistent between subjects (see Table 18). IFNγ ELISpot responses elicited by peptide pools were almost always increased by deamidation (see Table 17). But enhancement of bioactivity of pools by deamidation was not as marked as for P04722 77-93 Q85 (SEQ ID NO: 29), even for pools including homologues of A-gliadin 57-73. This suggests that Pepset peptides were partially deamidated during synthesis or in preparation, for example the Pepset peptides are delivered as salts of trifluoracetic acid (TFA) after lyophilisation from a TFA solution.

One hundred and seventy individual tTG-deamidated peptides from 21 of the most bioactive pools were separately assessed. Seventy-two deamidated peptides were greater than 10% as bioactive as P04722 77-93 QE85 (SEQ ID NO:27) at an equivalent concentration (20 µgimp (see Table 19). The five most potent peptides (85-94% bioactivity of P04722 QE85—SEQ ID NO:27) were previously identified α-gliadin homologues A-gliadin 57-73 (SEQ ID NO:10). Fifty of the bioactive peptides were not homologues of A-gliadin 57-73 (SEQ ID NO:10), but could be divided into six families of structurally related sequences (see Table 20). The most bioactive sequence of each of the peptide families were: PQQPQQPQQPFPQPQQPFPW (SEQ ID NO:31) (peptide 626, median 72% bioactivity of P04722 QE85—SEQ ID NO:27), QQPQQPFPQPQQPQLPFPQQ (SEQ ID NO:32) (343, 34%), QAFPQPQQTFPHQPQQQFPQ (SEQ ID NO:33) (355, 27%), TQQPQQPFPQQPQQPFPQTQ (SEQ ID NO:34) (396, 23%), PIQPQQPFPQQPQQPQQPFP (SEQ ID NO:35) (625, 22%), PQQSFSYQQQPFPQCIPYPQQ (SEQ ID NO:36) (618, 18%) (core sequences are underlined). All of these sequences include glutamine residues predicted to be susceptible to deamidation by transglutaminase (e.g. QXP, QXPF (SEQ ID NO:37), QXX[FY] (SEQ ID NO:38)) (see Vader et al 2002). Some bioactive peptides contain two core sequences from different families.

Consistent with the possibility that different T-cell populations respond to peptides with distinct core sequences, bioactivity of peptides from different families appear to be additive. For example, median bioactivity of tTG-treated Pool 81 was 141% of P04722 QE85 (SEQ ID NO:27), while bioactivity of individual peptides was in rank order: Peptide 631 (homologue of A-gliadin 57-73—SEQ ID NO:10) 61%, 636 (homologue of 626) 51%, and 635 19%, 629 16%, and 634 13% (all homologues of 396).

Although likely to be an oversimplification, the contribution of each "peptide family" to the summed IFNγ ELISpot response to gliadin peptides was compared in the HLA-DQ2+ coeliac subjects (see FIG. 32). Accordingly, the contribution of P04722 77-73 E85 (SEQ ID NO:27) to the summed response to gliadin peptides is between 1/5 and 2/3.

Using the peptide homology search programme, WWW PepPepSearch, which can be accessed through the world wide web of the internet at, for example, "cbrg.inf.ethz.ch/subsection3_1_5.html.", and by direct comparison with Genbank sequences for rye secalins, exact matches were found for the core sequences QQPFPQPQQPFP (SEQ ID NO:39) in barley hordeins (HOR8) and rye secalins (A23277, CAA26449, AAG35598), QQPFPQQPQQPFP (SEQ ID NO:40) in barley hordeins (HOG1 and HOR8), and for PIQPQQPFPQQP (SEQ ID NO:41) also in barley hordeins (HOR8).

HLA-DQ8-Associated Coeliac Disease

Seven HLA-DQ8+ coeliac subjects were studied before and after gluten challenge. Five of these HLA-DQ8+ (HLA-DQA0*0301-3, HLA-DQB0*0302) subjects also carried one or both of the coeliac disease-associated HLA-DQ2 complex (DQA0*05, DQB0*02). Two of the three subjects with both coeliac-associated HLA-DQ complexes had potent responses to gliadin peptide pools (and individual peptides including P04722 77-93 E85—SEQ ID NO:27) that were qualitatively and quantitatively identical to HLA-DQ2 coeliac subjects (see FIGS. 33 and 34, and Table 18). Deamidated peptide pool 74 was bioactive in both HLA-DQ2/8 subjects, but only in one of the 6 HLA-DQ2/X subjects. Pretreatment of pool 74 with tTG enhances bioactivity between 3.8 and 22-times, and bioactivity of tTG-treated pool 74 in the three responders is equivalent to between 78% and 350% the bioactivity of P04722 77-93

E85 (SEQ ID NO:27). Currently, it is not known which peptides are bioactive in Pool 74 in subject C02, C07, and C08.

Two of the four HLA-DQ8 coeliac subjects that lacked both or one of the HLA-DQ2 alleles associated with coeliac disease showed very weak IFNγ ELISpot responses to gliadin peptide pools, but the other two did respond to both protease-digested gliadin and specific peptide pools. Subject C12 (HLA-DQ7/8) responded vigorously to deamidated Pools 1-3 (see FIG. 35). Assessment of individual peptides in these pools identified a series of closely related bioactive peptides including the core sequence LQPQNPSQQQPQ (SEQ ID NO:42) (see Table 20). Previous work (by us) has demonstrated that three glutamine residues in this sequence are susceptible to tTG-mediated deamidation (underlined). Homology searches using WWW PepPepSearch have identified close matches to LQPQNPSQQQPQ (SEQ ID NO:43) only in wheat α-gliadins.

The fourth HLA-DQ8 subject (C11) had inducible IFNγ ELISpot responses to tTG-treated Pool 33 (see FIG. 36). Pools 32 and 33 include polymorphisms of a previously defined HLA-DQ8 restricted gliadin epitope (QQYPSG QGSFQPSQQNPQ (SEQ ID NO:44)) active after deamidation by tTG (underlined Gln are deamidated and convey bioactivity) (van der Wal et al 1998). Currently, it is not known which peptides are bioactive in Pool 33 in subject C11.

Comprehensive T cell epitope mapping in HLA-DQ2-associated coeliac disease using in vivo gluten challenge and a set of 652 peptides spanning all known 12 amino acid sequences in wheat gliadin has thus identified at least 72 peptides at 10% as bioactive as the known α-gliadin epitope, A-gliadin 57-73 E65. However, these bioactive peptides can be reduced to a set of perhaps as few as 5 distinct but closely related families of peptides. Almost all these peptides are rich in proline, glutamine, phenylalanine, and/or tyrosine and include the sequence PQ(QL)P(FY)P (SEQ ID NO:45). This sequence facilitates deamidation of Q in position 2 by tTG. By analogy with deamidation of A-gliadin 57-68 (Arentz-Hansen 2000), the enhanced bioactivity of these peptides generally found with deamidation by tTG may be due to increased affinity of binding for HLA-DQ2.

Cross-reactivity amongst T cells in vivo recognizing more than one of these bioactive gliadin peptides is possible. However, if each set of related peptides does activate a distinct T cell population in vivo, the epitope corresponding to A-gliadin 57-73 E65 (SEQ ID NO:2) is the most potent and is generally recognized by at least 40% of the peripheral blood T cells that secrete IFN-γ in response to gliadin after gluten challenge.

No gliadin-peptide specific responses were found in HLA-DQ2/8 coeliac disease that differed qualitatively from those in HLA-DQ2/X-associated coeliac disease. However, peripheral blood T cells in HLA-DQ8+ coeliac subjects without both HLA-DQ2 alleles did not recognize A-gliadin 57-73 E65 (SEQ ID NO:2) homologues. Two different epitopes were dominant in two HLA-DQ8+ coeliacs. The dominant epitope in one of these HLA-DQ8+ individuals has not been identified previously (LQPQNPSQQQPQ (SEQ ID NO:46)).

Given the teaching herein, design of an immunotherapy for coeliac disease utilizing all the commonly recognised T cell epitopes is practical and may include fewer than six distinct peptides. Epitopes in wheat γ- and ω-gliadins are also present in barley hordeins and rye secalins.

Example 14

Several ELI Spot assays were performed as previously described and yielded the following results and/or conclusions:

Examination of Multiple α-Gliadin Polymorphisms with PQLPY (SEQ ID NO: 12)

```
Potent agonists of A-gliadin 57-73QE (G01) (SEQ ID NO: 2) include
QLQPFPQPELPYPQPQS (G01)(SEQ ID NO: 2),
PQL-Y----------------------P (G10)(SEQ ID NO: 101, and
PQPQPFL---------------------  (G12)(SEQ ID NO: 781)
Less potent include
---------------------L------P (G04)(SEQ ID NO: 782),
----------R-----------------P (G05)(SEQ ID NO: 783), and
---------------------S------P (G06)(SEQ ID NO: 784).
Less potent yet include
--------L------------S------P (G07)(SEQ ID NO: 785),
--------S------------S------P (G08)(SEQ ID NO: 786),
------------------S--S------P (G09)(SEQ ID NO: 797), and
PQPQPFP-----------------(G13)(SEQ ID NO: 788).
Dashes indicate identity with the G01 sequence in the
particular position.
```

Gluten Challenge Induces A-Gliadin 57-73 QE65 (SEQ ID NO:2) T Cells Only After Two Weeks of Gluten-Free Diet in Newly Diagnosed Coeliac Disease Additional analyses indicated that tTG-deamidated gliadin responses change after two weeks of gluten-free diet in newly diagnosed coeliac disease. Other analyses indicated that deamidated gliadin-specific T cells are CD4$^+$α$_4$β$_7^+$ HLA-DQ2 restricted.

Optimal Epitope (Clones Versus Gluten Challenge)

A "dominant" epitope is defined by γIFN ELISpot after gluten challenge. QLQPFPQPELPYPQPQS (SEQ ID NO:2) (100% ELISpot response). Epitopes defined by intestinal T cell clones: QLQPFPQPELPY (SEQ ID NO:13) (27%), PQPELPYPQPELPY (SEQ ID NO:47) (52%), and QQLPQPEQPQQSFPEQERPF (SEQ ID NO:48)(9%).

Dominance Among Individual Peptide Responses

Dominance depends on wheat or rye. For wheat, dominant peptides include peptide numbers 89, 90 and 91 (referring to sequence numbers in Table 23) (SEQ ID NO: 195, SEQ ID NO:196 and SEQ ID NO:197 respectively). For rye, dominant peptides include peptide numbers 368, 369, 370, 371, and 372 (referring to sequence numbers in Table 23) (SEQ ID NO:474, SEQ ID NO:475, SEQ ID NO:476, SEQ ID NO:477 and SEQ ID NO:478 respectively). Some peptides, including 635 (SEQ ID NO:741) and 636 (SEQ ID NO:742) (referring to sequence numbers in Table 23) showed activity in both rye and wheat.

In Vivo Gluten Challenge Allows T Cell Epitope Hierarchy to be Defined for Coeliac Disease The epitope hierarchy is consistent among HLA-DQ2+ coeliacs but different for HLA-DQ8+ coeliacs. The hierarchy depends on what cereal is consumed. Deamidation generates almost all gliadin epitopes. HLA-DQ2, DQ8, and DR4 present deamidated peptides. HLA-DQ2/8-associated coeliac disease preferentially present DQ2-associated gliadin epitopes. Gliadin epitopes are sufficiently restricted to justify development of epitope-based therapeutics.

Other analyses indicated the following: HLA-DR3-DQ2 (85-95%) and HLA-DR4-DQ8 (5-15%).

Other analyses indicated the following:

|  | HLA-DQ | HLA-DQA1 allele | HLA-DQB1 allele | Duodenal histology | Gluten free | EMA on gluten (on GFD) |
|---|---|---|---|---|---|---|
| C01 | 2, 6 | 102/6, 501 | 201, 602 | SVA | 1 yr | +(−) |
| C02 | 2, 2 | 501 | 201 | SVA | 1 yr | +(−) |
| C03 | 2, 5 | 101/4/5, 501 | 201, 501 | PVA | 1 yr | +(−) |
| C04 | 2, 5 | 101/4/5, 501 | 201, 501 | SVA | 7 yr | +(−) |
| C05 | 2, 2 | 201, 501 | 201, 202 | SVA | 4 mo | +(ND) |
| C06 | 2, 2 | 201, 501 | 201, 202 | SVA | 2 yr | +(−) |
| C07 | 2, 8 | 301-3, 501 | 201, 302 | SVA | 1 yr | +(−) |
| C08 | 2, 8 | 301-3, 501 | 201, 302/8 | SVA | 11 yr | ND(−) |
| C09 | 2, 8 | 301-3, 501 | 201, 302 | SVA | 29 yr | +(−) |
| C10 | 2, 8 | 201, 301-3 | 202, 302 | IEL | 1 yr | +(−) |
| C11 | 6, 8 | 102/6, 301-3 | 602/15, 302/8 | IEL | 9 mo | −(ND) |
| C12 | 8, 7 | 301-3, 505 | 302, 301/9-10 | SVA | 2 yr | −(−) |
| C13 | 8, 8 | 301 | 302 | SVA | 1 yr | +(+) |

Another analysis was carried out to determine the bioactivity of individual tTG-deamidated peptides in pools 1-3 in subject C12. The results are as follows (sequence numbers refer to the peptides listed in Table 23): Sequence 8 (SEQ ID NO: 114) (100%), Sequence 5 (SEQ ID NO:111) (85%), Sequence 6 (SEQ ID NO: 112) (82%), Sequence 3 (SEQ ID NO: 109) (77%), Sequence 1 (SEQ ID NO:107) (67%), Sequence 2 (SEQ ID NO:108) (59%), Sequence 9 (SEQ ID NO:115) (49%), Sequence 7 (113) (49%), Sequence 10 (SEQ ID NO:116) (33%), Sequence 4 (SEQ ID NO:110) (15%), Sequence 12 (SEQ ID NO: 118) (8%), Sequence 11 (SEQ ID NO:117) (0%), Sequence 23 (SEQ ID NO:129) (26%), Sequence 14 (SEQ ID NO:120) (18%), Sequence 15 (SEQ ID NO:121) (18%), Sequence 17 (SEQ ID NO:123) (18%), Sequence 16 (SEQ ID NO:122) (13%), Sequence 14 (SEQ ID NO:120) (8%), Sequence 22 (SEQ ID NO:128) (5%), Sequence 18 (SEQ ID NO:124) (3%), Sequence 19 (SEQ ID NO:125) (3%), Sequence 20 (SEQ ID NO:126) (0%), Sequence 21 (SEQ ID NO:127) (0%). The predicted deamidated sequence is LQPENPSQEQPE (SEQ ID NO:22).

Individual ELISpot Responses by PBMC (Spot Forming Cells Determined by ELISpot Reader)

| Peptide (see TABLE 23) | C01 | C02 | C03 | C04 | C05 |
|---|---|---|---|---|---|
| 65 (SEQ ID NO: 171) | 16 | 2 | 1 | 2 | 3 |
| 66 (SEQ ID NO: 172) | 32 | 6 | 13 | 0 | 6 |
| 67 (SEQ ID NO: 173) | 16 | 3 | 4 | 0 | 4 |
| 68 (SEQ ID NO: 174) | 25 | 8 | 4 | 2 | 2 |
| 69 (SEQ ID NO: 175) | 4 | 0 | 0 | 0 | 0 |
| 70 (SEQ ID NO: 176) | 2 | 1 | 0 | 0 | 0 |
| 71 (SEQ ID NO: 177) | 1 | 1 | 0 | 0 | 1 |
| 72 (SEQ ID NO: 178) | 0 | 0 | 0 | 0 | 0 |
| 73 (SEQ ID NO: 179) | 95 | 21 | 42 | 31 | 31 |
| 74 (SEQ ID NO: 180) | 122 | 15 | 29 | 21 | 28 |
| 75 (SEQ ID NO: 181) | 5 | 1 | 2 | 2 | 5 |
| 76 (SEQ ID NO: 182) | 108 | 13 | 28 | 16 | 22 |
| 77 (SEQ ID NO: 183) | 3 | 0 | 1 | 0 | 1 |
| 78 (SEQ ID NO: 184) | 21 | 2 | 3 | 5 | 3 |
| 79 (SEQ ID NO: 185) | 20 | 0 | 2 | 0 | 2 |
| 80 (SEQ ID NO: 186) | 5 | 2 | 0 | 0 | 3 |
| 81 (SEQ ID NO: 187) | 4 | 1 | 2 | 3 | 1 |
| 82 (SEQ ID NO: 188) | 3 | 3 | 5 | 2 | 2 |
| 83 (SEQ ID NO: 189) | 14 | 2 | 0 | 0 | 1 |
| 84 (SEQ ID NO: 190) | 3 | 0 | 0 | 0 | 0 |
| 85 (SEQ ID NO: 191) | 14 | 1 | 2 | 1 | 2 |
| 86 (SEQ ID NO: 192) | 11 | 0 | 2 | 0 | 2 |

Cross-Reactivity

To deal with data from 652 peptides in 29 subjects, or to determine when a particular response is a true positive peptide-specific T-cell response, or to determine when a response to a peptide is due to cross-reactivity with another structurally related peptide, expression of a particular peptide response can be as a percentage of a "dominant" peptide response. Alternately, the expression can be a "relatedness" as correlation coefficients between peptide responses, or via bioinformatics.

Additional Epitopes

A representative result is as follows:

| Combination of peptides with P04722E (all 20 mcg/ml) (n = 4) | | |
|---|---|---|
|  | Alone | P04722E+ |
| Pep 626 (SEQ ID NO: 732) | 60 | 135 |
| P04722E (SEQ ID NO: 49) | 100 | 110 |
| HLAa | 0 | 85 |
| (expressed as percent P04722E) | | |

626 + tT: PQQPQQPQQPFPQPQQPFPW (SEQ ID NO: 31)
P04724E: QLQPFPQPELPYPQPQL (SEQ ID NO: 49)
TTG-deamidation of peptide 626 (n = 12)
No tTG = 100%
TTG = 170%

Substitution at Particular Positions

Substitution of Peptide 626
PQQP[Q1]QP[Q2]QPFPQP[Q3]QPFPV
(SEQ ID NO: 31)(n = 12)

|    | Glu | Arg |
|----|-----|-----|
| Q1 | 95  | 90  |
| Q2 | 145 | 80  |
| Q3 | 155 | 10  |

(expressed as percent wild-type peptide)

Bioactivity of tTG-treated 15 mers spanning
Peptide 626/627 (PQQPQQPQQPFPQPQQPFPWQP
(SEQ ID NO: 50))(n = 8)

| P1-15 | 5  |
|-------|----|
| P2-16 | 4  |
| P3-17 | 3  |
| P4-18 | 38 |
| P5-19 | 65 |
| P6-20 | 95 |
| P7-21 | 65 |
| P8-22 | 90 |

(expressed as percent of maximal 15 mer response)

Multiple Epitopes:

(SEQ ID NO: 51)
P04724E: QLQPFPQPQLPYPQPQL (SEQ ID NO: 31)
626 + tTG: PQQPQQPQQPFPQPQQPFPW (SEQ ID NO: 52)
Minimal epitope: QPQQPFPQPQQPFPW Immunomagnetic depletion of PBMC by beads coated with anti-CD4 and by anti-integrin β7 depleted IFNγ ELISpot responses, while immunomagnetic depletion of PBMC by beads coated with anti-CD8 or anti-alphaE integrin. Thus, the PBMC secreting IFNγ are CD4+ and $α_4β_7$+, associated with homing to the lamina propria in the gut.

Blocked by anti-DQ antibody but not by anti-DR antibody in heterozygotes and homozygotes for HLA-DQ2. This may imply multiple epitopes within one sequence.

T Cell Epitopes in Coeliac Disease

Other investigators have characterized certain intestinal T cell clone epitopes. See, e.g., Vader et al., Gastroenterology 2002, 122:1729-37; Arentz-Hansen et al., Gastroenterology 2002, 123:803-809. These are examples of epitopes whose relevance is at best unclear because of the in vitro techniques used to clone T cells.

Intestinal Versus Peripheral Blood Clones

Intestinal: 1) intestinal biopsies, 2) T cell clones raised against peptic-tryptic digest of gluten, 3) all HLA-DQ2 restricted, 4) clones respond to gliadin deamidated by transglutaminase.

Peripheral blood: 1) T cell clones raised against gluten are HLA-DR, DQ and DP restricted. Result: Intestinal T cell clones can be exclusively used to map coeliac disease associated epitopes GDA_9Wheat 307 aa Definition Alpha/Beta-Gliadin MM1 Precursor (Prolamin) Accession P18573—Genbank (which is incorporated herein by reference in its entirety)

Intestinal T Cell Clone Epitopes

A definition of intestinal T cell clone epitopes can be found in, for example, Arentz-Hansen et al., J Exp Med. 2000, 191:603-12. Also disclosed therein are gliadin epitopes for intestinal T cell clones. Deamidated QLQPFPQPQLPY (SEQ ID NO:53) is an epitope, with a deamidated sequence of QLQPFPQPELPY (SEQ ID NO:13). There is an HLA-DQ2 restriction. A homology search shows other bioactive rAlpha-gliadins include PQPQLPY(SEQ ID NO:4) singly or duplicated. A majority of T cell clones respond to either/or DQ2-αI: QLQPFPQPELPY(SEQ ID NO:13) DQ2-αII: PQPELPYPQPELPY(SEQ ID NO:47)

Dominant Gliadin T Cell Epitopes

All deamidated by transglutaminase.

Peripheral blood day 6 after gluten challenge: A-gliadin 57-73: QLQPFPQPELPYPQPQS(SEQ ID NO:2)

Intestinal T cell clones: DQ2-αI: QLQPFPQPELPY(SEQ ID NO:13) DQ2-αII: PQPELPYPQPELPY(SEQ ID NO:47)

Intestinal T-Cell Clone Epitope Mapping

| α-Gliadins | A1 | PFPQPQLPY(SEQ ID NO: 54) |
|---|---|---|
|  | A2 | PQPQLPYPQ(SEQ ID NO: 55) |
|  | A3 | PYPQPQLPY(SEQ ID NO: 56) |
|  | Glia-20 | PQQPYPQPQPQ(SEQ ID NO: 57) |
| Γ-Gliadins | G1 | PQQSFPQQQ(SEQ ID NO: 58) |
|  | G2 | IIPQQPAQ(SEQ ID NO: 59) |
|  | G3 | FPQQPQQPYPQQP(SEQ ID NO: 60) |
|  | G4 | FSQPQQQFPQPQ(SEQ ID NO: 61) |
|  | G5 | LQPQQPFPQQPQQPYFQQPQ (SEQ ID NO: 62) |
|  | Glu-21 | QSEQSQQPFPQQF(SEQ ID NO: 63) |
|  | Glu-5 | Q(LL)PQQPQQF(SEQ ID NO: 64) |
| Glutenin | Glt-156 | PFSQQQQSPF(SEQ ID NO: 65) |
|  | Glt-17 | PFSQQQQQ(SEQ ID NO: 66) |

Gluten Exposure and Induction of IFNγ-Secreting A-Gliadin 57-73QE65 (SEQ ID NO:2)-Specific T Cells in Peripheral Blood Untreated coeliac disease, followed by gluten free diet for 1, 2, or 8 weeks, followed by gluten exposure (3 days bread 200 g/day), followed by gluten free diet Result 1: Duration of gluten free diet and IFNγ ELISpot responses on day 0 and day 6 of gluten challenge: A-gliadin 57-73 QE65 (SEQ ID NO:2) (results expressed as IFNγ specific spots/million PPBMC)

Day 0: none (5), 1 week (1), 2 weeks (2), 8 weeks (1)

Day 6: none (0), 1 week (4), 2 weeks (28), 8 weeks (48)

Result 2: Duration of gluten free diet and IFNγ ELISpot responses on day 0 and day 6 of gluten challenge: tTG-gliadin (results expressed as IFNγ specific spots/million PPBMC)

Day 0: none (45), 1 week (62), 2 weeks (5), 8 weeks (5)

Day 6: none (0), 1 week (67), 2 weeks (40), 8 weeks (60)

Result 3: Duration of gluten free diet and IFNγ ELISpot responses on day 0 and day 6 of gluten challenge: A-gliadin 57-73 P65 (results expressed as IFNγ specific spots/million PPBMC)

Day 0: none (1), 1 week (2), 2 weeks (1), 8 weeks (1)

Day 6: none (0), 1 week (0), 2 weeks (0), 8 weeks (0)

Result 4: Duration of gluten free diet and IFNγ ELISpot responses on day 0 and day 6 of gluten challenge: PPD (results expressed as IFNγ specific spots/million PPBMC)

Day 0: none (90), 1 week (88), 2 weeks (210), 8 weeks (150)

Day 6: none (0), 1 week (100), 2 weeks (210), 8 weeks (100)

Result 5: Duration of gluten free diet and IFNγ ELISpot responses on day 0 and day 6 of gluten challenge: tTG (results expressed as IFNγ specific spots/million PPBMC)

Day 0: none (5), 1 week (4), 2 weeks (3), 8 weeks (2)

Day 6: none (0), 1 week (4), 2 weeks (1), 8 weeks (2)

Gluten Challenge in HLA-DQ2 Coeliac Disease on Long Term Gluten

Characterization of anti-gliadin T cell response was carried out in peripheral blood on day 6-8 after 3-day gluten challenge.

Result 1: PBMC Day 6 Long-term gluten free diet (preincubation with anti-HLA-DR and -DQ antibody) (expressed as % inhibition)

DR-: tTG-gliadin 100 mcg/ml (105), A-gliadin 57-73 QE65 (SEQ ID NO:2) 50 mcg/ml (90), PPD 5 mcg/ml (30)

DQ-: tTG-gliadin 100 mcg/ml (5), A-gliadin 57-73 QE65 (SEQ ID NO:2) 50 mcg/ml (22), PPD 5 mcg/ml (78).

Result 2: PBMC Day 6 Long-term gluten free diet (expressed as % CD8-depleted PBMC response)

B7 depletion: tTG-gliadin n=6 (7), A-gliadin 57-73 n=9 (6), PPD n=8 (62)

AE depletion: tTG-gliadin n=6 (120), A-gliadin 57-73 n=9 (80), PPD n=8 (110).

CD4 depletion: tTG-gliadin n=6 (10), A-gliadin 57-73 n=9 (9), PPD n=8 (10).

Therapeutic Peptides Include, but are not Limited to

```
QLQPFPQPQLPYPQPQS   (AG01)     (SEQ ID NO: 10)

QLQPFPQPQLPYPQPQP   (AG02)     (SEQ ID NO: 26)

QLQPFPQPQLPYPQPQL   (AG03)     (SEQ ID NO: 51)

QLQPFPQPQLPYLQPQP   (AG04)     (SEQ ID NO: 67)

QLQPFPRPQLPYPQPQP   (AG05)     (SEQ ID NO: 68)

QLQPFPQPQLPYSQPQP   (AG06)     (SEQ ID NO: 28)

QLQPFLQPQLPYSQPQP   (AG07)     (SEQ ID NO: 69)

QLQPFSQPQLPYSQPQP   (AG08)     (SEQ ID NO: 70)

QLQPFPQPQLSYSQPQP   (AG09)     (SEQ ID NO: 71)

PQLPYPQPQLPYPQPQP   (AG10)     (SEQ ID NO: 72)

PQLPYPQPQLPYPQPQL   (AG11)     (SEQ ID NO: 73)

PQPQPFLPQLPYPQPQS   (AG12)     (SEQ ID NO: 74)

PQPQPFPPQLPYPQPQS   (AG13)     (SEQ ID NO: 75)

PQPQPFPPQLPYPQYQP   (AG14)     (SEQ ID NO: 76)

PQPQPFPPQLPYPQPPP   (AG015)    (SEQ ID NO: 77)
```

Briefly after oral antigen challenge, specificities of peripheral blood T cells reflect those of intestinal T cell clones. In peripheral blood, epitopes of intestinal T cell clones are sub-optimal compared to A-gliadin 57-73 QE65 (SEQ ID NO:2), which is an optimal α-gliadin epitope.

Example 15

ELISpot assays were also carried out for mapping purposes as follows.

Fine-Mapping the Dominant DQ-8 Associated Epitope

```
Sequence / sfc              tTG-treated sequence / sfc

VPQLQPQNPSQQQPQEQV / 76     RWPVPQLQPQNPSQQ / 60
                            WPVPQLQPQNPSQQQ / 90
VPQLQPENPSQQQPQEQV / 3      PVPQLQPQNPSQQQP / 130
VPQLQPRNPSQQQPQEQV / 76     VPQLQPQNPSQQQPQ / 140
                            PQLQPQNPSQQQPQE / 59
VPQLQPQNPSQEQPQEQV / 100    QLQPQNPSQQQPQEQ / 95
VPQLQPQNPSQRQPQEQV / 1      LQPQNPSQQQPQEQV / 30
                            QPQNPSQQQPQEQVP / 4
VPQLQPQNPSQQQPEEQV / 71
YPQLQPQNPSQQQPREQV / 27     DQ8 Gliadin Epitope
                            GDA09 202Q / 6
VPQLQPQNPSQEQPEEQV / 81     GDA09 202E / 83
VPQLQPENPSQQQPEEQV / 2      GDA09 202Q + tTG / 17
VPQLQPENPSQEQPQEQV / 6      BI + tTG / 0
VPQLQPENPSQEQPEEQV / 5      BI / 0

A = SEQ ID NO: 78;
B = SEQ ID NO: 79;
C = SEQ ID NO: 80;
D = SEQ ID NO: 81;
E = SEQ ID NO: 82;
F = SEQ ID NO: 83;
G = SEQ ID NO: 84;
H = SEQ ID NO: 85;
I = SEQ ID NO: 86;
J = SEQ ID NO: 87;
K = SEQ ID NO: 88;
L = SEQ ID NO: 89;
M = SEQ ID NO: 90;
N = SEQ ID NO: 91;
O = SEQ ID NO: 92;
P = SEQ ID NO: 93;
Q = SEQ ID NO: 94;
R = SEQ ID NO: 95;
S = SEQ ID NO: 96;
```

Fine-Mapping Dominant Epitope (2)
Pool 33 (deamidated)/sfc
A2b3 301 QQYPSGQGFFQPSQQNPQAQ (SEQ ID NO:359)/2
A2b5 301 QQYPSGQGFFQPFQQNPQAQ (SEQ ID NO:360)/1
A3a1 301 QQYPSGQGFFQPSQQNPQAQ (SEQ ID NO:361)/0
A3b1 301 QQYPSSQVSFQPSQLNPQAQ (SEQ ID NO:362)/0
A3b2 301 QQYPSSQGSFQPSQQNPQAQ (SEQ ID NO:363)/2
A4a 301 EQYPSGQVSFQSSQQNPQAQ (SEQ ID NO:364)/28
A1b1 309 SFRPSQQNPLAQGSVQPQQL (SEQ ID NO:365)/2
A1a1 309 SFRPSQQNPQAQGSVQPQQL (SEQ ID NO:366)/2

Example 16

Bioactivity of Gliadin Epitopes in IFNγ-ELISpot (25 mcg/ml, n=6) (Expressed as % A-Gliadin 57-73 QE65 (SEQ ID NO2) Response)

DQ2-AII: wild type (WT) (4), WT+tTG (52), Glu-substituted (52)

DQ2-AI: wild type (WT) (2), WT+tTG (22), Glu-substituted (28)

GDA09: wild type (WT) (1), WT+tTG (7), Glu-substituted (8)

A-G31-49: wild type (WT) (2), WT+tTG (3), Glu-substituted (0)

Dose Response of A-Gliadin 57-73 QE65 (SEQ ID NO:2) (G01E) (n=8) (Expressed as % G01E Maximal Response)

0.025 mcg/ml (1), 0.05 mcg/ml (8), 0.1 mcg/ml (10), 0.25 mcg/ml (22), 0.5 mcg/ml (38), 1 mcg/ml (43), 2.5 mcg/ml (52), 5 mcg/ml (70), 10 mcg/ml (81), 25 mcg/ml (95), 50 mcg/ml (90), 100 mcg/ml (85).

IFNγ ELISpot response to gliadin epitopes alone or mixed with A-gliadin 57-75 (G01E) (all 50 mcg/ml, tTG-gliadin 100 mcg/ml, PPD 5 mcg/ml; n=9) (expressed as % G01E response)

Alone: DQ2-A1 (20), DQ2-A2 (55), Omega GI (50), tTG Gliadin (80), PPD (220), DQ2 binder (0)

G01E+: DQ2-A1 (90), DQ2-A2 (95), Omega GI (100), tTG Gliadin (120), PPD (280), DQ2 binder (80)

Effect of Alanine and Lysine Substitution of A-Gliadin 57-73 QE65 (SEQ ID NO:2) on IFNγ ELISpot Responses in Individual Coeliac Subjects (n=8)

Epitope sequence: QLQPFPQPELPYPQPQS (SEQ ID NO:2)

Alanine substitution at positions 57-59 and 72-73 showed little to no decrease in % A-gliadin 57-73 QE65 (SEQ ID NO:2) response. Alanine substitution at positions 60-62 and 68-71 showed moderate decrease in % A-gliadin 57-73 QE65 (SEQ ID NO:2) response. Alanine substitution at positions 63-67 showed most decrease in % A-gliadin 57-73 QE65 (SEQ ID NO:2) response.

Effect of lysine substitution of A-gliadin 57-73 QE65 (SEQ ID NO:2) on IFNγ ELISpot responses in individual coeliac subjects (n=8);

Epitope Sequence: QLQPFPQPELPYPQPQS(SEQ ID NO:2)

Lysine substitution at positions 57-59 and 71-73 showed little to no decrease in % A-gliadin 57-73 QE65 (SEQ ID NO:2) response. Lysine substitution at positions 60-61 and 69-70 showed moderate decrease in % A-gliadin 57-73 QE65 (SEQ ID NO:2) response. Lysine substitution at positions 62-68 showed most decrease in % A-gliadin 57-73 QE65 (SEQ ID NO:2) response.

Example 17

Table 24 shows the results of analyses examining the 652 peptides with several patients challenged with wheat or rye.

REFERENCES

1. Molberg O, et al. Nature Med. 4, 713-717 (1998).
2. Quarsten H, et al. Eur. J. Immunol. 29, 2506-2514 (1999).
3. Greenberg C S et al. FASEB 5, 3071-3077 (1991).
4. Mantzaris G, Jewell D. Scand. J. Gastroenterol. 26, 392-398 (1991).
5. Mauri L, et al. Scand. J. Gastroenterol. 31, 247-253 (1996).
6. Bunce M, et al. Tissue Antigens 46, 355-367 (1995).
7. Olerup O, et al. Tissue antigens 41, 119-134 (1993).
8. Mullighan C G, et al. Tissue-Antigens. 50, 688-92 (1997).
9. Plebanski M et al. Eur. J. Immunol. 28, 4345-4355 (1998).
10. Anderson D O, Greene F C. The alpha-gliadin gene family. II. DNA and protein sequence variation, subfamily structure, and origins of pseudogenes. Theor Appl Genet (1997) 95:59-65.
11. Arentz-Hansen H, Korner R, Molberg O, Quarsten H, Van der Wal Y, Kooy Y M C, Lundin K E A, Koning F, Roepstorff P, Sollid L M, McAdam S N. The intestinal T cell response to alpha-gliadin in adult celiac disease is focused on a single deamidated glutamine targeted by tissue transglutaminase. J Exp Med. 2000; 191:603-12.
12. Vader L W, de Ru A, van der Wal, Kooy Y M C, Benckhuijsen W, Mearin M L, Drijfhout J W, van Veelen P, Koning F. Specificity of tissue transglutaminase explains cereal toxicity in celiac disease. J Exp Med 2002; 195:643-649.
13. van der Wal Y, Kooy Y, van Veelan P, Pena S, Mearin L, Papadopoulos G, Koning F. Selective deamidation by tissue transglutaminase strongly enhances gliadin-specific T cell reactivity. J Immunol. 1998; 161:1585-8.
14. van der Wal Y, Kooy Y, van Veelan P, Pena S, Mearin L, Molberg O, Lundin K E A, Sollid L, Mutis T, Benckhuijsen W E, Drijfhout J W, Koning F. Proc Natl Acad Sci USA 1998; 95:10050-10054.
15. Vader W, Kooy Y, Van Veelen P et al. The gluten response in children with celiac disease is directed toward multiple gliadin and glutenin peptides. Gastroenterology 2002, 122:1729-37
16. Arentz-Ilansen H, McAdam S N, Molberg O, et al. Celiac lesion T cells recognize epitopes that cluster in regions of gliadin rich in proline residues. Gastroenterology 2002, 123:803-809.

Each of the PCT publications, U.S. patents, other patents, journal references, and any other publications cited or referred to herein is incorporated herein by reference in their entirety.

TABLE 1

A-Gliadin protein sequence (based on amino acid sequencing) (SEQ ID NO: 3)

| | | | | | | |
|---|---|---|---|---|---|---|
| VRVPVPQLQP | QNPSQQQPQE | QVPLVQQQQF | PGQQQQFPPQ | QPYPQPQPFP | SQQPYLQLQP | FPQPQLPYPQ |
| 1 | 11 | 21 | 31 | 41 | 51 | 61 |
| PQSFPPQQPY | PQPQPQYSQP | QQPISQQQAQ | QQQQQQQQQQ | QQQILQQILQ | QQLIPCMDVV | LQQHNIAHAR |
| 71 | 81 | 91 | 101 | 111 | 121 | 131 |
| SQVLQQSTYQ | LLQELCCQHL | WQIPEQSQCQ | AIHNVVHAII | LHQQQKQQQQ | PSSQVSFQQP | LQQYP LGQGS |
| 141 | 151 | 161 | 171 | 181 | 191 | 201 |
| FRPSQQNPQA | QGSVQPQQLP | QFEEIRNLAL | QTLPAMCNVY | IAPYCTIAPF | GIFGTN | |
| 211 | 221 | 231 | 241 | 251 | 261 | |

TABLE 2

| Coeliac disease subjects studied | | | | | |
|---|---|---|---|---|---|
| | Age Sex | Gluten free diet | HLA-DQ2 | Bread challenge | Symptoms with bread |
| 1 | 64 f | 14 yr | Homozygote | 3 days | Abdominal pain, lethargy, mouth ulcers, diarrhoea |
| 2 | 57 m | 1 yr | Heterozygote | 10 days | Lethargy, nausea |
| 3 | 35 f | 7 yr | Heterozygote | 3 days | Nausea |
| 4 | 36 m | 6 wk | Homozygote | 3 days | Abdominal |

TABLE 2-continued

Coeliac disease subjects studied

| Age Sex | Gluten free diet | HLA-DQ2 | Bread challenge | Symptoms with bread |
|---|---|---|---|---|
| 5  26 m | 19 yr | Heterozygote | 3 days | pain, mouth ulcers, diarrhoea None |
| 6  58 m | 35 yr | Heterozygote | 3 days | None |
| 7  55 m | 1 yr | Heterozygote | 3 days | Diarrhoea |
| 8  48 f | 15 yr | Homozygote | 3 days | Abdominal pain, diarrhoea |

TABLE 3

| Aminoacid at position 65 | Range | Mean |
|---|---|---|
| Glutamate | (100) | 100% |
| Asparagine | (50-84) | 70% |
| Aspartate | (50-94) | 65% |
| Alanine | (44-76) | 64% |
| Cysteine | (45-83) | 62% |
| Serine | (45-75) | 62% |
| Valine | (24-79) | 56% |
| Threonine | (46-66) | 55% |
| Glycine | (34-47) | 40% |
| Leucine | (8-46) | 33% |
| Glutamine | (16-21) | 19% |
| Isoleucine | (3-25) | 14% |
| Methionine | (3-32) | 14% |
| Phenylalanine | (0-33) | 12% |
| Histidine | (0-13) | 8% |
| Tyrosine | (0-17) | 8% |
| Tryptophan | (0-17) | 8% |
| Lysine | (0-11) | 4% |
| Proline | (0-4) | 2% |
| Arginine | (0-2) | 1% |

TABLE 4

| Elisopt No TG | response TG | Peptide sequence | Corresponding residues in gliadin protein sequences (Accession no.) |
|---|---|---|---|
| 13). | | QLQPFPQPQLPYPQPQS (SEQ ID NO: 796) | 57-73 α-Gliadin (T. aestivum) Q41545 |
| | 100(100) | QLQPFPQPELPYPQPQS (SEQ ID NO: 797) | 57-73 α-Gliadin (T. aestivum) Q41545 |
| 7) | 53(44-67) | QLQPFPQPQLPYSQPQP (SEQ ID NO: 28) | 77-93 α/β-Gliadin precursor (Tricetum aestivum) P02863 |
| | | | 76-92 α-Gliadin (T. aestivum) Q41528 |
| | | | 77-93 α-Gliadin storage protein (T. aestivum) Q41531 |
| | | | 57-73 α-Gliadin mature peptide (T. aestivum) Q41533 |
| | | | 77-93 α-Gliadin precursor (T. spelta) Q9ZP09 |
| -20) | 83 (61-113) | QLQPFPQPQLPYPQPQP (SEQ ID NO: 26) | 77-93 α/β-Gliadin A-II precursor (T. aestivum) P0472 |
| -337 | 83(74-97) | QLQPFPQPQLPYPQPQL (SEQ ID NO: 798) | 77-93 α/β-Gliadin A-IV precursor (T. aestivum) P04724 |
| | | | 77-93 α/β-Gliadin MM1 precursor (T. aestivum) P18573 |
| | 109(41-152)) | PQLPYPQPQLPYPQPQP (SEQ ID NO: 72) | 84-100 α/β-Gliadin A-I precursor (T. aestivum) P04724 |
| | | PQLPYPQPQLPYPQPQL (SEQ ID NO: 73) | 84-100 α/β-Gliadin MMI precursor (T. aestivum) P18573 |
| | 3(0-7) | QLQPFLQPQLPYSQPQP (SEQ ID NO: 69) | 77-93 α/β-Gliadin A-I precursor (T. aestivum) P04721 |
| | | | 77-93 α-Gliadin (T. aestivum) Q41509 |
| | 2(0-7) | QLQPFSQPQLPYSQPQP (SEQ ID NO: 70) | 77-93 α-Gliadin storage protein (T. aestivum) Q41530 |
| | | PQPQPFPPQLPYPQTQP (SEQ ID NO: 97) | 77-93 α/β-Gliadin A-III precursor (T. aestivum) P04723 |
| -40) | 24(11-43) | PQPQPFPPQLPYPQPQS (SEQ ID NO: 75) | 82-98 α/β-Gliadin A-V precursor (T. aestivum) P04725 |
| -30) | 19(11-33) | PQPQPFPPQLPYPQPPP (SEQ ID NO: 77) | 82-98 α/β-Gliadin clone PW1215 precursor (T. aestivum) P04726 |
| | | | 82-98 α/β-Gliadin (T. urartu) Q41632 |

TABLE 4-continued

| Elisopt No TG | response TG | Peptide sequence | Corresponding residues in gliadin protein sequences (Accession no.) |
|---|---|---|---|
| -30) | 21(11-33) | PQPQPFLPQLPYPQPQS (SEQ ID NO: 74) | 79-95 α/β-Gliadin clone PW8142 precursor (T. aestivum) P04726 |
| | | | 79-95 α-Gliadin (T. estivum) Q41529 |
| | | | 79-95 α/β-Gliadin precursor (T. aestivum) Q41546 |

TABLE 5

T cell epitopes described in coeliac disease

| Source | Restriction | Frequency | Sequence* |
|---|---|---|---|
| Gamma-gliadin | DQ2 | 3/NS (iTCC) | (SEQ ID NO: 48) QQLPQPEQPQQSFPEQERPF |
| Alpha-gliadin | DQ2 | 12/17 (iTCL) | (SEQ ID NO: 13) QLQPFPQPELPY |
| Alpha-gliadin | DQ2 | 11/17 (iTCL) | (SEQ ID NO: 47) PQPELPYPQPELPY |
| Alpha-gliadin | DQ2 | 1/23 (bTCC) | (SEQ ID NO: 98) LGQQQPFPPQQPYPQPQPF |
| Alpha-gliadin | DQ8 | 3/NS (iTCC) | (SEQ ID NO: 99) QQYPSGEGSFQPSQENPQ |
| Glutenin | DQ8 | 1/1 (iTCC) | (SEQ ID NO: 100) GQQGYYPTSPQQSGQ |
| Alpha-gliadin | DQ2 | 11/12 in vivo | (SEQ ID NO: 2) QLQPFPQPELPYPQPQS |

NS not stated in original publication, iTCC intestinal T cell clone, iTCL intestinal polyclonal T cell line, bTCC peripheral blood T cell clone
* All peptides are the products of transglutaminase modifying wild type gluten peptides except the fourth and sixth peptides

TABLE 6

Relative bioactivity of gliadin T cell epitopes in coeliac PBMC after gluten challenge ELISpot response as % A-gliadin 57-73 QE65 (SEQ ID NO: 2) (all 25 mcg/ml)

| Sequence* | Wild type | Wildtype + tTG | E-substituted |
|---|---|---|---|
| QQLPQPEQPQQSFPEQERPF (SEQ ID NO: 48) | 9 (3) | 18 (7) | 10 (5) |
| QLQPFPQPELPY (SEQ ID NO: 13) | 6 (2) | 19 (1) | 8 (3) |
| PQPELPYPQPELPY (SEQ ID NO: 47) | 13 (6) | 53 (8) | 48 (9) |
| QQYPSGEGSFQPSQENPQ (SEQ ID NO: 99) | 10 (3) | 9 (3) | 14 (8) |
| QLQPFPQPELPYPQPQS (SEQ ID NO: 2) | 18 (7) | 87 (7) | 100 |
| PQLPYPQPELPYPQPQP (SEQ ID NO: 101) | 14 (4) | 80 (17) | 69 (20) |

*sequence refers that of transglutaminase (tTG) modified peptide and the T cell epitope. Wild type is the unmodified gliadin peptide. Data from 4 subjects. Blank was 5 (1)%.

TABLE 7

Polymorphisms of A-gliadin 57-73

A. Sequences derived from Nordic autumn wheat strain Mjoelner

| Alpha-gliadin protein (single letter code refers to FIG. 14 peptides) | Polymorphism |
|---|---|
| Q41545 A-gliadin (from sequenced protein) 57-73 (A) | QLQPFPQPQLPYPQPQS (SEQ ID NO: 10) |
| Gli alpha 1, 6: (EMBL: AJ133605 & AJ133602 58-74) (J) | QPQPFPPPQLPYPQTQP (SEQ ID NO: 105) |
| Gli alpha 3, 4, 5: (EMBL: AJ133606, AJ133607, AJ133608 57-73) (I) | QLQPFPQPQLPLSYSQPQP (SEQ ID NO: 71) |
| Gli alpha 7: (EMBL: AJ133604 57-73) (E) | QLQPFPRPQLPYPQPQP (SEQ ID NO: 68) |
| Gli alpha 8, 9, 11: (EMBL:) (F) | QLQPFPQPQLPYSQPQP (SEQ ID NO: 28) |
| Gli alpha 10: (EMBL: AJ133610 57-73) (D) | QLQPFPQPQLPYLQPQS (SEQ ID NO: 104) |

B. SWISSPROT and TREMBL scan (10.12.99) for gliadins containing the sequence: XXXXXXXPQLPYXXXXX (SEQ ID NO: 799)

| Wheat (Triticum aestivum unless stated) gliadin accession number | Polymorphism |
|---|---|
| Q41545 A-gliadin (from sequenced protein) 5773 (A) | QLQPFPQPQLPYPQPQS (SEQ ID NO: 10) |
| SWISSPROT: | |
| GDA0_WHEAT P02863 7793 (F) | QLQPFPQPQLPYSQPQP (SEQ ID NO: 28) |
| GDA1_WHEAT P04721 7793 (G) | QLQPFLQPQLPYSQPQP (SEQ ID NO: 69) |
| GDA2_WHEAT P04722 7793 (B) | QLQPFPQPQLPYPQPQP (SEQ ID NO: 26) |
| GDA3_WHEAT P04723 7793 (O) | PQPQPFPPQLPYPQTQP (SEQ ID NO: 97) |
| GDA4_WHEAT P04724 7793 (C) | QLQPFPQPQLPYPQPQL (SEQ ID NO: 51) |
| GDA4_WHEAT P04724 84100 (K) | PQLPYPQPQLPYPQPQP (SEQ ID NO: 72) |
| GDA5_WHEAT P04725 8298 (N) | PQLPYFPPQLPYPQPQS (SEQ ID NO: 75) |
| GDA6_WHEAT P04726 8298 (P) | PQPQPFPPQLPYPQPPP (SEQ ID NO: 77) |
| GDA7_WHEAT P04727 7995 (M) | PQPQPFLPQLPYPQPQS (SEQ ID NO: 74) |
| GDA9_WHEAT P18573 7793 (C) | QLQPFPQPQLPYPQPQL (SEQ ID NO: 51) |
| GDA9_WHEAT P18573 84100 (L) | PQLPYPQPQLPYPQPQL (SEQ ID NO: 73) |
| GDA9_WHEAT P18573 91107 (K) | PQLPYPQPQLPYPQPQP (SEQ ID NO: 72) |
| TREMBL | |
| Q41509 ALPHA-GLIADLN 7793 (G) | QLQPFLQPQLPYSQPQP (SEQ ID NO: 69) |
| Q41528 ALPHA-GLIADIN 7692 (F) | QLQPFPQPQLPYSQPQP (SEQ ID NO: 28) |
| Q41529 ALPHA-GLIADIN 7995 (M) | PQPQPFLPQLPYPQPQS (SEQ ID NO: 74) |
| Q41530 ALPHA-GLIADIN 7793 (H) | QLQPFSQPQLPYSQPQP (SEQ ID NO: 70) |
| Q41531 ALPHA-GLIADIN 7793 (F) | QLQPFPQPQLPYSQPQP (SEQ ID NO: 28) |
| Q41533 ALPHA-GLIADLN 5773 (F) | QLQPFPQPQLPYSQPQP (SEQ ID NO: 28) |
| Q41546 ALPHA/BETA-GLIADIN 7995 (M) | PQPQPFLPQLPYPQPQS (SEQ ID NO: 74) |
| Q41632 ALPHA/BETA-TYPE GLIADIN. Triticum urartu 8298 (P) | PQPQPFPPQLPYPQPPP (SEQ ID NO: 77) |
| Q9ZP09 ALPHA-GLIADIN Triticum spelta 7793 (F) | QLQPFPQPQLPYSQPQP (SEQ ID NO: 28) |

TABLE 8

Bioactivity of substituted variants of A-gliadin 57-73 QE65 (SEQ ID NO: 2) (Subst) compared to unmodified A-gliadin 57-73 QE65 (SEQ ID NO: 2) (G) (mean 100%, 95% CI 97-104) and blank (no peptide, bl) (mean 7.1%, 95% CI: 5.7-8.5)

| Subst | % | P vs G |
|---|---|---|
| Super-agonists | | |
| Y61 | 129 | <0.0001 |
| Y70 | 129 | 0.0006 |
| Agonists | | |
| W70 | 119 | 0.017 |
| K57 | 118 | 0.02 |
| Y59 | 117 | 0.04 |
| A57 | 116 | 0.046 |
| S70 | 116 | 0.045 |
| K58 | 114 | 0.08 |
| W59 | 110 | 0.21 |
| A73 | 109 | 0.24 |
| I59 | 108 | 0.37 |
| G59 | 108 | 0.34 |
| A58 | 108 | 0.35 |
| A59 | 104 | 0.61 |
| K72 | 104 | 0.65 |
| S59 | 103 | 0.76 |
| K73 | 102 | 0.8 |
| A70 | 102 | 0.81 |
| Y60 | 101 | 0.96 |
| A72 | 100 | 0.94 |
| S63 | 98 | 0.67 |
| K59 | 96 | 0.46 |
| I60 | 96 | 0.5 |
| G70 | 95 | 0.41 |
| D65 | 95 | 0.44 |
| E70 | 93 | 0.27 |
| I63 | 92 | 0.19 |
| S60 | 92 | 0.23 |
| P59 | 88 | 0.08 |
| M63 | 87 | 0.03 |
| K71 | 85 | 0.047 |
| V62 | 84 | 0.04 |
| I70 | 84 | 0.04 |
| I61 | 83 | 0.01 |
| V68 | 82 | 0.0045 |
| E59 | 81 | 0.01 |
| Partial agonists | | |
| W61 | 79 | 0.002 |
| A60 | 78 | 0.002 |
| Y62 | 78 | 0.006 |
| G60 | 77 | 0.003 |
| A71 | 77 | 0.003 |
| W62 | 76 | 0.0009 |
| Q60 | 76 | 0.001 |

TABLE 8-continued

Bioactivity of substituted variants of A-gliadin 57-73 QE65 (SEQ ID NO: 2) (Subst) compared to unmodified A-gliadin 57-73 QE65 (SEQ ID NO: 2) (G) (mean 100%, 95% CI 97-104) and blank (no peptide, bl) (mean 7.1%, 95% CI: 5.7-8.5)

| Subst | % | P vs G |
|---|---|---|
| L63 | 74 | 0.0002 |
| I62 | 74 | 0.0005 |
| K70 | 74 | 0.001 |
| H61 | 72 | <0.0001 |
| W68 | 72 | <0.0001 |
| F62 | 71 | 0.001 |
| V63 | 70 | <0.0001 |
| S69 | 70 | <0.0001 |
| H63 | 70 | <0.0001 |
| F63 | 70 | 0.008 |
| P70 | 69 | <0.0001 |
| T62 | 69 | <0.0001 |
| L61 | 69 | <0.0001 |
| S61 | 69 | <0.0001 |
| T61 | 69 | <0.0001 |
| T63 | 69 | <0.0001 |
| M66 | 68 | <0.0001 |
| T69 | 67 | <0.0001 |
| K60 | 66 | <0.0001 |
| S62 | 66 | <0.0001 |
| M61 | 66 | <0.0001 |
| P61 | 65 | <0.0001 |
| M62 | 64 | <0.0001 |
| Q61 | 64 | <0.0001 |
| G61 | 64 | <0.0001 |
| A63 | 64 | <0.0001 |
| L62 | 60 | <0.0001 |
| I68 | 60 | <0.0001 |
| S67 | 59 | <0.0001 |
| N61 | 59 | <0.0001 |
| I69 | 59 | <0.0001 |
| V61 | 58 | <0.0001 |
| D61 | 58 | <0.0001 |
| E60 | 57 | <0.0001 |
| A61 | 57 | <0.0001 |
| Q62 | 56 | <0.0001 |
| F68 | 56 | <0.0001 |
| N65 | 56 | <0.0001 |
| A62 | 56 | <0.0001 |
| A68 | 53 | <0.0001 |
| P66 | 53 | <0.0001 |
| R61 | 53 | <0.0001 |
| S68 | 53 | <0.0001 |
| Y63 | 52 | <0.0001 |
| N69 | 51 | <0.0001 |
| E63 | 51 | <0.0001 |
| T64 | 51 | <0.0001 |
| T67 | 51 | <0.0001 |
| Y69 | 50 | <0.0001 |
| D63 | 50 | <0.0001 |
| A65 | 49 | <0.0001 |
| K61 | 49 | <0.0001 |
| I66 | 49 | <0.0001 |
| T68 | 48 | <0.0001 |
| S65 | 48 | <0.0001 |
| L68 | 48 | <0.0001 |
| Q68 | 48 | <0.0001 |
| H62 | 47 | <0.0001 |
| G69 | 47 | <0.0001 |
| N63 | 47 | <0.0001 |
| H68 | 47 | <0.0001 |
| M68 | 46 | <0.0001 |
| D68 | 46 | <0.0001 |
| V69 | 46 | <0.0001 |
| G63 | 45 | <0.0001 |
| V64 | 45 | <0.0001 |
| E61 | 45 | <0.0001 |
| A69 | 43 | <0.0001 |
| R62 | 42 | <0.0001 |
| G68 | 42 | <0.0001 |
| A64 | 42 | <0.0001 |
| C65 | 42 | <0.0001 |
| N67 | 41 | <0.0001 |
| W63 | 41 | <0.0001 |
| F69 | 41 | <0.0001 |
| N68 | 40 | <0.0001 |
| V66 | 40 | <0.0001 |
| H69 | 40 | <0.0001 |
| M69 | 40 | <0.0001 |
| R69 | 40 | <0.0001 |
| W69 | 40 | <0.0001 |
| Q69 | 39 | <0.0001 |
| L67 | 38 | <0.0001 |
| K69 | 38 | <0.0001 |
| K62 | 38 | <0.0001 |
| E67 | 37 | <0.0001 |
| L69 | 37 | <0.0001 |
| S64 | 36 | <0.0001 |
| G62 | 36 | <0.0001 |
| E69 | 36 | <0.0001 |
| E68 | 36 | <0.0001 |
| V67 | 35 | <0.0001 |
| D62 | 35 | <0.0001 |
| R68 | 34 | <0.0001 |
| Q66 | 34 | <0.0001 |
| A67 | 33 | <0.0001 |
| N62 | 32 | <0.0001 |
| F66 | 31 | <0.0001 |
| E62 | 31 | <0.0001 |
| D69 | 31 | <0.0001 |
| D67 | 30 | <0.0001 |
| M67 | 29 | <0.0001 |
| Y66 | 28 | <0.0001 |
| I67 | 28 | <0.0001 |
| H65 | 26 | <0.0001 |
| P68 | 26 | <0.0001 |
| Y64 | 25 | <0.0001 |
| EK65 | 25 | <0.0001 |
| T66 | 25 | <0.0001 |

| Subst | % | P vs G | P vs bl |
|---|---|---|---|
| N66 | 24 | <0.0001 | |
| R64 | 24 | <0.0001 | |
| K63 | 23 | <0.0001 | |
| V65 | 23 | <0.0001 | |
| H66 | 23 | <0.0001 | |
| H67 | 22 | <0.0001 | |
| L64 | 22 | <0.0001 | |
| S66 | 22 | <0.0001 | |
| F67 | 21 | <0.0001 | |
| W66 | 21 | <0.0001 | |
| G64 | 21 | <0.0001 | |
| G65 | 21 | <0.0001 | |
| D64 | 21 | <0.0001 | |
| I65 | 21 | <0.0001 | |
| M64 | 20 | <0.0001 | <0.0001 |
| G67 | 19 | <0.0001 | <0.0001 |
| T65 | 19 | <0.0001 | 0.003 |
| A66 | 19 | <0.0001 | <0.0001 |
| I64 | 19 | <0.0001 | 0.0003 |
| R63 | 19 | <0.0001 | <0.0001 |
| W67 | 19 | <0.0001 | <0.0001 |
| K68 | 18 | <0.0001 | <0.0001 |
| H64 | 18 | <0.0001 | <0.0001 |
| W64 | 18 | <0.0001 | 0.0001 |
| Q65 | 18 | <0.0001 | 0.0002 |
| F64 | 16 | <0.0001 | 0.0008 |
| L65 | 16 | <0.0001 | 0.0022 |
| N64 | 16 | <0.0001 | <0.0001 |
| F65 | 16 | <0.0001 | 0.12 |
| Q67 | 15 | <0.0001 | 0.0012 |
| M65 | 14 | <0.0001 | 0.015 |
| D66 | 14 | <0.0001 | 0.013 |
| R67 | 14 | <0.0001 | 0.002 |
| Non-agonists | | | |
| P63 | 13 | <0.0001 | 0.012 |
| E64 | 12 | <0.0001 | 0.053 |
| W65 | 11 | <0.0001 | 0.24 |

TABLE 8-continued

Bioactivity of substituted variants of A-gliadin 57-73 QE65 (SEQ ID NO: 2) (Subst) compared to unmodified A-gliadin 57-73 QE65 (SEQ ID NO: 2) (G) (mean 100%, 95% CI 97-104) and blank (no peptide, bl) (mean 7.1%, 95% CI: 5.7-8.5)

| Subst | | P | |
|---|---|---|---|
| Q64 | 11 | <0.0001 | 0.15 |
| G66 | 11 | <0.0001 | 0.07 |
| R65 | 11 | <0.0001 | 0.26 |
| Y67 | 10 | <0.0001 | 0.13 |
| E66 | 10 | <0.0001 | 0.17 |
| K66 | 10 | <0.0001 | 0.21 |
| R66 | 10 | <0.0001 | 0.23 |
| K67 | 10 | <0.0001 | 0.11 |
| P65 | 8 | <0.0001 | 0.57 |
| K64 | 8 | <0.0001 | 0.82 |
| K65 | 8 | <0.0001 | 0.63 |
| Y65 | 7 | <0.0001 | 0.9 |

TABLE 9

Antagonism of A-gliadin 57-73 QE65 (SEQ ID NO: 2) interferon gamma ELISPOT response by substituted variants of A-gliadin 57-73 QE65 (SEQ ID NO: 2) (Subst) (P is significance level in unpaired t-test). Agonist activity (% agonist) of peptides compared to A-gliadin 57-73 QE65 (SEQ ID NO: 2) is also shown.

| Subst | % Inhibit. | P | % agonist. |
|---|---|---|---|
| Antagonists | | | |
| 65T | 28 | 0.004 | 19 |
| 67M | 27 | 0.0052 | 29 |
| 64W | 26 | 0.007 | 18 |
| 67W | 25 | 0.0088 | 19 |
| Potential antagonists | | | |
| 67I | 24 | 0.013 | 10 |
| 67Y | 24 | 0.013 | 21 |
| 64G | 21 | 0.03 | 21 |
| 64D | 21 | 0.029 | 16 |
| 65L | 20 | 0.046 | 26 |
| 66N | 20 | 0.037 | 24 |
| 65H | 20 | 0.038 | 16 |
| 64N | 19 | 0.05 | 16 |
| 64Y | 19 | 0.06 | 25 |
| 66Y | 19 | 0.048 | 28 |
| 64E | 19 | 0.049 | 12 |
| 67A | 18 | 0.058 | 30 |
| 67H | 18 | 0.052 | 22 |
| Non-antagonists | | | |
| 65V | 17 | 0.07 | 23 |
| 65I | 17 | 0.086 | 21 |
| 66T | 17 | 0.069 | 25 |
| 65W | 15 | 0.11 | 11 |

TABLE 9-continued

Antagonism of A-gliadin 57-73 QE65 (SEQ ID NO: 2) interferon gamma ELISPOT response by substituted variants of A-gliadin 57-73 QE65 (SEQ ID NO: 2) (Subst) (P is significance level in unpaired t-test). Agonist activity (% agonist) of peptides compared to A-gliadin 57-73 QE65 (SEQ ID NO: 2) is also shown.

| Subst | % Inhibit. | P | % agonist. |
|---|---|---|---|
| 67R | 15 | 0.13 | 14 |
| 65P | 15 | 0.13 | 8 |
| 65K | 15 | 0.11 | 8 |
| 66W | 15 | 0.12 | 21 |
| 67G | 14 | 0.14 | 19 |
| 66A | 14 | 0.14 | 19 |
| 65R | 13 | 0.18 | 11 |
| 65M | 13 | 0.16 | 14 |
| 68P | 13 | 0.16 | 26 |
| 63R | 13 | 0.19 | 19 |
| 66G | 12 | 0.19 | 11 |
| 65Q | 12 | 0.2 | 18 |
| 65Y | 12 | 0.22 | 7 |
| 66S | 12 | 0.22 | 22 |
| 67F | 11 | 0.25 | 21 |
| 66R | 10 | 0.29 | 10 |
| 67K | 10 | 0.29 | 10 |
| 64F | 10 | 0.29 | 16 |
| 65F | 9 | 0.41 | 16 |
| 63P | 8 | 0.42 | 13 |
| 65EK | 8 | 0.39 | 25 |
| 64Q | 7 | 0.49 | 11 |
| 64I | 5 | 0.6 | 21 |
| 68K | 5 | 0.56 | 19 |
| 67Q | 5 | 0.61 | 18 |
| 65G | 5 | 0.62 | 15 |
| 64M | 4 | 0.7 | 20 |
| 66H | 4 | 0.66 | 23 |
| 66 E | 3 | 0.76 | 10 |
| 66D | 1 | 0.9 | 14 |
| 63K | 1 | 0.88 | 23 |
| 64H | 1 | 0.93 | 18 |
| 66K | 0 | 0.98 | 10 |
| 64K | −2 | 0.88 | 8 |
| 64L | −11 | 0.26 | 22 |

TABLE 10

Inhibition of A-gliadin 57-73 QE65 (SEQ ID NO: 2) interferon gamma ELISPOT response by peptides known to bind HLA-DQ2 (P is significance level in unpaired t-test).

| Peptide | % Inhibit. | P |
|---|---|---|
| TP | 31 | <0.0001 |
| HLA1a | 0 | 0.95 |

TABLE 11

Antagonism of A-gliadin 57-73 QE65 (SEQ ID NO: 2) interferon gamma ELISpot response by naturally occurring polymorphisms of A-gliadin 57-73 QE65 (SEQ ID NO: 2) (P issignificance level in unpaired t-test).

| A-gliadin 57-73 QE65 (SEQ ID NO: 2) | polymorphism | % Inhibit | P |
|---|---|---|---|
| P04725 82-98 QE90 (SEQ ID NO: 17) | PQPQPFPPELPYPQPQS | 19 | 0.009 |
| Q41509 77-93 QE85 (SEQ ID NO: 803) | QLQPFLQPELPYSQPQP | 11 | 0.15 |
| Gli α 1, 6 58-74 QE66 (SEQ ID NO: 804) | QPQPFPPPELPYPQTQP | 11 | 0.11 |

TABLE 11-continued

Antagonism of A-gliadin 57-73 QE65 (SEQ ID NO: 2) interferon gamma ELISpot response by naturally occurring polymorphisms of A-gliadin 57-73 QE65 (SEQ ID NO: 2) (P issignificance level in unpaired t-test).

| A-gliadin 57-73 QE65 (SEQ ID NO: 2) polymorphism | | % Inhibit | P |
|---|---|---|---|
| P04723 77-93 QE85 (SEQ ID NO: 805) | PQPQPFPPELPYPQTQP | 10 | 0.14 |
| Gil α 3-5 57-73 QE65 (SEQ ID NO: 806) | QLQPFPQPELSYSQPQP | 7 | 0.34 |
| P02863 77-93 QE85 (SEQ ID NO: 29) | QLQPFPQPELPYSQPQP | 6 | 0.35 |
| Q41509 77-93 QE85 (SEQ ID NO: 803) | QLQPFLQPELPYSQPQP | 6 | 0.41 |
| P04727 79-95 QE65 (SEQ ID NO: 807) | PQPQPFLPELPYPQPQS | 6 | 0.39 |
| P04726 82-98 QE90 (SEQ ID NO: 808) | PQPQPFPPELPYPQPPP | 5 | 0.43 |

TABLE 12

Prolamin homologues of A-gliadin 57-73 (excluding alpha/beta-gliadins)

| Prolamin | Accession number | Sequence | % Bioactivity* |
|---|---|---|---|
| Wheat: α-gliadin | A-gliadin (57-73) | QLQPFPQPQLPYPQPQS (SEQ ID NO: 10) | 100 (0) |
| Wheat: ω-gliadin | AAG17702 (141-157) | PQ.........................F......QSE (SEQ ID NO: 761) | 32 (6.4) |
| Barley: C-hordein | Q40055 (166-182) | ...QPFPL..............F...........Q (SEQ ID NO: 762) | 2.3 (2.0) |
| Wheat: γ-gliadin | P21292 (96-112) | ...QTFPQ..............F......QPQ (SEQ ID NO: 763) | 2.1 (4.2) |
| Rye: secalin | Q43639 (335-351) | ...QPSPQ..............F...........Q (SEQ ID NO: 764) | 1.6 (1.4) |
| Barley: γ-hordein | P80198 (52-68) | ...QPFPQ..............HQHQFP (SEQ ID NO: 765) | -1.0 (1.8) |
| Wheat: LMW glutenin | P16315 (67-83) | LQ...QPIL...........FS...Q...Q (SEQ ID NO: 766) | -0.9 (1.0) |
| Wheat: HMW glutenin | P08489 (718-734) | HGYYPTS.........SGQGQRP (SEQ ID NO: 767) | 6.4 (4.0) |
| Wheat: γ-gliadin | P04730 (120-136) | ...QCCQQL......I...QQSRYQ (SEQ ID NO: 768) | 0.7 (0.9) |
| Wheat: LMW glutenin | P10386 (183-199) | ...QCCQQL......I...QQSRYE (SEQ ID NO: 769) | -0.7 (0.5) |
| Wheat: LMW glutenin | O49958 (214-230) | ...QCCRQL......I...EQSRYD (SEQ ID NO: 770) | -1.1 (0.3) |
| Barley: B1-hordein | P06470 (176-192) | ...QCCQQL......I...EQFRHE (SEQ ID NO: 771) | 1.8 (1.4) |
| Barley: B-hordein | Q40026 (176-192) | ...QCCQQL......ISEQFRHE (SEQ ID NO: 772) | 0.5 (0.9) |

*Bioactivity is expressed as 100x(spot forming cells with peptide 25 mcg/ml plus tTG 8 mcg/ml minus blank)/(spot forming cells with A-gliadin 5773 25 mcg/ml plus tTG 8 mcg/ml minus blank) (mean (SEM), n = 5). Peptides were preincubated with tTG for 2 h 37° C.

Note,

Q is deamidated in A-gliadin 57-73 by tTG.

TABLE 13

Clinical details of coeliac subjects.

| | HLA-DQ | HLA-DQA1 alleles | HLA-DQB1 alleles | Duodenal histology | Gluten free | EMA on gluten (on GFD) |
|---|---|---|---|---|---|---|
| C01 | 2, 6 | 102/6, 501 | 201, 602 | SVA | 1 yr | +(−) |
| C02 | 2, 2 | 501 | 201 | SVA | 1 yr | +(−) |
| C03 | 2, 5 | 101/4/5, 501 | 201, 501 | PVA | 1 yr | +(−) |
| C04 | 2, 5 | 101/4-5, 501 | 201, 501 | SVA | 7 yr | +(−) |
| C05 | 2, 2 | 201, 501 | 201, 202 | SVA | 4 mo | +(ND) |
| C06 | 2, 2 | 201, 501 | 201, 202 | SVA | 2 yr | +(−) |
| C07 | 2, 8 | 301-3, 501 | 201, 302 | SVA | 1 yr | +(−) |
| C08 | 2, 8 | 301-3, 501 | 201, 302/8 | SVA | 11 yr | ND(−) |
| C09 | 2, 8 | 301-3, 501 | 201, 302 | SVA | 29 yr | +(−) |
| C10 | 2, 8 | 201, 301-3 | 202, 302 | IEL | 1 yr | +(−) |
| C11 | 6, 8 | 102/6, 301-3 | 602/15, 302/8 | IEL | 9 mo | −(ND) |
| C12 | 8, 7 | 301-3, 505 | 302, 301/9-10 | SVA | 2 yr | −(−) |
| C13 | 8, 8 | 301 | 302 | SVA | 1 yr | +(+) |

SVA subtotal villous atrophy,
PVA partial villous atrophy,
IEL increased intra-epithelial atrophy,
GFD gluten-free diet,
ND not done.

TABLE 14

HLA-DQ2+ Coeliac (C01-6) and healthy control (H01-10) IFNγ ELISpot responses to control peptides (20 μg/ml) and gliadin (500 μg/ml) before and after gluten challenge (sfc/million PBMC minus response to PBS alone)

| Peptide | Healthy Day 0 | Healthy Day 6 | Coeliac Day 0 | Coeliac Day 6 |
|---|---|---|---|---|
| P04722 77-93 (SEQ ID NO: 26) | 0 (−4 to 17) | 0 (−5 to 9) | −2 (−3 to 0) | 27 (0-100)* |
| P04722 77-93 (SEQ ID NO: 26) + tTG | 0 (−5 to 4) | 0 (−9 to 3) | 0 (−4 to 11) | 141 (8 to 290)** |
| P04722 77-93 QE85 (SEQ ID NO: 27) | 0 (−5 to 5) | 0 (−3 to 4) | 0 (−6 to 14) | 133 (10 to 297)* |
| P02863 77-93 (SEQ ID NO: 28) | 0 (−4 to 13) | 2 (−3 to 5) | −2 (−3 to 2) | 8 (−2 to 42)** |
| P02863 77-93 (SEQ ID NO: 28) + tTG | −1 (−5 to 4) | −1 (−4 to 11) | 1 (−4 to 6) | 65 (8-164)** |
| P02863 77-93 QE85 (SEQ ID NO: 29) | 0 (−4 to 13) | 0 (−4 to 14) | −1 (−4 to 6) | 42 (−2 to 176)* |
| Gliadin chymotrypsin | 2 (−5 to 20) | 18 (0 to 185)* | 20 (11 to 145) | 92 (50 to 154) |
| Gliadin chymotrypsin + tTG | 0 (−1 to 28) | 16 (−9 to 171)* | 55 (29 to 248) | 269 (206 to 384)** |
| Chymotrypsin | 0 (−4 to 5) | 1 (−4 to 11) | −2 (−5 to 5) | 1 (−4 to 8) |
| Chymotrypsin + tTG | 0 (−5 to 8) | 6 (0 to 29) | −2 (−3 to 11) | 2 (−3 to 18)* |
| Gliadin pepsin | 4 (−4 to 28) | 29 (0 to 189)*** | 44 (10 to 221) | 176 (54 to 265)** |
| Gliadin pepsin + tTG | 2 (−3 to 80) | 27 (−4 to 241)*** | 61 (8 to 172) | 280 (207 to 406)** |
| Pepsin | 0 (−4 to 10) | 0 (−3 to 12) | 0 (−2 to 3) | 2 (−2 to 8) |
| Pepsin + tTG | 0 (−3 to 8) | 0 (−5 to 9) | 1 (−6 to 3) | 0 (−3 to 14) |
| PBS alone | 4 (0 to 6) | 2 (0 to 6) | 4 (1 to 12) | 4 (0 to 4) |
| PBS + tTG | 3 (0 to 8) | 3 (0 to 11) | 4 (2 to 10) | 4 (2 to 11) |

Day 6 vs. Day 0:
*P < 0.05
**P, 0.02,
***P < 0.01 by one-tailed Wilcoxon Matched-Pairs Signed-Ranks test

TABLE 15

Effect of deamidation by tTG to gliadin (0.5 mg/ml) and A-gliadin 57-73 (SEQ ID NO: 10) homologues on IFNγ ELISpot responses in HLA-DQ2+ coeliac (C01-6) and healthy control subjects (H01-10) (median ratio tTG:no tTG pretreatment, range)

| Peptide | Healthy Day 6 | Coeliac Day 0 | Coeliac Day 6 |
|---|---|---|---|
| Gliadin chymotrypsin | 0.94 (0.4-9.0) | 2.1 (0.8-6.8)* | 3.2 (1.8-4.2)** |
| Gliadin pepsin | 1.4 (0.5-1.4) | 1.4 (0.8-4.0)* | 1.9 (1.1-4.4)** |
| P04722 77-93 Q85 (SEQ ID NO: 26) | | | 6.5 (2.3-12)** |
| P04722 77-93 E85 (SEQ ID NO: 27) | | | 0.7 (0.6-1.1) |
| P02863 77-93 Q85 (SEQ ID NO: 28) | | | 7.5 (3.9-19.9)** |
| P02863 77-93 E85 (SEQ ID NO: 29) | | | 1.0 (0.8-1.2) |

TTG > no tTG:
*P < 0.05
**P, 0.02,
***P < 0.01 by one-tailed Wilcoxon Matched-Pairs Signed-Ranks test

TABLE 16

Healthy subjects: IFNγ ELISpot Responses (>10 sfc/million PBMC and >4 × buffer only) to tTG-treated gliadin peptide Pools on Day 6 of gluten challenge (sfc/million PBMC) (italic: response also present on Day 0):
Group 1 - HLA-DQ2 (DQA1*0501-5, DQB1*0201)
Group 2 - HLA-DQ8 (DQA1*0301, DQB1*0302) and absent or "incomplete" DQ2 (only DQA1*0501-5 or DQB1*0201)

| | Group 1 | | | | | | | | | | Group 2 |
| --- | --- | --- | --- | --- | --- | --- | --- | --- | --- | --- | --- |
| Subject HLA-DQ | H01 2, 6 | H02 2, 7 | H03 2, 8 | H04 2, 5 | H05 2, 6 | H06 2, 6 | H07 2, 6 | H08 2, 7 | H09 2, 5 | H10 2, 5 | H11 8, 8 |
| Pool 1 | . | . | . | . | . | . | . | . | . | . | . |
| 2 | . | . | . | . | . | . | . | . | . | . | . |
| 3 | . | . | . | . | . | . | . | . | . | . | . |
| 4 | . | . | . | . | . | . | . | . | 13 | . | . |
| 5 | . | 17 | . | . | . | . | . | . | *24* | . | . |
| 6 | . | . | . | . | . | . | . | . | *31* | . | . |
| 7 | . | . | . | . | . | . | . | . | . | . | . |
| 8 | . | . | . | . | . | . | . | . | . | . | . |
| 9 | . | . | . | . | . | . | . | . | . | . | . |
| 10 | . | . | . | . | . | . | . | . | . | . | . |
| 11 | . | . | . | . | . | . | . | . | . | . | . |
| 12 | . | . | . | . | . | . | . | . | . | . | . |
| 13 | . | . | . | . | . | . | . | . | . | . | . |
| 14 | . | . | . | . | . | . | . | . | . | . | . |
| 15 | . | . | . | . | . | . | . | . | . | . | . |
| 16 | . | . | . | . | . | . | . | . | . | . | . |
| 17 | . | . | . | . | . | . | . | . | . | . | . |
| 18 | . | . | . | . | . | . | 20 | . | . | . | . |
| 19 | . | . | . | . | . | . | . | . | . | . | . |
| 20 | . | 11 | . | . | . | . | . | . | . | . | . |
| 21 | . | 11 | . | . | . | . | . | . | 27 | . | . |
| 22 | . | . | . | . | . | . | . | . | . | . | . |
| 23 | . | *43* | . | . | . | . | . | . | . | . | . |
| 24 | . | . | . | . | . | . | . | . | . | . | . |
| 25 | . | 11 | . | . | . | . | . | . | . | . | . |
| 26 | . | . | . | . | . | . | . | . | . | . | . |
| 27 | . | . | . | . | . | . | . | . | . | . | . |
| 28 | . | . | . | . | . | . | . | . | . | . | . |
| 29 | . | . | . | . | . | . | . | . | . | . | . |
| 30 | . | . | . | . | . | . | . | . | 23 | . | . |
| 31 | . | . | . | . | . | . | . | . | . | . | . |
| 32 | . | . | . | . | . | . | . | . | . | . | . |
| 33 | . | 20 | . | . | . | . | . | . | . | . | . |
| 34 | . | . | . | . | . | . | . | . | . | . | . |
| 35 | . | 11 | . | . | . | . | . | . | . | . | . |
| 36 | . | . | . | . | . | . | . | . | . | . | . |
| 37 | . | . | . | . | . | . | . | *18* | . | . | . |
| 38 | 14 | . | . | . | . | . | . | 12 | . | . | . |
| 39 | . | . | . | . | . | . | . | 11 | . | . | . |
| 40 | . | 14 | . | . | . | . | . | 17 | . | . | . |
| 41 | . | . | . | . | . | . | . | . | . | . | . |
| 42 | . | . | . | . | . | . | . | . | . | . | . |
| 43 | . | . | . | . | . | . | . | . | 11 | . | . |
| 44 | . | 14 | . | . | . | . | . | . | . | . | . |
| 45 | . | 11 | . | . | . | . | . | . | . | . | . |
| 46 | . | . | . | . | . | . | . | . | . | . | . |
| 47 | . | . | . | . | . | . | . | . | . | . | . |
| 48 | . | . | . | . | . | . | . | . | . | . | . |
| 49 | . | . | . | . | . | . | . | . | . | . | . |
| 50 | . | 14 | . | . | 12 | . | . | *22* | . | 14 | . |
| 51 | . | . | . | . | . | . | . | . | . | . | . |
| 52 | . | 14 | . | . | . | . | . | . | . | . | . |
| 53 | . | 26 | . | . | . | . | . | . | . | . | . |
| 54 | . | . | . | . | . | . | . | 12 | . | . | . |
| 55 | . | . | . | . | . | . | . | . | . | . | . |
| 56 | . | . | . | . | . | . | . | . | . | . | . |

TABLE 16-continued

Healthy subjects: IFNγ ELISpot Responses (>10 sfc/million PBMC and >4 × buffer only) to tTG-treated gliadin peptide Pools on Day 6 of gluten challenge (sfc/million PBMC) (italic: response also present on Day 0):
Group 1 - HLA-DQ2 (DQA1*0501-5, DQB1*0201)
Group 2 - HLA-DQ8 (DQA1*0301, DQB1*0302) and absent or "incomplete" DQ2 (only DQA1*0501-5 or DQB1*0201)

| | Group 1 | | | | | | | | | | Group 2 |
|---|---|---|---|---|---|---|---|---|---|---|---|
| Subject HLA-DQ | H01 2, 6 | H02 2, 7 | H03 2, 8 | H04 2, 5 | H05 2, 6 | H06 2, 6 | H07 2, 6 | H08 2, 7 | H09 2, 5 | H10 2, 5 | H11 8, 8 |
| 57 | . | 23 | . | . | . | . | 12 | . | . | . | . |
| 58 | . | 14 | . | . | . | . | . | . | . | . | . |
| 59 | . | . | . | . | . | . | . | . | . | . | . |
| 60 | . | . | . | . | . | . | . | . | . | . | . |
| 61 | . | 23 | . | . | . | . | . | *11* | *11* | . | . |
| 62 | . | . | . | . | . | . | . | . | . | . | . |
| 63 | . | . | . | . | . | . | . | . | . | . | . |
| 64 | . | 20 | . | . | . | . | . | . | . | . | . |
| 65 | . | . | . | . | . | . | . | . | . | . | . |
| 66 | . | 14 | . | . | . | . | . | . | . | . | . |
| 67 | . | 11 | . | . | . | . | . | . | . | . | . |
| 68 | . | 20 | . | . | . | . | . | *20* | . | . | . |
| 69 | . | 20 | . | . | . | . | . | . | . | . | . |
| 70 | . | . | . | . | . | . | . | . | . | . | . |
| 71 | . | . | . | . | . | . | . | . | . | . | 16 |
| 72 | . | 11 | . | . | . | . | . | . | . | . | . |
| 73 | . | 14 | . | . | . | . | . | . | . | . | . |
| 74 | . | . | . | . | . | . | . | . | . | . | . |
| 75 | . | . | . | . | . | . | . | . | . | . | . |
| 76 | . | 14 | . | . | . | . | . | . | . | . | . |
| 77 | . | . | . | . | . | . | . | . | . | . | . |
| 78 | . | 11 | . | . | . | . | . | . | . | . | . |
| 79 | . | 11 | . | . | 19 | . | . | . | . | . | . |
| 80 | . | . | . | . | . | . | . | . | . | . | . |
| 81 | . | . | . | . | . | . | . | . | . | . | . |
| 82 | . | . | . | . | . | . | . | . | . | . | . |
| 83 | . | . | . | . | . | . | . | . | . | . | . |
| P04722 77-93 | . | . | . | . | . | . | . | . | . | . | . |
| P04722 77-93 E | . | . | . | . | . | . | . | . | . | . | . |
| P04722 77-93 E | . | . | . | . | . | . | . | . | . | . | . |
| P02863 77-93 | . | . | . | . | . | . | . | . | 11 | . | . |
| P02863 77-93 E | . | . | . | . | . | . | . | . | . | . | . |
| Gliadin + C | *171* | 40 | 25 | 16 | 10 | . | 18 | 14 | . | 17 | *90* |
| Chymotrypsin | 29 | 26 | 18 | . | . | . | . | . | 22 | . | . |
| Gliadin + Pepsin Pepsin | *241* | 151 | 29 | 24 | 48 | . | 16 | 45 | . | 19 | 35 |

TABLE 17 tTG-deamidated gliadin peptide pools showing significant increase in IFN gamma responses between Day 0 and Day 6 of gluten challenge in HLA-DQ2 coeliac subjects C01-6 (Day 6-Day 0 response, and ratio of responses to tTG-deamidated pool and same pool without tTG treatment)

| Pool | IFNg ELISpot (Median sfc/million) | tTG: no tTG (Median) |
|---|---|---|
| 9 | 59*** | 1.0 |
| 10 | 116** | 1.7 |
| 11 | 24*** | 2.5 |
| 12 | 133*** | 1.1 |
| 13 | 26** | 2.1 |
| 42 | 30** | 1.2 |
| 43 | 32*** | 1.3 |
| 44 | 24*** | 1.5 |
| 45 | 10*** | 1.1 |
| 46 | 12*** | 2.1 |
| 48 | 17*** | 1.4 |
| 49 | 46*** | 1.4 |
| 50 | 50*** | 4.6 |
| 51 | 40*** | 1.7 |
| 52 | 30*** | 3.1 |
| 53 | 27** | 1.4 |
| 76 | 17*** | 1.1 |
| 79 | 20*** | 0.9 |
| 80 | 83*** | 1 |
| 81 | 141*** | 1.1 |
| 82 | 22*** | 1.5 |
| 83 | 16** | 1.8 |

Day 6 vs. Day 0 P < 0.02, *P < 0.01 by one-tailed Wilcoxon Matched-Pairs Signed-Ranks test

TABLE 18

Coeliac subjects: IFNγ ELISpot Responses >10 sfc/million PBMC and
>4 × buffer only to tTG-treated Pepset Pools on Day 6 of gluten challenge
(sfc/million PBMC) (italic: response also present on Day 0):
Group 1 - HLA-DQ2 (DQA1*0501-5, DQB1*0201/2),
Group 2 - HLA-DQ2/8 (DQA1*0501-5, *0301, and DQB1*0201/2, *0302), and
Group 3 - HLA-DQ8 (DQA1*0301, DQB1*0302) and absent or "incomplete"
DQ2 (only DQA1*0501-5 or DQB1*0201/2)

| | Group 1: | | | | | | Group 2: | | | Group 3 | | | |
|---|---|---|---|---|---|---|---|---|---|---|---|---|---|
| Subject | C01 | C02 | C03 | C04 | C05 | C06 | C07 | C08 | C09 | C10 | C11 | C12 | C13 |
| HLA-DQ | 2, 6 | 2, 2 | 2, 5 | 2, 5 | 2, 2 | 2, 2 | 2, 8 | 2, 8 | 2, 8 | 2, 8 | 6, 8 | 7, 8 | 8, 8 |
| Pool 1 | . | | | | | | 23 | | | | | 223 | |
| 2 | . | | | | | | | | | | | 155 | |
| 3 | . | | | | | | | | | | | 41 | |
| 4 | 11 | | | | | | | | | 22 | . | | |
| 5 | . | | | | | | | | | | | | |
| 6 | 18 | | | 21 | | | 20 | 17 | | . | . | | |
| 7 | . | | | | | | | 353 | | . | . | | |
| 8 | 11 | 64 | | | | 14 | 20 | 480 | | . | . | | 13 |
| 9 | 93 | 127 | | 92 | 25 | | 32 | 460 | | . | . | | 18 |
| 10 | 175 | 491 | 58 | 200 | 48 | | 84 | *787* | | . | . | | |
| 11 | 32 | 118 | | 33 | 14 | | 26 | 27 | | 12 | . | | |
| 12 | 204 | 379 | 54 | 225 | 61 | | 129 | 587 | | 12 | . | | |
| 13 | 93 | 142 | | 29 | 18 | | | *60* | | . | . | | 11 |
| 14 | . | 45 | | 21 | | | 17 | | | . | . | | |
| 15 | 18 | 30 | | | | | 38 | 43 | | . | . | | |
| 16 | . | | | | | | | 37 | | . | . | | |
| 17 | . | | | | | | | | | . | . | | |
| 18 | . | | | | | | | | | . | . | | |
| 19 | 11 | | | | | | | | | . | . | | |
| 20 | 11 | 215 | | | | | 51 | 167 | | . | . | | |
| 21 | . | | | | | | | | 11 | . | . | | |
| 22 | . | 21 | | | | | | | | . | . | | |
| 23 | . | 18 | | 21 | | | | | | 12 | . | | |
| 24 | . | 15 | | | | | | 10 | | . | . | | |
| 25 | . | *15* | | | | | | | | 12 | . | | |
| 26 | . | *18* | | | | | | 13 | | 12 | . | | |
| 27 | . | 15 | | | | | | | | . | . | | |
| 28 | . | | | | | | | | | . | . | | 11 |
| 29 | . | | | | | | 11 | | | . | . | | |
| 30 | 11 | | | | | | 11 | | | . | . | | |
| 31 | . | 70 | | | | | | | | . | . | | |
| 32 | . | 18 | | | | | 20 | | | . | . | | |
| 33 | 11 | | | 10 | | | *14* | | *11* | . | 40 | | *11* |
| 34 | . | | | | | | | | 11 | . | . | | |
| 35 | . | | | | | | | | | . | . | | |
| 36 | . | | | | | | | | | . | . | | |
| 37 | . | | | 23 | 14 | | | | | . | . | | |
| 38 | . | 24 | | 19 | | | 20 | | | . | . | | |
| 39 | . | 49 | | 15 | | | | | *11* | . | . | | |
| 40 | . | | | | | | 14 | | | . | . | | |
| 41 | . | 21 | | | | | | | | | | | |
| 42 | 39 | 42 | | 44 | 21 | | 11 | 63 | | 12 | . | | |
| 43 | 50 | 91 | 13 | 75 | 14 | | 190 | 113 | | . | . | 21 | |
| 44 | 32 | 97 | 17 | 96 | 13 | | 87 | 107 | | . | . | | |
| 45 | . | 21 | 10 | 100 | 11 | | 38 | 110 | | . | . | | |
| 46 | 14 | 55 | | 102 | 18 | | 63 | *163* | | . | . | | |
| 47 | 14 | 58 | | 38 | | | 223 | 97 | | . | . | 31 | |
| 48 | 21 | 106 | | 60 | 14 | | 144 | 353 | | . | . | 57 | |
| 49 | 75 | 170 | 17 | 142 | 30 | | 202 | 293 | | . | . | 39 | |
| 50 | 57 | *245* | 23 | 140 | 61 | *27* | 248 | *143* | | . | . | | 11 |
| 51 | 68 | 106 | 10 | 127 | | | 220 | *267* | | . | . | 29 | |
| 52 | 43 | 121 | | 79 | 13 | 16 | 175 | 180 | | . | . | | |
| 53 | 36 | 94 | | 92 | 29 | | 69 | 53 | | . | . | | |
| 54 | 36 | | | 35 | 11 | | 166 | 27 | | . | . | 19 | 13 |
| 55 | . | | | | | | | | | . | . | | |
| 56 | 29 | | | | | | | | *11* | . | . | | |
| 57 | . | 36 | | | | | 20 | 13 | | . | . | | |
| 58 | . | | | | | | | | | . | . | | |
| 59 | . | | 10 | | | | | 53 | | . | . | | |
| 60 | . | 18 | | 15 | | | 11 | 53 | | . | . | | |
| 61 | . | | | | | | 20 | | | . | . | | |
| 62 | 14 | 18 | | 13 | | | 60 | | | . | . | | |
| 63 | . | | 10 | | | 14 | | | | 28 | . | | |
| 64 | . | 15 | | | | | | | | 18 | . | | |
| 65 | | 36 | | 25 | *23* | | 35 | 27 | | . | *11* | | |
| 66 | | | | 31 | 11 | 10 | 17 | | | . | . | | |
| 67 | . | | | 17 | | | 17 | | | . | . | | |

TABLE 18-continued

Coeliac subjects: IFNγ ELISpot Responses >10 sfc/million PBMC and
>4 × buffer only to tTG-treated Pepset Pools on Day 6 of gluten challenge
(sfc/million PBMC) (italic: response also present on Day 0):
Group 1 - HLA-DQ2 (DQA1*0501-5, DQB1*0201/2),
Group 2 - HLA-DQ2/8 (DQA1*0501-5, *0301, and DQB1*0201/2, *0302), and
Group 3 - HLA-DQ8 (DQA1*0301, DQB1*0302) and absent or "incomplete"
DQ2 (only DQA1*0501-5 or DQB1*0201/2)

|  | Group 1: | | | | | | Group 2: | | | Group 3 | | | |
| --- | --- | --- | --- | --- | --- | --- | --- | --- | --- | --- | --- | --- | --- |
| Subject | C01 | C02 | C03 | C04 | C05 | C06 | C07 | C08 | C09 | C10 | C11 | C12 | C13 |
| HLA-DQ | 2, 6 | 2, 2 | 2, 5 | 2, 5 | 2, 2 | 2, 2 | 2, 8 | 2, 8 | 2, 8 | 2, 8 | 6, 8 | 7, 8 | 8, 8 |
| 68 | . | . | 19 | *127* | . | 14 | . | . | . | . | . | . | . |
| 69 | . | 15 | . | 10 | . | . | *20* | 20 | . | . | . | . | . |
| 70 | . | 12 | 31 | . | 13 | 10 | . | . | . | . | . | . | . |
| 71 | 11 | 21 | 13 | . | . | . | 14 | . | . | . | . | 18 | . |
| 72 | . | . | . | . | . | 16 | . | . | . | . | . | . | . |
| 73 | . | . | . | 13 | . | 14 | 11 | . | . | . | . | . | . |
| 74 | . | 239 | . | . | . | . | 254 | 447 | . | . | . | . | . |
| 75 | . | . | . | . | . | . | . | . | . | . | . | . | . |
| 76 | 18 | 21 | 19 | 15 | . | . | . | . | . | . | . | 12 | . |
| 77 | . | 88 | . | . | . | 10 | . | 13 | . | . | . | . | . |
| 78 | . | 18 | 17 | 69 | . | . | . | . | . | . | . | . | . |
| 79 | 11 | 85 | . | 44 | 29 | 12 | 44 | 43 | . | . | . | . | . |
| 80 | 132 | 133 | 33 | 240 | 39 | 12 | 208 | 467 | . | 12 | . | 70 | . |
| 81 | 171 | 318 | 113 | 367 | 104 | 12 | 211 | 530 | . | . | . | 74 | . |
| 82 | 18 | 300 | 17 | 125 | 32 | *16* | 241 | 723 | . | . | . | . | . |
| 83 | 14 | 164 | . | 31 | 21 | . | 163 | 277 | . | 15 | . | . | . |
| P04722 77-93 | 211 | 291 | 75 | 281 | 66 | . | 78 | *740* | . | . | . | . | . |
| P04722 77-93 E | 164 | 297 | 108 | 221 | 64 | 10 | 84 | 653 | . | . | . | . | . |
| P04722 77-93 E | 161 | 182 | 98 | 256 | 73 | *16* | 63 | 500 | . | . | . | . | . |
| P02863 77-93 | 139 | 164 | 35 | 94 | 36 | . | 29 | 603 | . | . | . | . | . |
| P02863 77-93 E | 46 | 176 | 19 | 88 | 41 | . | 23 | 520 | . | . | . | . | . |
| Gliadin + C Chymotrypsin | *214* | *273* | *265* | *360* | *384* | *206* *18* | *278* | *543* | 17 | . | *25* | *527* | *71* |
| Gliadin + Pepsin | *239* | *315* | *269* | *406* | *207* | *292* | *357* | *557* | . | *42* | *89* | *335* | *87* |
| Pepsin | . | . | . | . | . | 14 | . | . | . | . | . | . | . |

TABLE 19

Deamidated peptides with mean bioactivity > 10% of P04722 E85
(20 µg/ml) in HLA-DQ2 coeliac subjects C01-5

| Rank | No. | SEQ ID NO: | Sequence | Mean (SEM) | Rank | No. | SEQ ID NO: | Sequence | Mean (SEM) |
| --- | --- | --- | --- | --- | --- | --- | --- | --- | --- |
|  | 89 | 195 | PQLPYPQPQLPYPQPQLPYP | 94 (18) | 37 | 483 | 519 | SKQPQQPFPQPQQPQQSFPQ | 18 (4) |
| *2 | 91 | 197 | PQPFPPQQLPYPQPQLPYPQP | 89 (12) | 38 | 380 | 486 | QPQQPQQPFPQPQQPQLPFP | 18 (6) |
| *3 | 74 | 180 | MQLQPFPQPQLPYPQPQLPY | 88 (24) | 39 | 618 | 724 | PQQSFSYQQQPFFQQPYPQQ | 18 (7) |
| *4 | 90 | 196 | PQLPYPQPQLPYPQPQPFRP | 87 (16) | *40 | 78 | 184 | LQLQPFPRPQLPYPQPQPFR | 17 (8) |
| *5 | 76 | 182 | LQLQPFPQPQLPYPQPQPFR | 85 (15) | 41 | 390 | 496 | QQTYPQRPQQPFPQTQQPQQ | 17 (9) |
|  6 | 626 | 732 | PQQPQQPQQPFPQPQQPFPW | 72 (23) | 42 | 348 | 454 | QQTFPQPQQTPPHQPQQQFP | 16 (10) |
|  7 | 627 | 733 | QPPPQPQQPFPWQPQQPFPQ | 66 (30) | 43 | 409 | 515 | QPQQPFPQLQQPQQPLPQPQ | 16 (2) |
| *8 | 631 | 737 | FPQQPQQPFFQPQLPFPQQS | 61 (12) | 44 | 382 | 488 | QQPFPQQPQQPFPQTQQPQQ | 16 (6) |
|  9 | 636 | 742 | PQQPQQPFFQPQQPIPVQPQ | 51 (20) | 45 | 629 | 735 | PFPQTQQSFPLQPQQPFPQQ | 16 (5) |
| *10 | 73 | 179 | LQLQPFPQPQLPYPQPQLPY | 49 (22) | 46 | 643 | 749 | PLQPQQPFPQQPQQPFPQQP | 16 (6) |
| 11 | 412 | 518 | SQQPQQPFPQPQQQFPQPQQ | 34 (19) | 47 | 389 | 495 | QQPFPQTQQPQQPFPQQPQQ | 16 (6) |
| 12 | 343 | 449 | QQPQQPFPQPQQPQLPFPQQ | 34 (11) | 48 | 350 | 456 | QQIFPQPQQTFPHQPQQAFP | 15 (8) |
| *13 | 68 | 174 | LQLQPFPQPQLPYLPQPQFR | 33 (10) | 49 | 65 | 171 | PFPSQQPYPQPQPFPQPQPF | 15 (5) |
| *14 | 66 | 172 | LQLQPFPQPQLPYSQPQFFR | 32 (7) | 50 | 349 | 455 | QQIFPQPQQTFPHQPQQQFP | 15 (9) |
| *15 | 96 | 202 | PQPFPPQQLPYPQPQSFPPQQ | 28 (6) | 51 | 610 | 716 | PWQQQPLPPQQSPSQQPPFS | 15 (1) |

TABLE 19-continued

Deamidated peptides with mean bioactivity > 10% of P04722 E85 (20 µg/ml) in HLA-DQ2 coeliac subjects C01-5

| Rank | No. | SEQ ID NO: | Sequence | Mean (SEM) | Rank | No. | SEQ ID NO: | Sequence | Mean (SEM) |
|---|---|---|---|---|---|---|---|---|---|
| 16 | 393 | 499 | QLPFPQQPQQPFPQPQQPQQ | 27 (8) | *52 | 81 | 187 | PQPQPFPPQLPYPQTQPFPP | 15 (5) |
| 17 | 355 | 461 | QAFPQPQQTFPHQPQQQFPQ | 27 (15) | *53 | 75 | 181 | MQLQPFPQPQPFPPQLPYPQ | 14 (5) |
| *18 | 67 | 173 | LQLQPFPQPQLPYSQPQQFR | 26 (6) | 54 | 368 | 474 | QQFPQPQQPQQPFPQQPQQQ | 14 (7) |
| 19 | 335 | 441 | QQQQPFPQPQQPQQPFPQPQ | 25 (1) | *55 | 82 | 188 | PQPQPFPQPQPFPPQLPYPQ | 14 (3) |
| *20 | 95 | 201 | PQPFLPQLPYPQPQSFPPQQ | 24 (6) | *56 | 80 | 186 | LQLQPFPQPQPFPPQLPYPQ | 14 (4) |
| 21 | 396 | 502 | TQQPQQPFPQQPQQPFPQTQ | 23 (9) | 57 | 624 | 730 | FTQPQQPTPIQPQQPFPQQP | 14 (6) |
| 22 | 609 | 715 | SCISGLERPWQQQPLPPQQS | 23 (18) | 58 | 407 | 513 | QPQQPFPQSQQPQQPFPQPQ | 14 (5) |
| 23 | 385 | 491 | QQPFPQPQQPQLPFPQQPQQ | 23 (7) | 59 | 337 | 443 | QQQQPFPQPQQPFQQQPQRTI | 13 (4) |
| 24 | 375 | 481 | PQQPFPQPQQPQQPFPQPQQ | 23 (10) | 60 | 634 | 740 | PQQLQQPFPLQPQQPFPQQP | 13 (3) |
| 25 | 406 | 512 | QPQQPFPQLQQPQQPFPQPQ | 22 (8) | 61 | 388 | 494 | QQPYPQQPQQPFPQTQQPQQ | 13 (3) |
| 26 | 625 | 731 | PIQPQQPFPQQPQQPQQPFP | 22 (9) | 62 | 641 | 747 | TPELQQPIPQQPQQPFPLQP | 13 (7) |
| 27 | 378 | 484 | QQPQQPFPQQPQQQFPQPQQ | 22 (10) | 63 | 399 | 505 | QQPFPQTQQPQQPFPQLQQP | 13 (5) |
| 28 | 371 | 477 | PQQQFQQPQQPFPQQPQQTY | 22 (10) | 64 | 387 | 493 | QQTFPQQPQLPFPQQPQQPF | 13 (4) |
| 29 | 642 | 748 | PQQPQQPFFLQPQQPFPQQP | 20 (8) | 65 | 628 | 734 | PFPWQPQQPFPQTPPSFPLQ | 12 (4) |
| 30 | 635 | 741 | PLQPQQPFPQQPQQPFFQPQ | 19 (5) | *66 | 88 | 194 | PQPFPPQLPYSQPQPFRPQQ | 12 (3) |
| *31 | 93 | 199 | PQPFPPQLPYPQPQPFRPQQ | 19 (5) | 67 | 408 | 514 | QPQQPFPQSKQPQQPFFQPQ | 12 (5) |
| 32 | 377 | 483 | PQQQFPQPQQPQQPFPQQPQ | 19 (9) | *68 | 77 | 183 | LQLQPFPQPQPFPPQLPYPQ | 11 (4) |
| 33 | 411 | 517 | LQQPQQPFPQPQQQLPQPQQ | 19 (4) | 69 | 370 | 476 | PQQQFLQPQQPFFQQPQQPY | 11 (5) |
| 34 | 415 | 521 | SQQPQQPFPQPQQPQQSFPQ | 18 (5) | 70 | 79 | 185 | LQLQPFPQPQPFLPQLPYPQ | 11 (5) |
| *35 | 94 | 200 | PQPFPPQLPYPQPPPFSPQQ | 18 (3) | 71 | 379 | 485 | QQPQQQFPQPQQPQQPFPQP | 11 (5) |
| 36 | 329 | 435 | PSGQVQWPQQQPFFQPQQPF | 18 (4) | 72 | 397 | 503 | PQQPQQPFPQTQQPQQPFPQ | 11 (3) |

*Indicates homologue of A-gliadin 57-73 with the core sequence PQLP(Y/F)

TABLE 20

Peptides > 10% as bioactive as P04722 QE65 grouped structure.

| Rank | Peptide no. [SEQ ID NO:] (Pool) | Gliadin-subtype | Sequence | IFNg ELISpot response compared to P04722 77-93 QE85 (SEQ ID NO: 27): mean (SEM) |
|---|---|---|---|---|
| Group 1: Homologues of A-gliadin 57-73 |||||
|  | P04722 77-93 |  | QLQPFPQPQLPYPQPQP (SEQ ID NO: 26) |  |
| 1 | 89 (12) | α | PQL-Y----------LPYP | 94 (18) |
| 2 | 91 (12) | α | PQPFPPQL-Y-------- | 89 (12) |
| 3 | 74 (10) | α | M---------------LPY | 88 (14) |
| 4 | 90 (12) | α | PQL-Y----------FRP | 87 (16) |
| 5 | 76 (10) | α | L----------------FR | 85 (15) |
| 8 | 631 (81) | ω | FPQQPQ---------F-QS | 61 (12) |
| 10 | 73 (10) | α | L................LPY | 49 (11) |
| 13 | 68 (9) | α | L-----------L--QPFR | 33 (10) |
| 14 | 66 (9) | α | L-----------S----FR | 32 (7) |
| 18 | 67 (9) | α | L............S...QFR | 26 (6) |
| 20 | 95 (13) | α | PQPFL--------SFPPQQ | 24 (6) |

TABLE 20-continued

Peptides > 10% as bioactive as P04722 QE65 grouped structure.

| Rank | Peptide no. [SEQ ID NO:] (Pool) | Gliadin-subtype | Sequence | IFNg ELISpot response compared to P04722 77-93 QE85 (SEQ ID NO: 27): mean (SEM) |
|---|---|---|---|---|
| 31 | 93 (12) | α | PQPFP---------FRPQQ | 19 (5) |
| 35 | 94 (12) | α | PQPFP-------P-FSPQQ | 18 (3) |
| 40 | 78 (10) | α | L-------R---------FR | 17 (8) |
| 52 | 81 (11) | α | PQPPFP------T--FPP | 15 (8) |
| 53 | 75 (10) | α | MQLQPFPQPQPFP------ | 14 (5) |
| 55 | 82 (11) | α | PQPQPFPQPQPFP------ | 14 (3) |
| 56 | 80 (10) | α | LQLQPFPQPQPFP------ | 14 (4) |
| 66 | 88 (11) | α | PQPFP-----S---FRPQQ | 12 (3) |
| 68 | 77 (10) | α | LQLQPFPQPQPFP------ | 11 (4) |
| 70 | 79 (10) | α | LQLQPFPQPQPFL...... | 11 (5) |

Group 2: Homologues of peptide 626

QQPFPQPQQPFP (SEQ ID NO: 39)

| | | | | |
|---|---|---|---|---|
| 6 | 626 (80) | ω | PQQPQQP------------W | 72 (23) |
| 7 | 627 (80) | ω | ----------WPQQPFPQ | 66 (30) |
| 9 | 636 (81) | ω | PQQP----------I-VQPQ | 51 (10) |
| 11 | 412 (53) | γ | SQQP---------Q--QPQQ | 34 (19) |
| 33 | 411 (53) | γ | LQQP---------QL-QPQQ | 19 (4) |
| 36 | 329 (42) | γ | PSGQVQWPQ---------- | 18 (4) |
| 41 | 390 (50) | γ | QQTYPQRP-------T---QQ | 17 (9) |
| 59 | 337 (43) | γ | Q-----------CQQPQRTI | 13 (4) |
| 61 | 388 (50) | γ | QQPYPQQP------T---QQ | 13 (3) |

Group 3: Homologues of peptide 355

FPQPQQTFPHQPQQQFP (SEQ ID NO: 801)

| | | | | |
|---|---|---|---|---|
| 17 | 355 (46) | γ | QA---------------Q | 27 (15) |
| 42 | 348 (45) | γ | QQT-------------- | 16 (10) |
| 48 | 350 (45) | γ | QQI-------------A-- | 15 (8) |
| 50 | 349 (45) | γ | QQI............... | 15 (9) |

Group 4: Homologues of Peptide 396

QQPFPQQPQQPFP (SEQ ID NO: 40)

| | | | | |
|---|---|---|---|---|
| 21 | 396 (51) | γ | TQQP-------------QTQ | 23 (9) |
| 27 | 378 (49) | γ | QQP----------Q--QPQQ | 22 (10) |
| 28 | 371 (48) | γ | PQQQFIQP-----------TY | 22 (10) |
| 29 | 642 (82) | ω | PQQP-----L-------QQP | 20 (8) |
| 30 | 635 (81) | ω | PLQP-------------QPQ | 19 (5) |
| 44 | 382 (49) | γ | -------------QTQQPQQ | 16 (6) |
| 45 | 629 (81) | ω | PFPQT--S L-------QQ | 16 (5) |
| 46 | 643 (82) | ω | PLQP-------------QQP | 16 (6) |
| 60 | 634 (81) | ω | PQQL-----L-------QQP | 13 (3) |
| 64 | 387 (50) | γ | --T------L---QQPQQPF | 13 (4) |
| 62 | 641 (82) | ω | FPEL---I---------LQP | 13 (7) |

Group 5: Homologues of Peptide 343 (overlap Groups 2 and 4)

QQPFPQPQQPQLPFPQ (SEQ ID NO: 802)

| | | | | |
|---|---|---|---|---|
| 12 | 343 (44) | γ | QQP---------------Q | 34 (11) |
| 16 | 393 (51) | γ | QLPFPQQP-----------Q | 27 (8) |
| 19 | 335 (43) | γ | QQ-----------Q----PQ | 25 (11) |
| 23 | 385 (50) | γ | ------------------QPQQ | 23 (7) |
| 24 | 375 (48) | γ | P----------Q----PQQ | 23 (10) |
| 25 | 406 (52) | γ | QP------L----Q----PQ | 22 (8) |
| 32 | 377 (49) | γ | P-Q--------Q---QPQ | 19 (9) |
| 34 | 415 (53) | γ | SQQP-----------QS--- | 18 (5) |
| 37 | 413 (53) | γ | SKQP-----------QS--- | 18 (4) |
| 38 | 380 (49) | γ | QPQQP-------------- | 18 (6) |
| 43 | 409 (53) | γ | QP------L----Q-L--PQ | 16 (2) |
| 47 | 389 (50) | γ | ------T----Q----QPQQ | 16 (6) |
| 58 | 407 (52) | γ | QP------S----Q----PQ | 14 (5) |
| 63 | 399 (51) | γ | ------T----Q----LQQP | 13 (5) |
| 67 | 408 (52) | γ | QP------SK---Q----PQ | 12 (5) |
| 71 | 379 (49) | γ | QQP--Q--------Q----P | 11 (5) |
| 72 | 397 (51) | γ | PQQP------T----Q--- | 11 (3) |

TABLE 20-continued

Peptides > 10% as bioactive as P04722 QE65 grouped structure.

| Rank | Peptide no. [SEQ ID NO:] (Pool) | Gliadin-subtype | Sequence | IFNg ELISpot response compared to P04722 77-93 QE85 (SEQ ID NO: 27): mean (SEM) |
|---|---|---|---|---|
| | | | Group 6: Peptide 625 | |
| | | | PIQPQQPFPQQP (SEQ ID NO: 41) | |
| 26 | 625 (80) | ω | ------------QQPQQPFP | 22 (9) |
| 57 | 624 (80) | ω | FTQPQQPT------------ | 14 (6) |
| 65 | 628 (80) | ω | PF-W----------TQQSFPLQ | 12 (4) |
| | | | Group 7: Peptide 618 | |
| 39 | 618 (79) | ω | PQQSFSYQQQPFPQQPYPQQ | 18 (7) |

TABLE 21

Bioactivity of individual tTG-deamidated Pools 1-3 peptides in Subject C12:

| No. | Sequence | % | No | Sequence | % |
|---|---|---|---|---|---|
| 8 | AVRWPVP<u>QLQPQNPSQQQPQ</u> | 100 | 23 | <u>LQPQNPSQQQPQ</u>EQVPLMQQ | 26 |
| 5 | MVRVTVPQ.................................. | 85 | 14 | ................................EQVPLVQQ | 18 |
| 6 | AVRVSVPQ.................................. | 82 | 15 | ........................H.....EQVPLVQQ | 18 |
| 3 | MVRVPVPQ.................H....... | 77 | 17 | ................................KQVPLVQQ | 18 |
| 1 | AVRFPVPQ.................L....... | 67 | 16 | .........D..................EQVPLVQQ | 13 |
| 2 | MVRVPVPQ.................................. | 59 | 13 | ................................EQVPLVQQ | 8 |
| 9 | AVRVPVPQ......L........... | 49 | 22 | .......K..................EQVPLVQQ | 5 |
| 7 | AVRVPVPQ.................................. | 49 | 18 | .....L..................EQVPLVQE | 3 |
| 10 | MVRVPVPQ......L........... | 33 | 19 | .....L..................EQVPLVQE | 3 |
| 4 | MVRVPMPQ.........D....... | 15 | 20 | P.....................P.........GQVPLVQQ | 0 |
| 12 | AVRVPVPQ.......K........... | 8 | 21 | P.....................P.........RQVPLVQQ | 0 |
| 11 | AVRVPVPQP............P................ | 0 | | | |

Core sequence of epitope is underlined. Predicted deamidated sequence is: LQPENPSQEQPE (SEQ ID NO: 22)

TABLE 22

Phylogenetic groupings of wheat (*Triticum aestivum*) gliadins

Alpha/beta-gliadins (n = 61)

| | |
|---|---|
| A1a1 | AAA96525, EEWTA, P02863 |
| A1a2 | CAB76963 |
| A1a3 | AAA96276 |
| A1a4 | CAA26384, S07923 |
| A1a5 | AAA34280 |
| A1a6 | P04728 |
| A1b1 | CAB76962 |
| A1b2 | CAB76961 |
| A1b3 | BAA12318 |
| A1b4 | CAB76960 |
| A1b5 | CAB76958 |
| A1b6 | CAB76959 |
| A1b7 | CAB76955 |
| A1b8 | AAA96524 |
| A1b9 | CAA10257 |
| A1b10 | AAA96523, T06282 |
| A1b11 | AAA17741, S52124 |
| A1b12 | AAA34281 |
| A1b13 | B22364, P04271 |
| A2a1 | AAB23109, CAA35238, P18573, S10015 |
| A2a2 | CAB76964 |
| A2b1 | P04724, T06500, AAA348282 |
| A2b2 | D22364 |
| A2b3 | P04722, T06498, AAA34276 |
| A2b4 | C22364 |
| A2b5 | CAB76956 |
| A3a1 | AAA34277, CAA26383, P04726, S07361 |
| A3a2 | 1307187B, A27319, S13333 |
| A3b1 | AAA96522 |
| A3b2i | AAA34279, P04727, |

TABLE 22-continued

Phylogenetic groupings of wheat (*Triticum aestivum*) gliadins

| | |
|---|---|
| A3b2ii | CAA26385, S07924 |
| A3b3 | A22364, AAA34278, AAB23108, C61218, P04725 |
| A4a | P04723, AAA34283, T06504 |
| A4b | E22364 |
| A4c | CAB76957 |
| A4d | CAB76954 |
| Gamma-gliadins (n = 47) | |
| GI1a | P08079, AAA34288, PS0094, CAC11079, AAD30556, CAC11057, CAC11065, CAC11056 |
| GI1b | CAC11089, CAC11064, CAC11080, CAC11078, AAD30440 |
| GI1c | CAC11087 |
| GI1d | CAC11088 |
| GI1e | CAC11055 |
| GI2a | JS0402, P08453, AAA34289 |
| GI2b | AAF42989, AAK84779, AAK84779 |
| GI3a | AAK84778 |
| GI3b | CAB75404 |
| GI3c | BAA11251 |
| GI4 | EEWTG, P06659, AAA34274 |
| Gamma-gliadins | |
| GI5a | AAK84774, AAK84772 |
| GI5b | AAK84773 |
| GI5c | AAK84776 |
| GI6a | JA0153, P21292, AAA34272, 1507333A |
| GI6b | AAK84777 |
| GI6c | 1802407A, AAK84775, AAK84780 |
| GI7 | AAB31090 |
| GIIa | AAA34287, P04730, S07398 |
| GIIb | 1209306A |
| GIII1a | P04729 |
| GIII1b | AAA34286 |
| Omega-gliadins (n = 3) | |
| O1a | AAG17702 |
| O1b | P02865 |
| O1c | A59156 |

TABLE 23

Synthetic peptides spanning all known wheat gliadin 12 mers

| Protein | Position* | Sequence | SEQ ID NO: | Peptide No. |
|---|---|---|---|---|
| POOL 1 | | | | |
| A1A1 | 20 | AVRF PVPQ LQPQ NPSQ QLPQ | 107 | 1 |
| A1A2 | 20 | MVRV PVPQ LQPQ NPSQ QQPQ | 108 | 2 |
| A1B1 | 20 | MVRV PVPQ LQPQ NPSQ QHPQ | 109 | 3 |
| A1B2 | 20 | MVRV PMPQ LQPQ DPSQ QQPQ | 110 | 4 |
| A1B7 | 20 | MVRV TVPQ LQPQ NPSQ QQPQ | 111 | 5 |
| A1B8 | 20 | AVRV SVPQ LQPQ NPSQ QQPQ | 112 | 6 |
| A1B8 | 20 | AVRV PVPQ LQPQ NPSQ QQPQ | 113 | 7 |
| A1B10 | 20 | AVRW PVPQ LQPQ NPSQ QQPQ | 114 | 8 |
| POOL 2 | | | | |
| A2B3 | 20 | AVRV PVPQ LQLQ NPSQ QQPQ | 115 | 9 |
| A2B5 | 20 | MVRV PVPQ LQLQ NPSQ QQPQ | 116 | 10 |
| A3A1 | 20 | AVRV PVPQ PQPQ NPSQ PQPQ | 117 | 11 |
| A3B1 | 20 | AVRV PVPQ LQPK NPSQ QQPQ | 118 | 12 |
| A1A1 | 28 | LQPQ NPSQ QLPQ EQVP LVQQ | 119 | 13 |
| A1A2 | 28 | LQPQ NPSQ QQPQ EQVP LVQQ | 120 | 14 |
| A1B1 | 28 | LQPQ NPSQ QHPQ EQVP LVQQ | 121 | 15 |
| A1B2 | 28 | LQPQ DPSQ QQPQ EQVP LVQQ | 122 | 16 |
| POOL 3 | | | | |
| A2B1 | 28 | LQPQ NPSQ QQPQ KQVP LVQQ | 123 | 17 |
| A2B3 | 28 | LQLQ NPSQ QQPQ EQVP LVQE | 124 | 18 |
| A2B5 | 28 | LQLQ NPSQ QQPQ EQVP LVQE | 125 | 19 |
| A3A1 | 28 | PQPQ NPSQ PQPQ GQVP LVQQ | 126 | 20 |
| A3A2 | 28 | PQPQ NPSQ PQPQ RQVP LVQQ | 127 | 21 |
| A3B1 | 28 | LQPK NPSQ QQPQ EQVP LVQQ | 128 | 22 |
| A4A | 28 | LQPQ NPSQ QQPQ EQVP LMQQ | 129 | 23 |
| A1A1 | 36 | QLPQ EQVP LVQQ QQFL GQQQ | 130 | 24 |
| POOL 4 | | | | |
| A1B1 | 36 | QHPQ EQVP LVQQ QQFL GQQQ | 131 | 25 |
| A1B2 | 36 | QQPQ EQVP LVQQ QQFL GQQQ | 132 | 26 |
| A1B12 | 36 | QQPQ EQVP LVQQ QQFL GQQQ | 133 | 27 |
| A2A1 | 36 | QQPQ EQVP LVQQ QQFP GQQQ | 134 | 28 |
| A2B1 | 36 | QQPQ KQVP LVQQ QQFP GQQQ | 135 | 29 |
| A2B3 | 36 | QQPQ EQVP LVQE QQFQ GQQQ | 136 | 30 |
| A3A1 | 36 | PQPQ GQVP LVQQ QQFP GQQQ | 137 | 31 |
| A3A2 | 36 | PQPQ RQVP LVQQ QQFP GQQQ | 138 | 32 |
| POOL 5 | | | | |
| A4A | 36 | QQPQ EQVP LMQQ QQQF PGQQ | 139 | 33 |
| A1A1 | 44 | LVQQ QQEL GQQQ PFPP QQPY | 140 | 34 |
| A1B1 | 44 | LVQQ QQFL GQQQ SFPP QQPY | 141 | 35 |
| A1B12 | 44 | LVQQ QQFL GQQQ FFPP QQPY | 142 | 36 |
| A2A1 | 44 | LVQQ QQFP GQQQ PFPP QQPY | 143 | 37 |
| A2B3 | 44 | LVQE QQFQ GQQQ PFPP QQPY | 144 | 38 |
| A3A1 | 44 | LVQQ QQFP GQQQ QFPP QQPY | 145 | 39 |
| A4A | 44 | LMQQ QQQF PGQQ EQFP PQQP | 146 | 40 |
| POOL 6 | | | | |
| A4D | 44 | LMQQ QQQF PGQQ ERFP PQQP | 147 | 41 |
| A1A1 | 53 | GQQQ PFPP QQPY PQPQ PFPS | 148 | 42 |
| A1A3 | 53 | GQQQ PFPP QQPY PQPQ FPSQ | 149 | 43 |
| A1B1 | 53 | GQQQ SFPP QQPY PQPQ PFPS | 150 | 44 |
| A2B1 | 53 | GQQQ PFPP QQPY PQQQ PFPS | 151 | 45 |
| A3A1 | 53 | GQQQ QFPP QQPY PQPQ PFPS | 152 | 46 |
| A4A | 53 | GQQE QFPP QQPY PHQQ PFPS | 153 | 47 |
| A4D | 53 | GQQE RFPP QQPY PHQQ PFPS | 154 | 48 |
| POOL 7 | | | | |
| A1A1 | 61 | QQPY PQPQ PFPS QLPY LQLQ | 155 | 49 |
| A1A3 | 61 | QQPY PQPQ FPSQ LPYL QLQP | 156 | 50 |
| A1B1 | 61 | QQPY PQPQ PFPS QQPY LQLQ | 157 | 51 |
| A2B1 | 61 | QQPY PQQQ PFPS QQPY MQLQ | 158 | 52 |
| A4A | 61 | QQPY PHQQ PFPS QQPY PQPQ | 159 | 53 |
| A1A1 | 69 | PFPS QLPY LQLQ PFPQ PQLP | 160 | 54 |
| A1B1 | 69 | PFPS QQPY LQLQ PPPQ PQLP | 161 | 55 |
| A1B10 | 69 | PFPS QQPY LQLQ PFSQ PQLP | 162 | 56 |
| POOL 8 | | | | |
| A1B11 | 69 | PFPS QQPY LQLQ PFLQ PQLP | 163 | 57 |
| A1B12 | 69 | PFPS QQPY LQLQ PPLQ PQPF | 164 | 58 |
| A2A1 | 69 | PFPS QQPY LQLQ PEPQ PQLP | 165 | 59 |
| A2B1 | 69 | PFPS QQPY MQLQ PFPQ PQLP | 166 | 60 |
| A2B2 | 69 | PFPS QQPY MQLQ PFPQ PQPF | 167 | 61 |
| A2B4 | 69 | PFPS QQPY LQLQ PFPQ PQPF | 168 | 62 |
| A2B5 | 69 | PFPS QQPY LQLQ PFPR PQLP | 169 | 63 |
| A4A | 69 | PFPS QQPY PQPQ PFPP QLPY | 170 | 64 |
| POOL 9 | | | | |
| A4B | 69 | PFPS QQPY PQPQ PFPQ PQPF | 171 | 65 |
| A1A1 | 77 | LQLQ PFPQ PQLP YSQP QPFR | 172 | 66 |
| A1A4 | 77 | LQLQ PFPQ PQLP YSQP QPFR | 173 | 67 |
| A1B1 | 77 | LQLQ PFPQ PQLP YLQP QPFR | 174 | 68 |
| A1B4 | 77 | LQLQ PFPQ PQLS YSQP QPFR | 175 | 69 |
| A1B10 | 77 | LQLQ PFSQ PQLP YSQP QPFR | 176 | 70 |
| A1B11 | 77 | LQLQ PFLQ PQLP YSQP QPFR | 177 | 71 |
| A1B12 | 77 | LQLQ PFLQ PQPF PPQL PYSQ | 178 | 72 |
| POOL 10 | | | | |
| A2A1 | 77 | LQLQ PFPQ PQLP YPQP QLPY | 179 | 73 |
| A2B1 | 77 | MQLQ PFPQ PQLP YPQP QLPY | 180 | 74 |
| A2B2 | 77 | MQLQ PFPQ PQPF PPQL PYPQ | 181 | 75 |
| A2B3 | 77 | LQLQ PFPQ PQLP YPQP QPFR | 182 | 76 |

TABLE 23-continued

Synthetic peptides spanning all known wheat gliadin 12 mers

| Protein | Position* | Sequence | SEQ ID NO: | Peptide No. |
|---|---|---|---|---|
| A2B4 | 77 | LQLQ PFPQ PQPF PPQL PYPQ | 183 | 77 |
| A2B5 | 77 | LQLQ PPPR PQLP YPQP QPFR | 184 | 78 |
| A3B1 | 77 | LQLQ PFPQ PQPF LPQL PYPQ | 185 | 79 |
| A3B3 | 77 | LQLQ PFPQ PQPF PPQL PYPQ | 186 | 80 |
| POOL 11 | | | | |
| A4A | 77 | PQPQ PFPP QLPY PQTQ PFPP | 187 | 81 |
| A4B | 77 | PQPQ PFPQ PQPP PPQL PYPQ | 188 | 82 |
| A1A1 | 85 | PQLP YSQP QPFR PQQP YPQP | 189 | 83 |
| A1A6 | 85 | PQLP YSQP QQFR PQQP YPQP | 190 | 84 |
| A1B1 | 85 | PQLP YLQP QPFR PQQP YPQP | 191 | 85 |
| A1B4 | 85 | PQLS YSQP QPFR PQQP YPQP | 192 | 86 |
| A1B6 | 85 | PQLS YSQP QPFR PQQL YPQP | 193 | 87 |
| A1B12 | 85 | PQPF PPQL PYSQ PQPF RPQQ | 194 | 88 |
| POOL 12 | | | | |
| A2A1 | 85 | PQLP YPQP QLPY PQPQ LPYP | 195 | 89 |
| A2B1 | 85 | PQLP YPQP QLPY PQPQ PFRP | 196 | 90 |
| A2B2 | 85 | PQPF PPQL PYPQ PQLP PFRP | 197 | 91 |
| A2B3 | 85 | PQLP YPQP QPFR PQQP YPQP | 198 | 92 |
| A2B4 | 85 | PQPP PPQL PYPQ PQPF RPQQ | 199 | 93 |
| A3A1 | 85 | PQPF PPQL PYPQ PPPF SPQQ | 200 | 94 |
| POOL 13 | | | | |
| A3B1 | 85 | PQPP LPQL PYPQ PQSF PPQQ | 201 | 95 |
| A3B3 | 85 | PQPP PPQL PYPQ PQSF PPQQ | 202 | 96 |
| A4A | 85 | QLPY PQTQ PFPP QQPY PQPQ | 203 | 97 |
| A4B | 85 | PQPF PPQL PYPQ TQPF PPQQ | 204 | 98 |
| A2A1 | 106 | LPYP QPQP FRPQ QPYP QSQP | 205 | 99 |
| A2B1 | 106 | LPYP QPQP FRPQ QSYP QPQP | 206 | 100 |
| A3A1 | 106 | LPYP QPPP FSPQ QPYP QPQP | 207 | 101 |
| A3B1 | 106 | LPQL PYPQ PQSF PPQQ PYPQ | 208 | 102 |
| POOL 14 | | | | |
| A4A | 106 | PPQL PYPQ TQPF PPQQ PYPQ | 209 | 103 |
| A1A1 | 112 | QPPR PQQP YPQP QPQY SQPQ | 210 | 104 |
| A1B0 | 112 | QPPR PQQL YPQP QPQY SQPQ | 211 | 105 |
| A2A1 | 112 | QPFR PQQP YPQS QPQY SQPQ | 212 | 106 |
| A2B1 | 112 | QPFR PQQS YPQP QPQY SQPQ | 213 | 107 |
| A3A1 | 112 | PPFS PQQP YPQP QPQY PQPQ | 214 | 108 |
| A3B1 | 112 | QSFP PQQP YPQQ RPKY LQPQ | 215 | 109 |
| A3B2 | 112 | QSFP PQQP YPQQ RPMY LQPQ | 216 | 110 |
| POOL 15 | | | | |
| A3B3 | 112 | QSFP PQQP YPQQ QPQY LQPQ | 217 | 111 |
| A4A | 112 | QPFP PQQP YPQP QPQY PQPQ | 218 | 112 |
| A1A1 | 120 | YPQP QPQY SQPQ QPIS QQQQ | 219 | 113 |
| A1B3 | 120 | YPQP QPQY SQPQ EPIS QQQQ | 220 | 114 |
| A2A1 | 120 | YPQS QPQY SQPQ QPIS QQQQ | 221 | 115 |
| A3A1 | 120 | YPQP QPQY PQPQ QPIS QQQA | 222 | 116 |
| A3B1 | 120 | YPQQ RPKY LQPQ QPIS QQQA | 223 | 117 |
| A3B2 | 120 | YPQQ RPMY LQPQ QPIS QQQA | 224 | 118 |
| POOL 16 | | | | |
| A3B3 | 120 | YPQQ QPQY LQPQ QPIS QQQA | 225 | 119 |
| A1A1 | 128 | SQPQ QPIS QQQQ QQQQ QQQQ | 226 | 120 |
| A1B3 | 128 | SQPQ EPIS QQQQ QQQQ QQQI | 227 | 121 |
| A3A1 | 128 | PQPQ QPIS QQQA QQQQ QQQQ | 228 | 122 |
| A1A1 | 138 | QQQQ QQQQ QQQQ QQQQ ILQQ | 229 | 123 |
| A1A6 | 138 | QQQQ QQQQ QQQQ QEQQ ILQQ | 230 | 124 |
| A1B11 | 138 | QQQQ QQQQ QQQQ QQQQ IIQQ | 231 | 125 |
| A2A1 | 138 | QQQQ QQQQ QQKQ QQQQ QQQI | 232 | 126 |
| POOL 17 | | | | |
| A4B | 139 | AQQQ QQQQ QQQQ QQQQ TLQQ | 233 | 127 |
| A1A1 | 146 | QQQQ QQQQ ILQQ ILQQ QLIP | 234 | 128 |
| A1A1 | 146 | QQQQ QQQQ ILQQ ILQQ QLIP | 235 | 129 |
| A1B6 | 146 | QQQQ QEQQ ILQQ MLQQ QLIP | 236 | 130 |
| A1B10 | 146 | QQQQ QEQQ ILQQ ILQQ QLTP | 237 | 131 |
| A1B11 | 146 | QQQQ QQQQ IIQQ ILQQ QLIP | 238 | 132 |
| A2A1 | 146 | QQKQ QQQQ QQQI LQQI LQQQ | 239 | 133 |
| A3A2 | 146 | QQQQ QQQQ ILPQ ILQQ QLIP | 240 | 134 |
| A4A | 146 | QQQQ QQQQ TLQQ ILQQ QLIP | 241 | 135 |
| A1A1 | 163 | ILQQ ILQQ QLIP CMDV VLQQ | 242 | 136 |
| A1B6 | 163 | ILQQ MLQQ QLIP CMDV VLQQ | 243 | 137 |
| A1B10 | 163 | ILQQ QLTP CMDV VLQQ | 244 | 138 |
| A2B1 | 163 | ILQQ ILQQ QLIP CRDV VLQQ | 245 | 139 |
| A3A2 | 163 | ILPQ ILQQ QL1P CRDV VLQQ | 246 | 140 |
| A4A | 163 | TLQQ ILQQ QLIP CRDV VLQQ | 247 | 141 |
| A1A1 | 171 | QLIP CMDV VLQQ HNIA HGRS | 248 | 142 |
| POOL 19 | | | | |
| A1A3 | 171 | QLIP CMDV VLQQ HNKA HGRS | 249 | 143 |
| A1B2 | 171 | QLIP CMDV VLQQ HNLA HGRS | 250 | 144 |
| A1B7 | 171 | QLIP CMDV VLQQ HNIV HGRS | 251 | 145 |
| A1B10 | 171 | QLTP CMDV VLQQ HNIA RGRS | 252 | 146 |
| A1B1 | 171 | QLIP CMDV VLQQ HNIV HGKS | 253 | 147 |
| A2A1 | 171 | QLIP CRDV VLQQ HSIA YGSS | 254 | 148 |
| A2B1 | 171 | QLIP CRDV VLQQ HSIA HGSS | 255 | 149 |
| A2B3 | 171 | QLIP CRDV VLQQ HNIA HGSS | 256 | 150 |
| POOL 20 | | | | |
| A3A1 | 171 | QLIP CRDV VLQQ HNIA HARS | 257 | 151 |
| A3B1 | 171 | QLIP CRDV VLQQ HNIA HASS | 258 | 152 |
| A1A1 | 179 | VLQQ HNIA HGRS QVLQ QSTY | 259 | 153 |
| A1A3 | 179 | VLQQ HNKA HGRS QVLQ QSTY | 260 | 154 |
| A1B2 | 179 | VLQQ HNLA HGRS QVLQ QSTY | 261 | 155 |
| A1B7 | 179 | VLQQ HNIV HGRS QVLQ QSTY | 262 | 156 |
| A1B10 | 179 | VLQQ HNIA RGRS QVLQ QSTY | 263 | 157 |
| A1B11 | 179 | VLQQ HNIV HGKS QVLQ QSTY | 264 | 158 |
| POOL 21 | | | | |
| A2A1 | 179 | VLQQ HSIA YGSS QVLQ QSTY | 265 | 159 |
| A2B1 | 179 | VLQQ HSIA HGSS QVLQ QSTY | 266 | 160 |
| A2B3 | 179 | VLQQ HNIA HGSS QVLQ ESTY | 267 | 161 |
| A3A1 | 179 | VLQQ HNIA HARS QVLQ QSTY | 268 | 162 |
| A3B1 | 179 | VLQQ HNIA HASS QVLQ QSTY | 269 | 163 |
| A4A | 179 | VLQQ HNIA HASS QVLQ QSSY | 270 | 164 |
| A1A1 | 187 | HGRS QVLQ QSTY QLLQ ELCC | 271 | 165 |
| A1A3 | 187 | HGRS QVLQ QSTV QLLR ELCC | 272 | 166 |
| POOL 22 | | | | |
| A1B8 | 187 | HGRS QVLQ QSTY QLLR ELCC | 273 | 167 |
| A1B11 | 187 | HGKS QVLQ QSTY QLLQ ELCC | 274 | 168 |
| A2A1 | 187 | YGSS QVLQ QSTY QLVQ QLCC | 275 | 169 |
| A2B1 | 187 | HGSS QVLQ QSTY QLVQ QFCC | 276 | 170 |
| A2B3 | 187 | HGSS QVLQ ESTY QLVQ QLCC | 277 | 171 |
| A3A1 | 187 | HARS QVLQ QSTY QPLQ QLCC | 278 | 172 |
| A3B1 | 187 | HASS QVLQ QSTY QLLQ QLCC | 279 | 173 |
| A4A | 187 | HASS QVLQ QSSY QQLQ QLCC | 280 | 174 |
| POOL 23 | | | | |
| A1A1 | 195 | QSTY QLLQ ELCC QHLW QIPE | 281 | 175 |
| A1A3 | 195 | QSTY QLLR ELCC QHLW QIPE | 282 | 176 |
| A1B8 | 195 | QSTY QLLR ELCC QHLW QIPE | 283 | 177 |
| A2A1 | 195 | QSTY QLVQ QLCC QQLW QIPE | 284 | 178 |
| A2B1 | 195 | QS1Y QLVQ QFCC QQLW QIPE | 285 | 179 |
| A3A1 | 195 | QSTY QPLQ QLCC QQLW QIPE | 286 | 180 |
| A3B1 | 195 | QSTY QLLQ QLCC QQLL QIPE | 287 | 181 |
| A4A | 195 | QSSY QQLQ QLCC QQLF QIPE | 288 | 182 |
| POOL 24 | | | | |
| A1A1 | 203 | ELCC QHLW QIPE QSQC QAIH | 289 | 183 |
| A1B6 | 203 | ELCC QHLW QILE QSQC QAIH | 290 | 184 |
| A1B10 | 203 | ELCC QHLW QIPE KLQC QAIH | 291 | 185 |
| A2A1 | 203 | QLCC QQLW QIPE QSRC QAIH | 292 | 186 |
| A2B1 | 203 | QFCC QQLW QIPE QSRC QAIH | 293 | 187 |
| A3B1 | 203 | QLCC QQLL QIPE QSRC QAIH | 294 | 188 |
| POOL 25 | | | | |
| A3B3 | 203 | GLCC QQLL QIPE QSQC QAIH | 295 | 189 |
| A4A | 203 | QLCC QQLF QIPE QSRC QAIH | 296 | 190 |
| A1A1 | 211 | QIPE QSQC QAIH NVVH AIIL | 297 | 191 |
| A1B3 | 211 | QIPE QSQC QAIQ NVVH AIIL | 298 | 192 |

TABLE 23-continued

Synthetic peptides spanning all known wheat gliadin 12 mers

| Protein | Position* | Sequence | SEQ ID NO: | Peptide No. |
|---|---|---|---|---|
| A1B6 | 211 | QILE QSQC QAIH NVVH AIIL | 299 | 193 |
| A1B9 | 211 | QIPE QSQC QAIH KVVH AIIL | 300 | 194 |
| A1B10 | 211 | QIPE KLQC QAIH NVVH AIIL | 301 | 195 |
| A2A1 | 211 | QIPE QSRC QAIH NVVH AIIL | 302 | 196 |
| POOL 26 | | | | |
| A3B3 | 211 | QIPE QSQC QAIH HVAH AIIM | 303 | 197 |
| A4A | 211 | QIPE QSRC QAIH NVVH AIIL | 304 | 198 |
| A1A1 | 219 | QAIH NVVH AIIL HQQQ KQQQ | 305 | 199 |
| A1A6 | 219 | QAIH NVVH AIIL HQQQ QKQQ | 306 | 200 |
| A1B3 | 219 | QAIQ NVVH AIIL HQQQ KQQQ | 307 | 201 |
| A109 | 219 | QAIH KVVH AIIL HQQQ KQQQ | 308 | 202 |
| A1013 | 219 | QAIH NVVH AIIL HQQQ QQQQ | 309 | 203 |
| A2B3 | 219 | QAIH NVVH AIIL HQQH HHHQ | 310 | 204 |
| POOL 27 | | | | |
| A3A1 | 219 | QAIH NVVH AIIL HQQQ RQQQ | 311 | 205 |
| A3B1 | 219 | QAIH NVVH AIIM HQQE QQQQ | 312 | 206 |
| A3B3 | 219 | QAIH NVAH AIIM HQQQ QQQQ | 313 | 207 |
| A4A | 219 | QAIH NVVH AIIL HHHQ QQQQ | 314 | 208 |
| A1A1 | 227 | AIIL HQQQ KQQQ QPSS QVSF | 315 | 209 |
| A1A6 | 227 | AIIL HQQQ QKQQ QPS SQFS | 316 | 210 |
| A1B2 | 227 | AIIL HQQQ KQQQ QLSS QVSF | 317 | 211 |
| A1B10 | 227 | AIIL HQQQ KQQQ PSSQ VSPQ | 318 | 212 |
| POOL 28 | | | | |
| A1B13 | 227 | AIIL HQQQ QQQQ EQKQ QLQQ | 319 | 213 |
| A2A1 | 227 | AIIL HQQQ QQQQ QQQQ QPLS | 320 | 214 |
| A2B3 | 227 | AIIL HQQH HHHQ QQQQ QPLS | 321 | 215 |
| A2B4 | 227 | AIIL HQQH HHHQ EQKQ QLQQ | 322 | 216 |
| A3A1 | 227 | AIIL HQQQ RQQQ PSSQ VSLQ | 323 | 217 |
| A3B1 | 227 | AIIM HQQE QQQQ LQQQ QQQQ | 324 | 218 |
| A3B3 | 227 | AIIM HQQQ QQQQ EQKQ QLQQ | 325 | 219 |
| A4A | 227 | AIIM HHHQ QQQQ QPSS QVSY | 326 | 220 |
| POOL 29 | | | | |
| A1A1 | 235 | KQQQ QPSS QVSF QQPL QQYP | 327 | 221 |
| A1A6 | 235 | KQQQ QPSF QFSF QQPL QQYP | 328 | 222 |
| A1B2 | 235 | KQQQ QLSS QVSF QQPL QQYP | 329 | 223 |
| A1010 | 235 | KQQQ PSSQ VSEQ QPQQ QYPL | 330 | 224 |
| A1B13 | 235 | QQQQ EQKQ QLQQ QQQQ QQQL | 331 | 225 |
| A2B4 | 235 | HHHQ EQKQ QLQQ QQQQ QQQL | 332 | 226 |
| A3A1 | 235 | RQQQ PSSQ VSLQ QPQQ QYPS | 333 | 227 |
| A3B1 | 235 | QQQQ LQQQ QQQQ LQQQ QQQQ | 334 | 228 |
| POOL 30 | | | | |
| A4A | 235 | QQQQ QPSS QVSY QQPQ EQYP | 335 | 229 |
| A1B13 | 243 | QLQQ QQQQ QQQL QQQQ QKQQ | 336 | 230 |
| A1B13 | 251 | QQQL QQQQ QKQQ QQPS SQVS | 337 | 231 |
| A2A1 | 260 | QQQQ QQQQ QPLS QVSF QQPQ | 338 | 232 |
| A2B1 | 260 | QQQQ QQQQ QPLS QVCF QQSQ | 339 | 233 |
| A2B3 | 260 | HHHQ QQQQ QQQQ QPLS QVSF | 340 | 234 |
| A3B1 | 260 | QQQQ QQQQ QPSS QVSI QQPQ | 341 | 235 |
| A2A1 | 289 | QPLS QVSP QQPQ QQYP SGQG | 342 | 236 |
| POOL 31 | | | | |
| A231 | 289 | QPLS QVCF QQSQ QQYP SGQG | 343 | 237 |
| A3B1 | 289 | QPSS QVSF QQPQ QQYP SSQV | 344 | 238 |
| A1A1 | 293 | QVSF QQPL QQYP LGQG SFRP | 345 | 239 |
| A1A6 | 293 | QFSF QQPL QQYP LGQG SFRP | 346 | 240 |
| A1B2 | 293 | QVSF QQPQ QQYP LGQG SFRP | 347 | 241 |
| A2A1 | 293 | QVSF QQPQ QQYP SGQG SPQP | 348 | 242 |
| A2B1 | 293 | QVCF QQSQ QQYP SGQG SFQP | 349 | 243 |
| A2B3 | 293 | QVSF QQPQ QQYP SGQG FPQP | 350 | 244 |
| POOL 32 | | | | |
| A2B5 | 293 | QVSF QQPQ QQYP SGQG FFQP | 351 | 245 |
| A3A1 | 293 | QVSL QQPQ QQYP SGQG FPQP | 352 | 246 |
| A3B1 | 293 | QVSP QQPQ QQYP SSQV SFQP | 353 | 247 |
| A3B2 | 293 | QVSF QQPQ QQYP SSQQ SFQP | 354 | 248 |
| A4A | 293 | QVSY QQPQ EQYP SGQV SFQS | 355 | 249 |
| A1A1 | 301 | QQYP LGQG SFRP SQQN SQAQ | 356 | 250 |
| A1B2 | 301 | QQYP LGQG SFRP SQQN SQAQ | 357 | 251 |
| A2A1 | 301 | QQYP SGQG SEQP SQQN PQAQ | 358 | 252 |
| POOL 33 | | | | |
| A2B3 | 301 | QQYP SGQG FFQP SQQN PQAQ | 359 | 253 |
| A2B5 | 301 | QQYP SGQG FFQP FQQH PQAQ | 360 | 254 |
| A3A1 | 301 | QQYP SGQG FFQP SQQN PQAQ | 361 | 255 |
| A3B1 | 301 | QQYP SSQV SFQP SQLN PQAQ | 362 | 256 |
| A3B2 | 301 | QQYP SGQG SFQP SQQN PQAQ | 363 | 257 |
| A4A | 301 | EQYP SGQV SFQS SQQN PQAQ | 364 | 258 |
| A1B1 | 309 | SFRP SQQN PLAQ GSVQ PQQL | 365 | 259 |
| A1A1 | 309 | SFRP SQQN PQAQ GSVQ PQQL | 366 | 260 |
| POOL 34 | | | | |
| A1A3 | 309 | SFRP SQQN PQTQ GSVQ PQQL | 367 | 261 |
| A1B2 | 309 | SFRP SQQN SQAQ GSVQ PQQL | 368 | 262 |
| A1B3 | 309 | SFRP SQQN PQDQ GSVQ PQQL | 369 | 263 |
| A1B4 | 309 | SFRP SQQN PRAQ GSVQ PQQL | 370 | 264 |
| A2A1 | 309 | SFQP SQQN PQAQ GSVQ PQQL | 371 | 265 |
| A2B3 | 309 | FFQP SQQN PQAQ GSFQ PQQL | 372 | 266 |
| A2B5 | 309 | FFQP FQQN PQAQ GSFQ PQQL | 373 | 267 |
| A3A1 | 309 | FFQP FQQN PQAQ GSVQ PQQL | 374 | 268 |
| Pool 35 | | | | |
| A3B1 | 309 | SFQP SQLN PAQG SVQP QQL | 375 | 269 |
| A3B1 | 309 | SFQP SQLN PAQG SVQP QQL | 376 | 270 |
| A3B2 | 309 | SEQP SQQN PQAQ GSVQ PQQL | 377 | 271 |
| A4A | 309 | SFQS SQQN PQAQ GSVQ PQQL | 378 | 272 |
| A1A1 | 317 | PQAQ GSVQ PQQL PQPE EIRN | 379 | 273 |
| A1A3 | 317 | PQTQ GSVQ PQQL PQPE EIRN | 380 | 274 |
| A1A6 | 317 | PQAQ GSVQ PQQL PQEE IRNL | 381 | 275 |
| A1B1 | 317 | PLAQ GSVQ PQQL PQFE EIRN | 382 | 276 |
| POOL 36 | | | | |
| A1B3 | 317 | PQDQ GSVQ PQQL PQFE EIRN | 383 | 277 |
| A1B4 | 317 | PRAQ GSVQ PQQL PQFE EIRN | 384 | 278 |
| A2A1 | 317 | PQAQ GSFQ PQQL PQFE EIRN | 385 | 279 |
| A2B5 | 317 | PQAQ GSPQ PQQL PQFE AIRN | 386 | 280 |
| A3B1 | 317 | OQAQ GSVQ PQQL PQEA EIRN | 387 | 281 |
| A4A | 317 | PQAQ GSVQ PQQL PQFQ EIRN | 388 | 282 |
| Pool 37 | | | | |
| A1A1 | 325 | PQQL PQFE EIRN LALQ TLPA | 389 | 283 |
| A1A6 | 325 | PQQL PQFE IRNL ALQT LPAM | 390 | 284 |
| A1B12 | 325 | PQQL PQFE EIRN LARK | 391 | 285 |
| A2A1 | 325 | PQQL PQFE EIRN LALE TLPA | 392 | 286 |
| A2B5 | 325 | PQQL PQFE AIRN LALQ TLPA | 393 | 287 |
| A3B1 | 325 | PQQL PQFA EIRN LALQ TLPA | 394 | 288 |
| A4A | 325 | PQQL PQFQ ERIN LALQ TLPA | 395 | 289 |
| A1A1 | 333 | EIRN LALQ TLPA MCNV YIPP | 396 | 290 |
| POOL 38 | | | | |
| A1A3 | 333 | EIRN LALQ TLPS MCNV YIPP | 397 | 291 |
| A2A1 | 333 | EIRN LALE TLPA MCNV YIPP | 398 | 292 |
| A3A1 | 333 | EIRN LALQ TLPR MCNV YIPP | 399 | 293 |
| A1A1 | 341 | TLPA MCNV YIPP YCTI APFG | 400 | 294 |
| A1A3 | 341 | TLPS MCNV YIPP YCTI APFG | 401 | 295 |
| A1B1 | 341 | TLPA MCNV YIPP YCTI VPFG | 402 | 296 |
| A1B4 | 341 | TLPA MCNV YIPP YCTI APFG | 403 | 297 |
| A1B9 | 341 | TLPA MCNV YIPP YCTI TPFG | 404 | 298 |
| Pool 39 | | | | |
| A2A1 | 341 | TLPA MCNV YIPP YCTI APVG | 405 | 299 |
| A2B2 | 341 | TLPA MCNV YIPP YCST TIAP | 406 | 300 |
| A3A1 | 341 | TLPR MCNV YIPP YCST TIAP | 407 | 301 |
| A3A2 | 341 | TLPR MCNV YIPP YCST TTAP | 408 | 302 |
| A3A1 | 341 | TLPA MCNV YIPP HCST TIAP | 409 | 303 |
| A1A1 | 349 | YIPP YCTI APFG IFGT NYR | 410 | 304 |
| A1B1 | 349 | YIPP YCTI VPPG IFGT NYR | 411 | 305 |
| A1B4 | 349 | YIPP YCAM APFG IFGT NYR | 412 | 306 |

TABLE 23-continued

Synthetic peptides spanning all known wheat gliadin 12 mers

| Protein | Position* | Sequence | SEQ ID NO: | Peptide No. |
|---|---|---|---|---|
| Pool 40 | | | | |
| A1B5 | 349 | YIPP YCTM APFG IFGT NYR | 413 | 307 |
| A1B9 | 349 | YIPP YCTI TPFG IFGT N | 414 | 308 |
| A2A1 | 349 | YIPP YCTI APVG IFGT NYR | 415 | 309 |
| A2B2 | 349 | YIPP YCST TIAP VGIF GTN | 416 | 310 |
| A3A2 | 349 | YIPP YCST TTAP FGIF GTN | 417 | 311 |
| A3B1 | 349 | YIPP HCST TIAP FGIF GTN | 418 | 312 |
| A3B3 | 349 | YIPP HCST TIAP FGIS GTN | 419 | 313 |
| A4D | 350 | IPPY CSTT IAPF GIFG TNYR | 420 | 314 |
| Pool 41 | | | | |
| GI1A | 17 | GTAN MQVD PSSQ VQWP QQQP | 421 | 315 |
| GI2A | 17 | GTAN IQVD PSGQ VQWL QQQL | 422 | 316 |
| GI3A | 17 | ATAN MQVD PSGQ VPWP QQQP | 423 | 317 |
| GI3B | 19 | MN IQVD PSGQ VPWP QQQP FP | 424 | 318 |
| GI4 | 17 | ATAN MQAD PSGQ VQWP QQQP | 425 | 319 |
| GI5A | 17 | TTAN IQVD PSGQ VQWP QQQP | 426 | 320 |
| GI5C | 17 | ATAN MQVD PSGQ VQWP QQQQ | 427 | 321 |
| GI7 | 20 | QIVF PSGQ VQWP QQQQ PFP | 428 | 322 |
| Pool 42 | | | | |
| GI1A | 25 | PSSQ VQWP QQQP VPQP HQPF | 429 | 323 |
| GI2A | 25 | PSGQ VQWL QQQL VPQL QQPL | 430 | 324 |
| GI3A | 25 | PSGQ VPWP QQQP FPQP HQPF | 431 | 325 |
| GI4 | 25 | PSGQ VQWP QQQP FLQP HQPF | 432 | 326 |
| GI5A | 25 | PSGQ VQWP QQQQ PFPQ PQQP | 433 | 327 |
| GI5C | 25 | PSGQ VQWP QQQP FRQP QQPF | 434 | 328 |
| GI6A | 25 | PSGQ VQWP QQQP FPQP QQPF | 435 | 329 |
| GI1A | 33 | QQQP VPQP HQPF SQQP QQTF | 436 | 330 |
| POOL 43 | | | | |
| GI2A | 33 | QQQL VPQL QQPL SQQP QQTF | 437 | 331 |
| GI3A | 33 | QQQP FPQP HQPF SQQP QQTF | 438 | 332 |
| GI4 | 33 | QQQP FLQP HQPF SQQP QQIF | 439 | 333 |
| GI5A | 33 | QQQQ PFPQ PQQP FSQQ PQQI | 440 | 334 |
| GI5B | 33 | QQQQ PFPQ PQQP QQPE PQPQ | 441 | 335 |
| GI5C | 33 | QQQP FRQP QQPY QQPH QHTF | 442 | 336 |
| GI6A | 33 | QQQP FPQP QQPF CQQP QRTI | 443 | 337 |
| GI6C | 42 | QQQP FPQP QQPP CEQP QRTI | 444 | 338 |
| POOL 44 | | | | |
| GI1A | 42 | HQPF SQQP QQTF PQPQ QTFP | 445 | 339 |
| GI2A | 42 | QQPL SQQP QQTF PQPQ QTFP | 446 | 340 |
| GI4 | 42 | HQPF SQQP QQIF PQPQ QTFP | 447 | 341 |
| GI5A | 42 | QQPF SQQP QQIF PQPQ QTFP | 448 | 342 |
| GI5B | 42 | QQPQ QPFP QPQQ PQLP FPQQ | 449 | 343 |
| GI5C | 42 | QQPF YQQP QHTF PQPQ QTCP | 450 | 344 |
| GI6A | 42 | QQPF CQQP QRTI PQPH QTFH | 451 | 345 |
| GI6B | 42 | QQPP CQQP QQTI PQPH QTFH | 452 | 346 |
| POOL 45 | | | | |
| GI6C | 42 | QQPF CEQP QRTI PQPH QTFH | 453 | 347 |
| GI1A | 50 | QQTP QQTF PQPQ HQPF QQFP | 454 | 348 |
| GI4 | 50 | QQIF PQPQ QTFP HQPQ QQFP | 455 | 349 |
| GI5A | 50 | QQIF PQPQ QTFP HQPQ QAFP | 456 | 350 |
| GI6A | 50 | QRTI PQPH QTFH HQPQ QTFP | 457 | 351 |
| GI5A | 58 | QTFP HQPQ QAFP QPQQ TFPH | 458 | 352 |
| GI6A | 58 | QTFH HQPQ QTFP HQPQ TYPH | 459 | 353 |
| GI6C | 58 | QTFH HQPQ QTFP QPEQ TYPH | 460 | 354 |
| POOL 46 | | | | |
| GI5A | 66 | QAFP QPQQ TFPH QPQQ QFPQ | 461 | 355 |
| GI5C | 66 | QHTF PQPQ QTCP HQPQ QQFP | 462 | 356 |
| GI6A | 66 | QTFP HQPQ TYPH QPQQ QFPQ | 463 | 357 |
| GI6C | 66 | QTFP QPEQ TYPH QPQQ QFPQ | 464 | 358 |
| GI1A | 73 | QTFP HQPQ QQFP QPQQ PQQQ | 465 | 359 |
| GI2A | 73 | QTPP HQPQ QVP QQQ PQQP | 466 | 360 |
| GI3A | 73 | QTFP HQPQ QFS QQQ PQQQ | 467 | 361 |
| GI5C | 73 | QTCP HQPQ QQFP QPQQ PQQP | 468 | 362 |
| POOL 47 | | | | |
| GI6A | 73 | QTYP HQPQ QQFP QTQQ PQQP | 469 | 363 |
| GI1A | 81 | QQFP QPQQ PQQQ FLQP QQPP | 470 | 364 |
| GI2A | 81 | QQVP QPQQ PQQP FLQP QQPF | 471 | 365 |
| GI3A | 81 | QQFS QPQQ PQQQ FIQP QQPF | 472 | 366 |
| GI4 | 81 | QQFP QPQQ PQQQ FLQP RQPF | 473 | 367 |
| GI5A | 81 | QQFP QPQQ PQQP PPQQ PQQQ | 474 | 368 |
| GI6A | 81 | QQFP QTQQ PQQP FPQP QQTE | 475 | 369 |
| GI1A | 89 | PQQQ FLQP QQPF PQQP QQPY | 476 | 370 |
| POOL 48 | | | | |
| GI3A | 89 | PQQQ FIQP QQPP PQQP QQTY | 477 | 371 |
| GI3B | 89 | PQQQ FIQP QQPQ QTYP QRPQ | 478 | 372 |
| GI4 | 89 | PQQQ FLQP RQPE PQQP QQPY | 479 | 373 |
| GI5A | 89 | QQPP FPQQ PQQQ FPQP QQPQ | 480 | 374 |
| GI5C | 89 | PQQP FPQP QQPQ QPPP QPQQ | 481 | 375 |
| GI6A | 89 | PQQP FPQP QQTF PQQP QLPF | 482 | 376 |
| POOL 49 | | | | |
| GI5A | 97 | PQQQ FPQP QQPQ QPFP QQPQ | 483 | 377 |
| GI5A | 105 | QQPQ QPPP QPQQ QQFP QQPQ | 484 | 378 |
| GI5A | 113 | QQPQ QQFP QQPQ QQQP FPQP | 485 | 379 |
| GI5A | 121 | QPQQ QQQP FPQP QQPQ LPFP | 486 | 380 |
| GI1A | 126 | QQPF PQQP QQPY PQQP QQPP | 487 | 381 |
| GI2A | 126 | QQPF PQQP QQPF PQTQ QPQQ | 488 | 382 |
| GI3A | 126 | QQPF PQQP QQTY PQRP QQPP | 489 | 383 |
| GI4 | 126 | RQPF PQQP QQPY PQQP QQPP | 490 | 384 |
| POOL 50 | | | | |
| GI5A | 126 | QQPF PQPQ QPQL PFPQ QPQQ | 491 | 385 |
| GI5C | 126 | QQPF PQPQ QAQL PFPQ QPQQ | 492 | 386 |
| GI6A | 126 | QQTF PQQP QLPF PQQP QQPF | 493 | 387 |
| GI1A | 134 | QQPY PQQP QQPF PQTQ QPQQ | 494 | 388 |
| GI2A | 134 | QQPF PQQP QQPF PFTQ QPQQ | 495 | 389 |
| GI3A | 134 | QQTY PQRP QQPF PQTQ QPQQ | 496 | 390 |
| GI5A | 134 | QPQL PFPQ QPQQ PFPQ QPFQ | 497 | 391 |
| GI5C | 134 | QAQL PFPQ QPQQ PLPQ PQQP | 498 | 392 |
| POOL 51 | | | | |
| GI6A | 134 | QLPF PQQP QQPF PQPQ QPQQ | 499 | 393 |
| GI2A | 142 | QPQQ PFPQ QPQQ PFPQ TQQP | 500 | 394 |
| GI2A | 150 | QPQQ PFPQ TQQP QQPF PQQP | 501 | 395 |
| GI2A | 158 | TQQP QQPF PQQP QQPF PQTQ | 502 | 396 |
| GI2A | 166 | PQQP QQPF PQTQ QPQQ PFPQ | 503 | 397 |
| GI1A | 170 | QQPF PQTQ QPQQ LFPQ SQQP | 504 | 398 |
| GI2A | 170 | QQPF PQTQ QPQQ PFPQ LQQP | 505 | 399 |
| GI3A | 170 | QQPF PQTQ QPQQ PFPQ SQQP | 506 | 400 |
| POOL 52 | | | | |
| GI4 | 170 | QQPE PQTQ QPQQ PFPQ SKQP | 507 | 401 |
| GI5A | 170 | QQPF PQPQ QPQQ PFPQ LQQP | 508 | 402 |
| C15C | 170 | QQPL PQPQ QPQQ PEPQ QQPP | 509 | 403 |
| GI6A | 170 | QQPF PQPQ QPQQ PFPQ SQQP | 510 | 404 |
| GI1A | 178 | QPQQ LFPQ SQQP QQQF SQPQ | 511 | 405 |
| GI2A | 178 | QPQQ PFPQ LQQP QQPF PQPQ | 512 | 406 |
| GI3A | 178 | QPQQ PFPQ SQQP QQPF PQPQ | 513 | 407 |
| GI4 | 178 | QPQQ PFPQ SKQP QQPF PQPQ | 514 | 408 |
| POOL 53 | | | | |
| GI5A | 178 | QPQQ PFPQ LQQP QQPL PQPQ | 515 | 409 |
| GI1A | 186 | SQQP QQQF SQPQ QPFP QPQQ | 516 | 410 |
| GI2A | 186 | LQQP QQPF PQPQ QLP QPQQ | 517 | 411 |
| GI1A | 186 | SQQP QQPF PQPQ QPQQ PFPQ | 518 | 412 |
| GI4 | 186 | SKQP QQPF PQPQ QPQQ SFPQ | 519 | 413 |
| GI5A | 186 | LQQP QQPL PQPQ QPQQ PFPQ | 520 | 414 |
| GI5C | 186 | SQQP QQPF PQPQ QPQQ SFPQ | 521 | 415 |
| GI1A | 194 | SQPQ QQFP QPQQ PQQS FPQQ | 522 | 416 |
| POOL 54 | | | | |
| GI2A | 194 | PQPQ QQLP QPQQ PQQS FPQQ | 523 | 417 |
| GI3A | 194 | PQPQ QQFP QPQQ PQQS FPQQ | 524 | 418 |
| GI4 | 194 | PQPQ QPQQ SFPQ QQPS LIQQ | 525 | 419 |

TABLE 23-continued

Synthetic peptides spanning all known wheat gliadin 12 mers

| Protein | Position* | Sequence | SEQ ID NO: | Peptide No. |
|---|---|---|---|---|
| GI5A | 194 | PQPQ QPQQ PFPQ QQQP LIQP | 526 | 420 |
| GI5C | 194 | PQPQ QPQQ SFPQ QQQP LIQP | 527 | 421 |
| GI1A | 202 | QPQQ PQQS FPQQ QPPF IQPS | 528 | 422 |
| GI2A | 202 | QPQQ PQQS FPQQ QRPF IQPS | 529 | 423 |
| GI3A | 202 | QPQQ PQQS FPQQ QPSL IQQS | 530 | 424 |
| POOL 55 | | | | |
| GI1A | 210 | FPQQ QPPP IQPS LQQQ VNPC | 531 | 425 |
| GI2A | 210 | FPQQ QRPF IQPS LQQQ LNPC | 532 | 426 |
| GI3A | 210 | FPQQ QPSL IQQS LQQQ LNPC | 533 | 427 |
| GI5A | 210 | FPQQ QPPL IQPY LQQQ MNPC | 534 | 428 |
| GI6A | 210 | FPQQ QQPA IQSF LQQQ MNPC | 535 | 429 |
| GI1A | 218 | IQPS LQQQ VNPC KNFL LQQC | 536 | 430 |
| GI2A | 218 | IQPS LQQQ LNPC KNIL LQQS | 537 | 431 |
| GI3A | 218 | IQQS LQQQ LNPC KNFL LQQC | 538 | 432 |
| POOL 56 | | | | |
| GI5A | 218 | IQPY LQQQ MNPC KNYL LQQC | 539 | 433 |
| GI6A | 218 | IQSF LQQQ MNPC KNFL LQQC | 540 | 434 |
| GI1A | 226 | VNPC KNFL LQQC KPVS LVSS | 541 | 435 |
| GI2A | 226 | LNPC KNIL LQQS KPAS LVSS | 542 | 436 |
| GI3A | 226 | LNPC KNFL LQQC KPVS LVSS | 543 | 437 |
| GI5A | 226 | MNPC KNYL LQQC NPVS LVSS | 544 | 438 |
| GI6A | 226 | MNPC KNFL LQQC NHVS LVSS | 545 | 439 |
| GI1A | 234 | LQQC KPVS LYSS LWSM IWPQ | 546 | 440 |
| POOL 57 | | | | |
| GI2A | 234 | LQQS KPAS LVSS LWSI IWPQ | 547 | 441 |
| GI3A | 234 | LQQC KPVS LVSS LWSM ILPR | 548 | 442 |
| GI5A | 234 | LQQC NPVS LVSS LVSM ILPR | 549 | 443 |
| GI6A | 234 | LQQC NHVS LVSS LVSI ILPR | 550 | 444 |
| GI1A | 242 | LYSS LWSM IWPQ SDCQ VMRQ | 551 | 445 |
| GI2A | 242 | LVSS LWSI IWPQ SDCQ VMRQ | 552 | 446 |
| GI3A | 242 | LVSS LWSM ILPR SDCQ VMRQ | 553 | 447 |
| GI4 | 242 | LVSS LWSI ILPP SDCQ VMRQ | 554 | 445 |
| POOL 58 | | | | |
| GI5A | 242 | LVSS LVSM ILPR SDCK VMRQ | 555 | 449 |
| GI5C | 242 | LVSS LVSM ILPR SDCQ VMQQ | 556 | 450 |
| GI6A | 242 | LVSS LVSI ILPR SDCQ VMQQ | 557 | 451 |
| GI1A | 250 | IWPQ SDCQ VMRQ QCCQ QLAQ | 558 | 452 |
| GI3A | 250 | ILPR SDCQ VMRQ QCCQ QLAQ | 559 | 453 |
| GI4 | 250 | ILPP SDCQ VMRQ QCCQ QLAQ | 560 | 454 |
| GI5A | 250 | ILPR SDCK VMRQ QCCQ QLAR | 561 | 455 |
| GI5C | 250 | ILPR SDCQ VMQQ QCCQ QLAQ | 562 | 456 |
| POOL 59 | | | | |
| GI1A | 258 | VMRQ QCCQ QLAQ IPQQ LQCA | 563 | 457 |
| GI5A | 258 | VMRQ QCCQ QLAR IPQQ LQCA | 564 | 458 |
| GI5C | 258 | VMQQ QCCQ QLAQ IPRQ LQCA | 565 | 459 |
| GI6A | 258 | VMQQ QCCQ QLAQ IPQQ LQCA | 566 | 460 |
| GI1A | 266 | QLAQ IPQQ LQCA AIHT VIHS | 567 | 461 |
| GI1B | 266 | QLAQ IPQQ LQCA AIHT VIHS | 568 | 462 |
| GI2A | 266 | QLAQ IPQQ LQCA AIHS VVHS | 569 | 463 |
| GI3A | 266 | QLAQ IPQQ LQCA AIHS IVHS | 570 | 464 |
| POOL 60 | | | | |
| GI5A | 266 | QLAR IPQQ LQCA AIHG IVHS | 571 | 465 |
| GI5C | 266 | QLAQ IPRQ LQCA AIHS VVHS | 572 | 466 |
| GI6A | 266 | QLAQ IPQQ LQCA AVHS VAHS | 573 | 467 |
| GI1A | 274 | LQCA AIHT IIHS IIMQ QEQQ | 574 | 468 |
| GI1B | 274 | LQCA AIHT VIHS IIMQ QEQQ | 575 | 469 |
| GI2A | 274 | LQCA AIHS VVHS IIMQ QQQQ | 576 | 470 |
| POOL 61 | | | | |
| GI3A | 274 | LQCA AIHS IVHS IIMQ QEQQ | 577 | 471 |
| GI4 | 274 | LQCA AVHS VVHS IIMQ QEQQ | 578 | 472 |
| GI5A | 274 | LQCA AIHG IVHS IIMQ QEQQ | 579 | 473 |
| GI6A | 274 | LQCA AVHS VAHS IIMQ QEQQ | 580 | 474 |
| GI1A | 282 | IIHS IIMQ QEQQ EQQQ GMHI | 581 | 475 |
| GI1B | 282 | VIHS IIMQ QEQQ QGMH ILLP | 582 | 476 |
| GI2A | 282 | VVHS IIMQ QQQQ QQQQ QGID | 583 | 477 |
| GI3A | 282 | IVHS IIMQ QEQQ EQRQ OVQI | 584 | 478 |
| GI4 | 282 | VVHS IIMQ QEQQ EQLQ OVQI | 585 | 479 |
| GI5A | 282 | IVHS IIMQ QEQQ QQQQ QQQQ | 586 | 480 |
| GI5C | 282 | VVHS IVMQ QEQQ QGIQ ILRP | 587 | 481 |
| GI6A | 282 | VARS IIMQ QEQQ QOVP ILRP | 588 | 482 |
| GI1A | 290 | QEQQ EQQQ GMHI LLPL YQQQ | 589 | 483 |
| GI2A | 290 | QQQQ QQQQ QGID IFLP LSQH | 590 | 484 |
| GI2B | 290 | QQQQ QQQQ QGMH IFLP LSQQ | 591 | 485 |
| GI3A | 290 | QEQQ EQRQ GVQI LVPL SQQQ | 592 | 486 |
| POOL 63 | | | | |
| GI4 | 290 | QEQQ EQLQ GVQI LVPL SQQQ | 593 | 487 |
| GI5A | 290 | QEQQ QQQQ QQQG IQIM | 594 | 488 |
| GI5C | 290 | QEQQ QGIQ ILRP LFQL VQGQ | 595 | 489 |
| GI6A | 290 | QEQQ QGVP ILRP LPQL AQGL | 596 | 490 |
| GI5A | 29B | QQQQ QQQO IQIM RPLF QLVQ | 597 | 491 |
| GI1A | 305 | GMHI LLPL YQQQ QVGQ GTLV | 598 | 492 |
| GI2A | 305 | GIDI FLPL SQHE QVGQ GSLV | 599 | 493 |
| GI2B | 305 | GMHI FLPL SQQQ QVGQ GSLV | 600 | 494 |
| POOL 64 | | | | |
| GI3A | 305 | GVQI LVPL SQQQ QVOQ GTLV | 601 | 495 |
| GI4 | 305 | GVQI LVPL SQQQ QVGQ GILV | 602 | 496 |
| GI5A | 305 | GIQI MRPL FQLV QGQG IIQP | 603 | 497 |
| GI5C | 305 | GQIQ LRPL FQLV QGQG IIQP | 604 | 498 |
| GI6A | 305 | GVPI LRPL FQLA QGLG IIQP | 605 | 499 |
| GI1A | 313 | YQQQ QVOQ GTLV QGQG IIQP | 606 | 500 |
| GI2A | 313 | SQHE QVGQ GSLV QGQG IIQP | 607 | 501 |
| GI2B | 313 | SQQQ QVGQ GSLV QGQG IIQP | 608 | 502 |
| POOL 65 | | | | |
| GI3A | 313 | SQQQ QVGQ GTLV QGQG IIQP | 609 | 503 |
| GI4 | 313 | SQQQ QVGQ GTLV QGQG IIQP | 610 | 504 |
| GI1A | 321 | GTLV QGQG IIQP QQPA QLEA | 611 | 505 |
| GI2A | 321 | GSLV QGQG IIQP QQPA QLEA | 612 | 506 |
| GI5A | 321 | FQLV QGQG IIQP QQPA QLEV | 613 | 507 |
| GI6A | 321 | FQLA QGLG IIQP QQPA QLEG | 614 | 508 |
| GI1A | 329 | IIQP QQPA QLEA IRSL VLQT | 615 | 509 |
| GI3A | 329 | IIQP QQPA QLEV IRSL VLQT | 616 | 510 |
| POOL 66 | | | | |
| G13C | 329 | IIQP QQPA QLEV IRSS VLQT | 617 | 511 |
| GI5C | 329 | IIQP QQPA QYEV IRSL VLRT | 618 | 512 |
| GI6A | 329 | IIQP QQPA QLEG IRSL VLKT | 619 | 513 |
| GI1A | 337 | QLEA IRSL VLQT LPTM CNVY | 620 | 514 |
| GI2A | 337 | QLEA IRSL VLQT LPSM CNVY | 621 | 515 |
| GI3A | 337 | QLEV IRSL VLQT LATM CNVY | 622 | 516 |
| G13C | 337 | QLEV IRSS VLQT LATM CNVY | 623 | 517 |
| GI5A | 337 | QLEV IRSL VLGT LPTM CNVF | 624 | 518 |
| POOL 67 | | | | |
| GI5C | 337 | QYEV IRSL VIRT LPNM CNVY | 625 | 519 |
| GI6A | 337 | QLEG IRSL VLKT LPTM CNVY | 626 | 520 |
| GI1A | 345 | VLQT LPTM CNVY VPPE CSII | 627 | 521 |
| GI2A | 345 | VLQT LPSM CNVY VPPE CSIM | 628 | 522 |
| GI3A | 345 | VLQT LATM CNVY VPPY CSTI | 629 | 523 |
| GI5A | 345 | VLGT LPTM CNVF VPPE CSTT | 630 | 524 |
| GI5C | 345 | VLRT LPNM CNVY VRPD CSTI | 631 | 525 |
| GI6A | 345 | VLKT LPTM CNVY VPPD CSTI | 632 | 526 |
| POOL 68 | | | | |
| GI1A | 353 | CNVY VPPE CSII KAPF SSVV | 633 | 527 |
| GI1A | 353 | CNVY VPPE CSII RAPF ASIV | 634 | 528 |
| GI3A | 353 | CNVY VPPY CSTI RAPP ASIV | 635 | 529 |
| GI5A | 353 | CNVF VPPE CSTF RAPF ASIV | 636 | 530 |
| GI5C | 353 | CNVY VRPD CSTI NAPP ASIV | 637 | 531 |
| GI6A | 353 | CNVY VPPD CSTI NVPY ANID | 638 | 532 |
| GI1A | 361 | CSII KAPF SSVV AGIG GQ | 639 | 533 |
| GI2A | 361 | CSIM RAPF ASIV AGIG GQ | 640 | 534 |

TABLE 23-continued

Synthetic peptides spanning all known wheat gliadin 12 mers

| Protein | Position* | Sequence | SEQ ID NO: | Peptide No. |
|---|---|---|---|---|
| POOL 69 | | | | |
| GI3A | 361 | CSTI RAPF ASIV AGIG GQYR | 641 | 535 |
| GI4 | 361 | CSTI RAPF ASIV ASIG GQ | 642 | 536 |
| GI5A | 361 | CSTT KAPF ASIV ADIG GQ | 643 | 537 |
| GI5C | 361 | CSTI NAPF ASIV AGIS GQ | 644 | 538 |
| GI6A | 361 | CSTI NVPY ANID AGIG GQ | 645 | 539 |
| GII | 1 | PQQP FPLQ PQQS PLWQ SQQP | 646 | 540 |
| GII | 9 | PQQS FLWQ SQQP FLQQ PQQP | 647 | 541 |
| GII | 17 | SQQP PLQQ PQQP SPQP QQVV | 648 | 542 |
| POOL 70 | | | | |
| GII | 25 | PQQP SPQP QQVV QIIS PATP | 649 | 543 |
| GII | 33 | QQVV QIIS PATP TTIP SAGK | 650 | 544 |
| GII | 41 | PATP TTIP SAGK PTSA PFPQ | 651 | 545 |
| GII | 49 | SAGK PTSA PFPQ QQQQ HQQL | 652 | 546 |
| GII | 57 | PFPQ QQQQ HQQL AQQQ IPVV | 653 | 547 |
| GII | 65 | HQQL AQQQ IPVV QPSI LQQL | 654 | 548 |
| GII | 73 | IPVV QPSI LQQL NPCK VFLQ | 655 | 549 |
| GII | 81 | LQQL NPCK VFLQ QQCS PVAM | 656 | 550 |
| POOL 71 | | | | |
| GII | 89 | VFLQ QQCS PVAM PQRL ARSQ | 657 | 551 |
| GII | 97 | PVAM PQRL ARSQ MLQQ SSCH | 658 | 552 |
| GII | 105 | ARSQ MLQQ SSCH VMQQ QCCQ | 659 | 553 |
| GII | 113 | SSCH VMQQ QCCQ QLPQ IPQQ | 660 | 554 |
| GII | 121 | QCCQ QLPQ IPQQ SRYQ AIRA | 661 | 555 |
| GII | 127B | PQIP QQSR YEAI RAII YSII | 662 | 556 |
| GII | 129 | IPQQ SRYQ AIRA ILYS IILQ | 663 | 557 |
| GII | 137 | AIRA IIYS ILLQ EQQQ VQGS | 664 | 558 |
| POOL 72 | | | | |
| GII | 145 | IILQ EQQQ VQGS IQSQ QQQP | 665 | 559 |
| GII | 153 | VQGS IQSQ QQQP QQLG QCVS | 666 | 560 |
| GII | 161 | QQQP QQLG QCVS QPQQ QSQQ | 667 | 561 |
| GII | 169 | QCVS QPQQ QSQQ QLGQ QPQQ | 668 | 562 |
| GII | 177 | QSQQ QLGQ QPQQ QQLA QGTF | 669 | 563 |
| GII | 185 | QPQQ QQLA QGTF LQPH QIAQ | 670 | 564 |
| POOL 73 | | | | |
| GII | 193 | QGTF LQPH QIAQ LEVM TSIA | 671 | 565 |
| GII | 201 | QIAQ LEVM TSIA LRIL PTMC | 672 | 566 |
| GII | 209 | TSIA LRIL PTMC SVNV PLYR | 673 | 567 |
| GII | 217 | PTMC SVNV PLYR TTTS VPFG | 674 | 568 |
| GII | 225 | PLYR TTTS VPPG VGTG VGAY | 675 | 569 |
| GIII 1A | 1 | TTTR TFPI PTIS SNNN HHFR | 676 | 570 |
| GIII 1A | 9 | PTIS SNNN HHFR SNSN HHFH | 677 | 571 |
| GIII 1A | 17 | HHFR SNSN HHFH SNNN QFYR | 678 | 572 |
| POOL 74 | | | | |
| GIII 1A | 25 | HHPH SNNN QFYR NNNS PGHN | 679 | 573 |
| GIII 1A | 33 | QFYR NNNS PGHN NPLN NNNS | 680 | 574 |
| GIII 1A | 41 | PGHN NPLN NNNS PNNN SPSN | 681 | 575 |
| GIII 1A | 49 | NNNS PNNN SPSN HHNN SPNN | 682 | 576 |
| GIII 1A | 57 | SPSN HHNN SPNN NFQY HTHP | 683 | 577 |
| GIII 1A | 65 | SPNN NFQY HTHP SNHK NLPH | 684 | 578 |
| GIII 1A | 73 | HTHP SNHK NLPH TNNI QQQQ | 685 | 579 |
| GIII 1A | 81 | NLPH TNNI QQQQ PPFS QQQQ | 686 | 580 |
| POOL 75 | | | | |
| GIII 1A | 89 | QQQQ PPPS QQQQ PPFS QQQQ | 687 | 581 |
| GIII 1A | 97 | QQQQ PPFS QQQQ PVLP QQSP | 688 | 582 |
| GIII 1A | 105 | QQQQ PVLP QQSP FSQQ QQLV | 689 | 583 |
| GIII 1A | 113 | QQSP FSQQ QQLV LPPQ QQQQ | 690 | 584 |
| GIII 1A | 121 | QQLV LPPQ QQQQ QLVQ QQIP | 691 | 585 |
| GIII 1A | 129 | QQQQ QLVQ QQIP IVQP SVLQ | 692 | 586 |
| GIII 1A | 137 | QQIP IVQP SVLQ QLNP CKVF | 693 | 587 |
| GIII 1A | 145 | SVLQ QLNP CKVF LQQQ CSPV | 694 | 588 |
| POOL 76 | | | | |
| GIII 1A | 153 | CKVF LQQQ CSPV AMPQ RLAR | 695 | 589 |
| GIII 1A | 161 | CSPV AMPQ RLAR SQMW QQSS | 696 | 590 |
| GIII 1A | 169 | RLAR SQMW QQSS CHVM QQQC | 697 | 591 |
| GIII 1A | 177 | QQSS CHVM QQQC CQQL QQIP | 698 | 592 |
| GIII 1A | 185 | QQQC CQQL QQIP CQSR YEAI | 699 | 593 |
| GIII 1A | 193 | QQIP EQSR YEAI RAII YSII | 700 | 594 |
| GIII 1A | 201 | YEAI RAII YSII LQEQ QQGF | 701 | 595 |
| GIII 1A | 209 | YSII LQEQ QQGF VQPQ QQQP | 702 | 596 |
| POOL 77 | | | | |
| GIII 1A | 217 | QQQF VQPQ QQQP QQSG QGVS | 703 | 597 |
| GIII 1A | 225 | QQQP QQSG QGVS QSQQ QSQQ | 704 | 598 |
| GIII 1A | 233 | QGVS QSQQ QSQQ QLGQ CSFQ | 705 | 599 |
| GIII 1A | 241 | QSQQ QLGQ CSFQ QPQQ QLGQ | 706 | 600 |
| GIII 1A | 249 | CSFQ QPQQ QLGQ QPQQ QQQQ | 707 | 601 |
| GIII 1A | 257 | QLGQ QPQQ QQQQ QVLQ GTFL | 708 | 602 |
| GIII 1A | 263 | QQQQ QVLQ GTFL QPHQ LAHL | 709 | 603 |
| GIII 1A | 271 | GTFL QPHQ IAHL EAVT SIAL | 710 | 604 |
| POOL 78 | | | | |
| GIII 1A | 279 | IAHL EAVT SIAL RTLP TMCS | 711 | 605 |
| GIII 1A | 287 | SIAL RTLP TMCS VNVP LYSA | 712 | 606 |
| GIII 1A | 295 | TMCS VNVP LYSA TTSV PFGV | 713 | 607 |
| GIII 1A | 303 | LYSA TTSV PFGV GTGV GAY | 714 | 608 |
| GIII 1B | 26 | SCIS GLER PWQQ QPLP PQQS | 715 | 609 |
| GIII 1B | 34 | PWQQ QPLP PQQS FSQQ PPFS | 716 | 610 |
| GIII 1B | 42 | PQQS FSQQ PPFS QQQQ QPLP | 717 | 611 |
| GIII 1B | 50 | PPFS QQQQ QPLP QQPS FSQQ | 718 | 612 |
| Pool 79 | | | | |
| GIII 1B | 58 | QPLP QQPS FSQQ QPPF SQQQ | 719 | 613 |
| GIII 1B | 66 | FSQQ QPPP SQQQ PILS QQPP | 720 | 614 |
| GIII 1B | 74 | SQQQ PILS QQPP FSQQ QQPV | 721 | 615 |
| O 1A | 17 | ATAA RELN PSNK ELQS PQQS | 722 | 616 |
| O 1A | 25 | PSNK ELQS PQQS FSYQ PQQS | 723 | 617 |
| O 1A | 33 | PQQS PSYQ QQPF PQQP YPQQ | 724 | 618 |
| O 1A | 41 | QQPF PQQP YPQQ PYPS QQPY | 725 | 619 |
| O 1A | 49 | YPQQ PYPS QQPY PSQQ PFPT | 726 | 620 |
| POOL 80 | | | | |
| O 1A | 57 | QQPY PSQQ PFPT PQQQ FPEQ | 727 | 621 |
| O 1A | 65 | PFPT PQQQ FPEQ SQQQ FTQP | 728 | 622 |
| O 1A | 73 | FPEQ SQQQ FTQP QQPT PIQP | 729 | 623 |
| O 1A | 81 | FTQP QQPT PIQP QQPF PQQP | 730 | 624 |
| O 1A | 89 | PIQP QQPF PQQP QQPQ QPFP | 731 | 625 |
| O 1A | 97 | PQQP QQPQ QPFP QPQQ PFPW | 732 | 626 |
| O 1A | 105 | QPFP QPQQ PFPW QPQQ PFLQ | 733 | 627 |
| O 1A | 113 | PFPW QPQQ PFPQ TQQS FPLQ | 734 | 628 |
| POOL 81 | | | | |
| O 1A | 121 | PFPQ TQQS FPLQ PQQP FPQQ | 735 | 629 |
| O 1A | 129 | FPLQ PQQP FPQQ PQQP FPQP | 736 | 630 |
| O 1A | 137 | FPQQ PQQP PFQP QLPF PQQS | 737 | 631 |
| O 1A | 145 | PPQP QLPF PQQS EQII PQQL | 738 | 632 |
| O 1A | 153 | PQQS EQII PQQL QQPF PLQP | 739 | 633 |
| O 1A | 161 | PQQL QQPF PQQP QQPF PQPQ | 740 | 634 |
| O 1A | 169 | PQQP QQPF PQPQ QQPF PQPQ | 741 | 635 |
| O 1A | 177 | PQQP QQPF PQPQ QPIP VQPQ | 742 | 636 |
| POOL 82 | | | | |
| O 1A | 185 | PQPQ QPIP VQPQ QSFP QQSQ | 743 | 637 |
| O 1A | 193 | VQPQ QSFP QQSQ QSQQ PFAQ | 744 | 638 |
| O 1A | 201 | QQSQ QSQQ PFAQ PQQL FPEL | 745 | 639 |
| O 1A | 209 | PFAQ PQQL FPEL QQPL PQQP | 746 | 640 |
| O 1A | 217 | FPEL QQPI PQQP QQPF PLQP | 747 | 641 |
| O 1A | 225 | PQQP QQPF PLQP QQPF PQPQ | 748 | 642 |
| O 1A | 233 | PLQP QQPF PQQP QQPF PQPQ | 749 | 643 |
| O 1A | 241 | PQQP QQPF PQQP QQSF PQQP | 750 | 644 |
| POOL 83 | | | | |
| O 1A | 249 | PQQP QQSF PQQP QQPY PQQQ | 751 | 645 |
| O 1A | 257 | PQQP QQPY PQQQ PYGS SLTS | 752 | 646 |
| O 1A | 265 | PQQQ PYGS SLTS IGGQ | 753 | 647 |
| O 1B | 1 | ARQL NPSD QELQ SPQQ LYPQ | 754 | 648 |
| O 1B | 9 | QELQ SPQQ LYPQ QPYP QQPY | 755 | 649 |
| O 1C | 1 | SRLL SPRG KELH TPQE QFPQ | 756 | 650 |

TABLE 23-continued

Synthetic peptides spanning all known wheat gliadin 12 mers

| Protein | Position* | Sequence | SEQ ID NO: | Peptide No. |
|---|---|---|---|---|
| O 1C | 9 | KELH TPQE QFPQ QQQF PQPQ | 757 | 651 |
| O 1C | 17 | QFPQ QQQF PQPQ QFPQ | 758 | 652 |

*Position of N-terminal residue in α-, γ1-, γ2-, γ3-, or ω consensus sequence

The invention claimed is:

1. A method of treating coeliac disease in a subject in need thereof, the method comprising administering to the subject a therapeutically effective amount of a peptide comprising an amino acid sequence of transglutaminase-treated QQP-FPQPQQPFPWQP (SEQ ID NO:779), wherein the peptide is 15 amino acids in length and wherein the subject is tolerised to a gliadin protein.

* * * * *